US009796685B2

(12) United States Patent
Boersen et al.

(10) Patent No.: US 9,796,685 B2
(45) Date of Patent: Oct. 24, 2017

(54) FORMULATIONS OF 2-(TERT-BUTYLAMINO)- 4-((1R,3R,4R)-3-HYDROXY-4-METHYLCYCLOHEXYLAMINO)-PYRIMIDINE-5-CARBOXAMIDE

(71) Applicant: Signal Pharmaceuticals, LLC, San Diego, CA (US)

(72) Inventors: Nathan Andrew Boersen, Summit, NJ (US); Indrajit Ghosh, Hillsborough, NJ (US); Lianfeng Huang, Basking Ridge, NJ (US); Daozhong Zou, Raritan, NJ (US)

(73) Assignee: Signal Pharmaceuticals, LLC, San Diego, CA (US)

(*) Notice: Subject to any disclaimer, the term of this patent is extended or adjusted under 35 U.S.C. 154(b) by 0 days.

(21) Appl. No.: 14/969,750

(22) Filed: Dec. 15, 2015

(65) Prior Publication Data
US 2016/0168105 A1  Jun. 16, 2016

Related U.S. Application Data

(60) Provisional application No. 62/196,044, filed on Jul. 23, 2015, provisional application No. 62/092,537, filed on Dec. 16, 2014.

(51) Int. Cl.
A61K 31/505 (2006.01)
C07D 239/48 (2006.01)

(52) U.S. Cl.
CPC .................................. *C07D 239/48* (2013.01)

(58) Field of Classification Search
USPC ......................................................... 514/275
See application file for complete search history.

(56) References Cited

U.S. PATENT DOCUMENTS

| | | | |
|---|---|---|---|
| 3,845,055 A | 10/1974 | Hoegerle et al. | |
| 6,432,963 B1 | 8/2002 | Hisamichi et al. | |
| 7,169,798 B2 | 1/2007 | Green et al. | |
| 7,449,456 B2 | 11/2008 | Nagashima et al. | |
| 7,517,886 B2 | 4/2009 | Singh et al. | |
| 7,524,849 B2 | 4/2009 | Zhang et al. | |
| 7,589,200 B2 | 9/2009 | Singh et al. | |
| 7,601,714 B2 | 10/2009 | Barbosa et al. | |
| 7,718,653 B2 | 5/2010 | Barlaam et al. | |
| 7,893,074 B2 | 2/2011 | Garcia-Echeverria et al. | |
| 7,956,060 B2 | 6/2011 | Arai et al. | |
| 8,338,439 B2 | 12/2012 | Singh et al. | |
| 8,513,242 B2 | 8/2013 | Chiang et al. | |
| 8,519,129 B2 | 8/2013 | Marsilje et al. | |
| 8,580,805 B2 | 11/2013 | Maehr | |
| 8,853,230 B2 | 10/2014 | Bauer et al. | |
| 8,969,336 B2 | 3/2015 | Shimada et al. | |
| 9,139,534 B2 * | 9/2015 | Bennett | C07D 239/48 |
| 9,365,524 B2 * | 6/2016 | Man | C07D 239/42 |
| 2008/0139531 A1 | 6/2008 | Yanni et al. | |
| 2009/0036440 A1 | 2/2009 | Barlaam et al. | |
| 2011/0130415 A1 | 6/2011 | Singh et al. | |
| 2011/0159019 A1 | 6/2011 | Tanaka et al. | |
| 2015/0210650 A1 | 7/2015 | Ferretti et al. | |

FOREIGN PATENT DOCUMENTS

| | | |
|---|---|---|
| EP | 1 184 376 | 3/2002 |
| EP | 1 518 855 | 3/2005 |
| JP | 2006/124387 | 5/2006 |
| WO | WO 99/31073 | 6/1993 |
| WO | WO 00/12485 | 3/2000 |
| WO | WO 00/76980 | 12/2000 |
| WO | WO 03/063794 | 8/2003 |
| WO | WO 03/078404 | 9/2003 |
| WO | WO 03/082855 | 9/2003 |
| WO | WO 2004/014382 | 2/2004 |
| WO | WO 2004/054617 | 7/2004 |
| WO | WO 2004/002964 | 8/2004 |
| WO | WO 2004/067516 | 8/2004 |
| WO | WO 2006/027377 | 3/2006 |
| WO | WO 2006/027378 | 3/2006 |
| WO | WO 2006/035069 | 4/2006 |
| WO | WO 2006/091737 | 8/2006 |
| WO | WO 2008/009458 | 1/2008 |
| WO | WO 2008/129380 | 10/2008 |
| WO | WO 2009/012421 | 1/2009 |
| WO | WO 2009/131687 | 10/2009 |
| WO | WO 2009/136995 | 11/2009 |
| WO | WO 2009/143389 | 11/2009 |
| WO | WO 2009/145856 | 12/2009 |

(Continued)

OTHER PUBLICATIONS

Adeyeye, M. C. et al. (Eds.), *Preformulation in Solid Dosage Form Development*, CRC Press, 2008, pp. 239-240.
Bogoyevitch et al., 2010, "c-Jun N-terminal kinase (JNK) signaling: Recent advances and challenges," Biochimica et Biophysica Acta 1804:4630475.
Bosseray et al., PubMed Abstract (Pathol Biol (Paris) 50(8):483-92), Oct. 2002.
Bundgaard, "Design of prodrugs: Bioreversible derivatives for various functional groups and chemical entities," Design of Prodrugs, Chapter 1, p. 1, 1985.
Cohen P. 2001, "The role of protein phosphorylation in human health and disease." The Sir Hans Krebs Medal Lecture. Eur J Biochem. 268(19):5001-10.
Cohen P. 2002, "Protein kinases—the major drug targets of the twenty-first century?" Nat Rev Drug Discov. 1(4):309-15.

(Continued)

Primary Examiner — Rei-Tsang Shiao
(74) Attorney, Agent, or Firm — Jones Day

(57) ABSTRACT

Provided are pharmaceutical compositions and dosage forms of 2-(tert-butylamino)-4-((1R,3R,4R)-3-hydroxy-4-methylcyclohexylamino)-pyrimidine-5-carboxamide, or a pharmaceutically acceptable stereoisomer, tautomer, solid form, polymorph, salt, hydrate, clathrate, or solvate thereof. Also provided are methods of treating, managing, or preventing various disorders, such as diseases or disorders treatable or preventable by inhibition of a JNK pathway in mammals using such pharmaceutical compositions or dosage forms. Further provided are salts of 2-(tert-butylamino)-4-((1R,3R,4R)-3-hydroxy-4-methylcyclohexylamino)-pyrimidine-5-carboxamide and methods of preparation of such salts.

7 Claims, 108 Drawing Sheets

(56) References Cited

FOREIGN PATENT DOCUMENTS

| WO | WO 2009/158571 | 12/2009 |
|---|---|---|
| WO | WO 2010/024430 | 3/2010 |
| WO | WO 2010/032875 | 3/2010 |
| WO | WO 2010/038081 | 4/2010 |
| WO | WO 2010/051223 | 5/2010 |
| WO | WO 2010/080864 | 7/2010 |
| WO | WO 2010/090875 | 8/2010 |
| WO | WO 2010/097248 | 9/2010 |
| WO | WO 2010/129802 | 11/2010 |
| WO | WO 2010/144468 | 12/2010 |
| WO | WO 2011/016472 | 2/2011 |
| WO | WO 2011/065800 | 6/2011 |
| WO | WO 2011/090760 | 7/2011 |
| WO | WO 2012/012619 | 1/2012 |
| WO | WO 2012/044936 | 4/2012 |
| WO | WO 2012/045010 | 4/2012 |
| WO | WO 2012/045020 | 4/2012 |
| WO | WO 2012/145569 | 4/2012 |

OTHER PUBLICATIONS

Das et al., 1996, "Activation of raf-1, MEK, and MAP kinase in prolactin responsive mammary cells," Breast Cancer Res. Treat., 40(2):141-149.
Davis RJ., 1994, "MAPKs: new JNK expands the group." Trends Biochem Sci., 19(11):470-3.
Douglas, Jr., 1996, "Introduction to Viral Diseases," Cecil Textbook of Medicine, 20th Edition, vol. 2, pp. 1739-1747.
Eferl et al., 2008, "Development of pulmonary fibrosis through a pathway involving the transcription factor Fra-2/AP-1," PNAS, 105(30):10525-10530.
Fanger et al., 1997, "MEKKs, GCKs, MLKs, PAKs, TAKs, and tpls: upstream regulators of the c-Jun amino-terminal kinases?" Curr Opin Genet Dev. 7(1):67-74.
Gaestel et al., 2007, "Protein kinases as small molecule inhibitor targets in inflammation." Curr Med Chem. 14(21):2214-34.
Goff, PubMed Abstract (J Gene Med 3(6):517-28), No—Dec. 2001.
Grimminger et al., 2010, "Targeting non-malignant disorders with tyrosine kinase inhibitors," Nat Rev Drug Sisc., 9(12):956-970.
Hirabayashi et al., 2008, "A novel Syk family kinase inhibitor: design, synthesis, and structure-activity relationship of 1,2,4-triazolo[4,3-c]pyrimidine and 1,2,4-triazolo[1,5-c]pyrimidine derivatives," Bioorg Med Chem., 16:7347-7357.
Hirosumi et al., 2002, "A central role for JNK in obesity and insulin resistance," Nature, 420:333-336.
Hisamichi et al., 2005, "Synthetic studies on novel Syk inhibitors. Part 1: Synthesis and structure-activity relationships of pyrimidine-5-carboxamide derivatives," Bioorg Med Chem., 13:4936-4951.
Hisamichi et al., 2005, "Corrigendum to Synthetic studies on novel Syk inhibitors. Part 1: Synthesis and structure-activity relationships of pyrimidine-5-carboxamide derivatives," Bioorg. Med. Chem., 13:6277-6279.
Hu et al., 2000, "Prolonged activation of the mitogen-activated protein kinase pathway is required for macrophage-like differentiation of a human myeloid leukemic cell line," Cell Growth Differ., 11(4):191-200.
Hulikal, "L15 Deuterium Labeled Compounds in Drug Discovery Process," Abstract, 2010.
Ichijo H., 1999, "From receptors to stress-activated MAP kinases." Oncogene. 18(45):6087-93.
Jones et al., 2012, Phase 1 Results From a Study of Romidepsin in Combination With Gemcitabine in Patients With Advanced Solid Tumors, Cancer Investigation, 30:481-486.
Kaneto et al., 2007, "Oxidative stress and the JNK pathway are involved in the development of type 1 and type 2 diabetes," Curr Mol Med., 7:674-686.
Katayama et al., 2008, "Identification of a key element for hydrogen-bonding patterns between protein kinases and their inhibitors," Proteins, 73:795-801.

Kluwe et al., 2010, "Modulation of hepatic fibrosis by c-Jun-N-terminal kinase inhibition," Gastroenterology 138:347-359.
Kodama et al., 2009, "c-Jun N-terminal kinase-1 from hematopoietic cells mediates progression from hepatic steatosis to steatohepatitis and fibrosis in mice," Gastroenterology, 137:1467-1477.e5.
Kyriakis JM., 2000, "MAP kinases and the regulation of nuclear receptors." Sci STKE. (48):pe1.
Le Jeune et al., 2006, "Evaluation of imatinib mesylate effects on glioblastoma aggressiveness with SPECT radiotracer 99mTc-(v)-DMSA." Eur J Cancer. 42(8):1004-13.
Liddle et al., 2011, "Discovery of GSK143, a highly potent, selective and orally efficacious spleen tyrosine kinase inhibitor," Bioorg Chem Chem Lett., 21:6188-6194.
Malhi et al., 2006, "Free fatty acids induce JNK-dependent hepatocyte lipoapoptosis," J Biol Chem., 281:12093-12101.
Malhi et al., 2008, "Molecular mechanisms of lipotoxicity in nonalcoholic fatty liver disease," Semin Liver Dis., 28(4):360-369.
Nagashima et al., 2007, "Synthesis and evaluation of 2-{[2-(4-hydroxyphenyl)-ethyl]amino}pyrimidine-5-carboxamide derivatives as novel STAT6 inhibitors," Bioorg Med Chem., 15:1044-1055.
Nagashima et al., 2008, "Identification of 4-benzylamino-2[4-morpholin-4-ylphenyl)amino]pyrimidine-5-carboxamide derivatives as potent and orally bioavailable STAT6 inhibitors," Biorg Med Chem., 16:6509-6521.
Nagashima et al., 2009, "Novel 7H-pyrrolo[2,3-d]pyrimidine derivatives as potent and orally active STAT6 inhibitors," Bioorg Med Chem., 17:6926-6936.
Ohga et al., 2008, "YM-341619 suppresses the differentiation of spleen T cells into Th2 cells in vitro, eosinophilia, and airway hyperresponsiveness in rat allergic models," Eur J Pharmacol., 590:409-416.
Papp et al., 2007, "Steady state kinetics of spleen tyrosine kinase investigated by a real time fluorescence assay," Biochemistry, 46:15103-15114.
Pimlott, PubMed Abstract (Nucl Med Commun. 26(3):183-8), 2005.
Razonable et al., PubMed Abstract (Herpes 10(3):60-5), Dec. 2003.
Reilly et al., 2011, "PRT-060318, a novel Syk inhibitor, prevents heparin-induced thrombocytopenia and thrombosis in a transgenic mouse model," Blood, 117(7):2241-2246.
Sanam et al., 2009, "Discovery of potential ZAP-70 kinase inhibitors: pharmacophore design, database screening and docking studies," Eur J Med Chem., 44:4793-4800.
Sanchez-Tillo et al., 2007, "JNK1 is required for the induction of Mkp1 expression in macrophages during proliferation and lipopolysaccharide-dependent activation," J Biol Chem., 282(17):12566-73.
Schramek H., 2002, "MAP kinases from intracellular signals to physiology and disease." News Physiol Sci. 17:62-7.
Schwabe et al., 2004, "Differential requirement for c-Jun NH2-terminal kinase in TNF-α—and Fas-mediated apoptosis in hepatocytes," FASEB J. 18(6):720-722.
Seger and Krebs, 1995, "The MAPK signaling cascade." FASEB J. 9(9):726-35.
Silverman, 1992, "Prodrugs and Drug Delivery Systems," The Organic Chemistry of Drug Design and Drug action, Chapter 8, pp. 352-400.
Singh et al., 2009, "Differential effects of JNK1 and JNK2 inhibition on murine steatohepatitis and insulin resistance," Hepatology, 49(1):87-96.
Singh et al., 2012, "Discovery and development of spleen tyrosine kinase (SYK) inhibitors," J Med Chem., 55:3614-1643.
Sridhar et al., 2000, "Protein kinases as therapeutic targets," Pharm Res., 17(11):1345-1353.
Storey, R. A. et al. (Eds.), *Solid State Characterization of Pharmaceuticals*, Wiley-Blackwell, 2011, pp. 473-491, 490.
Uehara et al., 2004, "c-Jun N-Terminal Kinase Mediates Hepatic Injury after Rat Liver Transplantation," Transplantation, 78(3):324-332.
Vallerie et al., 2010, "The role of JNK proteins in metabolism," Sci Transl Med., 2(60):1-7.

(56) References Cited

OTHER PUBLICATIONS

Villasenor et al., 2009, "Structural insights for design of potent spleen tyrosine kinase inhibitors from crystallographic analysis of three inhibitor complexes," Chem Biol Drug Des., 73:466-470.
Virkamaki et al., 1999, "Protein-protein interaction in insulin signaling and the molecular mechanisms of insulin resistance," J Clin Invest., 103(7):931-943.
Whitmarsh AJ, et al. 1999, "Signal transduction by MAP kinases regulation by phosphorylation-dependent switches." Sci. STKE. (1):pe1.
Xie et al., 2009, "Pharmacophore modeling study based on known spleen tyrosine kinase inhibitors together with virtual screening for identifying novel inhibitors," Bioorg Med Chem Lett., 19:1944-1949.

* cited by examiner

Note: Treatment A: 60 mg Compound 1 as AIC, QD x 6 days
Treatment B: 160 mg Compound 1 as AIC, QD x 6 days
Treatment C: 400 mg Compound 1 as AIC, QD x 6 days

FORMULATIONS OF 2-(TERT-BUTYLAMINO)-4-((1R,3R,4R)-3-HYDROXY-4-METHYLCYCLOHEXYLAMINO)-PYRIMIDINE-5-CARBOXAMIDE

This application claims the benefit of U.S. Provisional Application No. 62/196,044, filed Jul. 23, 2015, and U.S. Provisional Application No. 62/092,537, filed Dec. 16, 2014, the contents of each of which are incorporated by reference herein in their entirety.

1. FIELD

Provided herein are pharmaceutical compositions, dosage forms and salts of 2-(tert-butylamino)-4-((1R,3R,4R)-3-hydroxy-4-methylcyclohexylamino)-pyrimidine-5-carboxamide. Methods for using the pharmaceutical compositions, dosage forms and salts are also provided herein.

2. BACKGROUND

The connection between abnormal protein phosphorylation and the cause or consequence of diseases has been known for over 20 years. Accordingly, protein kinases have become a very important group of drug targets. (See Cohen, *Nature*, 1:309-315 (2002), Gaestel et al. *Curr. Med. Chem.* 14: 2214-223 (2007); Grimminger et al. *Nat. Rev. Drug Disc.* 9(12):956-970 (2010)). Various protein kinase inhibitors have been used clinically in the treatment of a wide variety of diseases, such as cancer and chronic inflammatory diseases, including rheumatoid arthritis and psoriasis. (See Cohen, *Eur. J. Biochem.*, 268:5001-5010 (2001); Protein Kinase Inhibitors for the Treatment of Disease: The Promise and the Problems, *Handbook of Experimental Pharmacology*, Springer Berlin Heidelberg, 167 (2005)).

JNK is a ubiquitously expressed serine/threonine kinase belonging, together with ERK (extracellular-regulated kinase) and p38, to the family of mitogen-activated protein kinases (MAPKs). (Kyriakis J M, *Sci. STKE* (48):pe1 (2000); Whitmarsh A J, et al. *Sci. STKE* (1):pe1 (1999); Schramek H, *News Physiol. Sci.* 17:62-7 (2002); Ichijo H, *Oncogene* 18(45):6087-93 (1999)). MAPKs are important mediators of signal transduction from the cell surface to the nucleus, using phosphorylation cascades to generate a coordinated response by a cell to an external stimulus by phosphorylation of selected intracellular proteins, including transcription factors. Additionally, JNK also phosphorylates non-nuclear proteins, for example, IRS-1, and Bcl-2 family members. (Davis R J, *Trends Biochem. Sci.* 9(11):470-473 (1994); Seger R et al., *FASEB J.;* 9(9):726-35 (1995); Fanger G R et al., *Curr. Opin. Genet. Dev.;* 7(1):67-74 (1997)).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways.

The compound chemically named 2-(tert-butylamino)-4-((1R,3R,4R)-3-hydroxy-4-methylcyclohexylamino)-pyrimidine-5-carboxamide (alternatively named 2-[(1,1-dimethylethyl)amino]-4-[[(1R,3R,4R)-3-hydroxy-4-methylcyclohexyl]amino]-5-pyrimidinecarboxamide) and tautomers thereof are disclosed in U.S. Patent Application Publication No. 2013/0029987, published on Jan. 31, 2013, and International Pub. No. WO2012/145569, the entireties of each of which are incorporated by reference herein.

The identification and selection of a formulation of a pharmaceutical compound is complex, given that a change in formulation may affect a variety of physical and chemical properties, which may provide benefits or drawbacks in safety, processing, stability, solubility and bioavailability, among other important pharmaceutical characteristics.

Notably, the various excipients employed in a formulation of a pharmaceutical compound can have a profound effect on the manufacturing process, wherein characteristics such as flowability (e.g., blend flow), hardness, compressibility, sticking, filming and capping can be affected by the identity and amount of the excipients employed.

Citation or identification of any reference in Section 2 of this application is not to be construed as an admission that the reference is prior art to the present application.

3. SUMMARY

Provided herein are pharmaceutical compositions and dosage forms comprising:

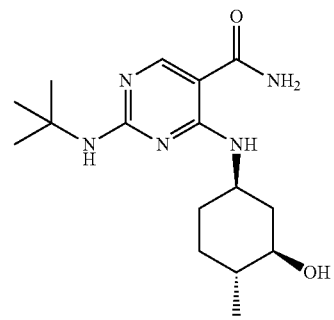

having the name 2-(tert-butylamino)-4-((1R,3R,4R)-3-hydroxy-4-methylcyclohexylamino)-pyrimidine-5-carboxamide (alternatively named 2-[(1,1-dimethylethyl)amino]-4-[[(1R,3R,4R)-3-hydroxy-4-methylcyclohexyl]amino]-5-pyrimidinecarboxamide) (Compound 1), or a pharmaceutically acceptable salt, stereoisomer, tautomer, solid form, polymorph, hydrate, clathrate, or solvate thereof (collectively referred to herein as "Compound A").

Further provided herein are pharmaceutically acceptable salts of Compound 1, including hydrochloride, sulfate, phosphate, L-tartrate, L-malate, L-lactate, succinate, p-toluenesulfate (tosylate), methanesulfate (mesylate), benzensulfate (besylate), fumarate and citrate salts.

Further provided herein are methods for using the pharmaceutical compositions, and dosage forms of Compound A for treating or preventing diseases or disorders treatable or preventable by inhibition of a JNK pathway, as described herein. Also provided herein is a pharmaceutical composition of Compound A for use in a method of treating diseases or disorders treatable or preventable by inhibition of a JNK pathway, as described herein. Also provided herein is a dosage form of Compound A for use in a method of treating diseases or disorders treatable or preventable by inhibition of a JNK pathway, as described herein. Also provided herein is a pharmaceutical composition of Compound A for use in a method of preventing diseases or disorders treatable or preventable by inhibition of a JNK pathway, as described herein. Also provided herein is a dosage form of Compound A for use in a method of preventing diseases or disorders treatable or preventable by inhibition of a JNK pathway, as described herein. In some embodiments, the diseases or disorders include, but are not limited to, interstitial pulmonary fibrosis, systemic sclerosis, scleroderma, chronic allograft nephropathy, antibody mediated rejection, or lupus. In other embodiments, the diseases or disorders include, but are not limited to, liver fibrotic disorders, or diabetes and/or metabolic syndrome leading to liver fibrotic disorders, as described herein.

Also provided are methods of preparing, isolating, and characterizing the salts.

The present embodiments can be understood more fully by reference to the detailed description and examples, which are intended to exemplify non-limiting embodiments.

4. BRIEF DESCRIPTION OF THE DRAWINGS

Figure 6:
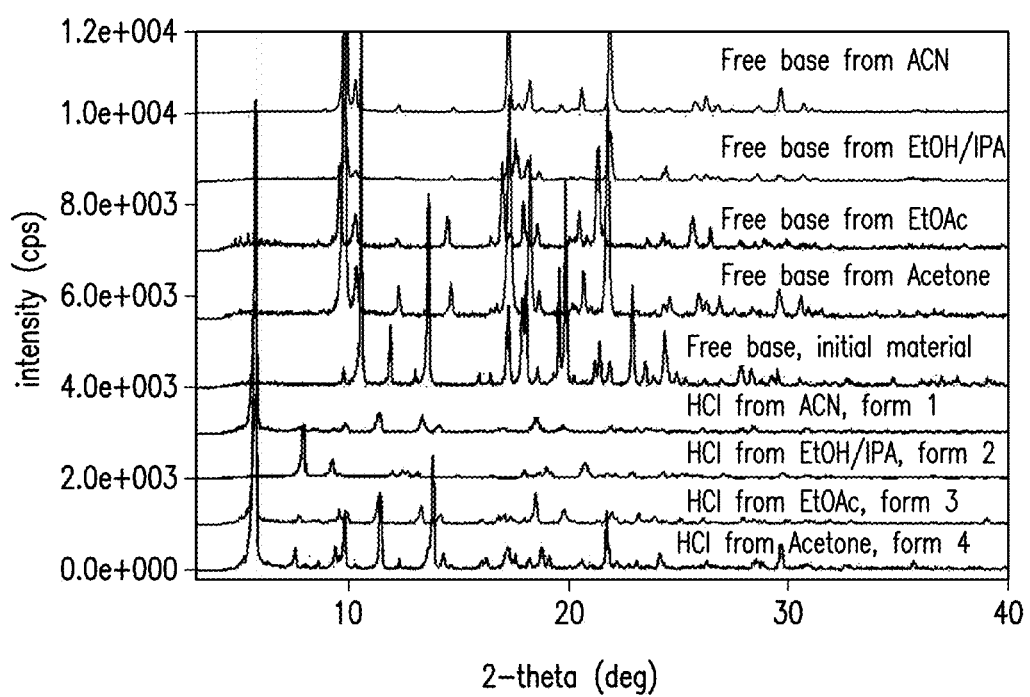

FIG. 6 depicts an overlay of X-ray powder diffractogram (XRPD) patterns of Compound 1 (free base) isolated from ACN (previously named Form C), EtOH/IPA (previously named Form C), EtOAc (previously named Form G) or acetone (previously named Form B), Form A (initial material) and HCl salt forms 1-4 of Compound 1 isolated from ACN, EtOH/IPA, EtOAc or acetone (from top to bottom). The free base Forms A (labeled initial material in FIGS. 6-13, 16-29), Form B, Form C and Form G were previously described in U.S. Provisional Patent Application No. 61/933,636, filed on Jan. 30, 2014, and U.S. Provisional Patent Application No. 62/025,161, filed on Jul. 16, 2014.

Figure 7:
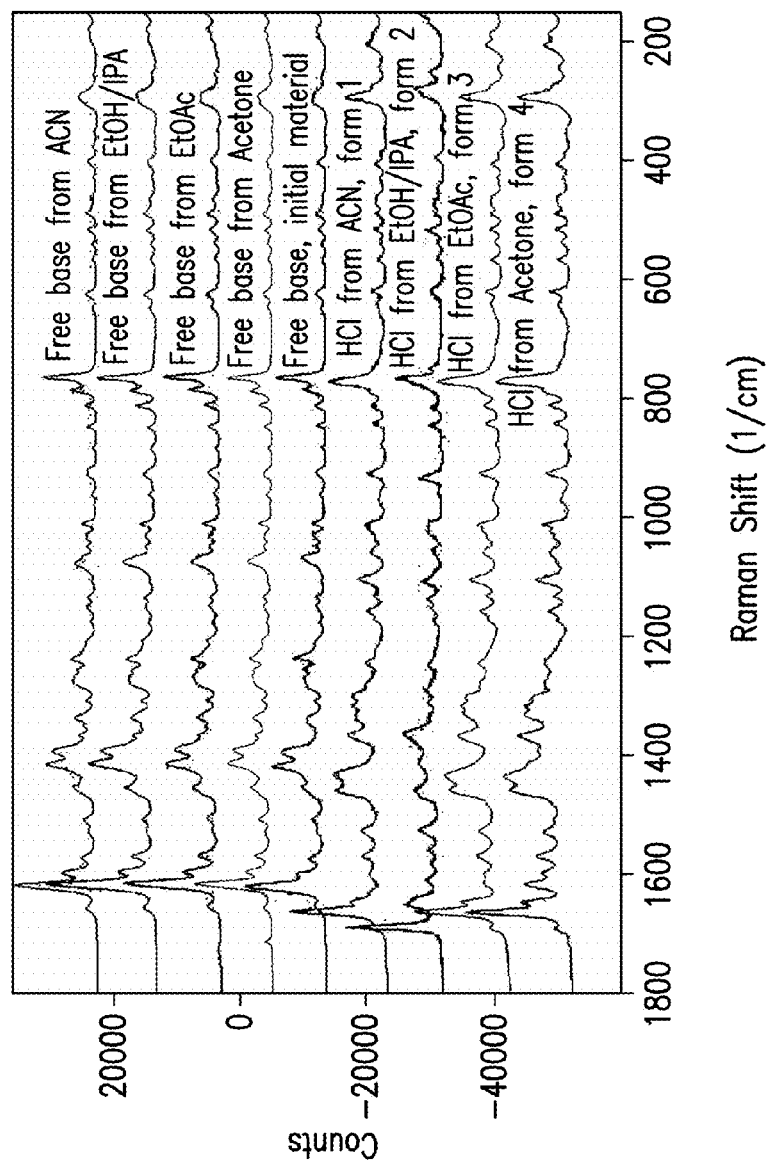

FIG. 7 depicts an overlay of Raman spectra of Compound 1 (free base) isolated from ACN, EtOH/IPA, EtOAc or acetone, Form A (initial material) and HCl salt forms 1-4 of Compound 1 isolated from ACN, EtOH/IPA, EtOAc or acetone (from top to bottom).

Figure 8:
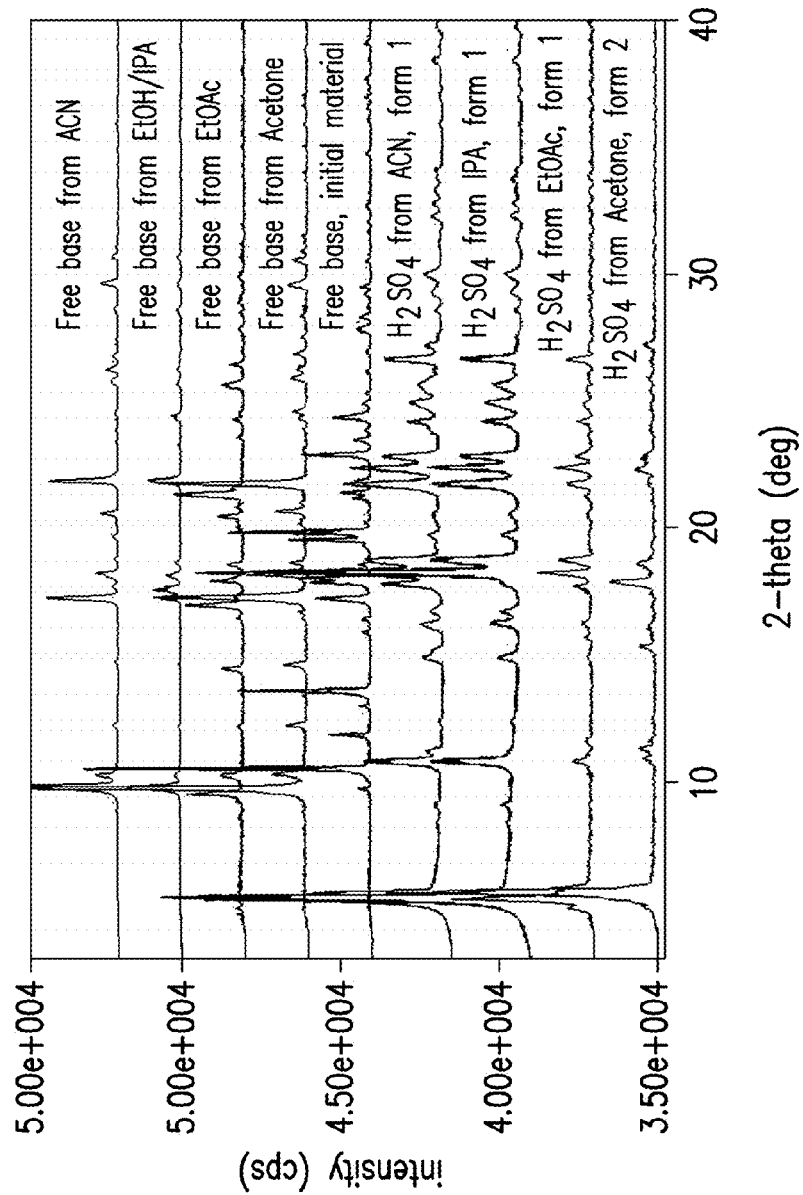

FIG. 8 depicts an overlay of XRPD patterns of Compound 1 (free base) isolated from ACN, EtOH/IPA, EtOAc or acetone, Form A (initial material) and $H_2SO_4$ salt forms 1-2 of Compound 1 isolated from ACN, IPA, EtOAc or acetone (from top to bottom).

Figure 9:
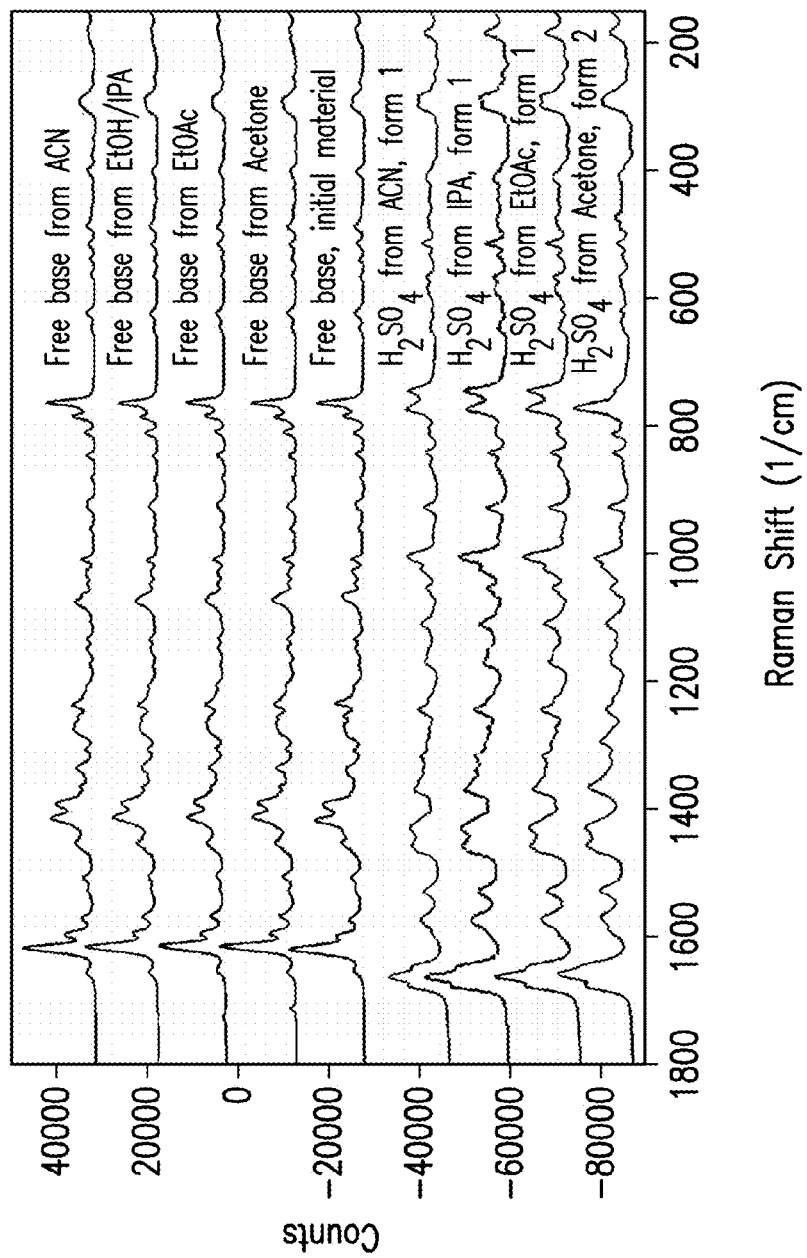

FIG. 9 depicts an overlay of Raman spectra of Compound 1 (free base) isolated from ACN, EtOH/IPA, EtOAc or acetone, Form A (initial material) and $H_2SO_4$ salt forms 1-2 of Compound 1 isolated from ACN, IPA, EtOAc or acetone (from top to bottom).

Figure 10:
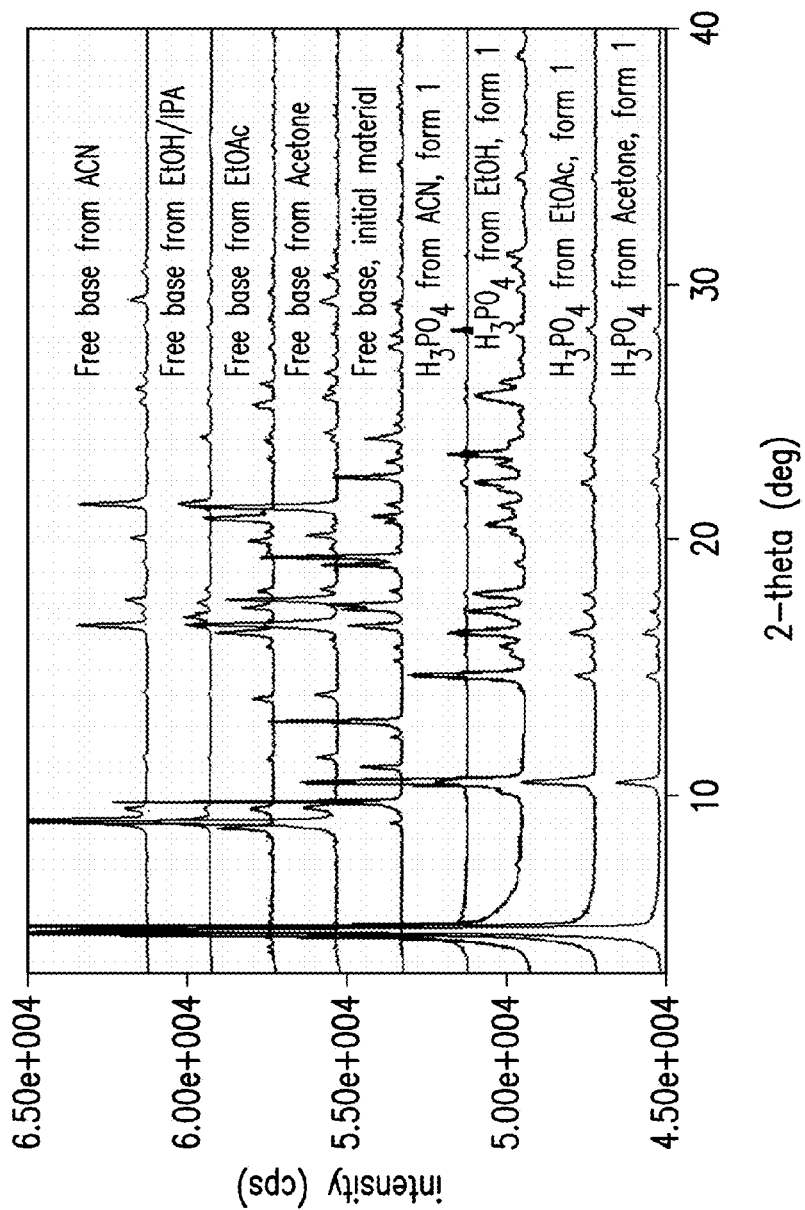

FIG. 10 depicts an overlay of XRPD patterns of Compound 1 (free base) isolated from ACN, EtOH/IPA, EtOAc or acetone, Form A (initial material) and the $H_3PO_4$ salt of Compound 1 isolated from ACN, EtOH, EtOAc or acetone (from top to bottom).

Figure 11:
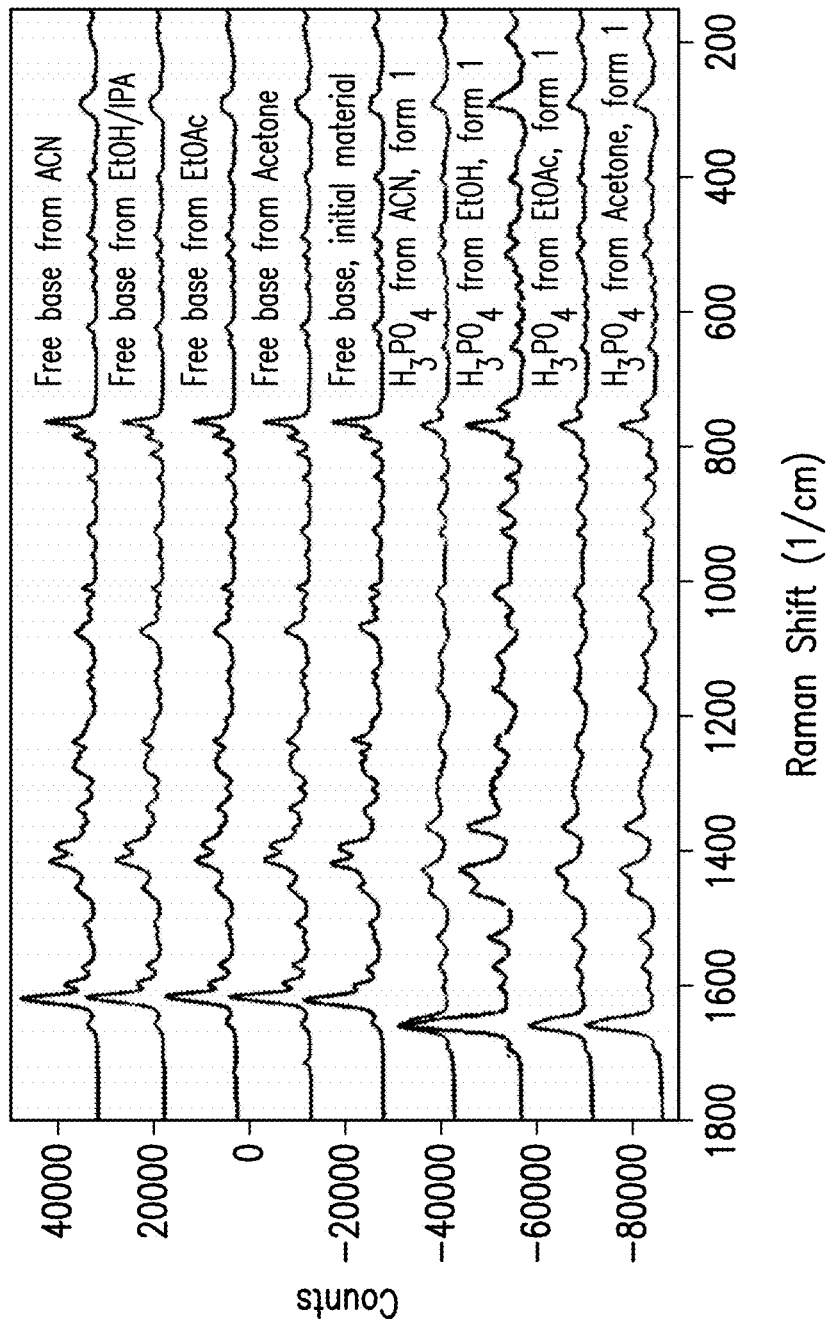

FIG. 11 depicts an overlay of Raman spectra of Compound 1 (free base) isolated from ACN, EtOH/IPA, EtOAc or acetone, Form A (initial material) and the $H_3PO_4$ salt of Compound 1 isolated from ACN, EtOH, EtOAc or acetone (from top to bottom).

Figure 12:
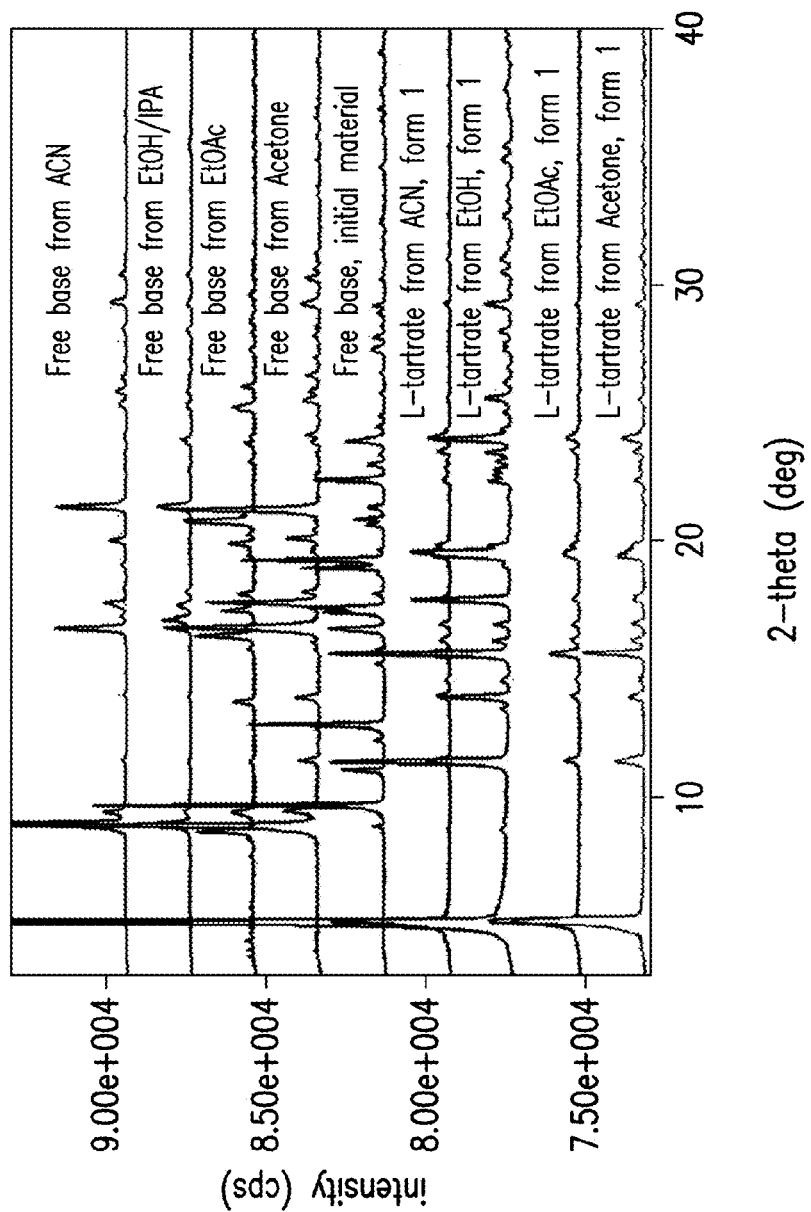

FIG. 12 depicts an overlay of XRPD patterns of Compound 1 (free base) isolated from ACN, EtOH/IPA, EtOAc or acetone, Form A (initial material) and the L-tartrate salt of Compound 1 isolated from ACN, EtOH, EtOAc or acetone (from top to bottom).

Figure 13:
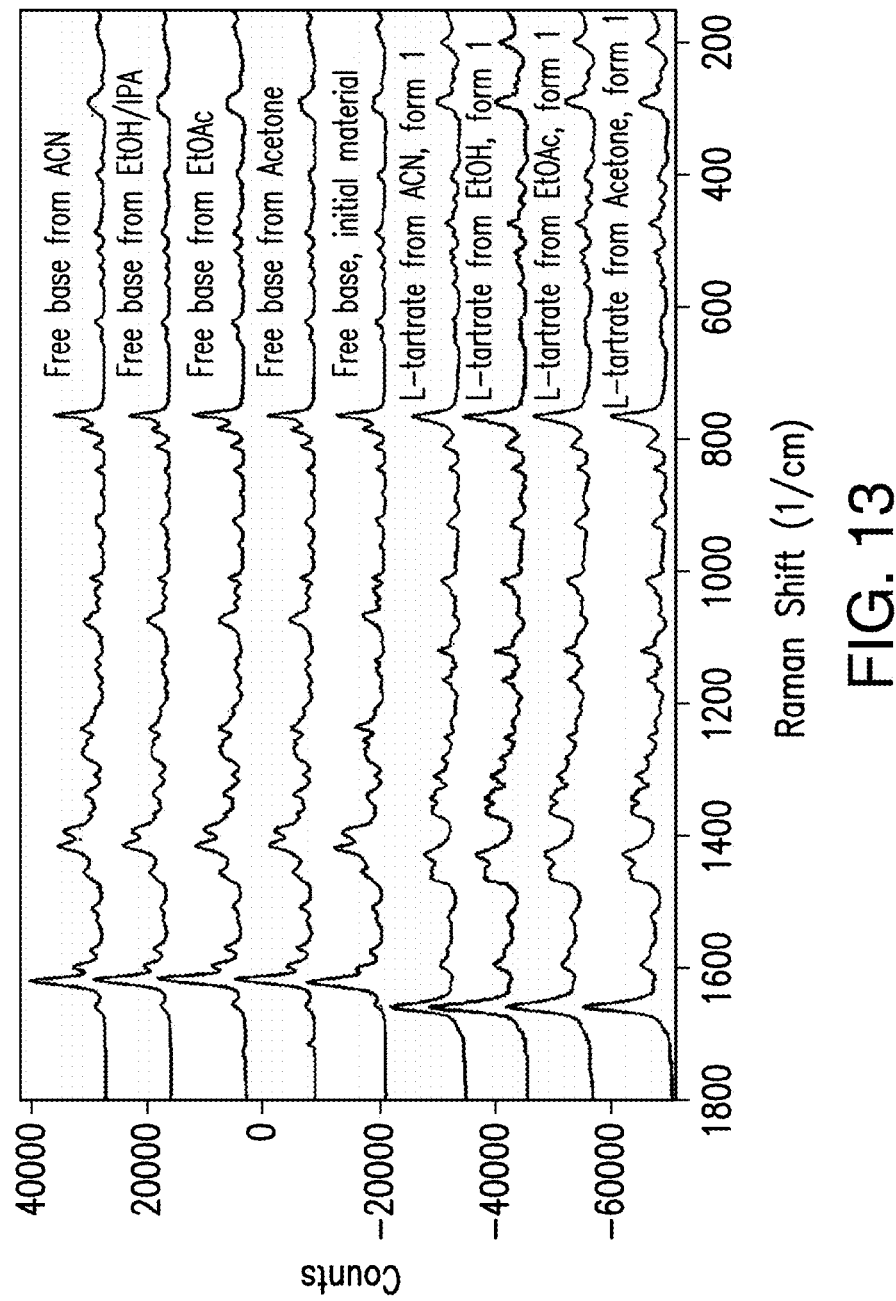

FIG. 13 depicts an overlay of Raman spectra of Compound 1 (free base) isolated from ACN, EtOH/IPA, EtOAc or acetone, Form A (initial material) and the L-tartrate salt of Compound 1 isolated from ACN, EtOH, EtOAc or acetone (from top to bottom).

Figure 14:
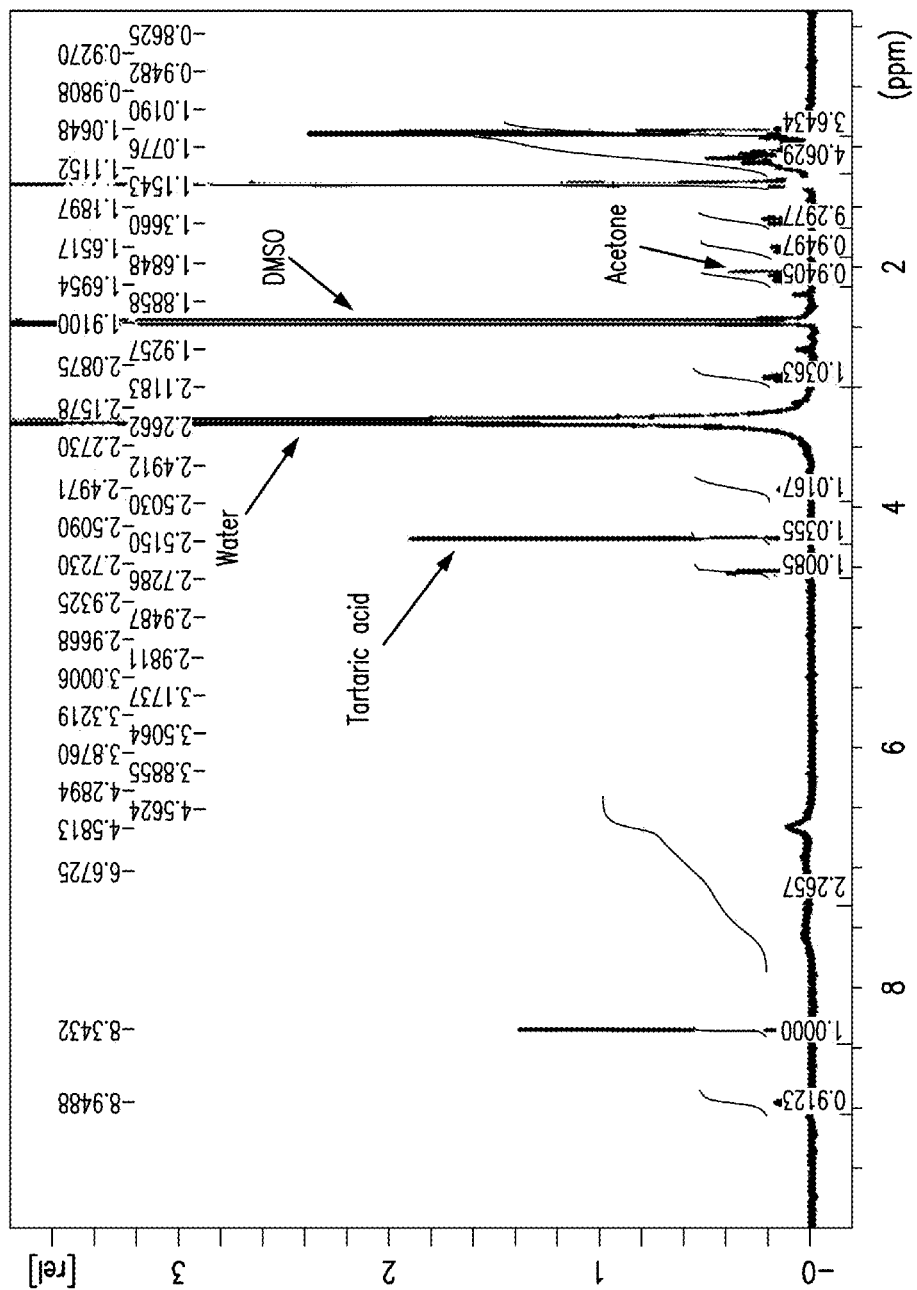

FIG. 14 depicts a $^1$H NMR spectrum of the L-tartrate salt of Compound 1 prepared from acetone.

Figure 15:
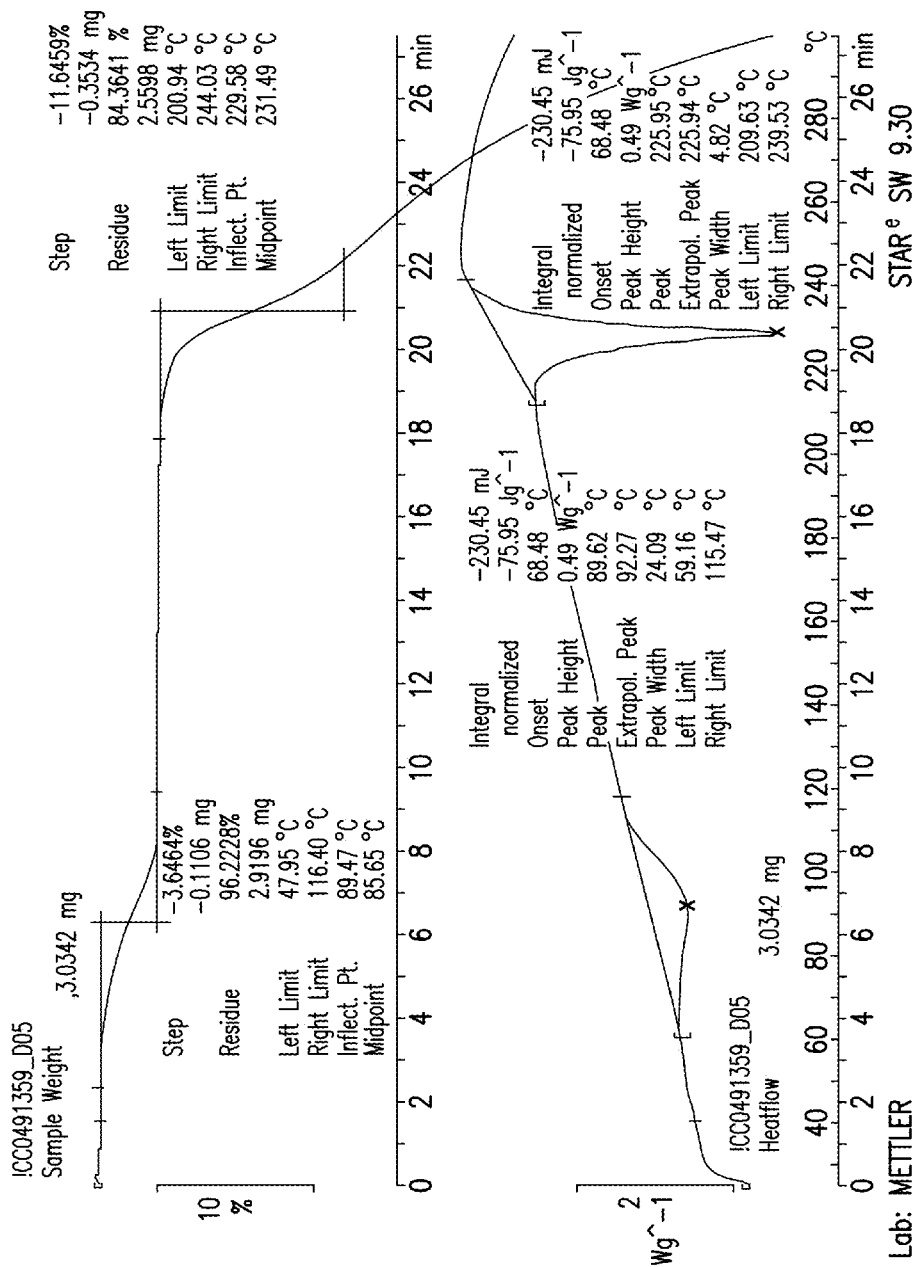

FIG. 15 depicts a TGA/DSC thermogram of the L-tartrate salt of Compound 1 prepared from acetone.

Figure 16:
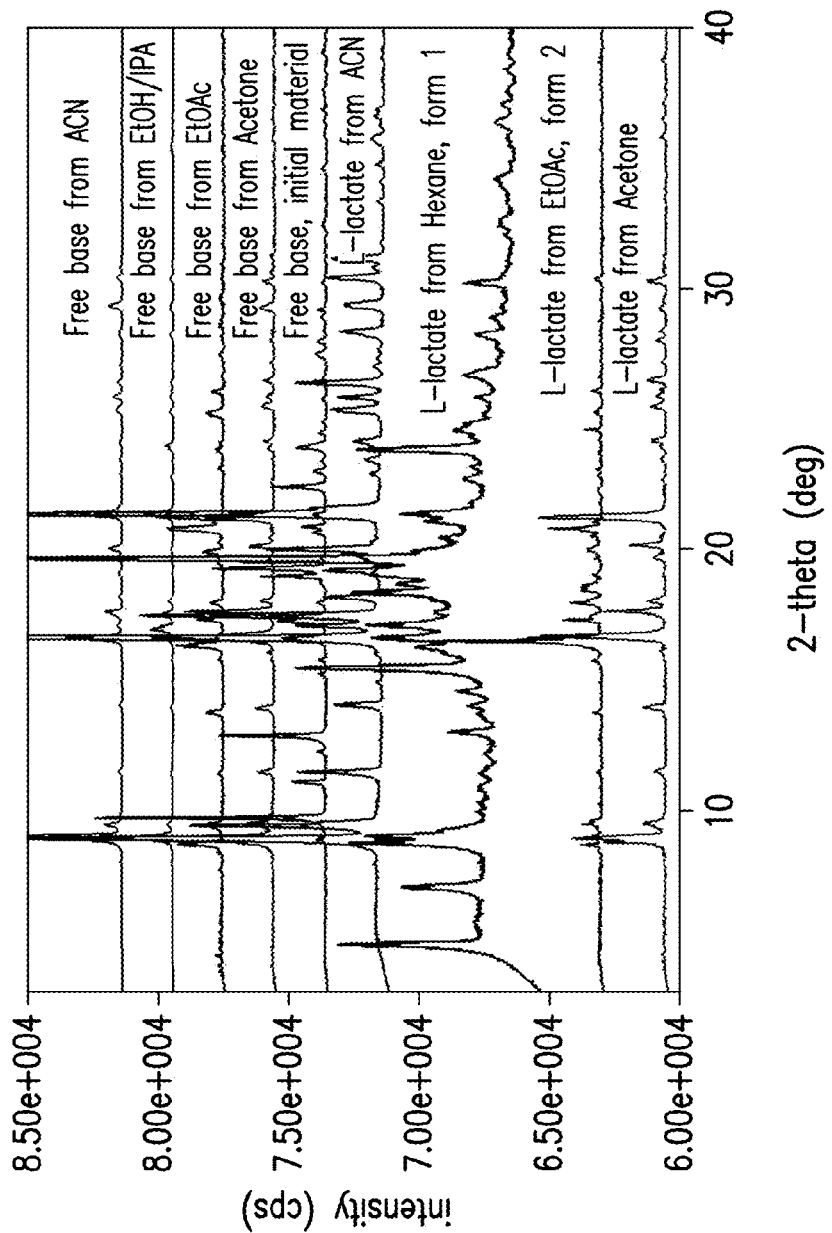

FIG. 16 depicts an overlay of XRPD patterns of Compound 1 (free base) isolated from ACN, EtOH/IPA, EtOAc or acetone, Form A (initial material) and L-lactate salt forms 1-2 of Compound 1 isolated from ACN, hexane, EtOAc or acetone (from top to bottom).

Figure 17:
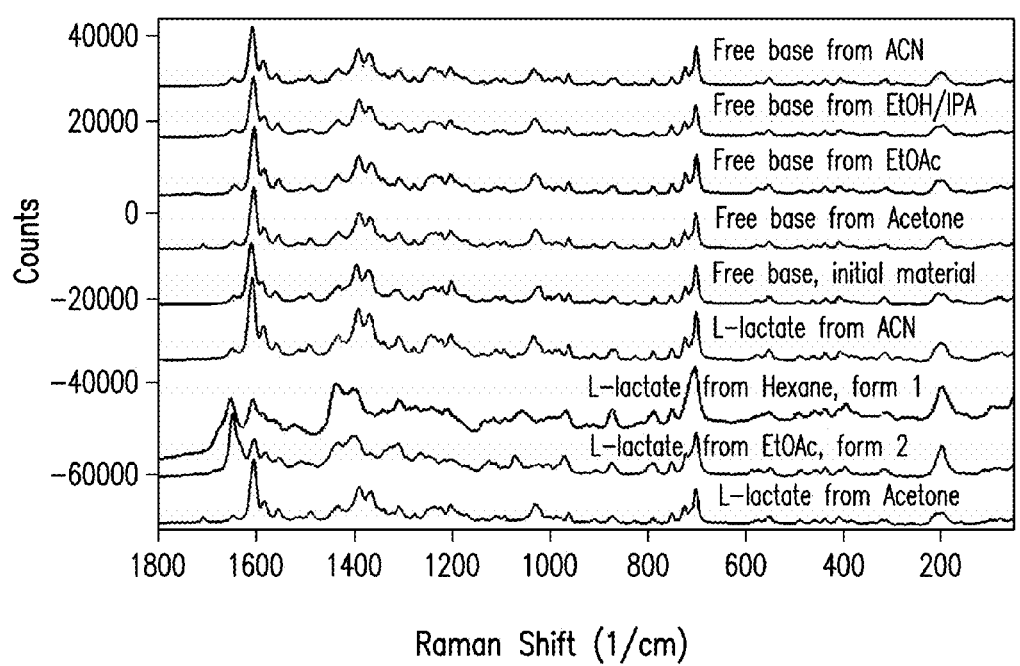

FIG. 17 depicts an overlay of Raman spectra of Compound 1 (free base) isolated from ACN, EtOH/IPA, EtOAc or acetone, Form A (initial material) and L-lactate salt forms 1-2 of Compound 1 isolated from ACN, hexane, EtOAc or acetone (from top to bottom).

Figure 18:
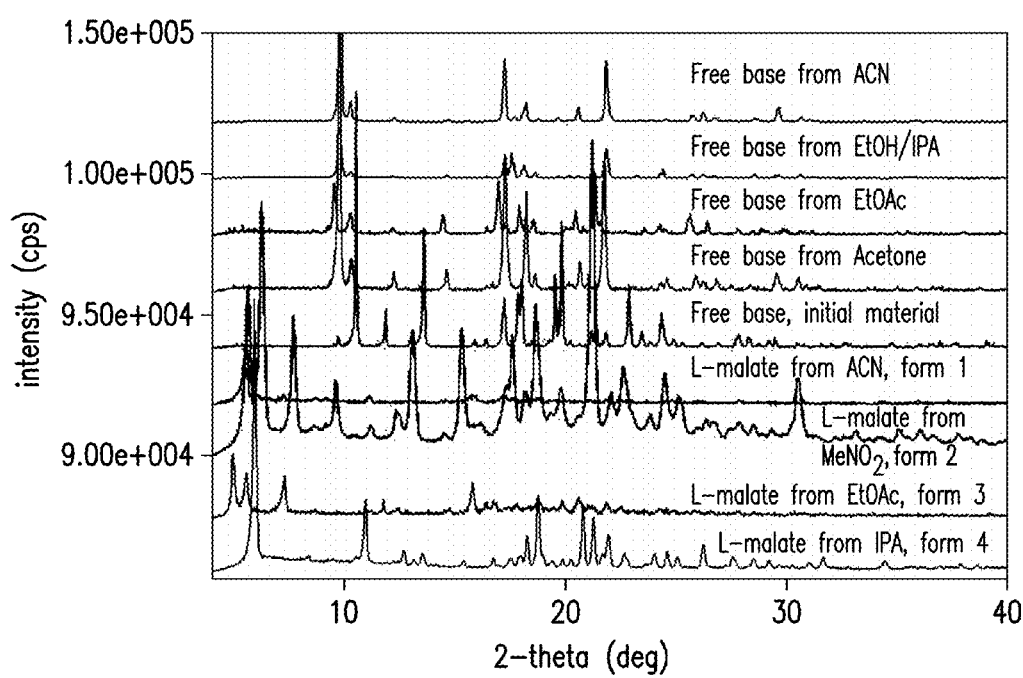

FIG. 18 depicts an overlay of XRPD patterns of Compound 1 (free base) isolated from ACN, EtOH/IPA, EtOAc or acetone, Form A (initial material) and L-malate salt forms 1-4 of Compound 1 isolated from ACN, $MeNO_2$, EtOAc or IPA (from top to bottom).

Figure 19:
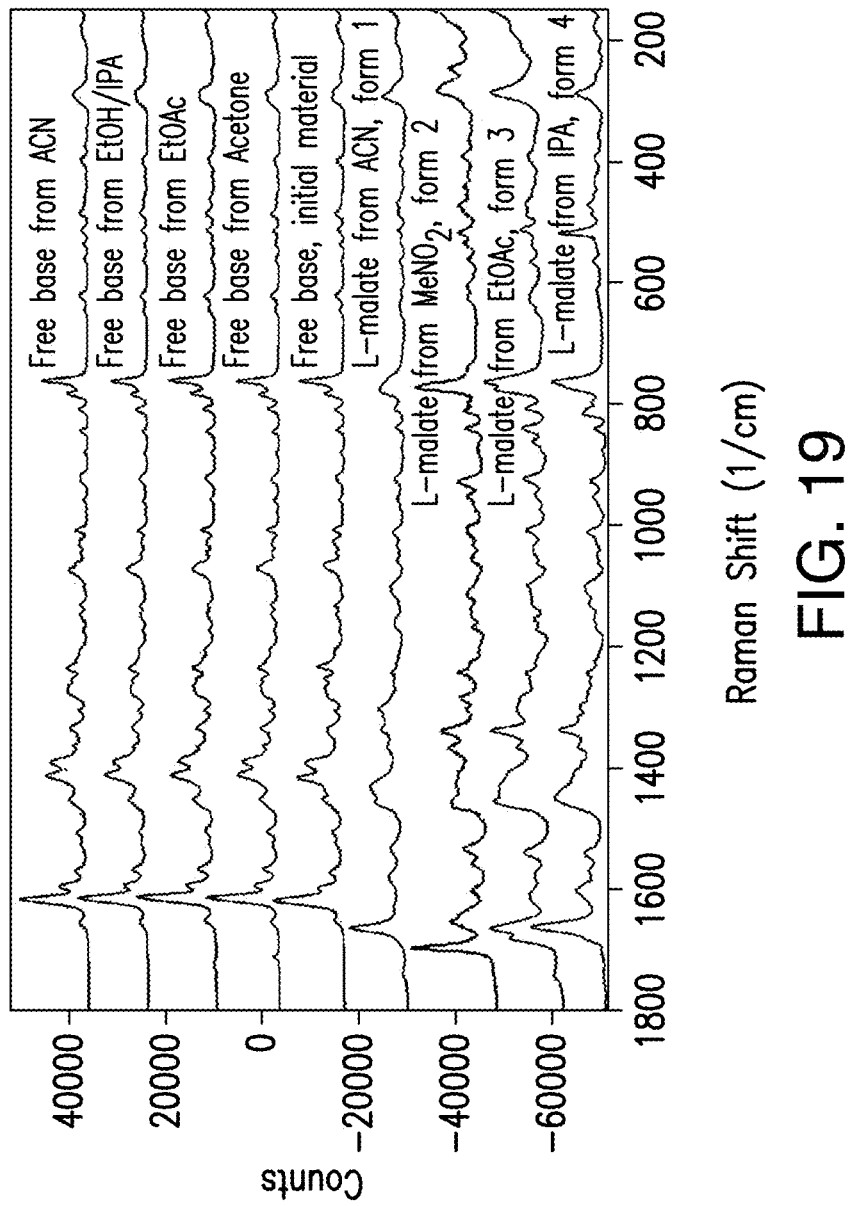

FIG. 19 depicts an overlay of Raman spectra of Compound 1 (free base) isolated from ACN, EtOH/IPA, EtOAc or acetone, Form A (initial material) and L-malate salt forms 1-4 of Compound 1 isolated from ACN, $MeNO_2$, EtOAc or IPA (from top to bottom).

Figure 20:
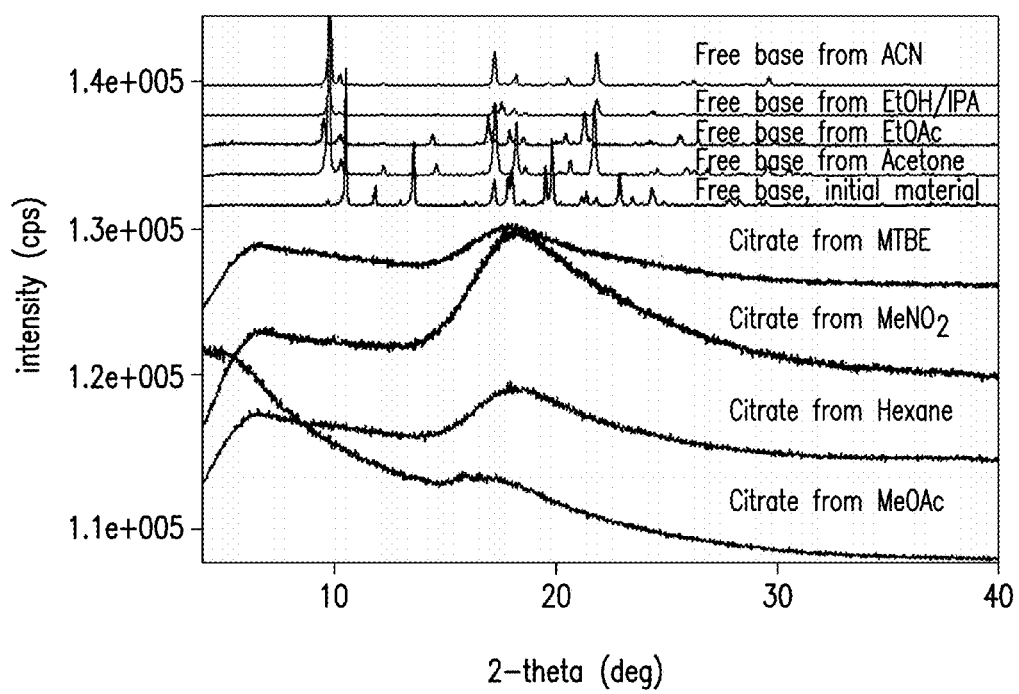

FIG. 20 depicts an overlay of XRPD patterns of Compound 1 (free base) isolated from ACN, EtOH/IPA, EtOAc or acetone, Form A (initial material) and the L-malate salt of Compound 1 isolated from MTBE, $MeNO_2$, hexane or MeOAc (from top to bottom).

Figure 21:
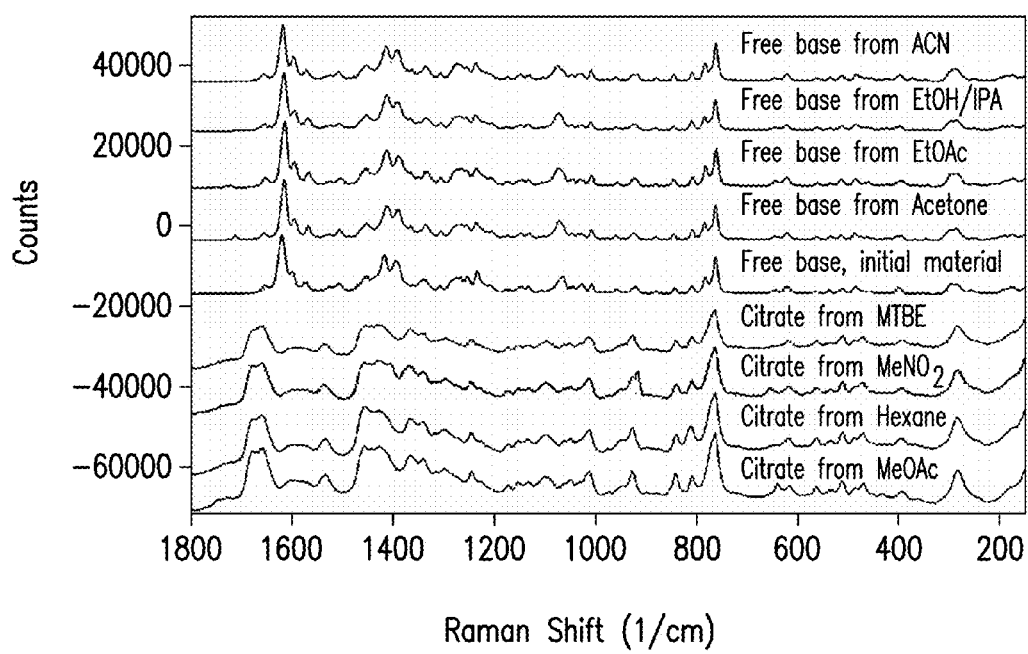

FIG. 21 depicts an overlay of Raman spectra of Compound 1 (free base) isolated from ACN, EtOH/IPA, EtOAc or acetone, Form A (initial material) and the L-malate salt of Compound 1 isolated from MTBE, $MeNO_2$, hexane or MeOAc (from top to bottom).

Figure 22:
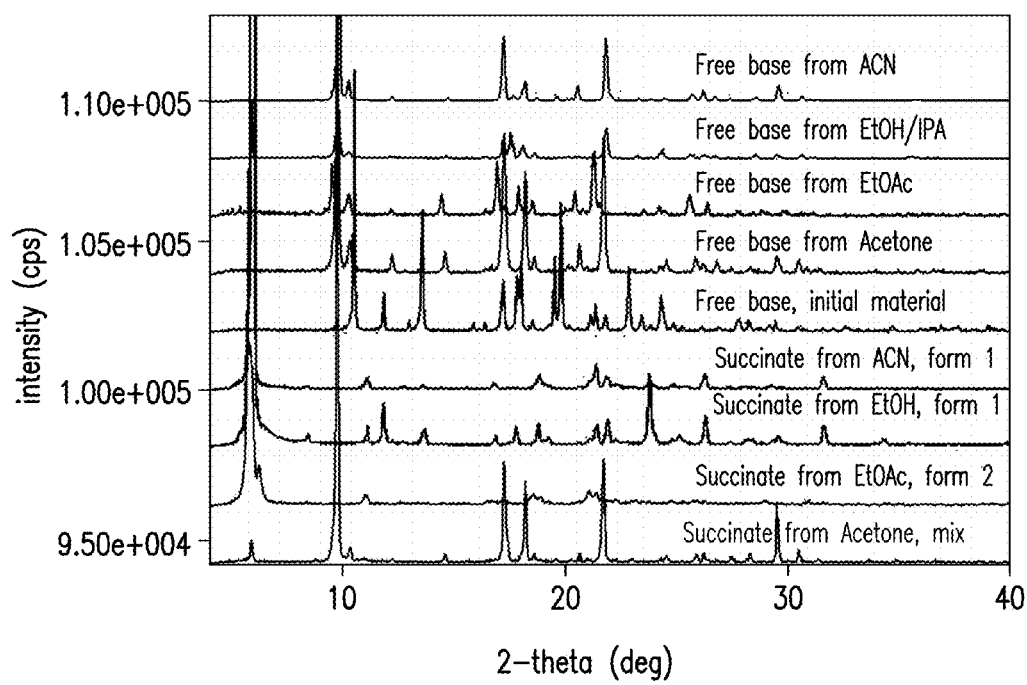

FIG. 22 depicts an overlay of XRPD patterns of Compound 1 (free base) isolated from ACN, EtOH/IPA, EtOAc or acetone, Form A (initial material) and succinate salt forms 1-2 and their mixture of Compound 1 isolated from ACN, EtOH, EtOAc or acetone (from top to bottom).

Figure 23:
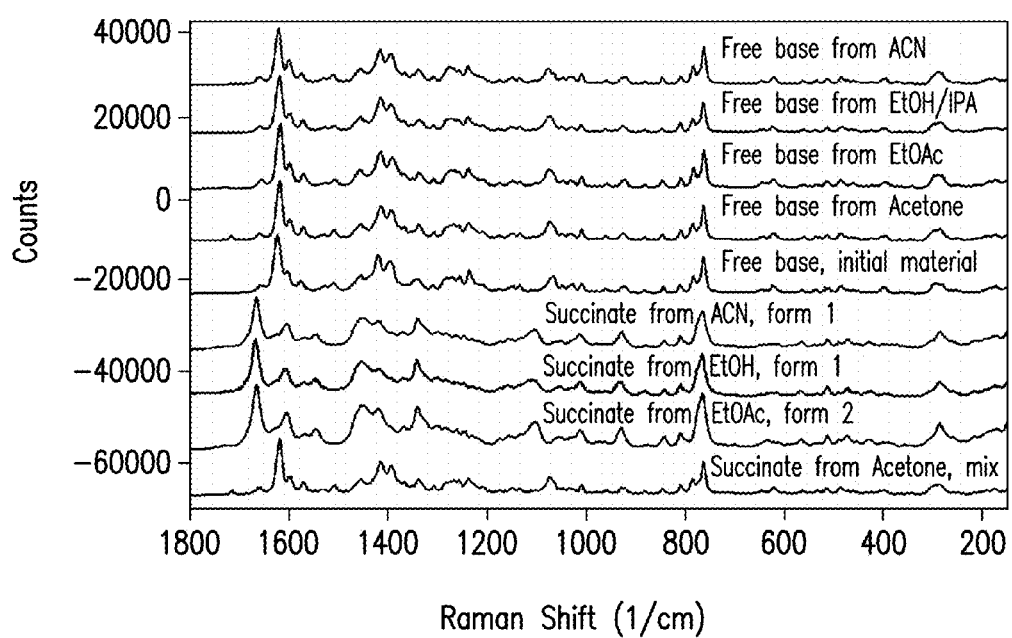

FIG. 23 depicts an overlay of Raman spectra of Compound 1 (free base) isolated from ACN, EtOH/IPA, EtOAc or acetone, Form A (initial material) and succinate salt forms 1-2 and their mixture of Compound 1 isolated from ACN, EtOH, EtOAc or acetone (from top to bottom).

Figure 24:
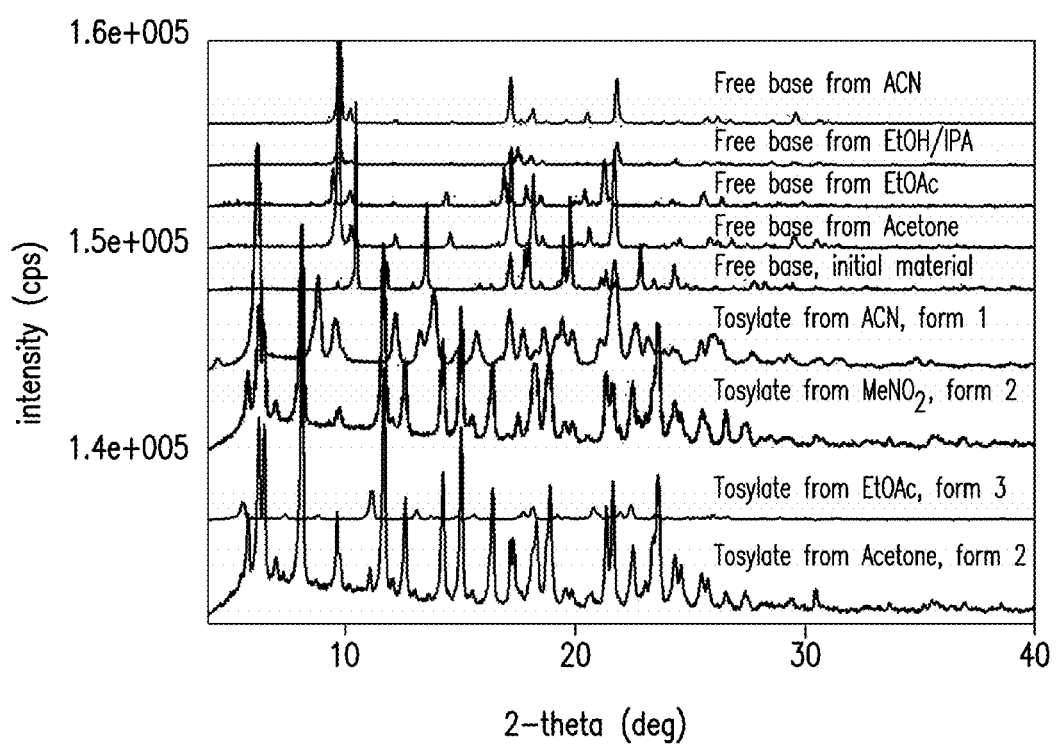

FIG. 24 depicts an overlay of XRPD patterns of Compound 1 (free base) isolated from ACN, EtOH/IPA, EtOAc or acetone, Form A (initial material) and tosylate salt forms 1-3 of Compound 1 isolated from ACN, $MeNO_2$, EtOAc or acetone (from top to bottom).

Figure 25:
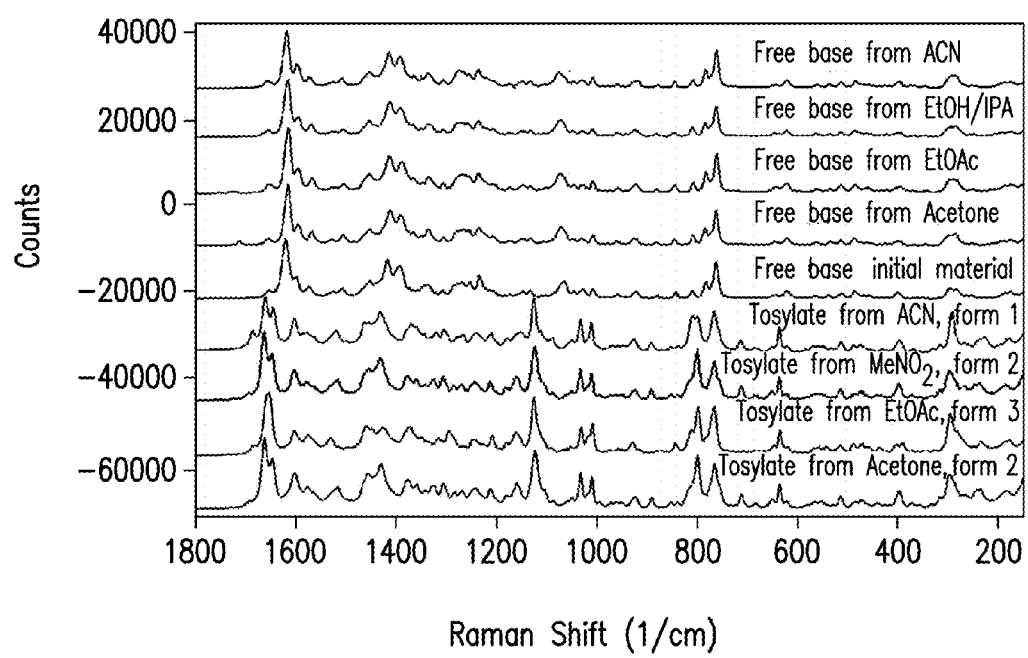

FIG. 25 depicts an overlay of Raman spectra of Compound 1 (free base) isolated from ACN, EtOH/IPA, EtOAc or acetone, Form A (initial material) and tosylate salt forms 1-3 of Compound 1 isolated from ACN, $MeNO_2$, EtOAc or acetone (from top to bottom).

Figure 26:
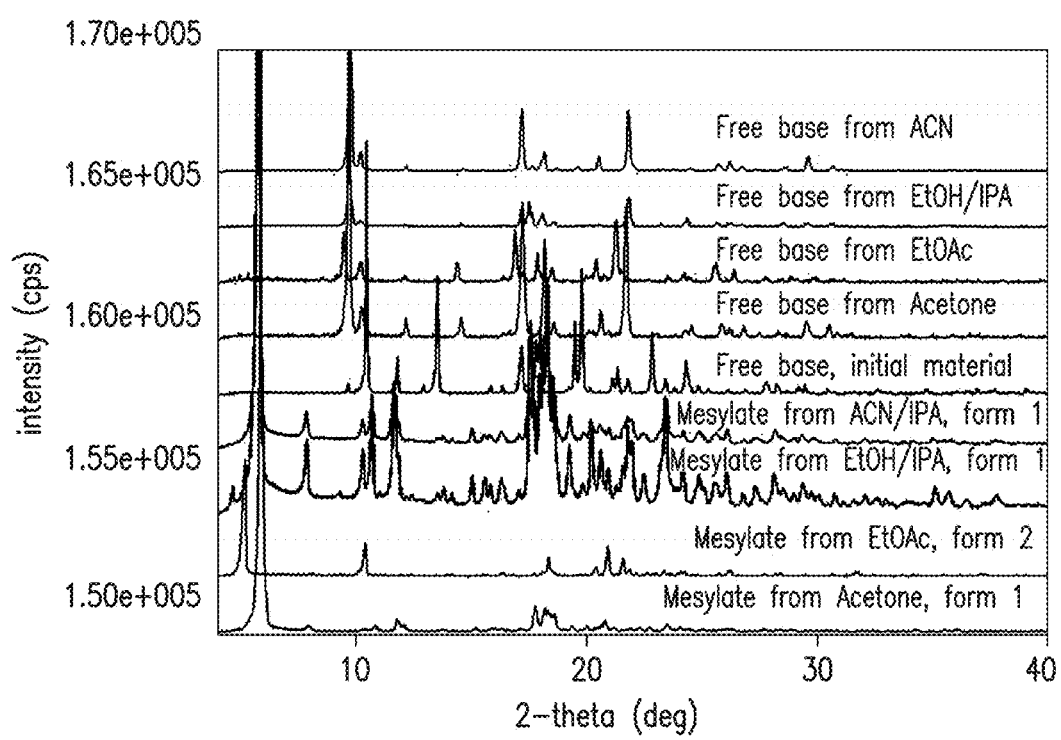

FIG. 26 depicts an overlay of XRPD patterns of Compound 1 (free base) isolated from ACN, EtOH/IPA, EtOAc or acetone, Form A (initial material) and mesylate salt forms 1-2 of Compound 1 isolated from ACN/IPA, EtOH/IPA, EtOAc or acetone (from top to bottom).

Figure 27:
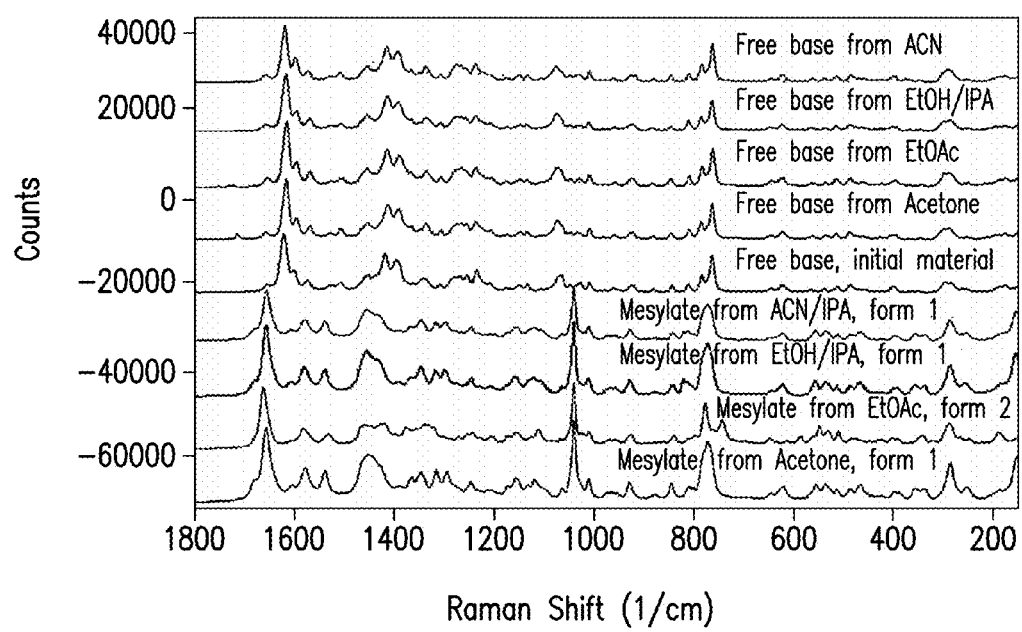

FIG. 27 depicts an overlay of Raman spectra of Compound 1 (free base) isolated from ACN, EtOH/IPA, EtOAc or acetone, Form A (initial material) and mesylate salt forms 1-2 of Compound 1 isolated from ACN/IPA, EtOH/IPA, EtOAc or acetone (from top to bottom).

Figure 28:
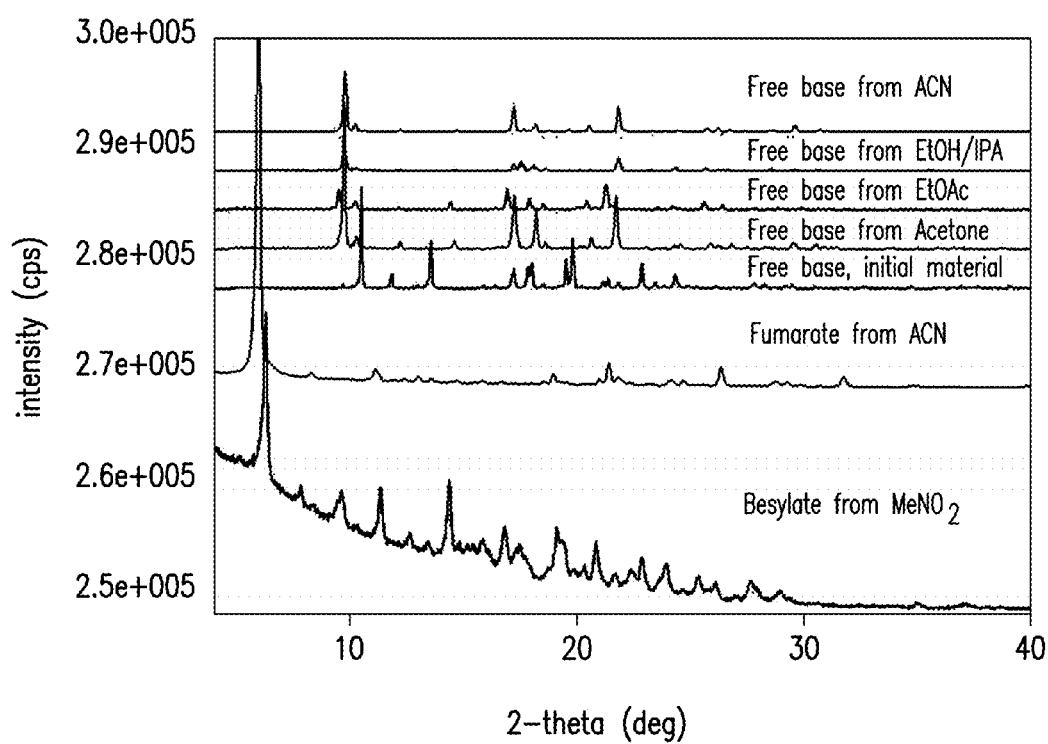

FIG. 28 depicts an overlay of XRPD patterns of Compound 1 (free base) isolated from ACN, EtOH/IPA, EtOAc or acetone, Form A (initial material) and the fumarate salt isolated from ACN and the besylate salt isolated from MeNO$_2$ (from top to bottom).

Figure 29:
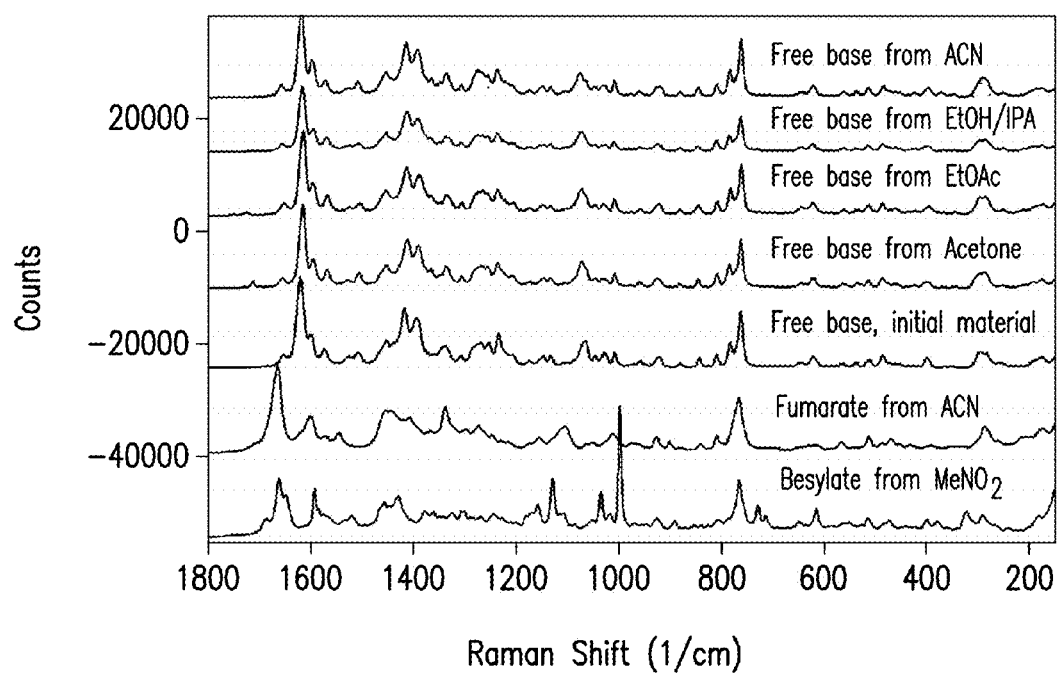

FIG. 29 depicts an overlay of Raman spectra of Compound 1 (free base) isolated from ACN, EtOH/IPA, EtOAc or acetone, Form A (initial material), the fumarate salt isolated from ACN and the besylate salt isolated from MeNO$_2$ (from top to bottom).

Figure 30:
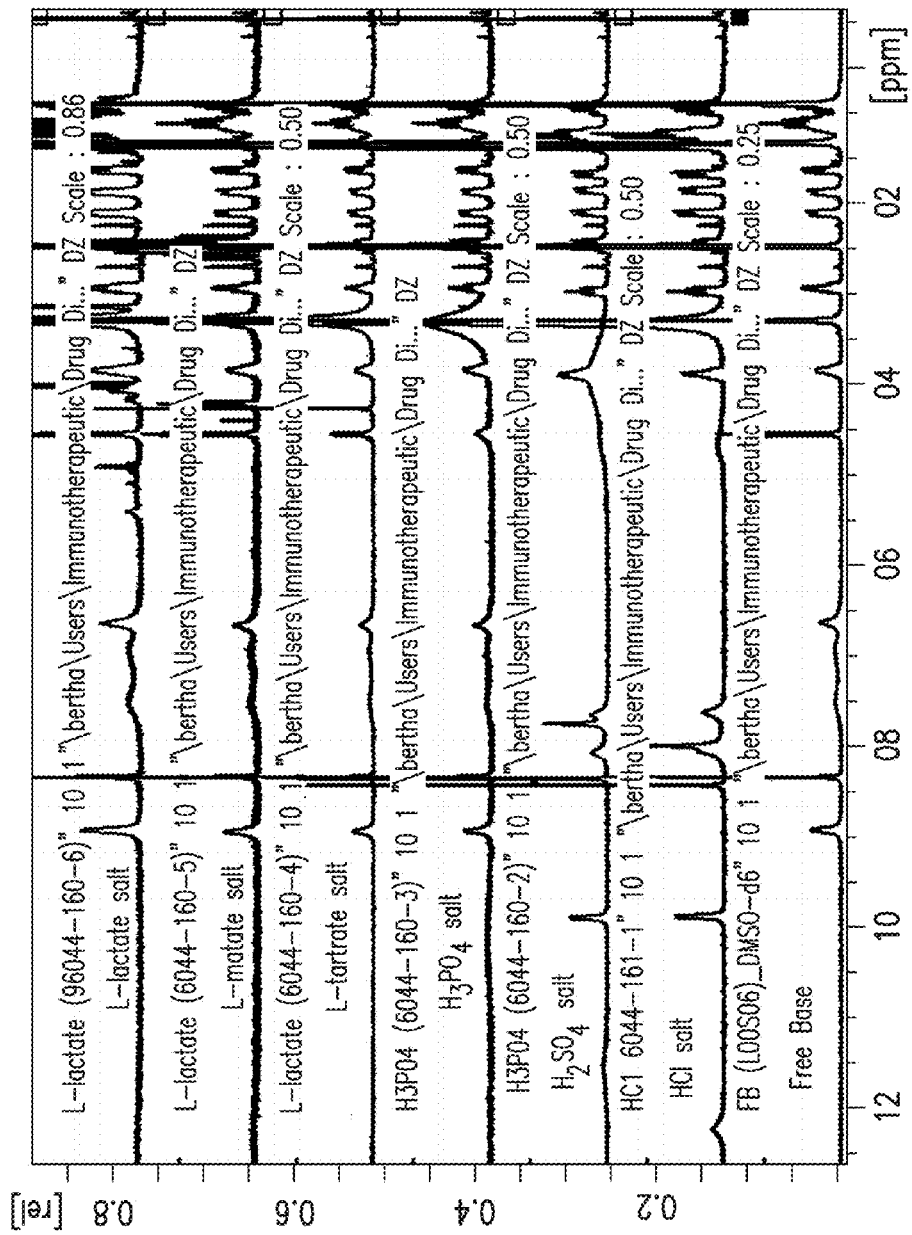

FIG. 30 depicts an overlay of $^1$H NMR spectra of the L-lactate salt, L-malate salt, L-tartrate salt, H$_3$PO$_4$ salt, H$_2$SO$_4$ salt, HCl salt and Compound 1 (free base) (from top to bottom).

Figure 31:
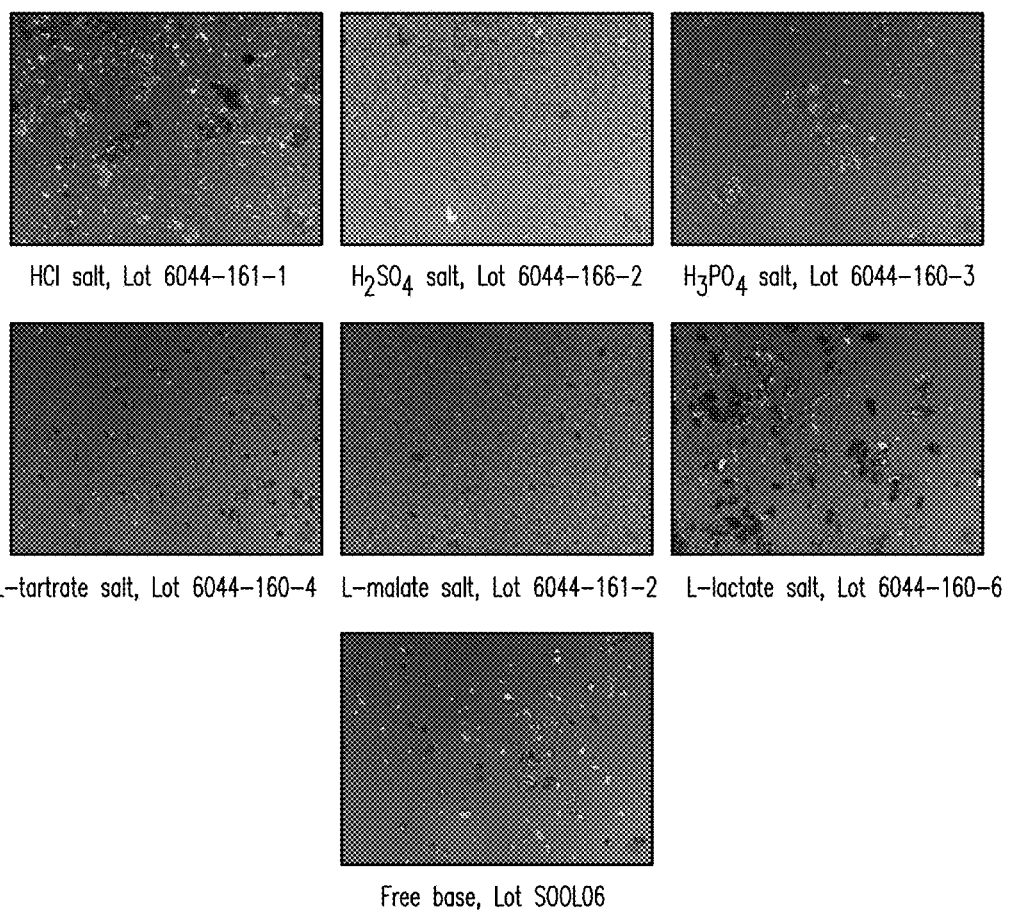

FIG. 31 depicts photomicrographs of the HCl salt, H$_2$SO$_4$ salt, H$_3$PO$_4$ salt, L-tartrate salt, L-malate salt, L-lactate salt and Compound 1 (free base) (from left to right, and top to bottom).

Figure 32:
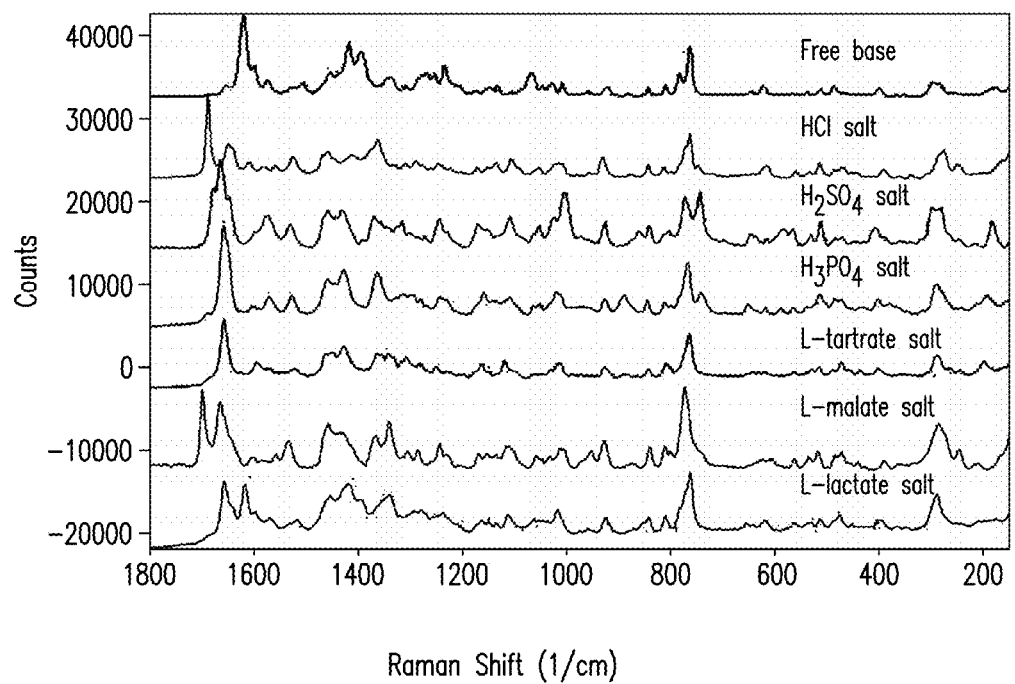

FIG. 32 depicts an overlay of Raman spectra of Compound 1 (free base), the HCl salt, H$_2$SO$_4$ salt, H$_3$PO$_4$ salt, L-tartrate salt, L-malate salt and L-lactate salt (from top to bottom).

Figure 33:
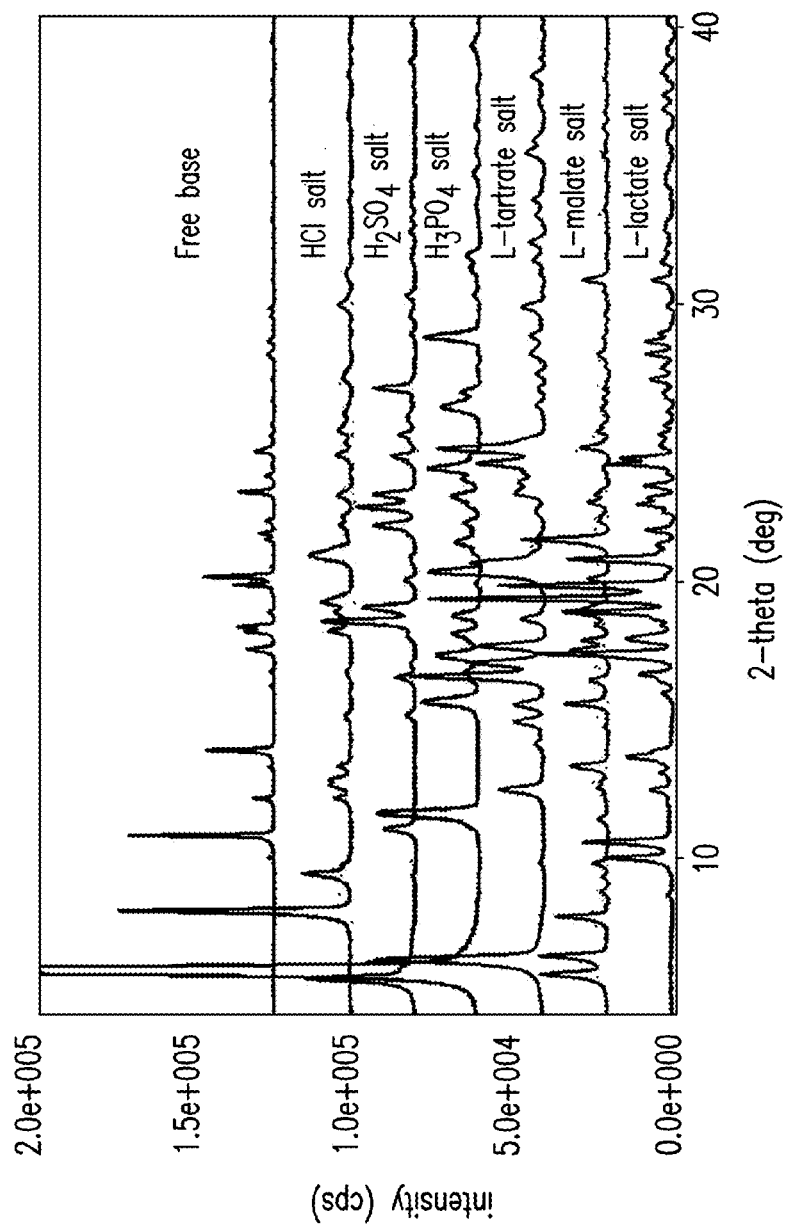

FIG. 33 depicts an overlay of XRPD patterns of Compound 1 (free base), the HCl salt, H$_2$SO$_4$ salt, H$_3$PO$_4$ salt, L-tartrate salt, L-malate salt and L-lactate salt (from top to bottom).

Figure 34:
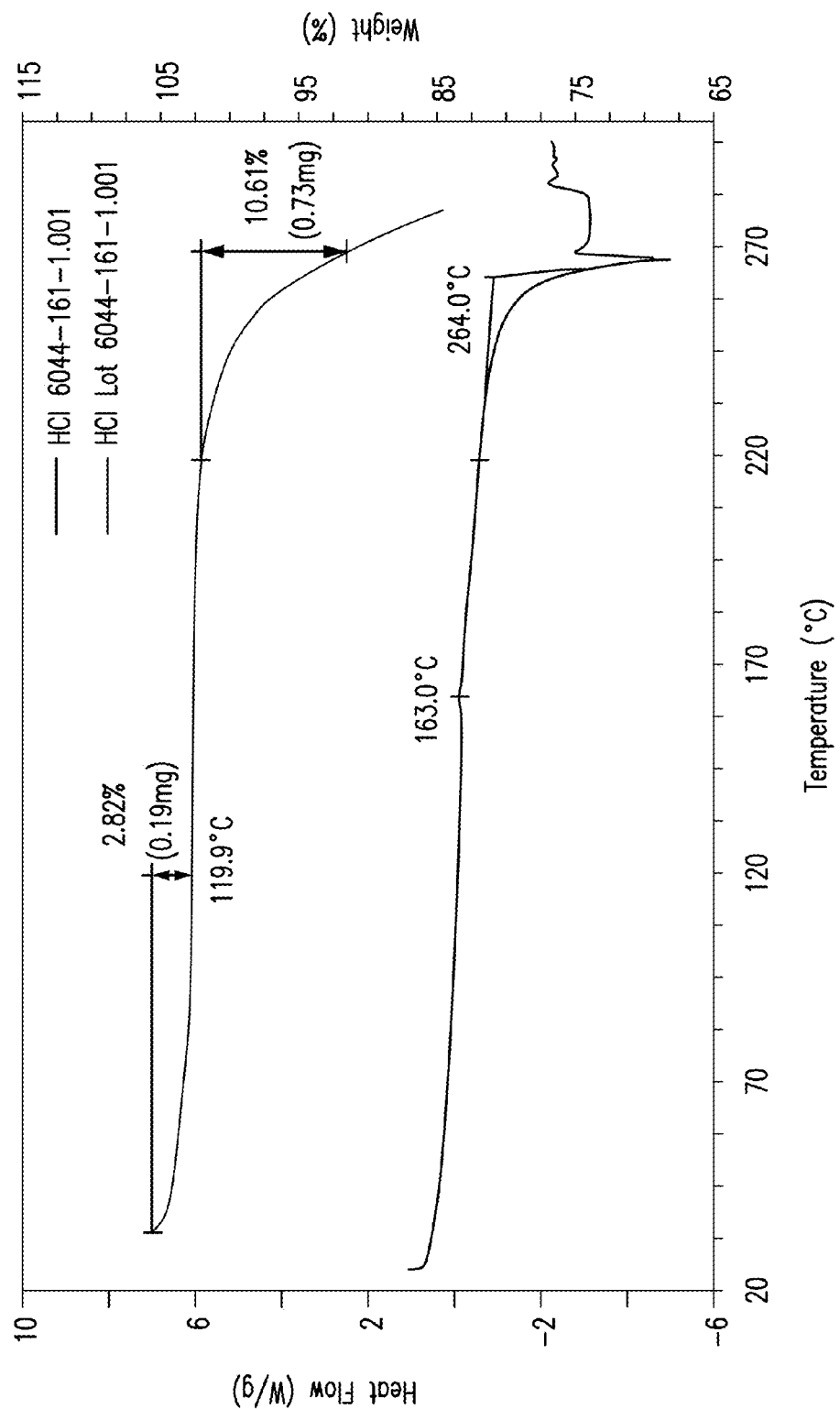

FIG. 34 depicts a TGA/DSC thermogram of form 2 of the HCl salt of Compound 1.

Figure 35:
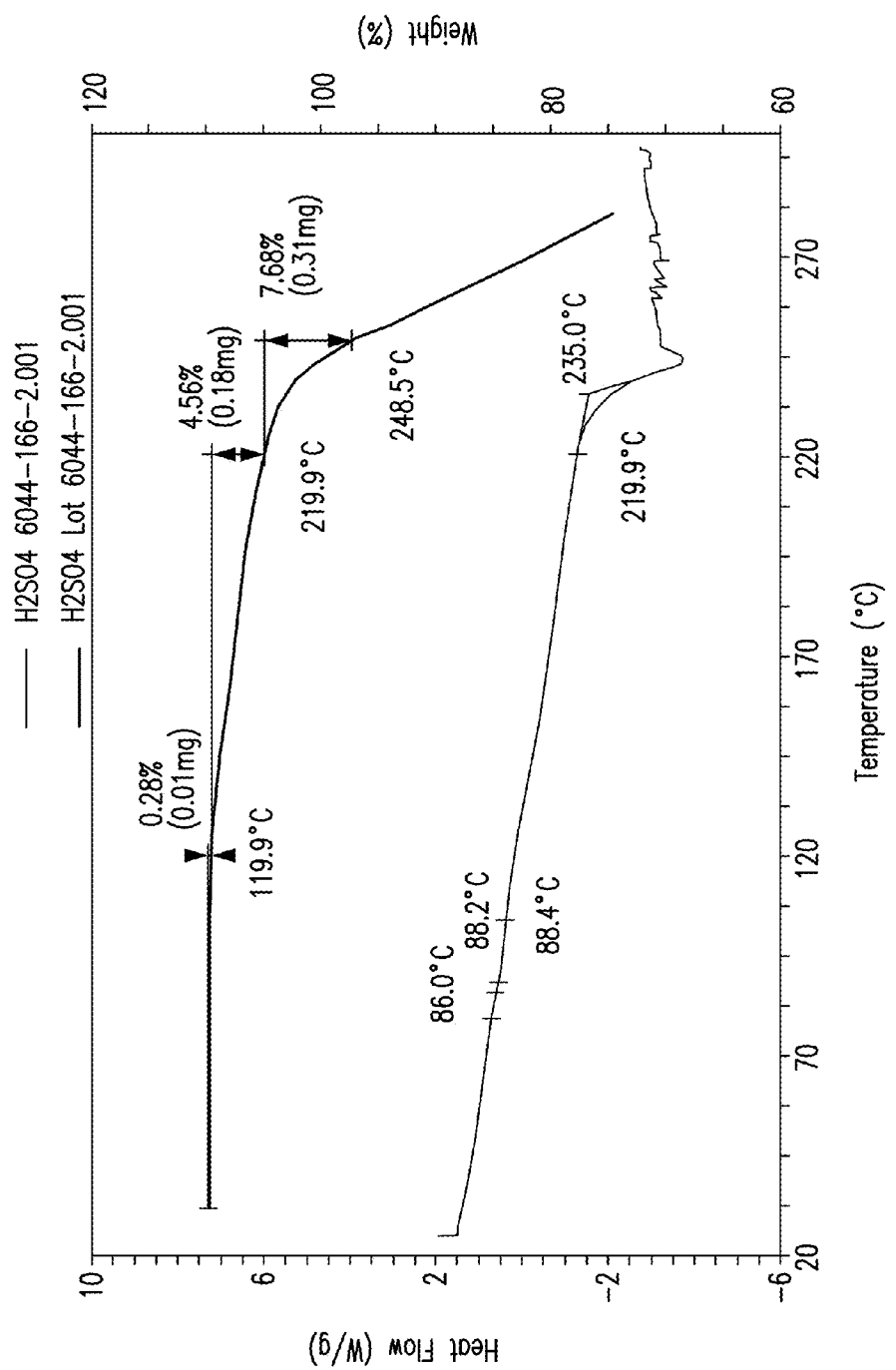

FIG. 35 depicts a TGA/DSC thermogram of the H$_2$SO$_4$ salt of Compound 1.

Figure 36:
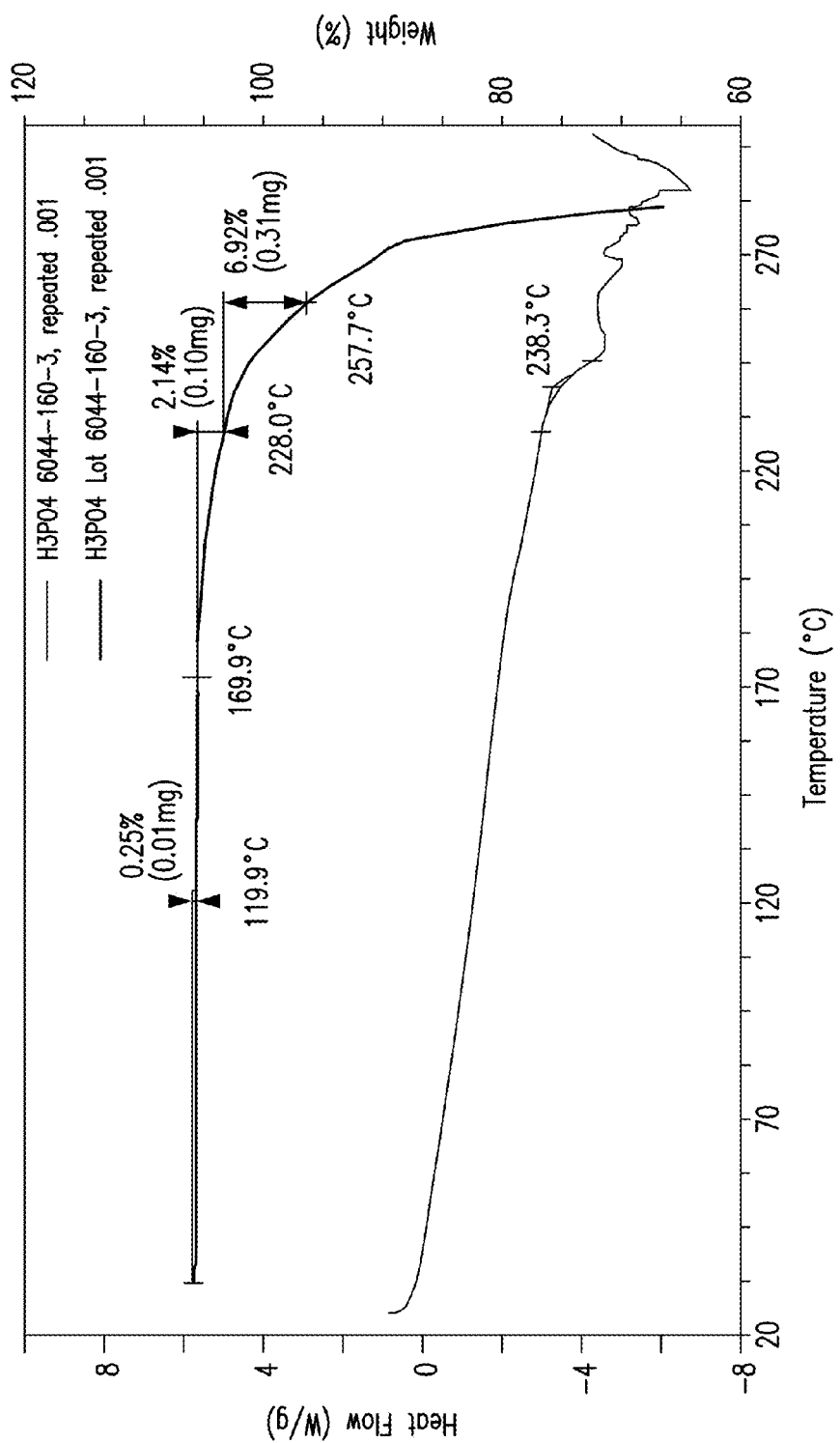

FIG. 36 depicts a TGA/DSC thermogram of the H$_3$PO$_4$ salt of Compound 1.

Figure 37:
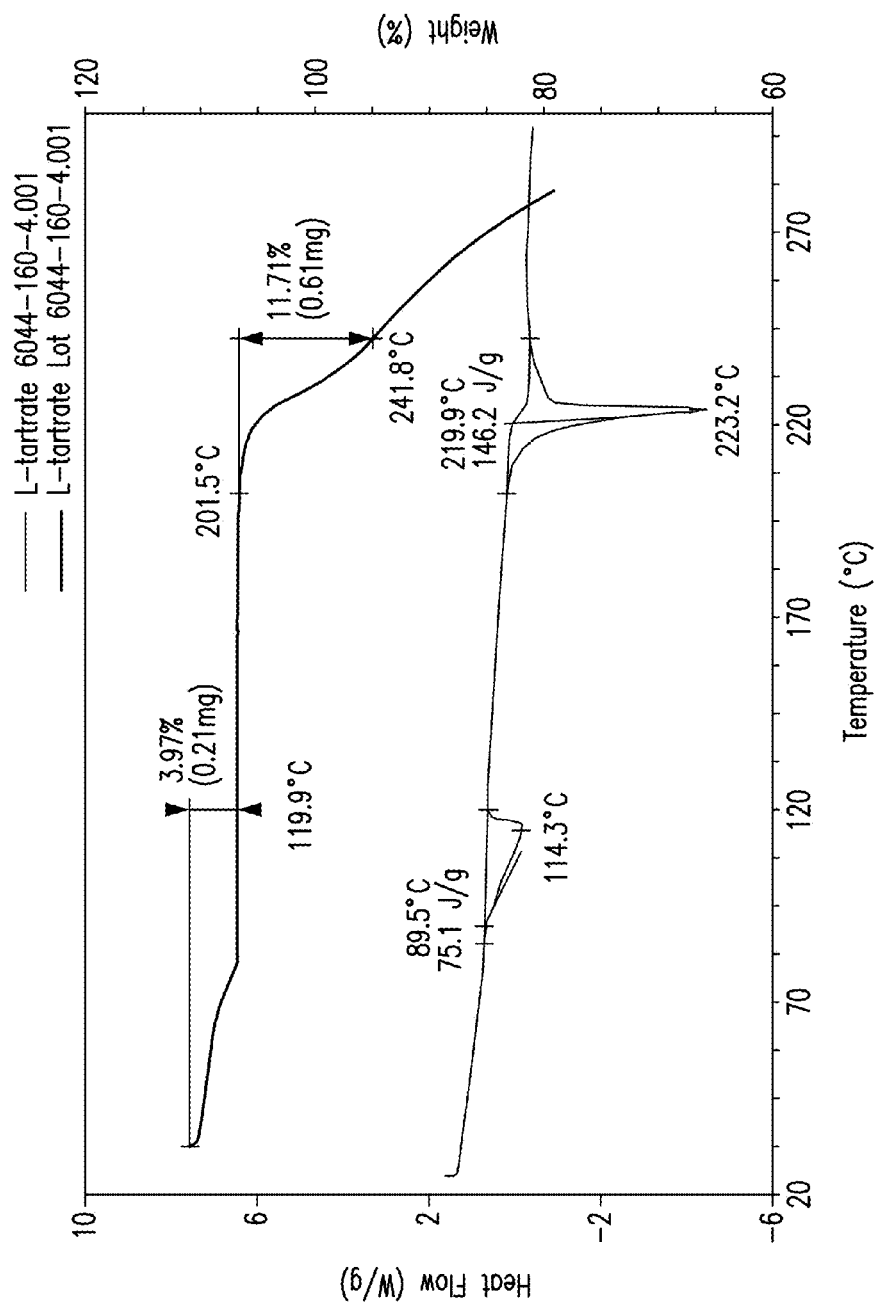

FIG. 37 depicts a TGA/DSC thermogram of the L-tartrate salt of Compound 1.

Figure 38:
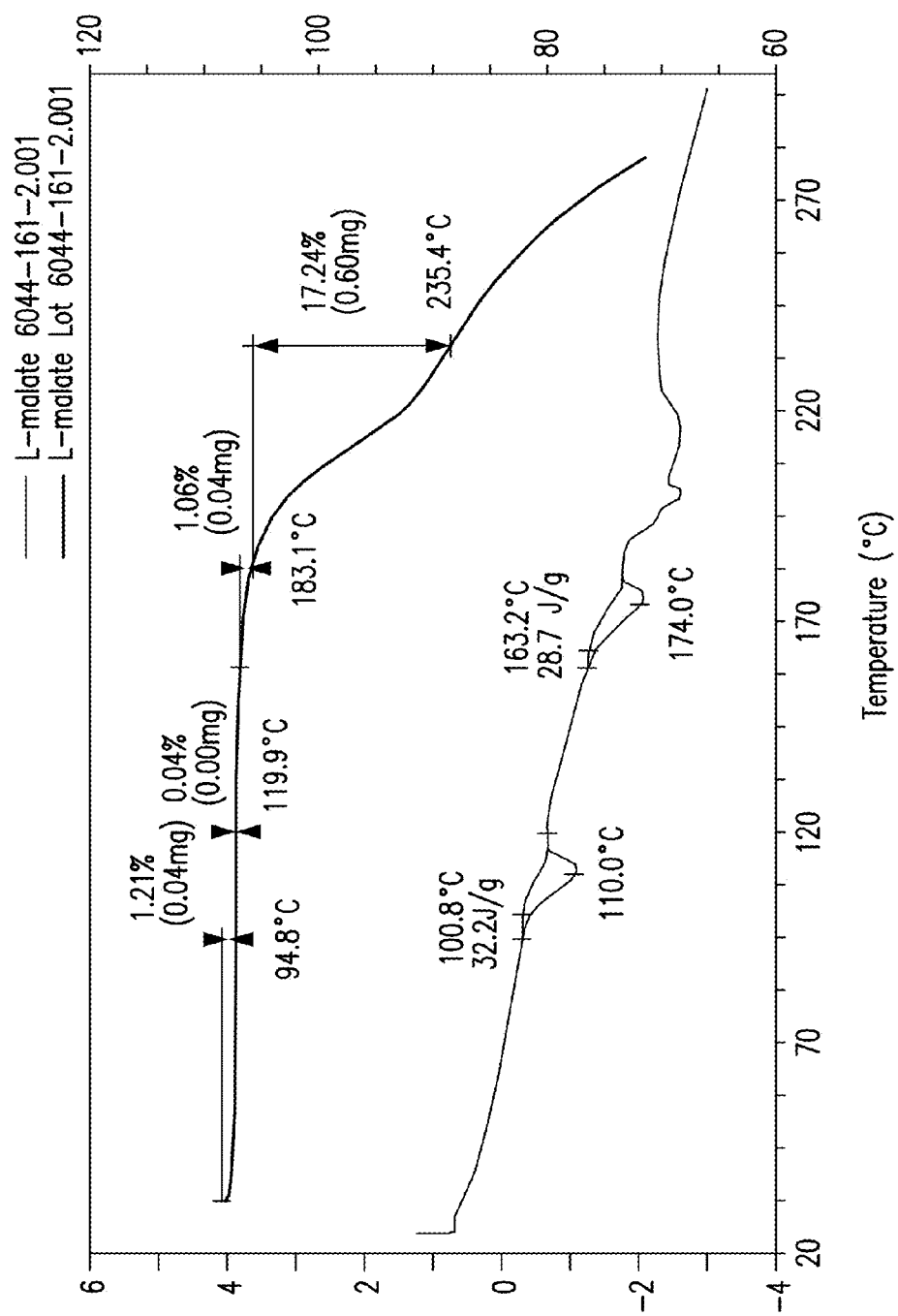

FIG. 38 depicts a TGA/DSC thermogram of the L-malate salt of Compound 1.

Figure 39:
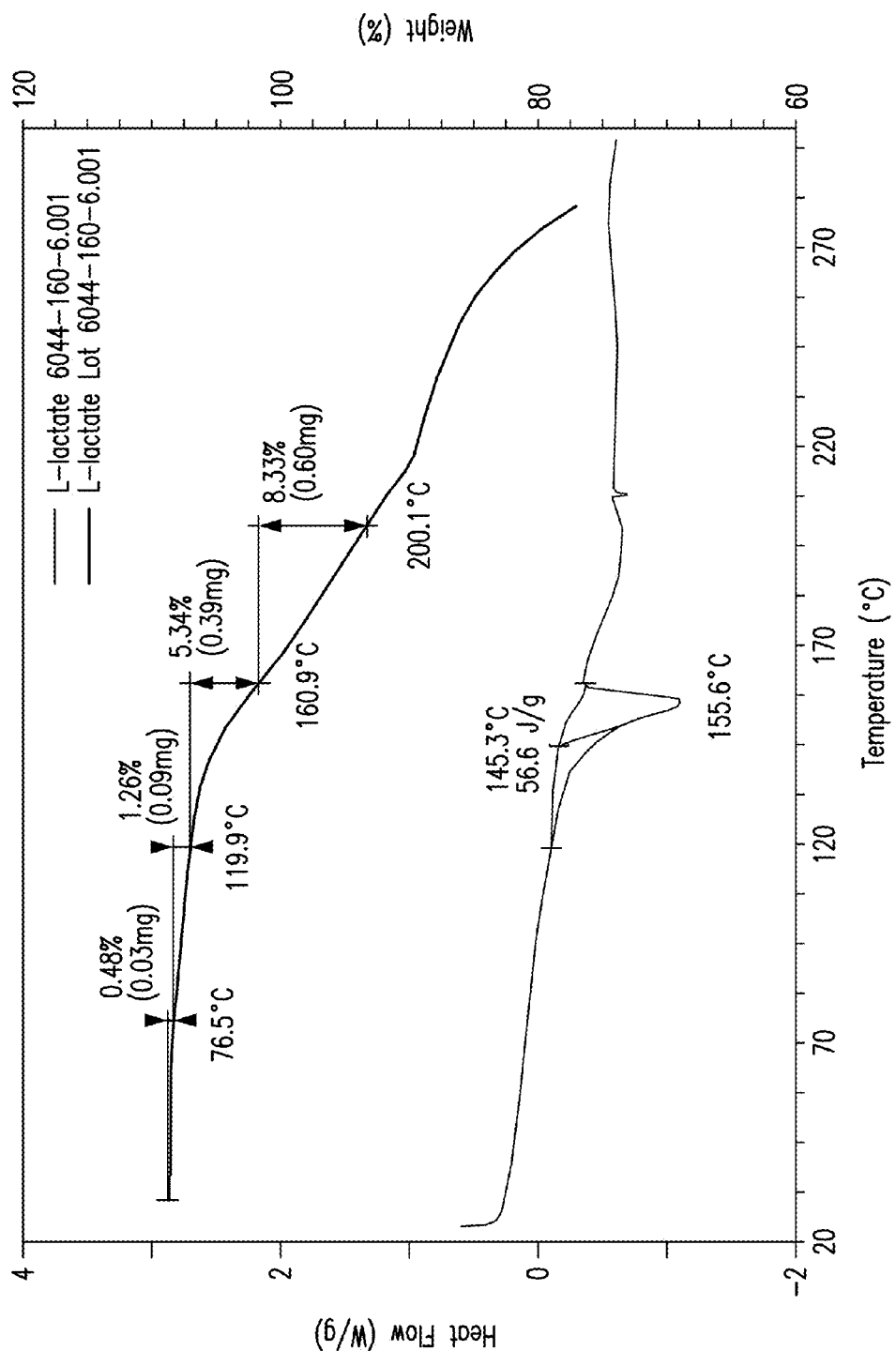

FIG. 39 depicts a TGA/DSC thermogram of the L-lactate salt of Compound 1.

Figure 40:
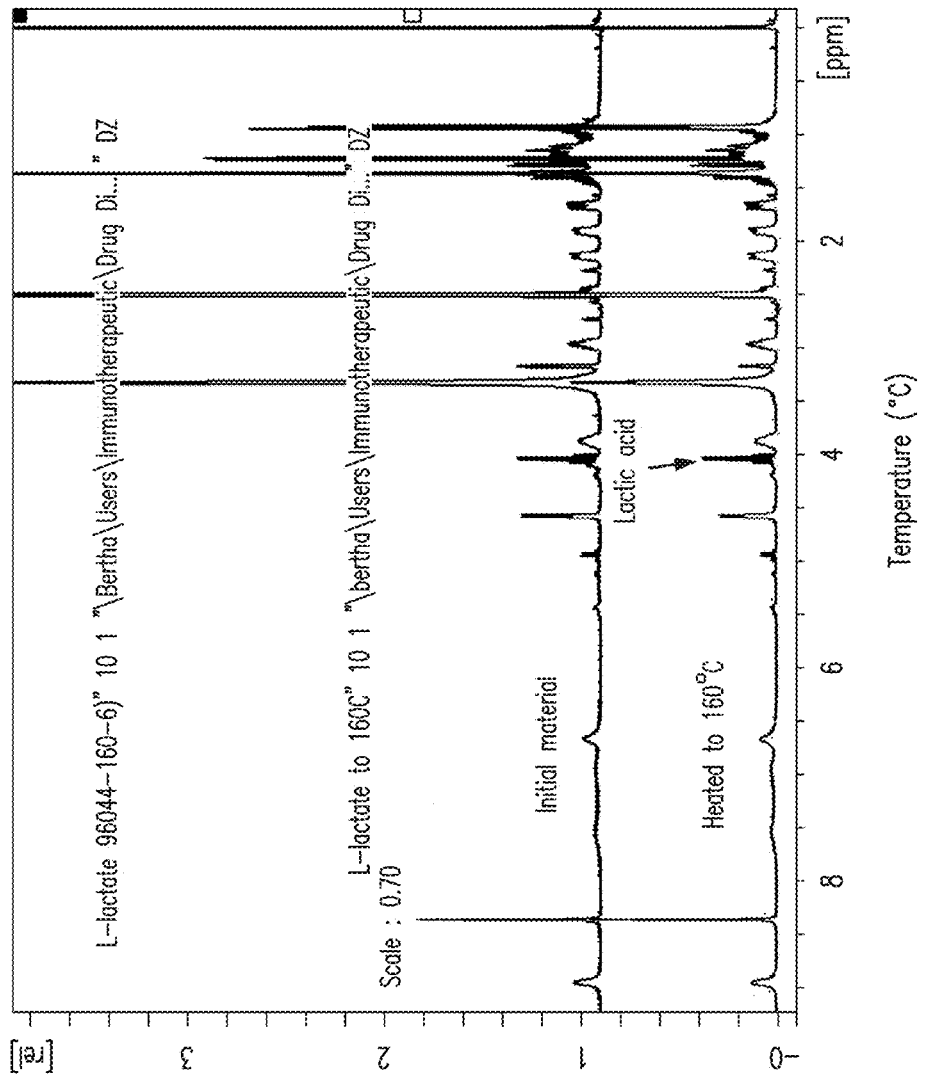

FIG. 40 depicts an overlay of $^1$H NMR spectra of the L-lactate salt before and after heating (from top to bottom).

Figure 41:
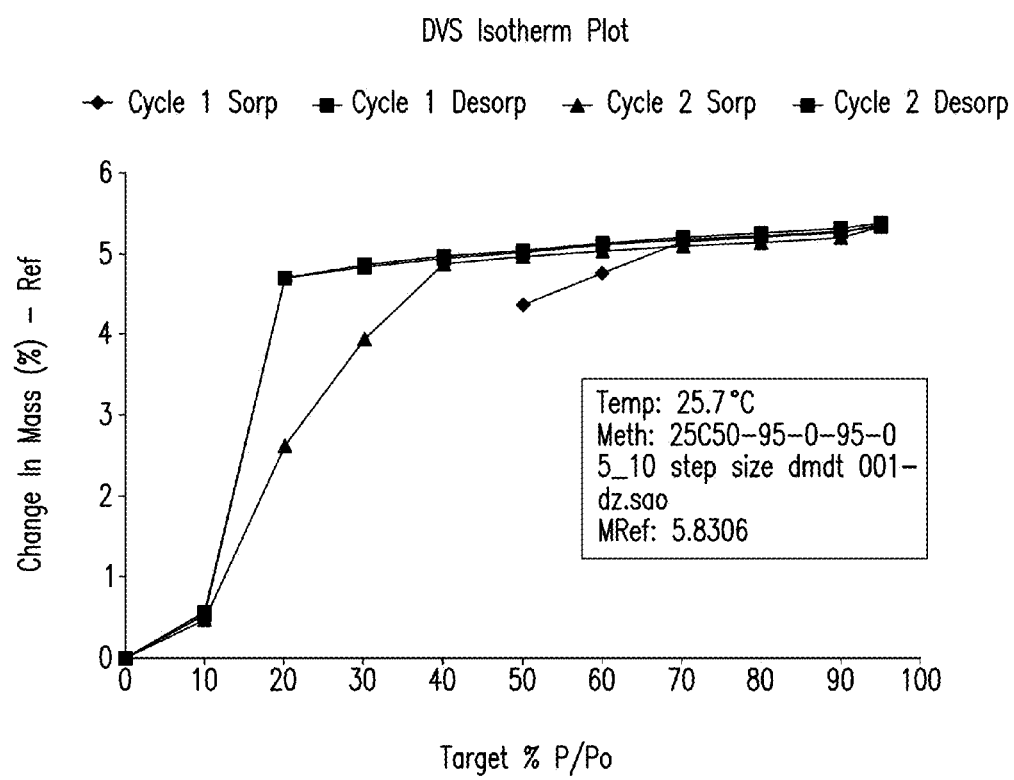

FIG. 41 depicts a DVS thermogram of the HCl salt of Compound 1.

Figure 42:
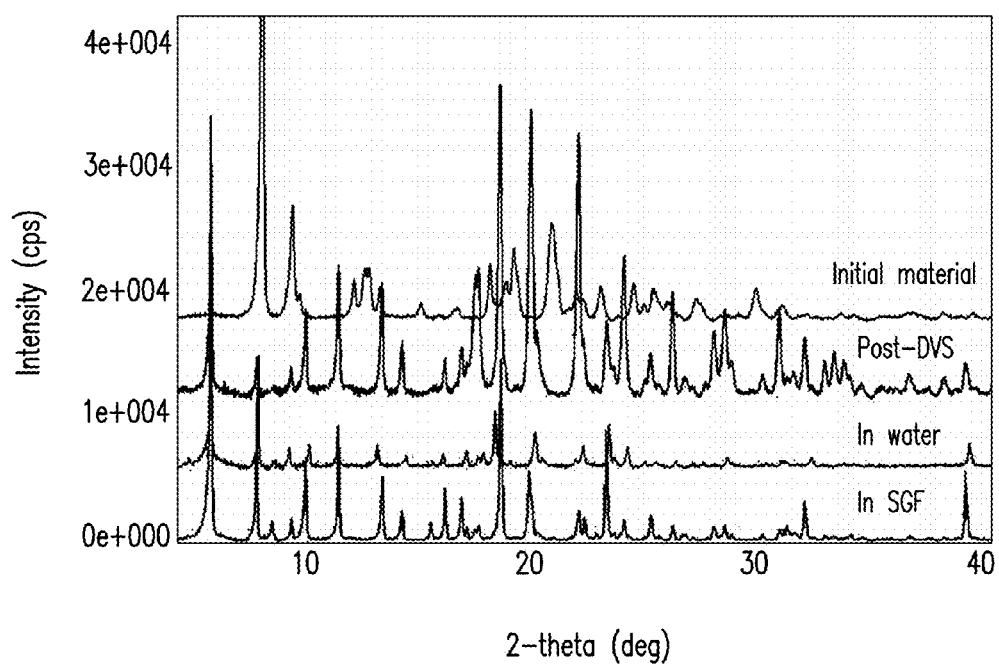

FIG. 42 depicts an overlay of XRPD patterns of the HCl salt, the post-DVS HCl salt, the HCl salt in water and the HCl salt in Simulated Gastric Fluid (SGF) (from top to bottom).

Figure 43:
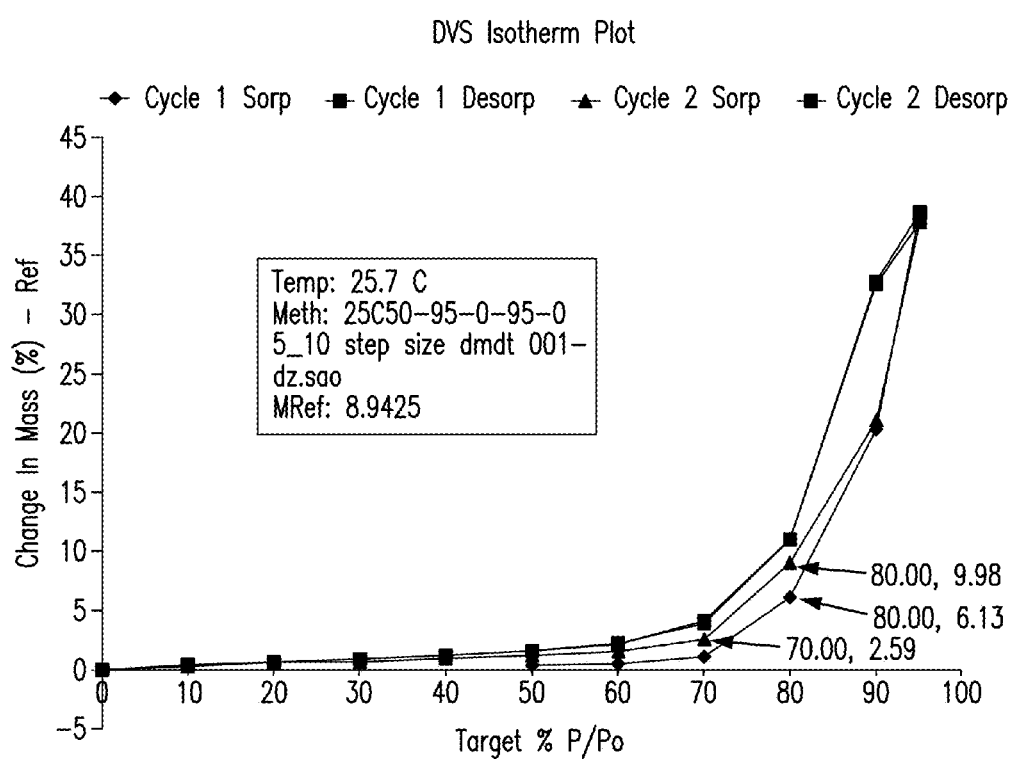

FIG. 43 depicts a DVS thermogram of the H$_2$SO$_4$ salt of Compound 1.

Figure 44:
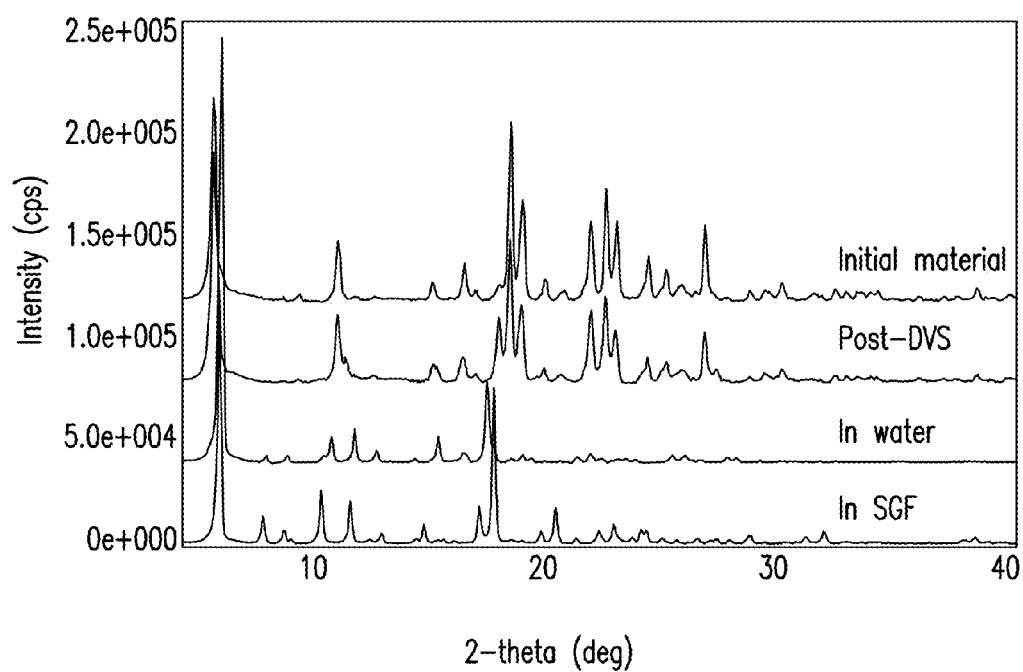

FIG. 44 depicts an overlay of XRPD patterns of the H$_2$SO$_4$ salt, the post-DVS H$_2$SO$_4$ salt, the H$_2$SO$_4$ salt in water and the H$_2$SO$_4$ salt in SGF (from top to bottom).

Figure 45:
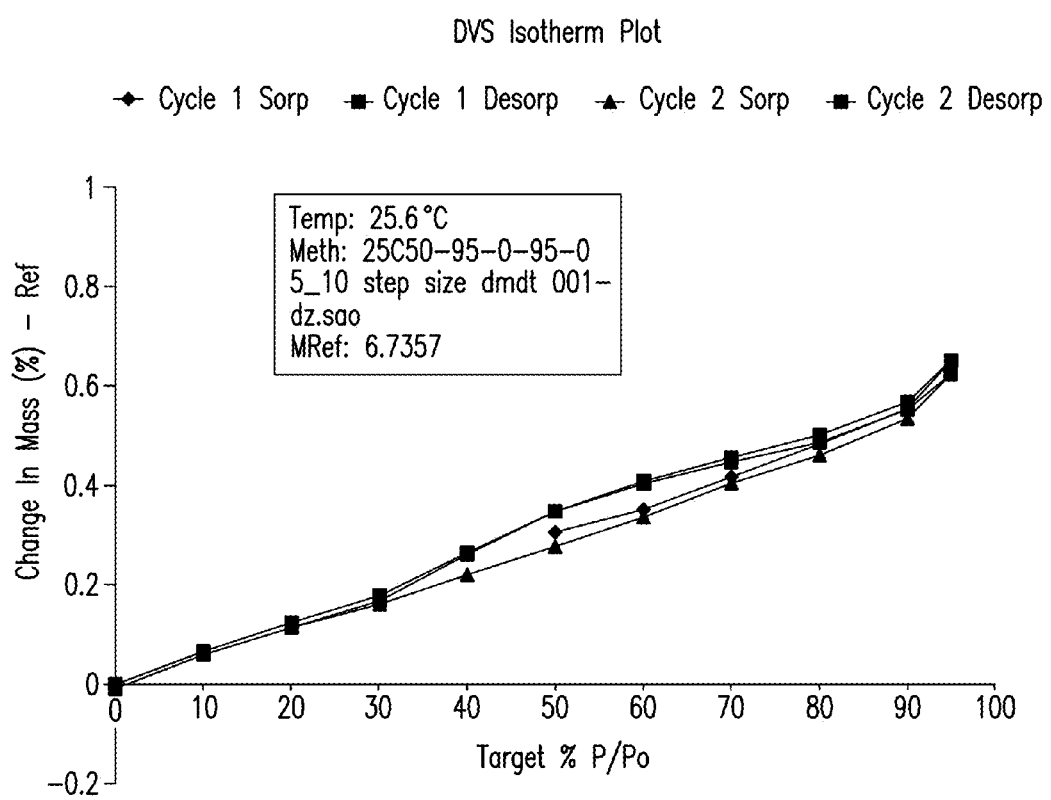

FIG. 45 depicts a DVS thermogram of the H$_3$PO$_4$ salt of Compound 1.

Figure 46:
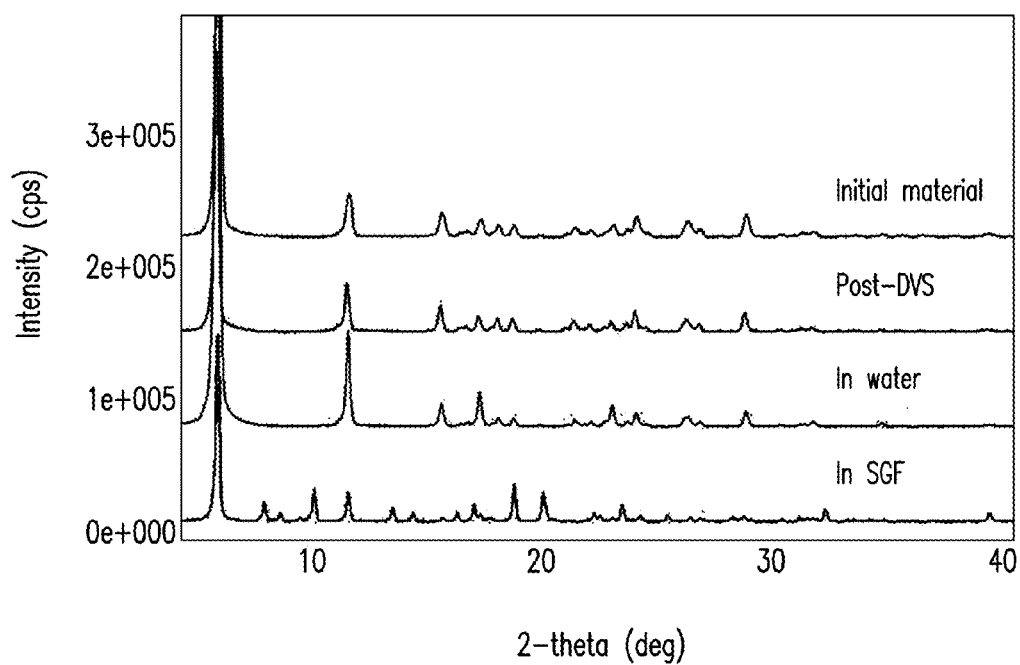

FIG. 46 depicts an overlay of XRPD patterns of the H$_3$PO$_4$ salt, the post-DVS H$_3$PO$_4$ salt, the H$_3$PO$_4$ salt in water and the H$_3$PO$_4$ salt in SGF (from top to bottom).

Figure 47:
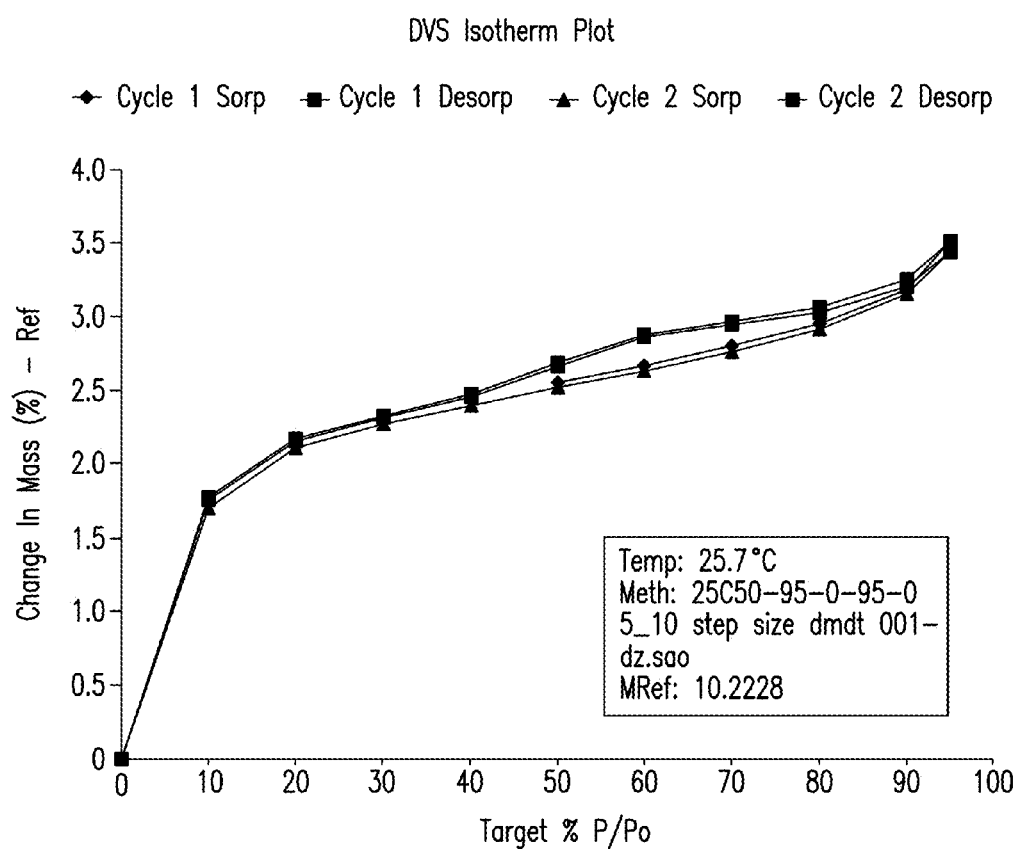

FIG. 47 depicts a DVS thermogram of the L-tartrate salt of Compound 1.

Figure 48:
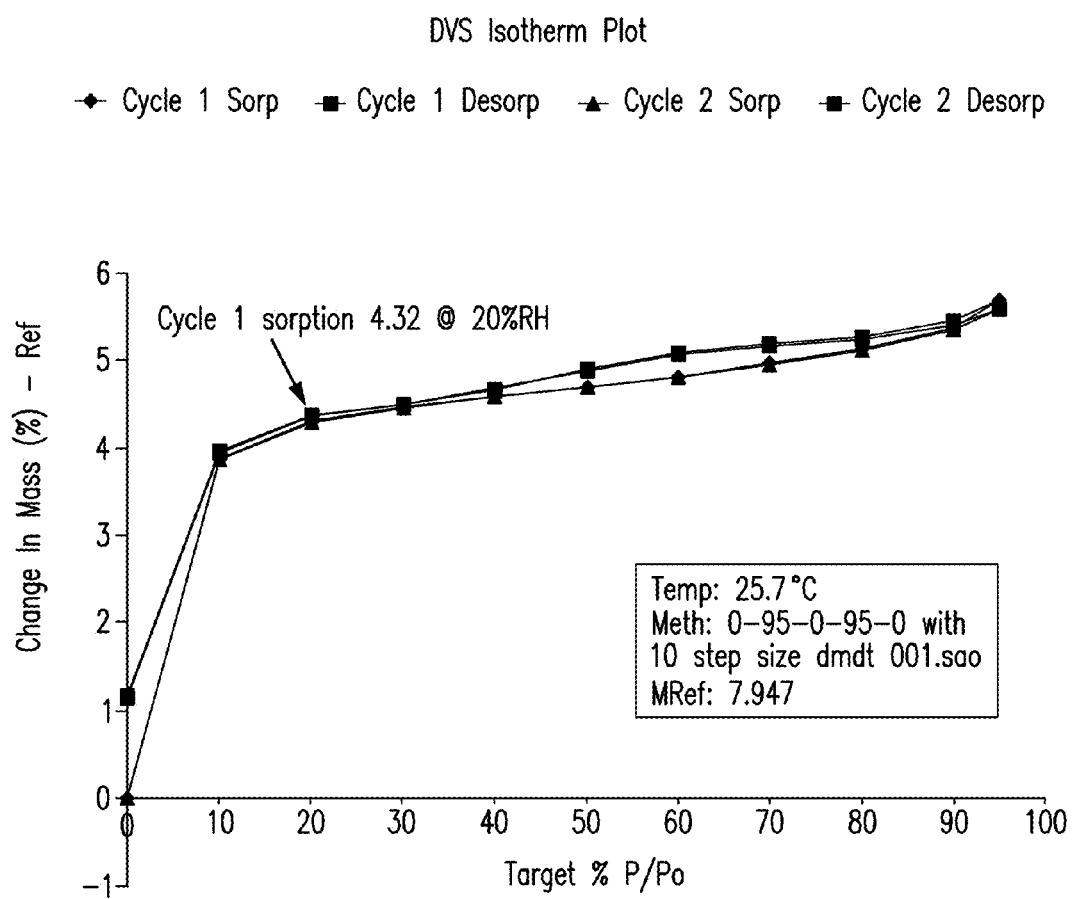

FIG. 48 depicts a DVS thermogram of the L-tartrate salt of Compound 1 after preheated at 50° C. for 3 hours. (from top to bottom).

Figure 49:
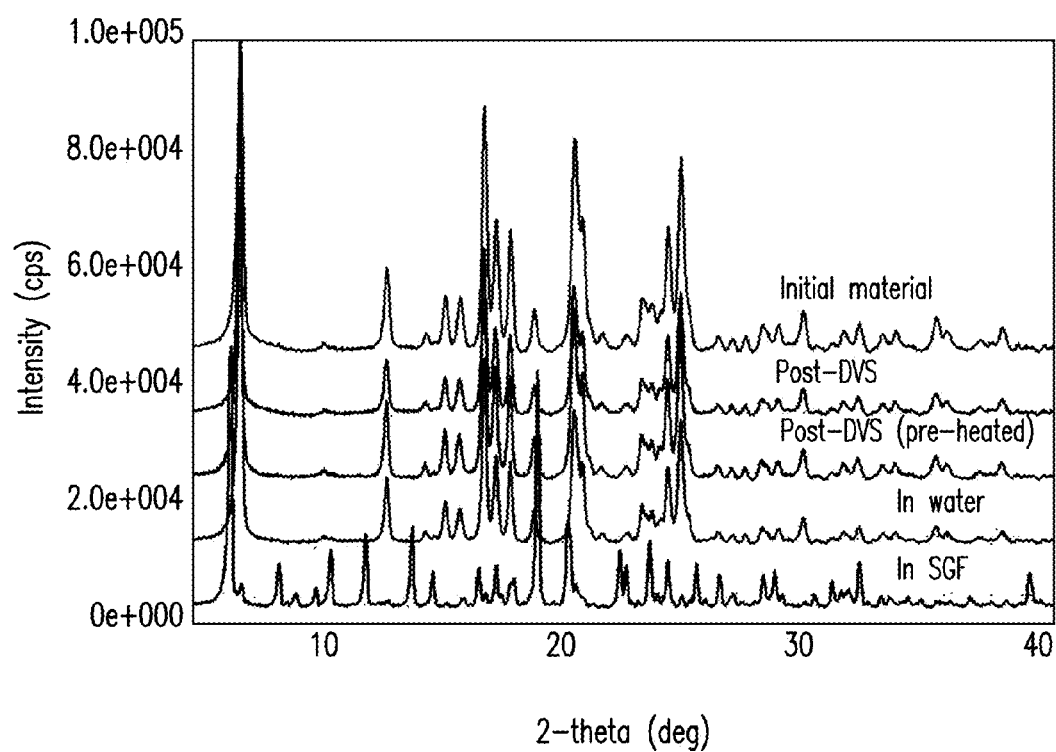

FIG. 49 depicts an overlay of XRPD patterns of the L-tartrate salt, the post-DVS L-tartrate salt, the post-DVS L-tartrate salt after preheated at 50° C. for 3 hours, the L-tartrate salt in water and the L-tartrate salt in SGF (from top to bottom).

Figure 50:
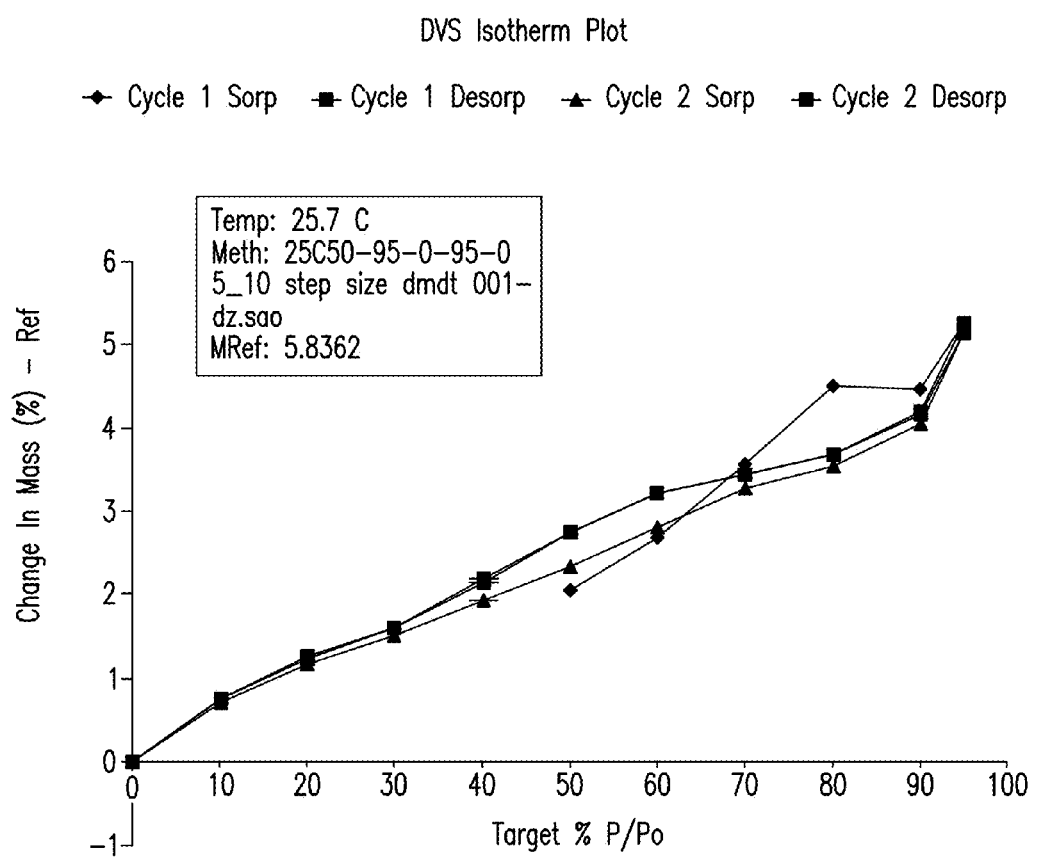

FIG. 50 depicts a DVS thermogram of the L-malate salt of Compound 1.

Figure 51:
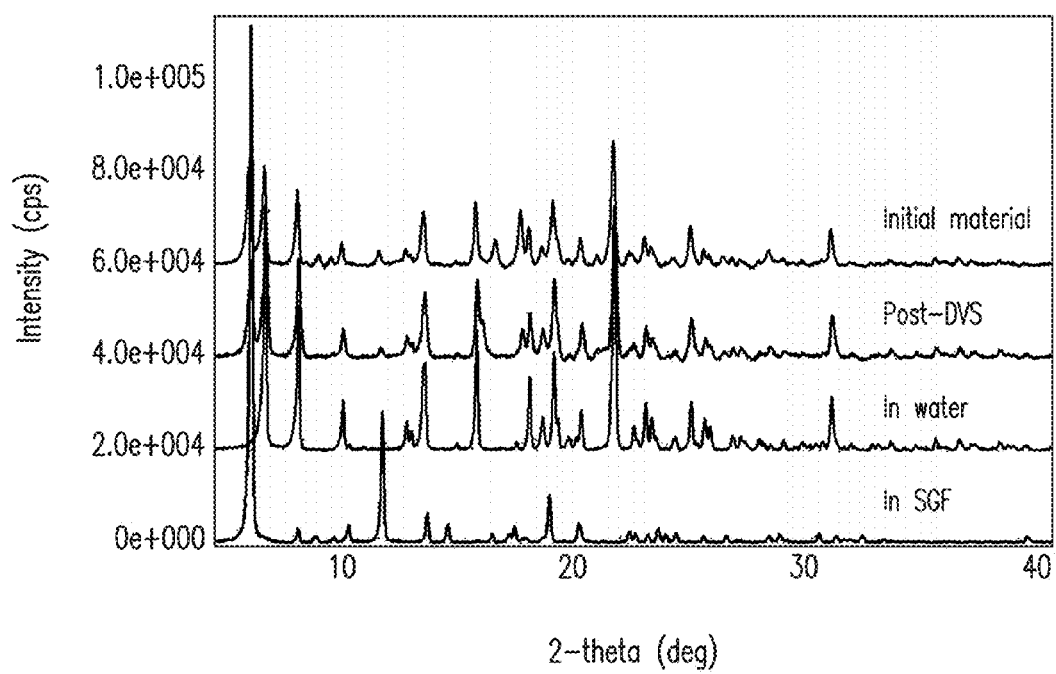

FIG. 51 depicts an overlay of XRPD patterns of the L-malate salt, the post-DVS L-malate salt, the L-malate salt in water and the L-malate salt in SGF (from top to bottom).

Figure 52:
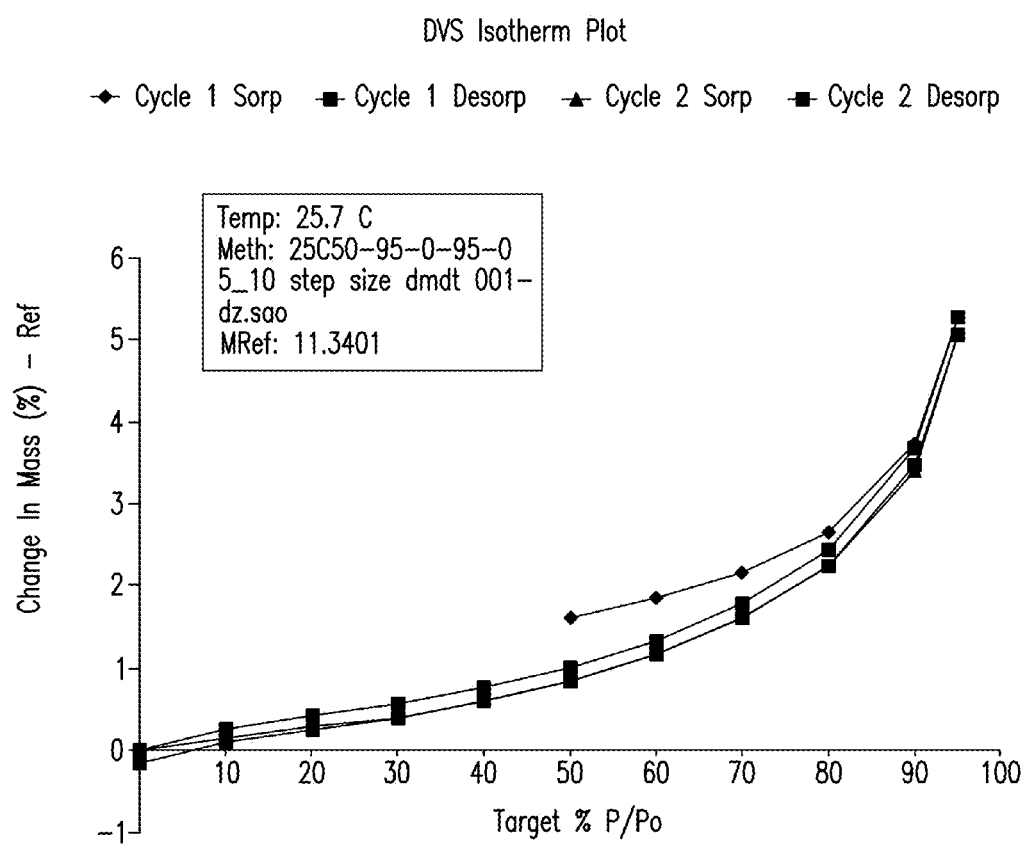

FIG. 52 depicts a DVS thermogram of the L-lactate salt of Compound 1.

Figure 53:
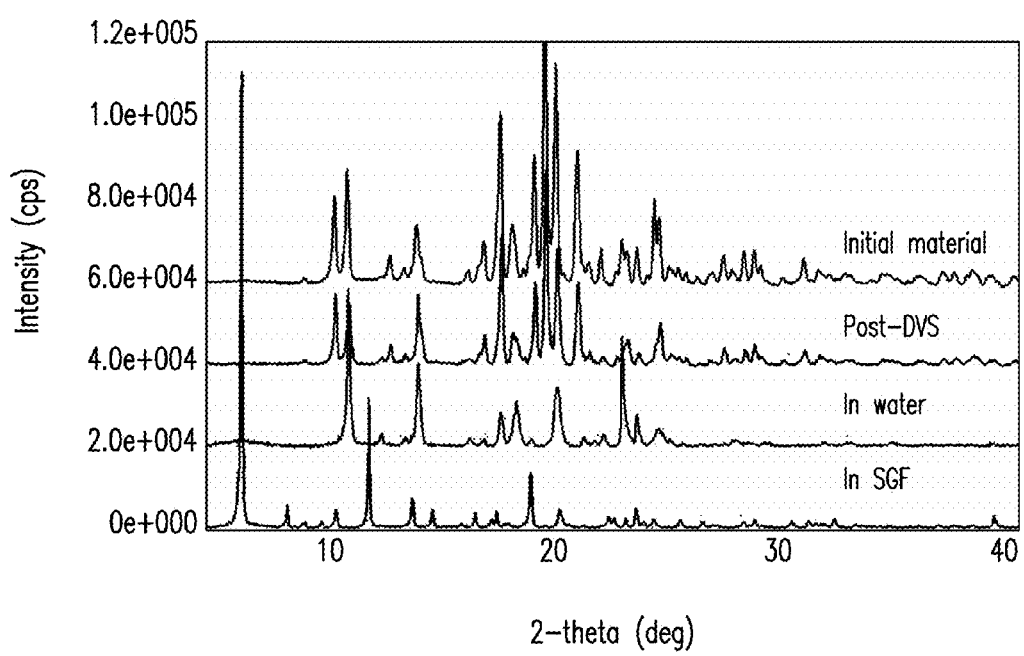

FIG. 53 depicts an overlay of XRPD patterns of the L-lactate salt, the post-DVS L-lactate salt, the L-lactate salt in water and the L-lactate salt in SGF (from top to bottom).

Figure 54:
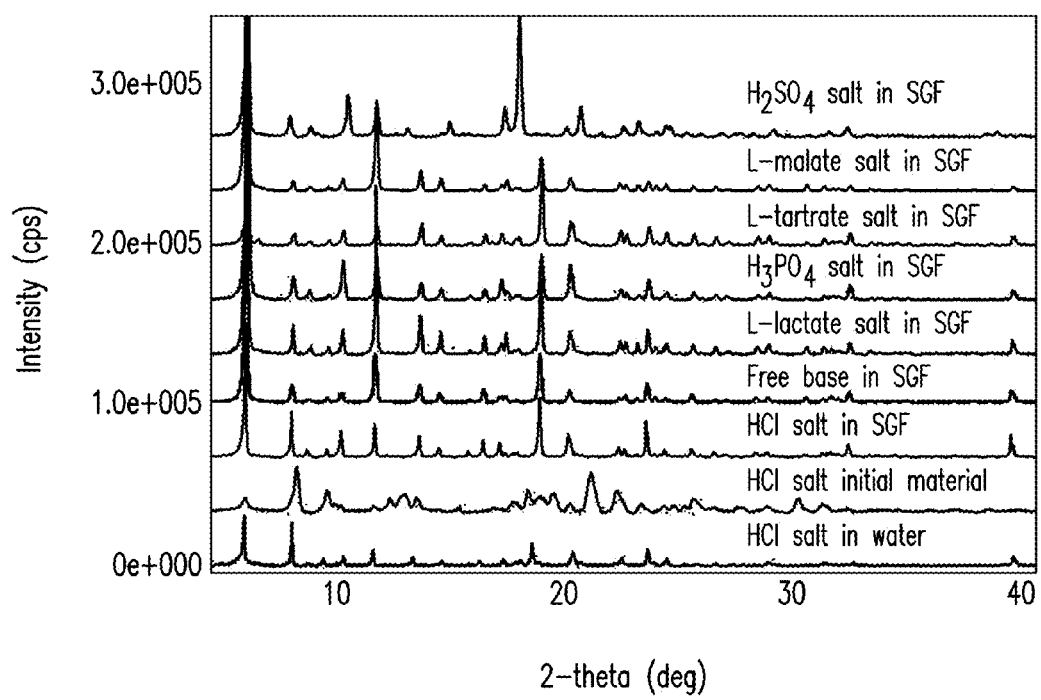

FIG. 54 depicts an overlay of XRPD patterns of the L-H$_2$SO$_4$ salt in SGF, the L-malate salt in SGF, the L-tartrate salt in SGF, the H$_3$PO$_4$ salt, the L-lactate salt in SGF, Compound 1 (free base) in SGF, the HCl salt in SGF, the HCl salt and the HCl salt in water (from top to bottom).

Figure 55:
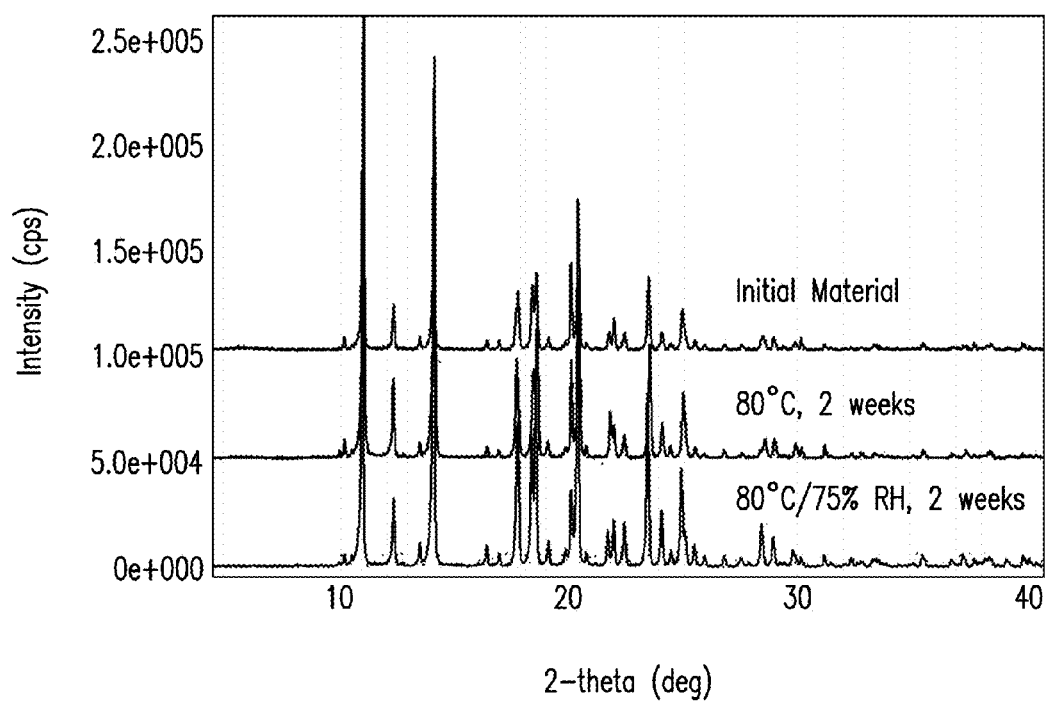

FIG. 55 depicts an overlay of XRPD patterns of the HCl salt, the HCl salt stored at 80° C. for 2 weeks and the HCl salt stored at 80° C. under 75% relative humidity for two weeks (from top to bottom).

Figure 56:
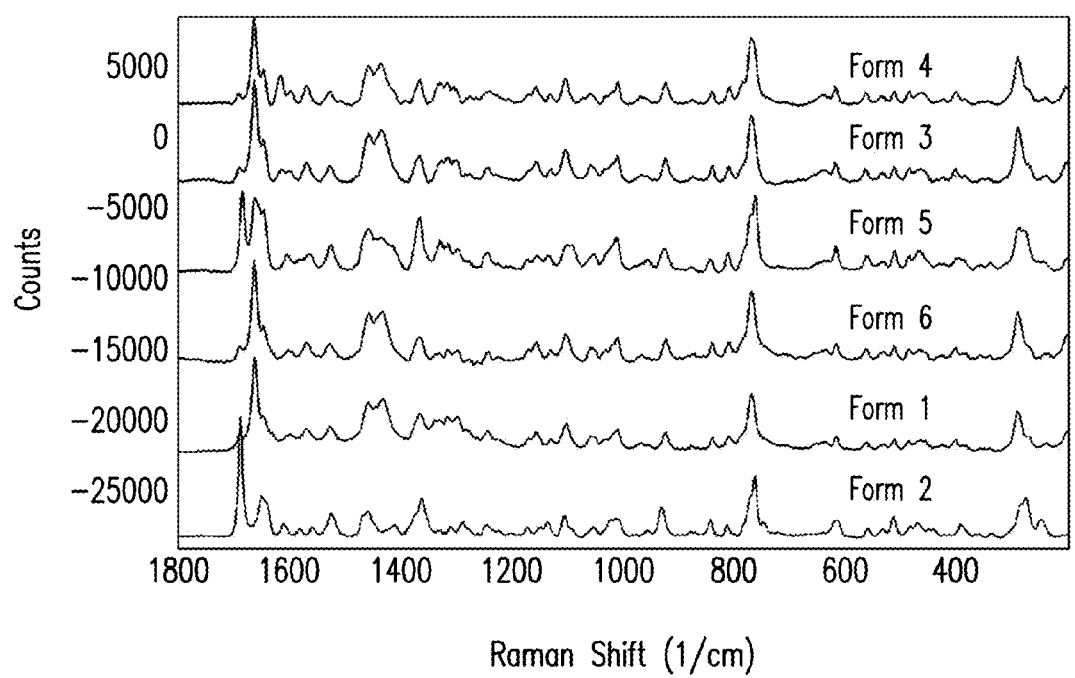

FIG. 56 depicts an overlay of Raman spectra of form 4, form 3, form 5, form 6, form 1 and form 2 of the HCl salt (from top to bottom).

Figure 57:
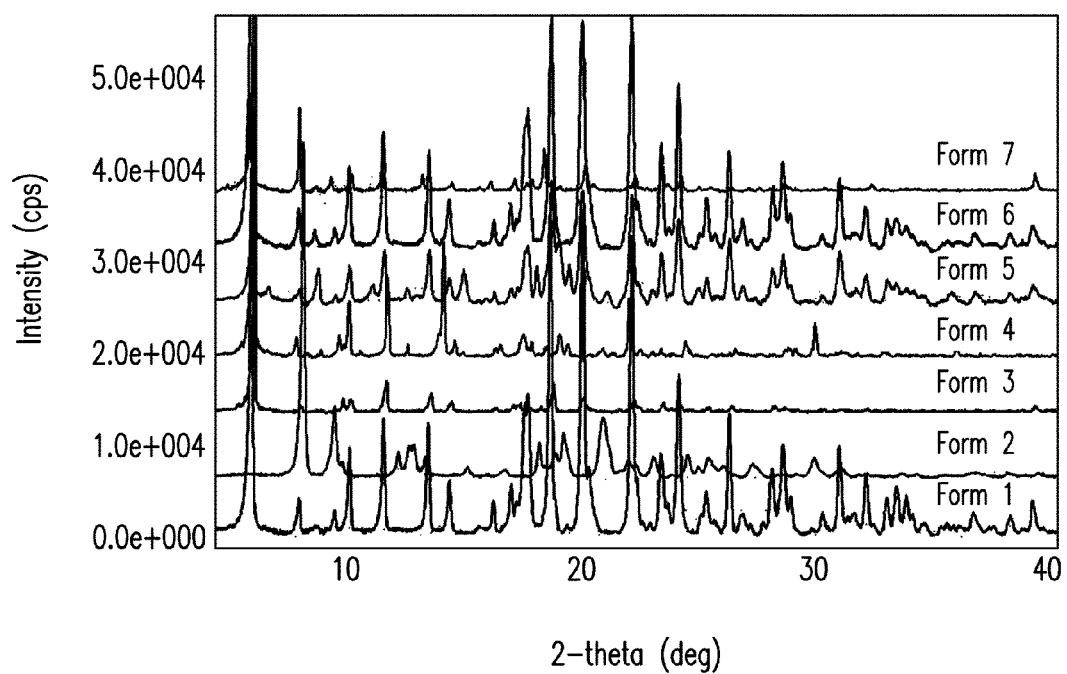

FIG. 57 depicts an overlay of XRPD patterns of form 7, form 6, form 5, form 4, form 3, form 2 and form 1 of the HCl salt (from top to bottom).

Figure 58:
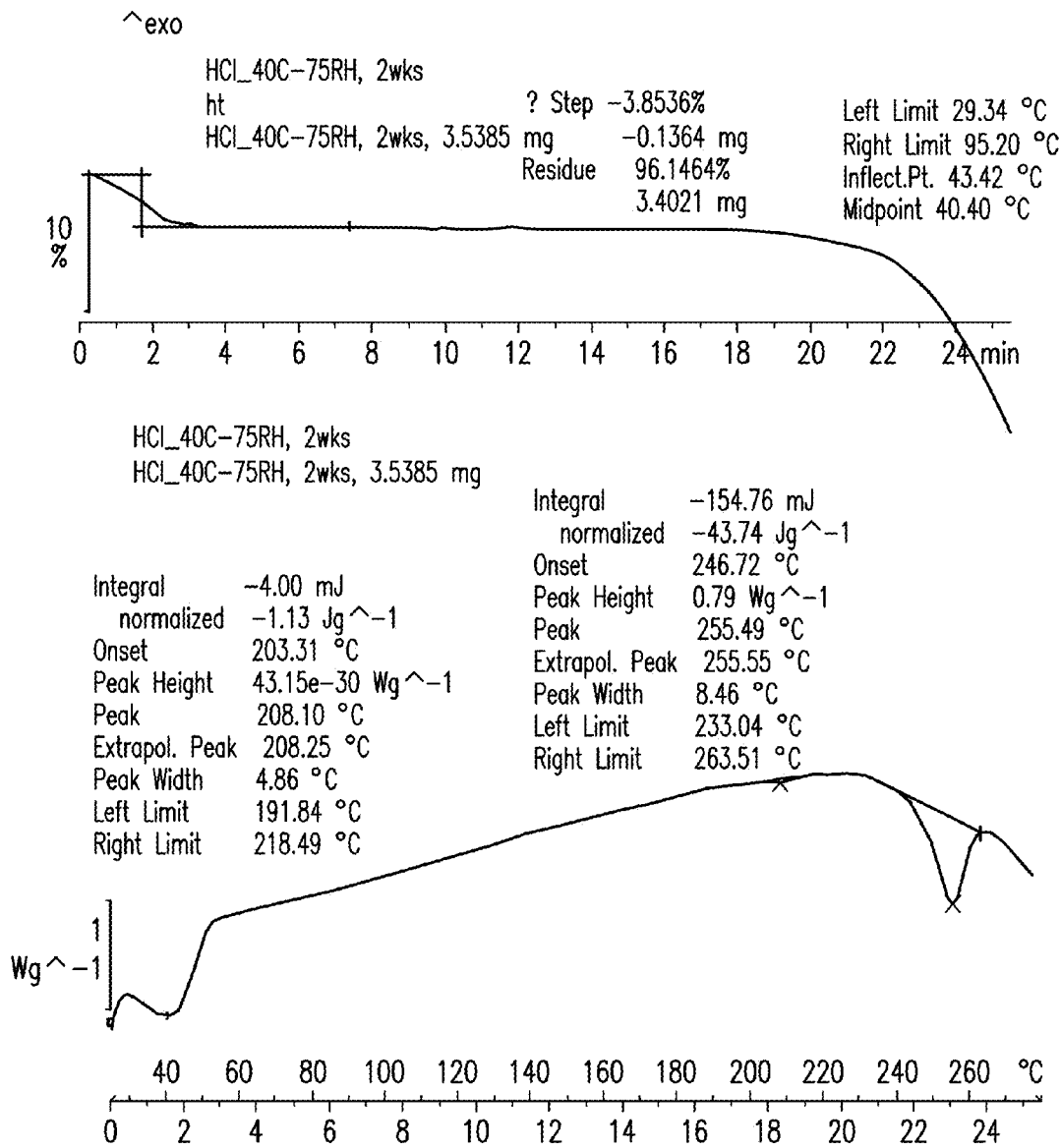

FIG. 58 depicts a TGA/DSC thermogram of the HCl salt stored under 40° C./75% relative humidity for two weeks.

Figure 59:
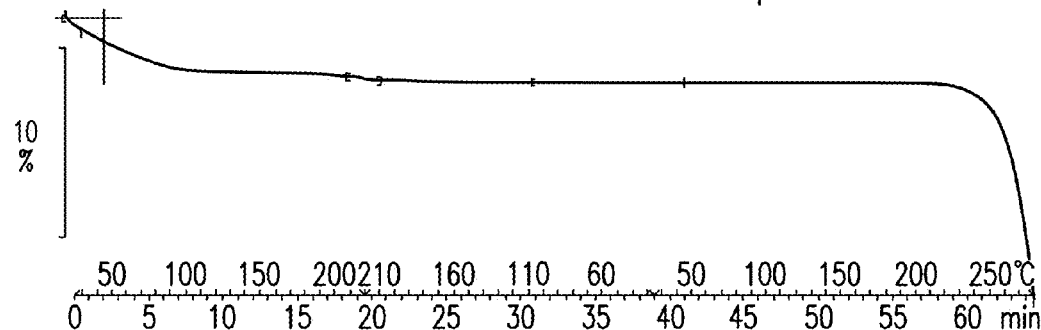
Figure 59:
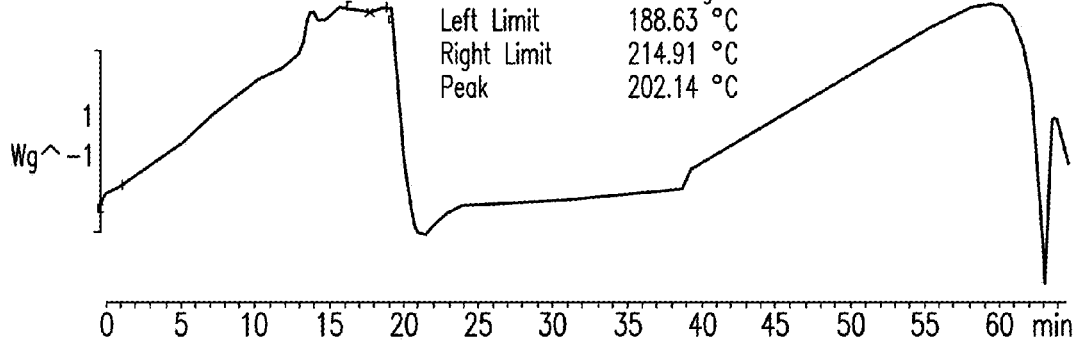

FIG. 59 depicts a TGA/DSC thermogram of form 6 of the HCl salt.

Figure 60:
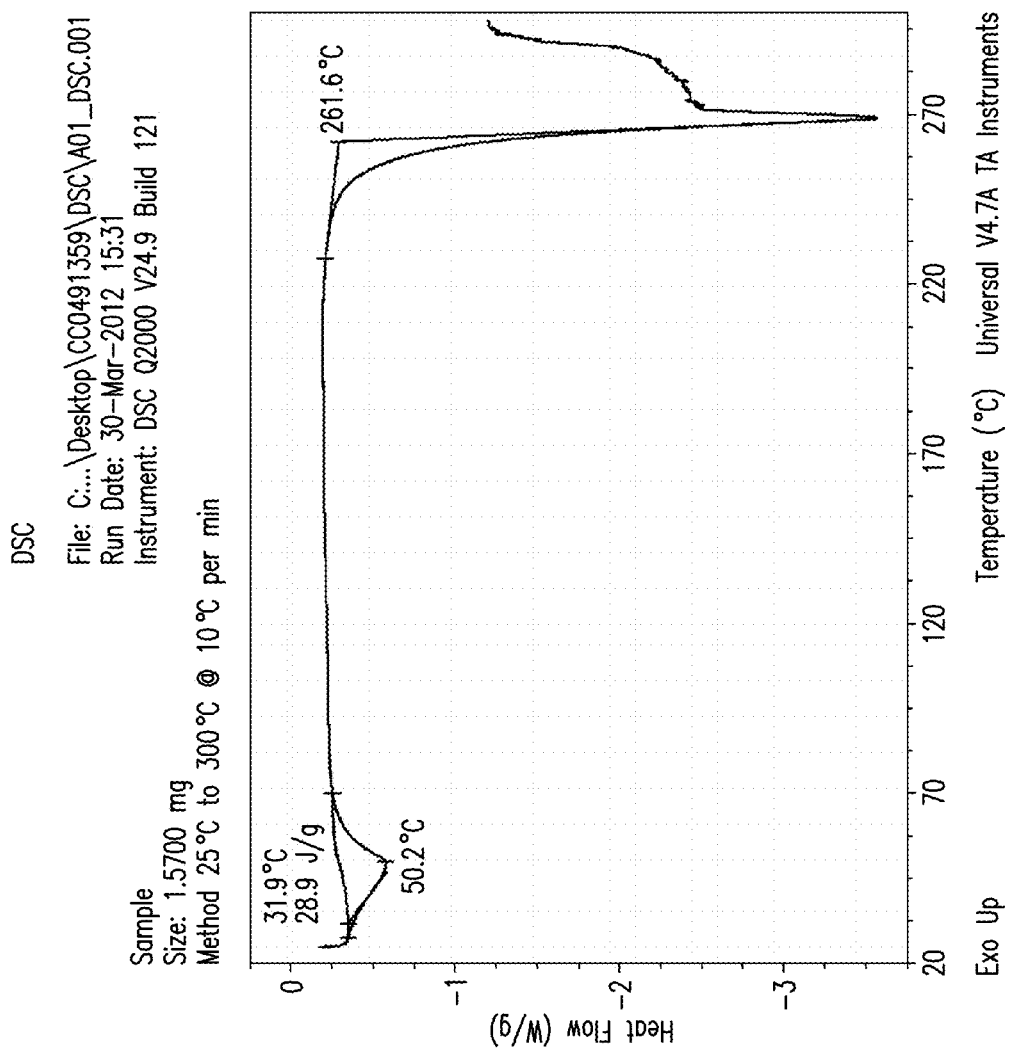

FIG. 60 depicts a DSC thermogram of form 1 of the HCl salt.

Figure 61:
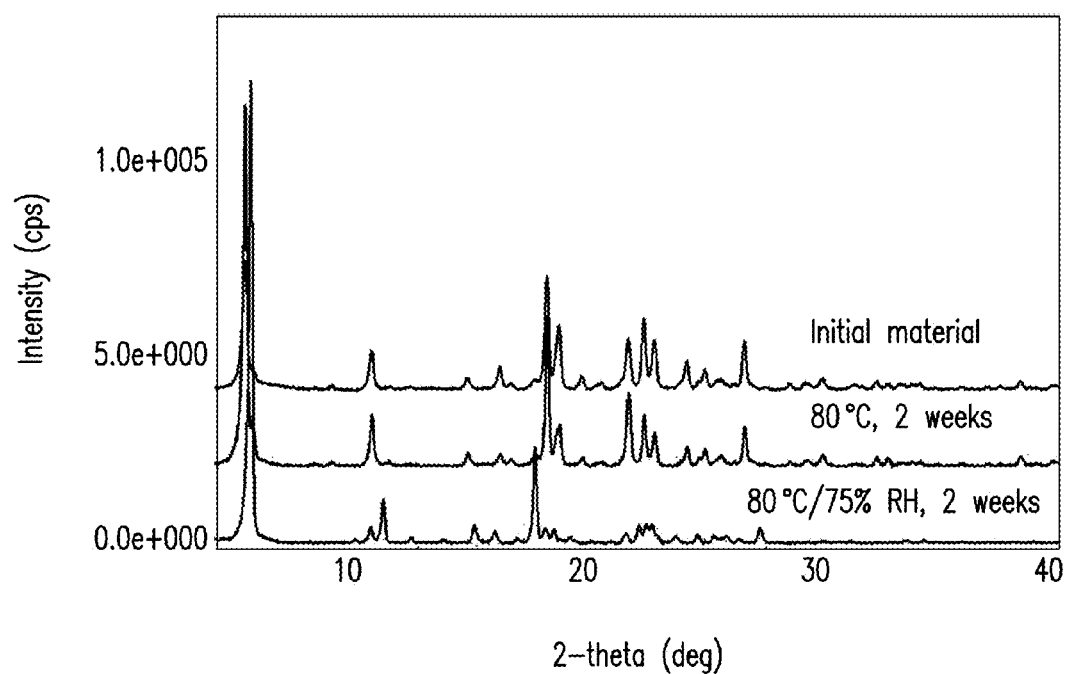

FIG. 61 depicts an overlay of XRPD patterns of the H$_2$SO$_4$ salt, the H$_2$SO$_4$ salt stored at 80° C. for 2 weeks and the H$_2$SO$_4$ salt stored at 80° C. under 75% relative humidity for two weeks (from top to bottom).

Figure 62:
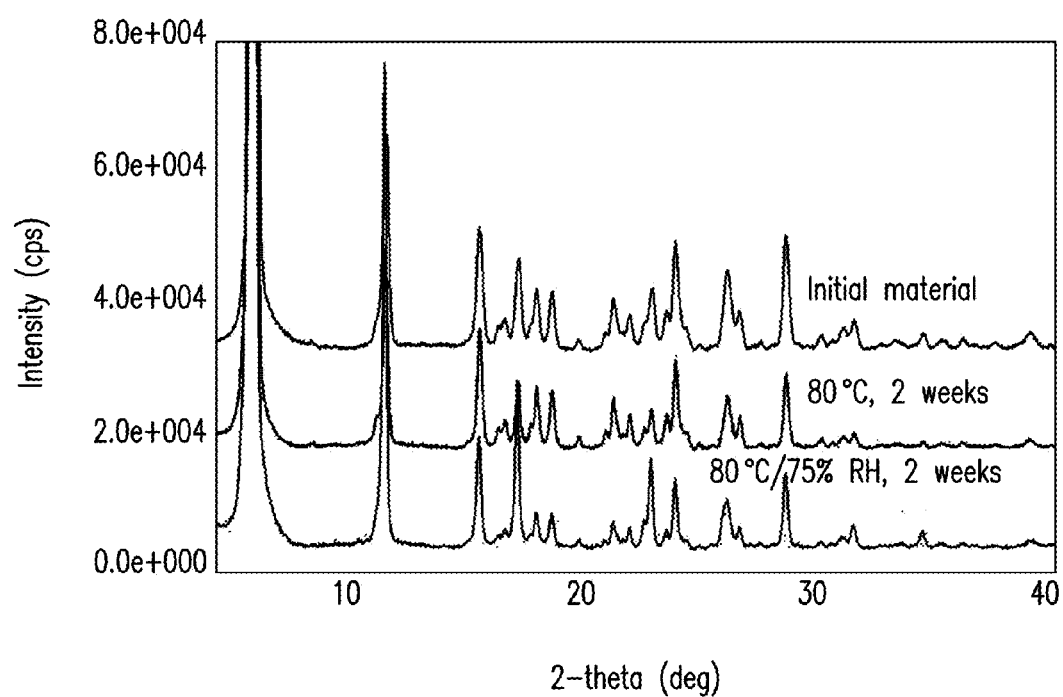

FIG. 62 depicts an overlay of XRPD patterns of the H$_3$PO$_4$ salt, the H$_3$PO$_4$ salt stored at 80° C. for 2 weeks and the H$_3$PO$_4$ salt stored at 80° C. under 75% relative humidity for two weeks (from top to bottom).

Figure 63:
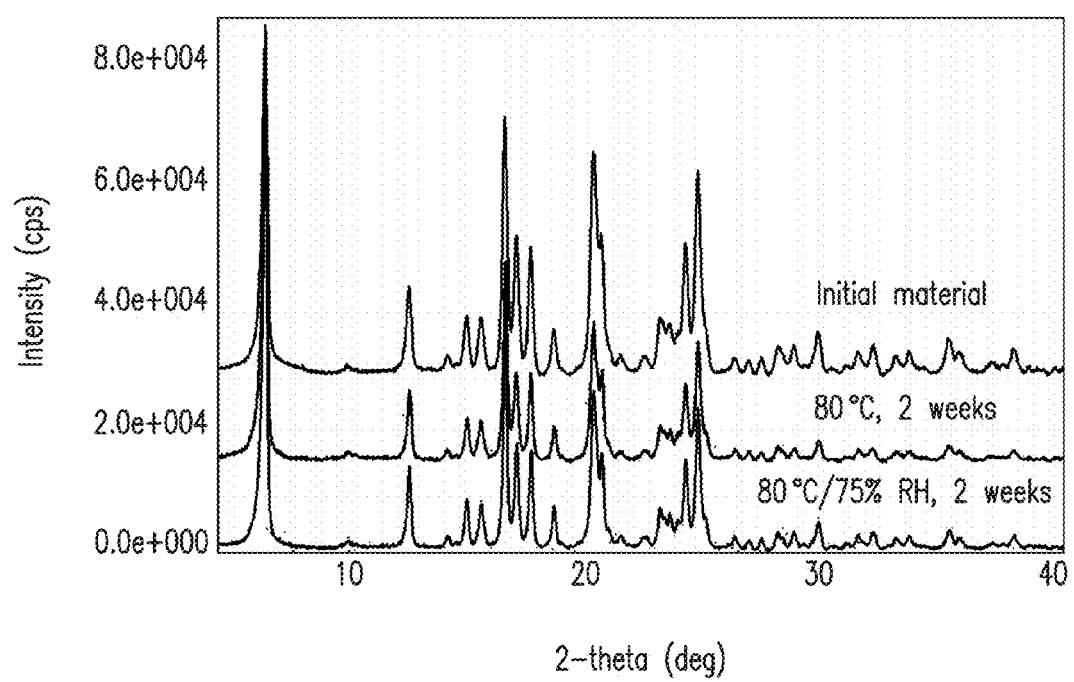

FIG. 63 depicts an overlay of XRPD patterns of the L-tartrate salt, the L-tartrate salt stored at 80° C. for 2 weeks and the L-tartrate salt stored at 80° C. under 75% relative humidity for two weeks (from top to bottom).

Figure 64:
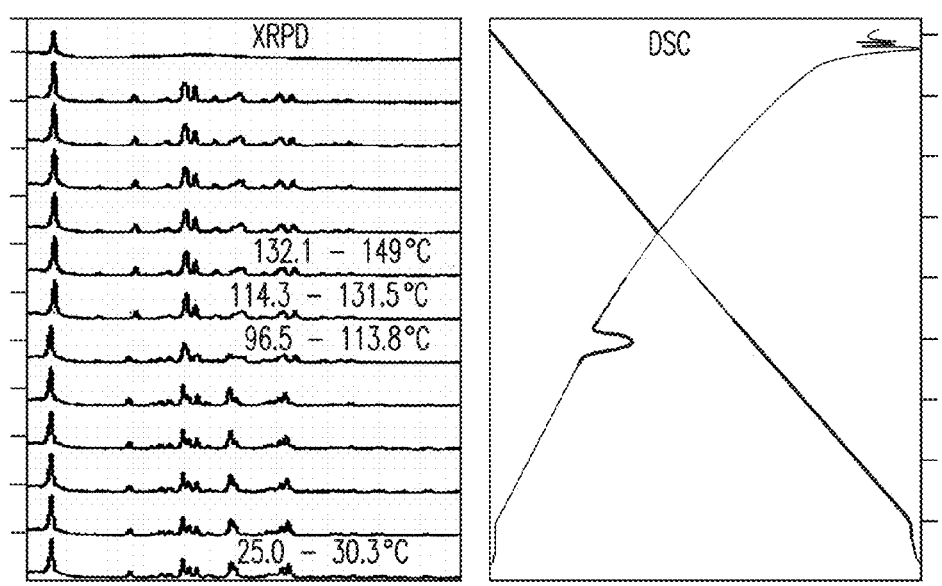

FIG. 64 depicts an overlay of XRPD-DSC patterns of the L-tartrate salt.

Figure 65:
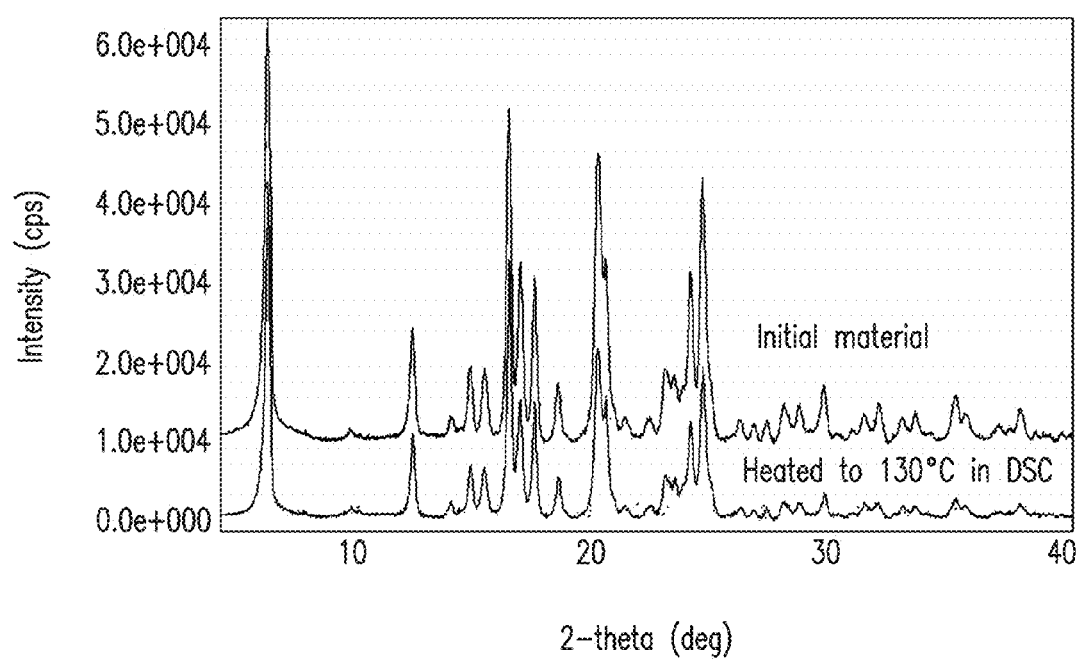

FIG. 65 depicts an overlay of XRPD patterns of the L-tartrate salt before and after heated to 130° C.

Figure 66:
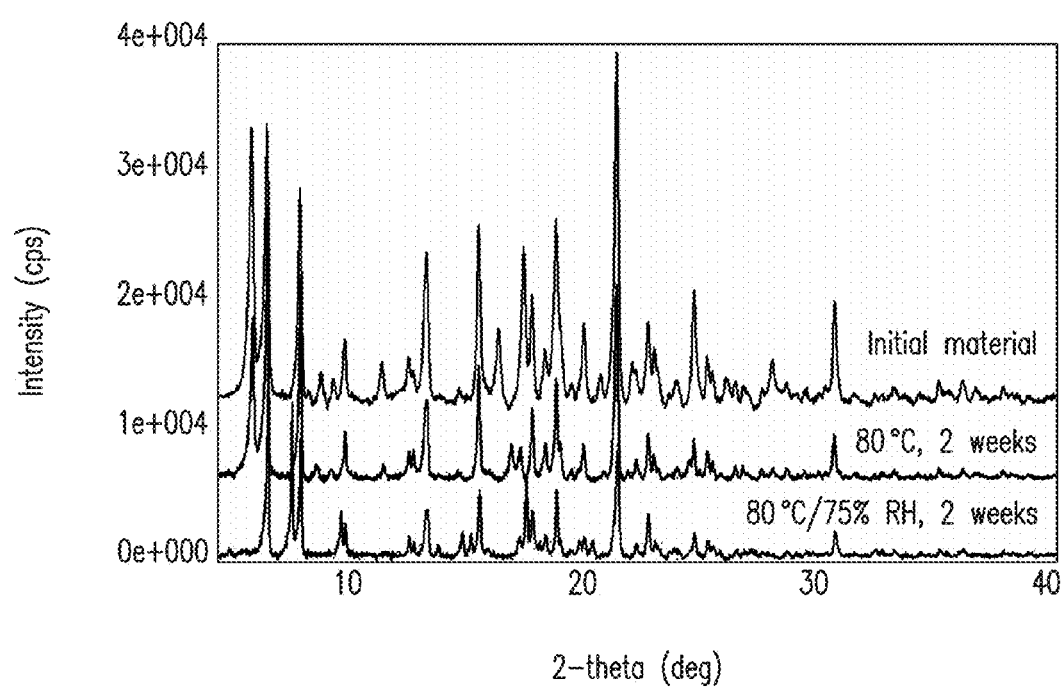

FIG. 66 depicts an overlay of XRPD patterns of the L-malate salt, the L-malate salt stored at 80° C. for 2 weeks and the L-malate salt stored at 80° C. under 75% relative humidity for two weeks (from top to bottom).

Figure 67:
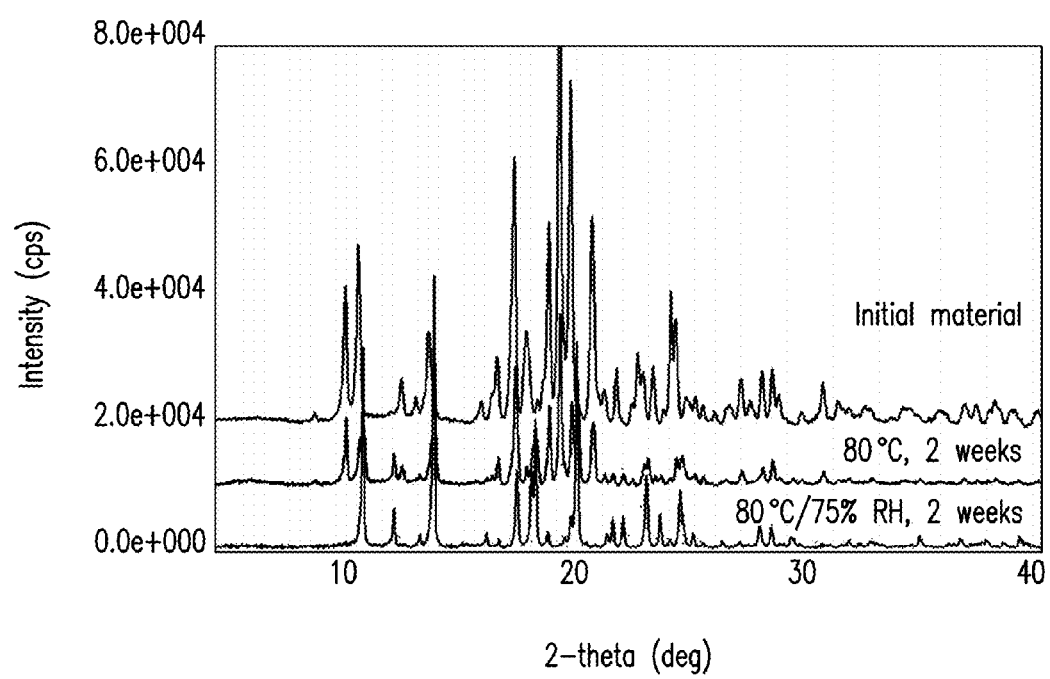

FIG. 67 depicts an overlay of XRPD patterns of the L-lactate salt, the L-lactate salt stored at 80° C. for 2 weeks and the L-lactate salt stored at 80° C. under 75% relative humidity for two weeks (from top to bottom).

Figure 68:
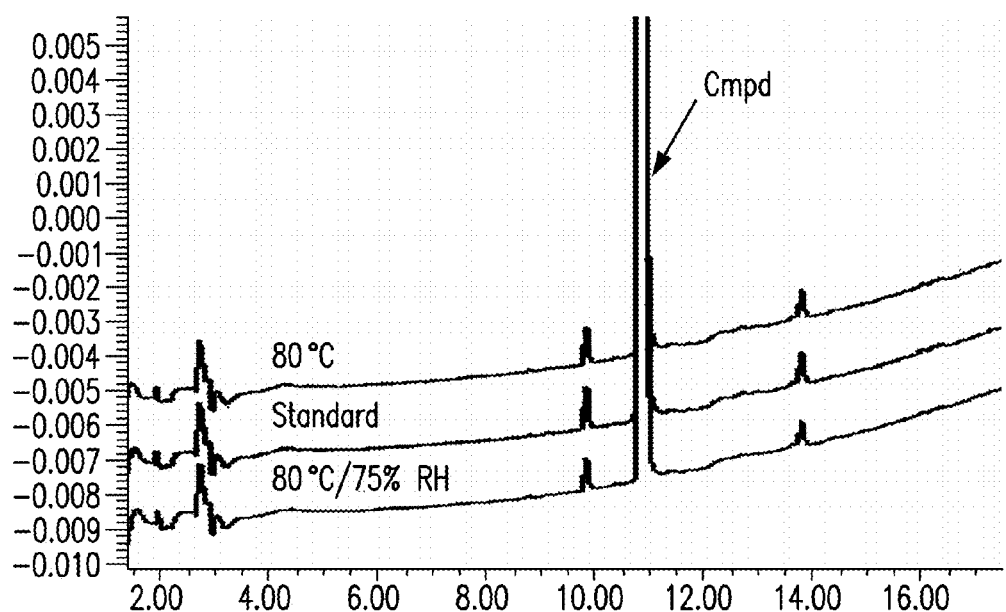

FIG. 68 depicts an overlay of HPLC chromatograms of the Compound 1 (free base) stored at 80° C. for 2 weeks, Compound 1 (free base) and the Compound 1 (free base) stored at 80° C. under 75% relative humidity for two weeks (from top to bottom).

Figure 69:
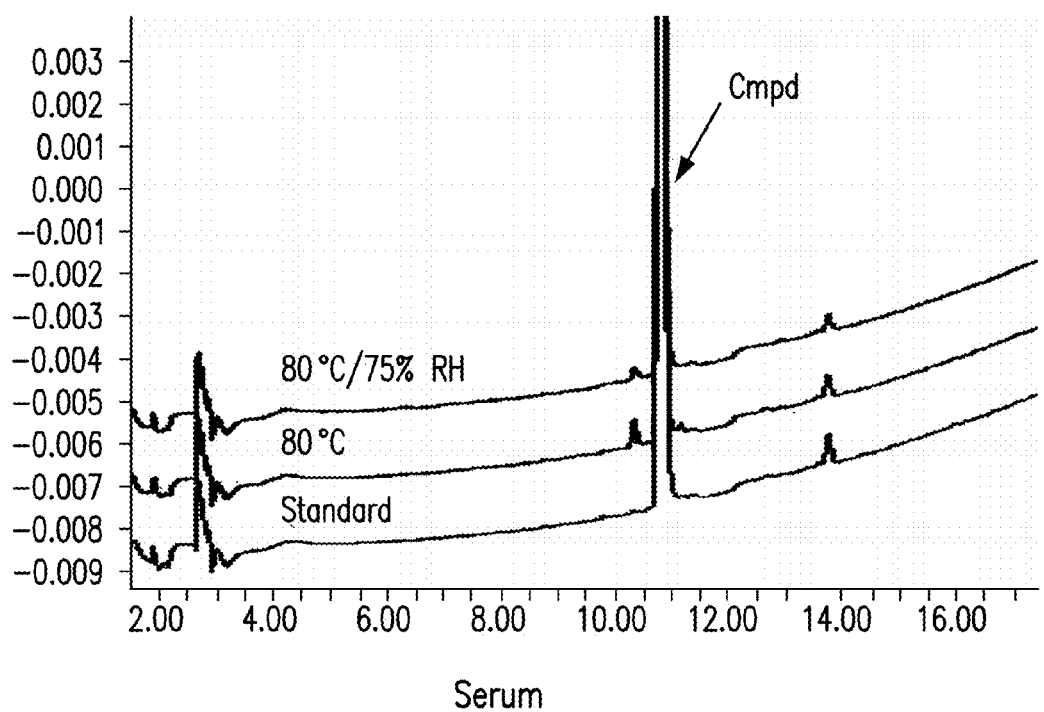

FIG. 69 depicts an overlay of HPLC chromatograms of the HCl salt stored at 80° C. under 75% relative humidity for two weeks, the HCl salt stored at 80° C. for 2 weeks and the HCl salt (from top to bottom).

Figure 70:
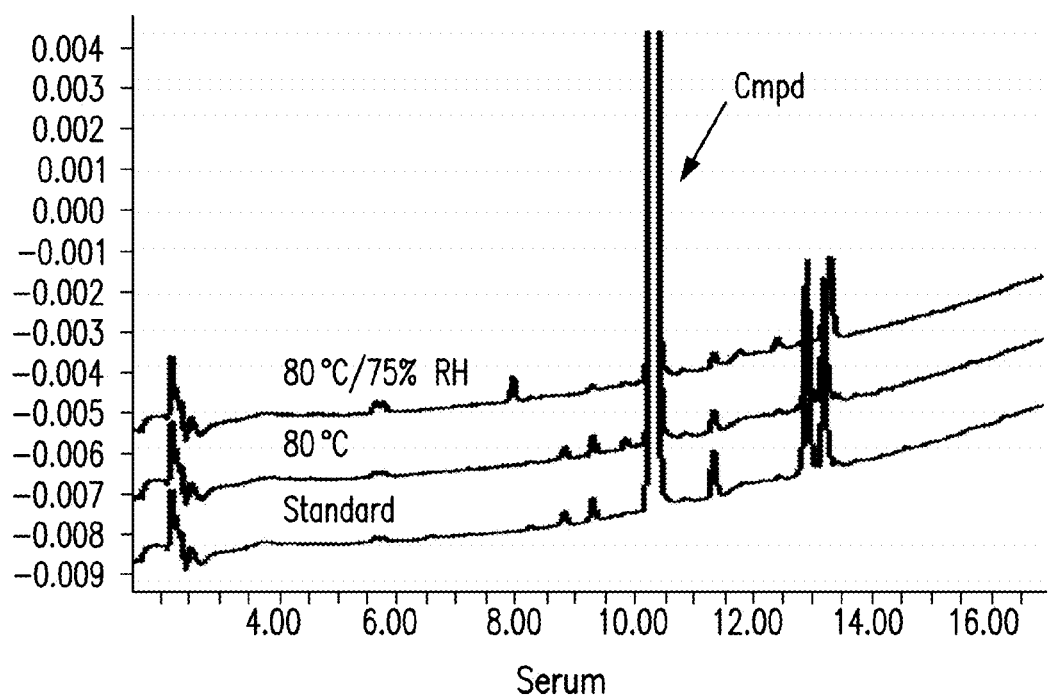

FIG. 70 depicts an overlay of HPLC chromatograms of the H$_2$SO$_4$ salt stored at 80° C. under 75% relative humidity for two weeks, the H$_2$SO$_4$ salt stored at 80° C. for 2 weeks and the H$_2$SO$_4$ salt (from top to bottom).

Figure 71:
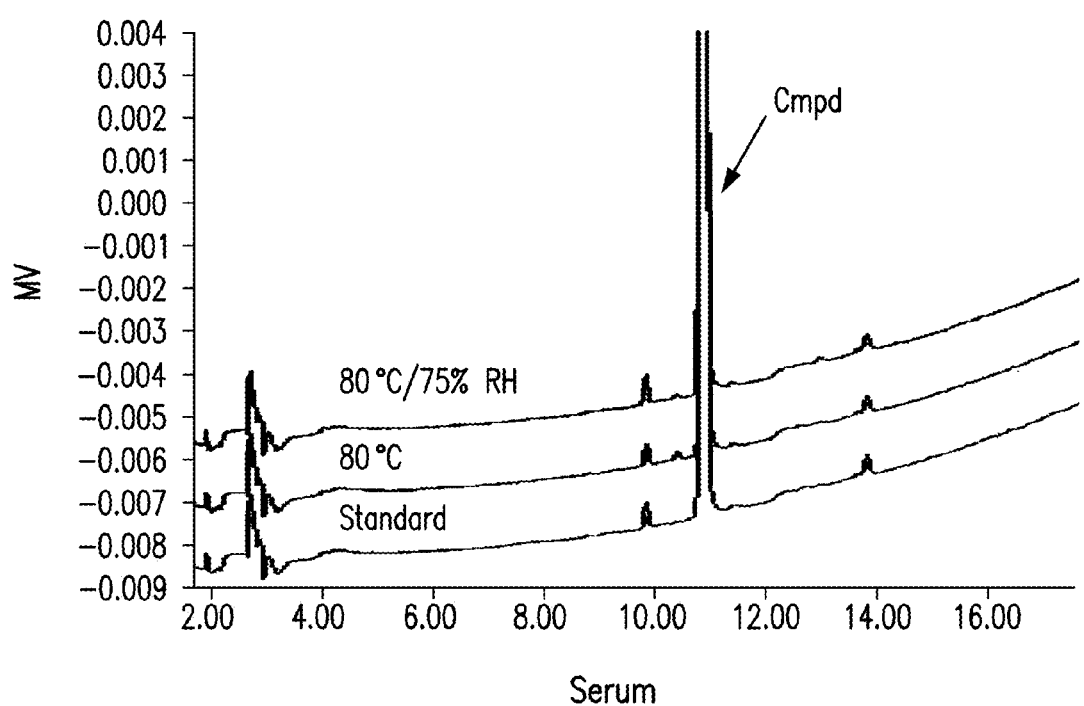

FIG. 71 depicts an overlay of HPLC chromatograms of the H$_3$PO$_4$ salt stored at 80° C. under 75% relative humidity for two weeks, the H$_3$PO$_4$ salt stored at 80° C. for 2 weeks and the H$_3$PO$_4$ salt (from top to bottom).

Figure 72:
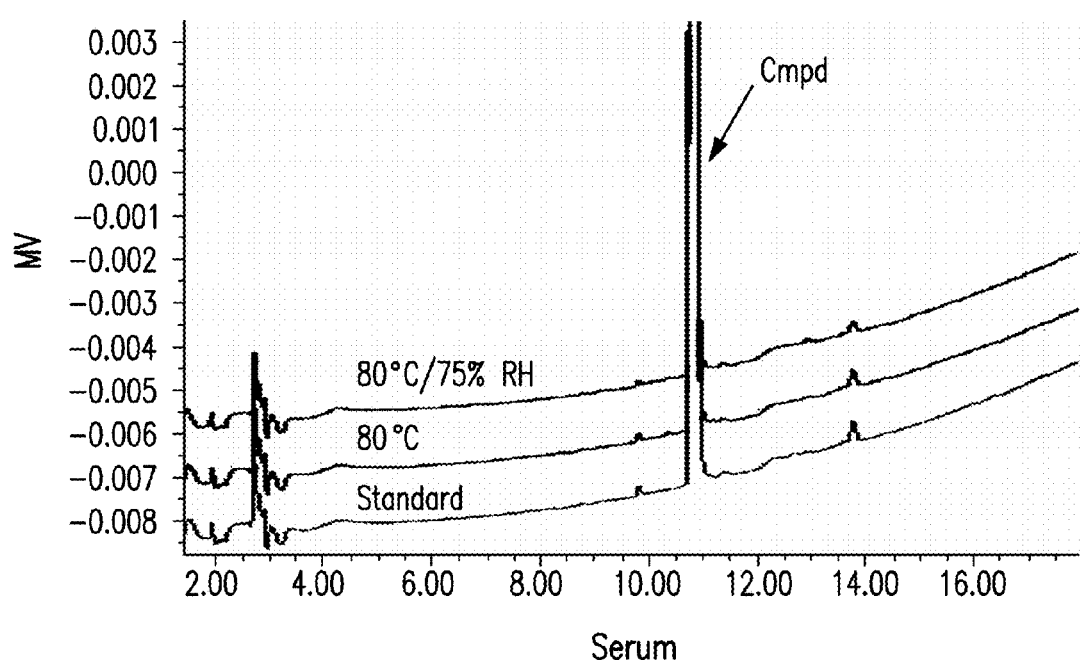

FIG. 72 depicts an overlay of HPLC chromatograms of the L-tartrate salt stored at 80° C. under 75% relative humidity for two weeks, the L-tartrate salt stored at 80° C. for 2 weeks and the L-tartrate salt (from top to bottom).

Figure 73:
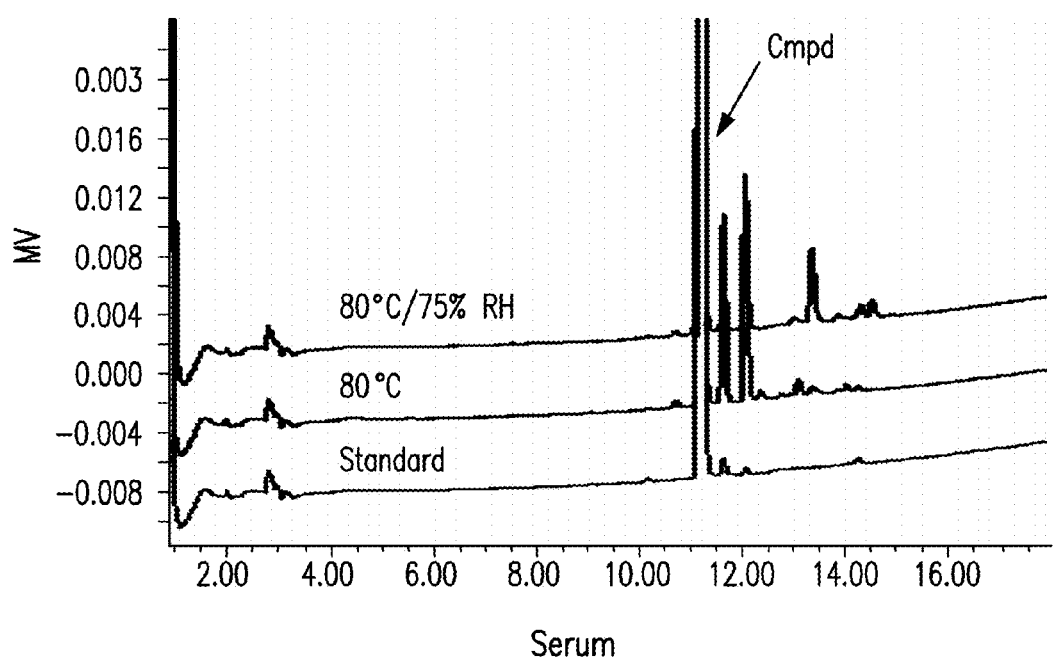

FIG. 73 depicts an overlay of HPLC chromatograms of the L-malate salt stored at 80° C. under 75% relative humidity for two weeks, the L-malate salt stored at 80° C. for 2 weeks and the L-malate salt (from top to bottom).

Figure 74:
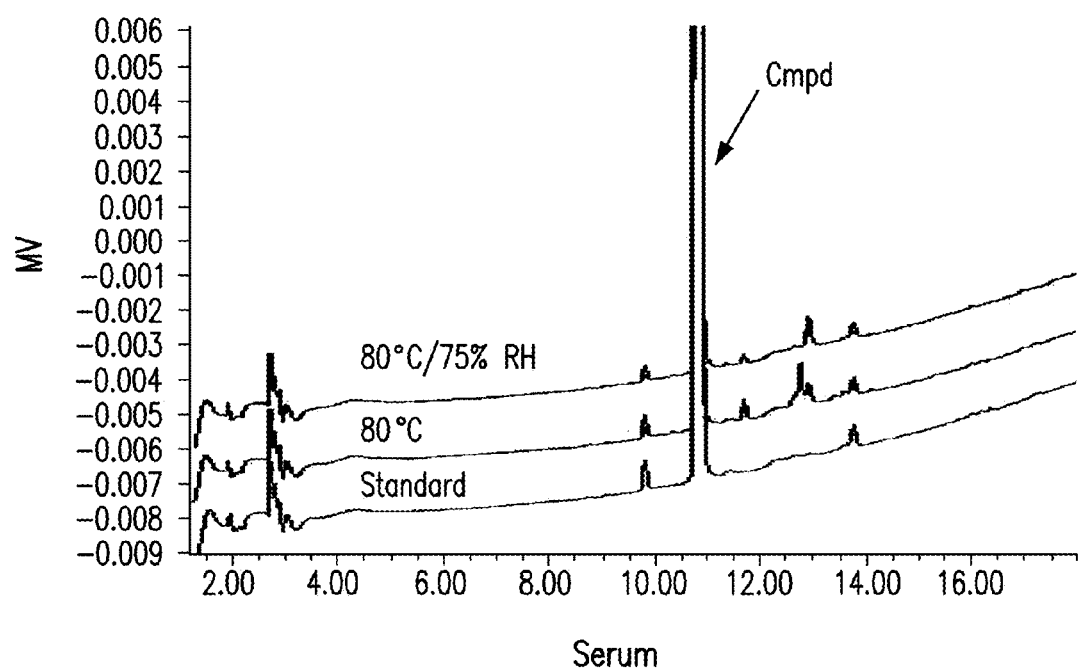

FIG. 74 depicts an overlay of HPLC chromatograms of the L-lactate salt stored at 80° C. under 75% relative humidity for two weeks, the L-lactate salt stored at 80° C. for 2 weeks and the L-lactate salt (from top to bottom).

Figure 75:
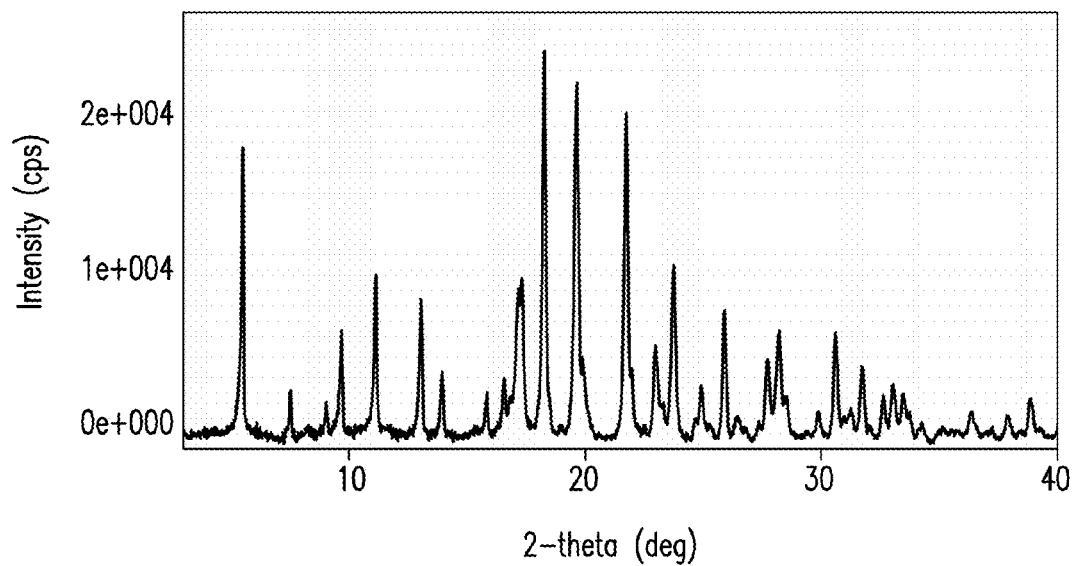
Figure 76:
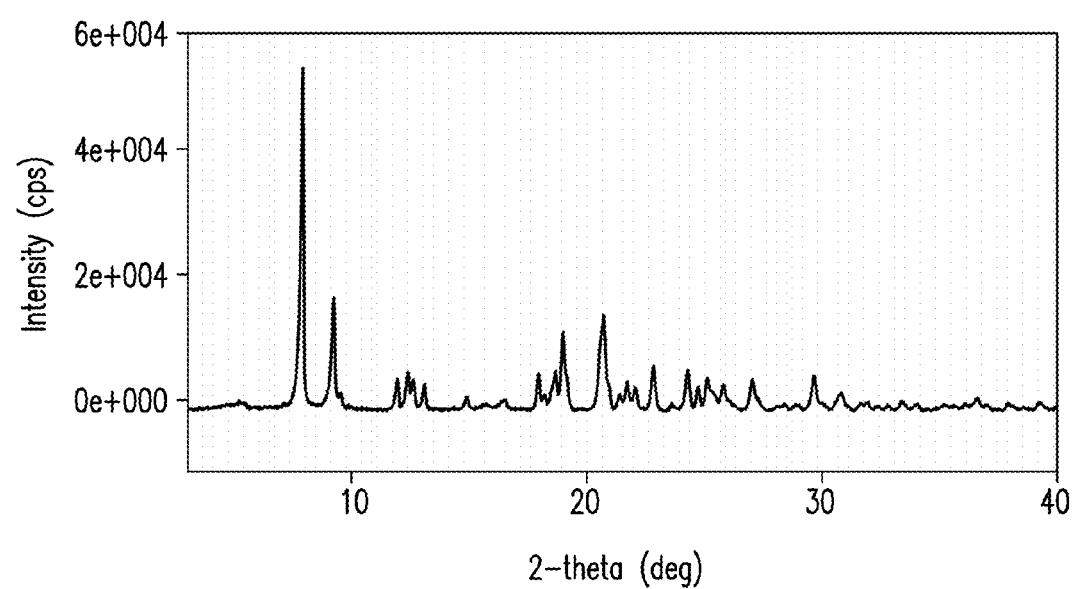
Figure 77:
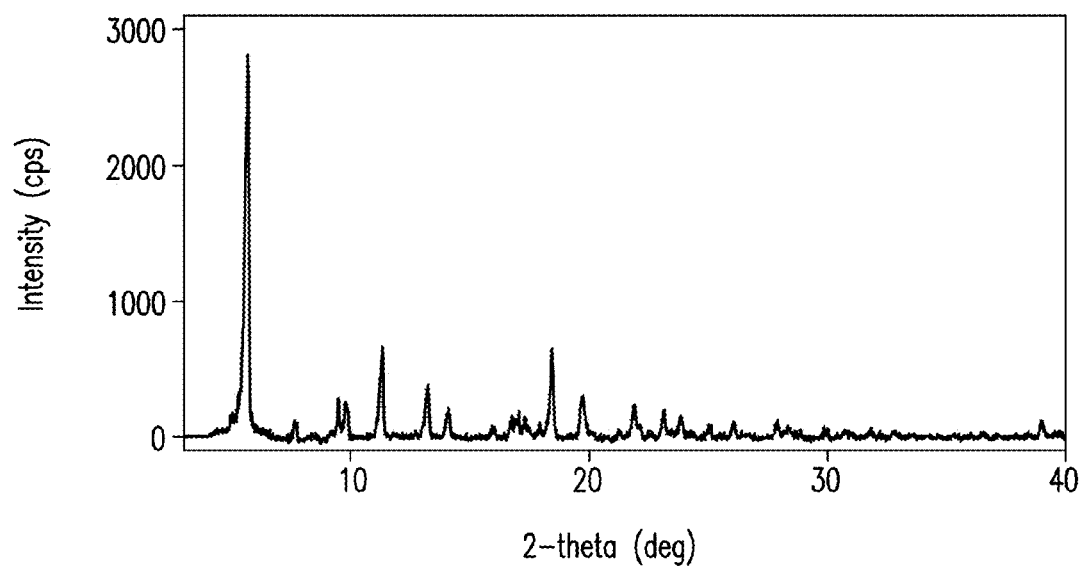
Figure 78:
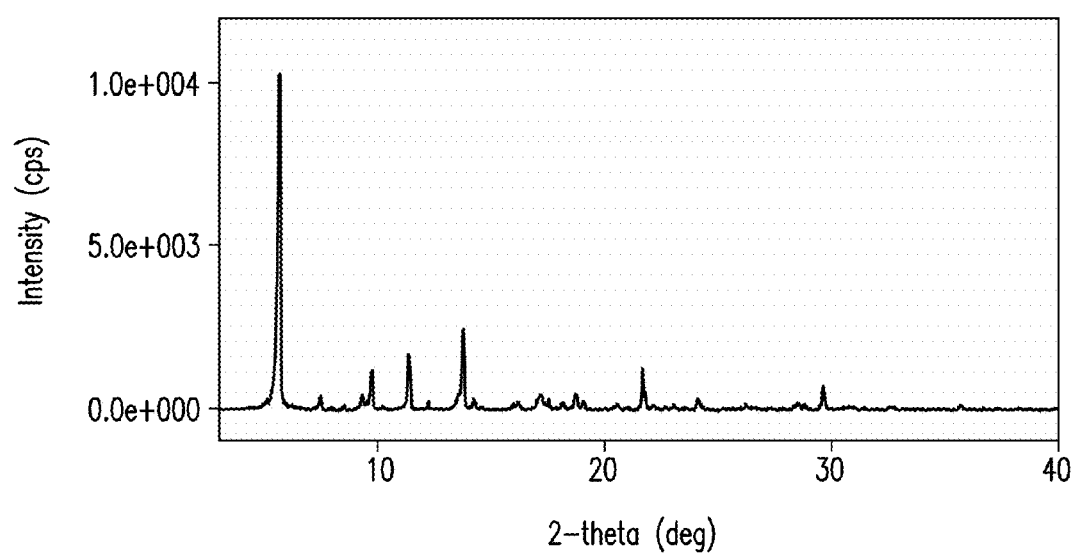
Figure 79:
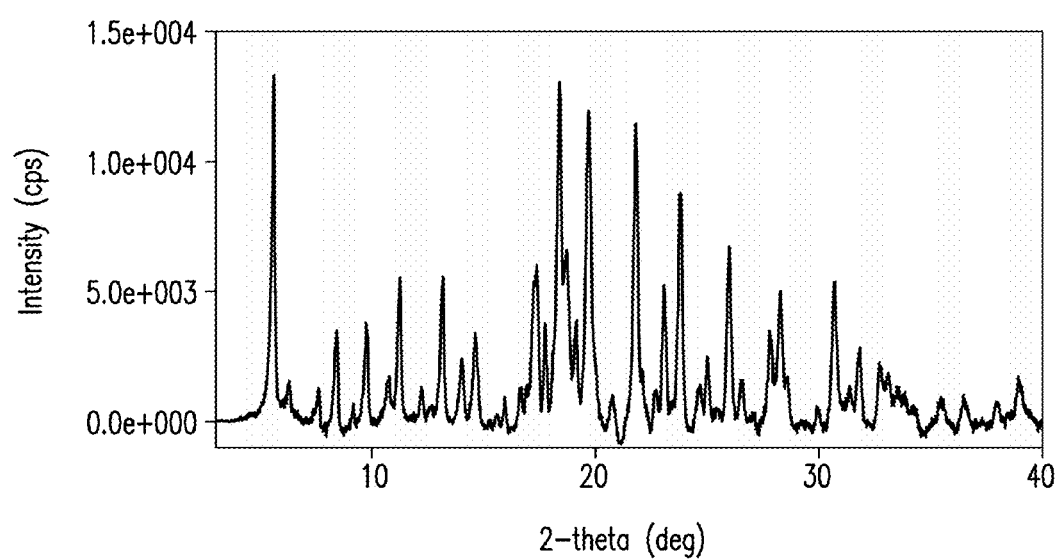
Figure 80:
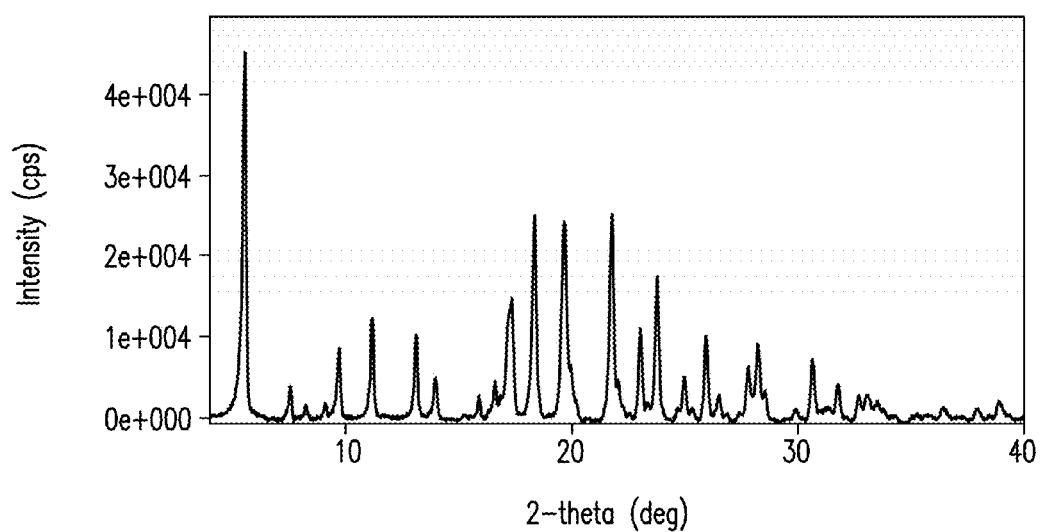
Figure 81:
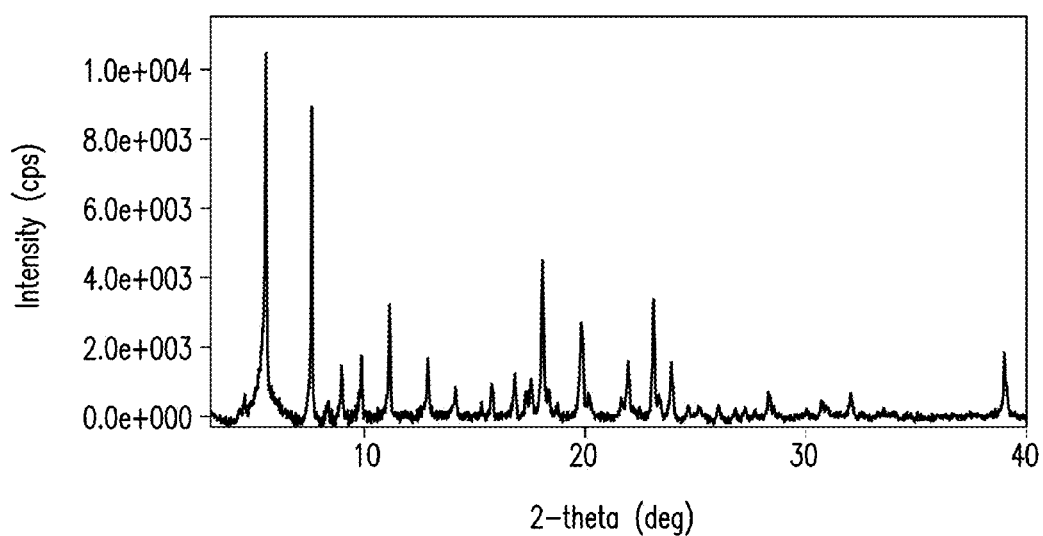
Figure 82:
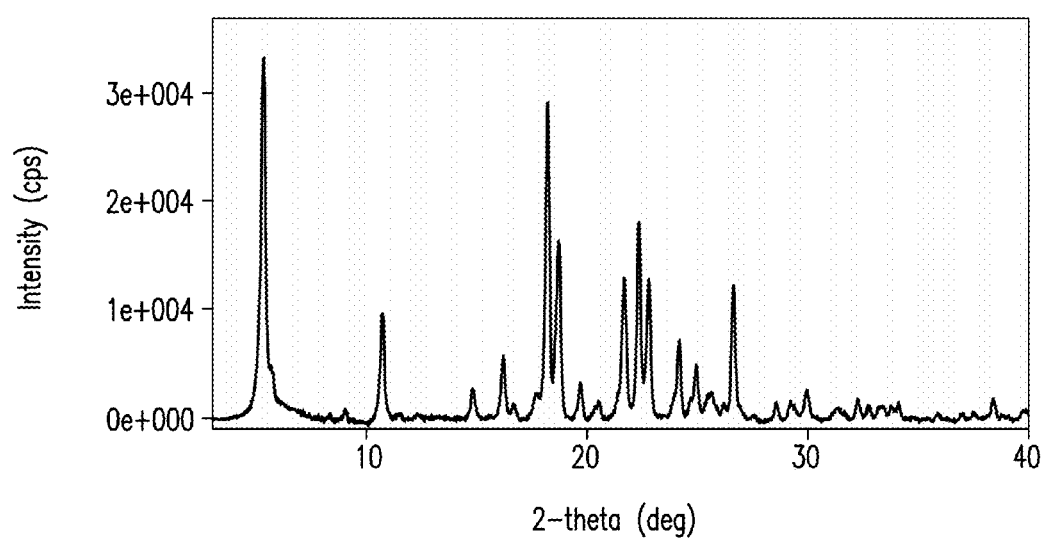
Figure 83:
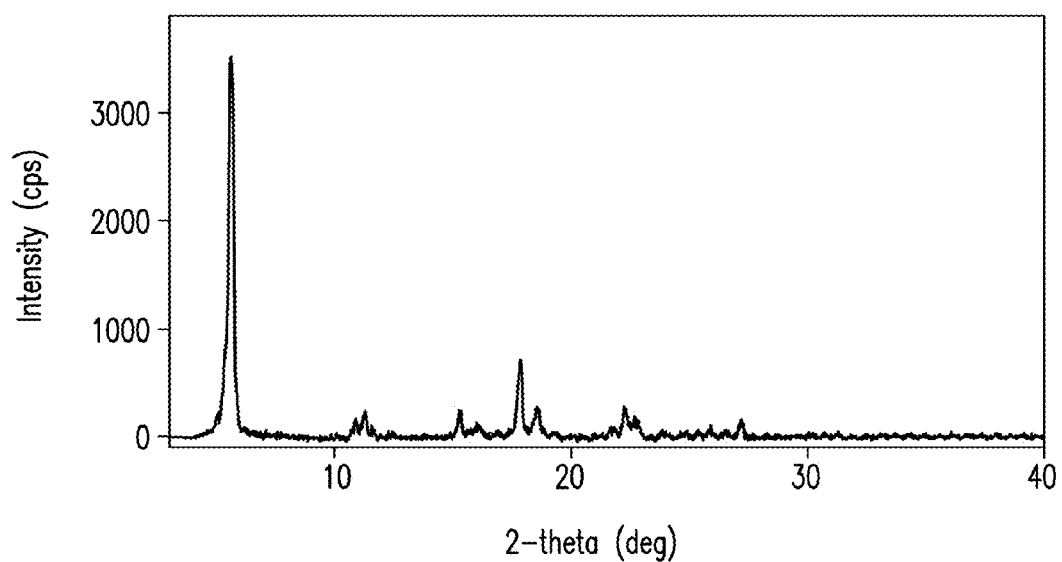
Figure 84:
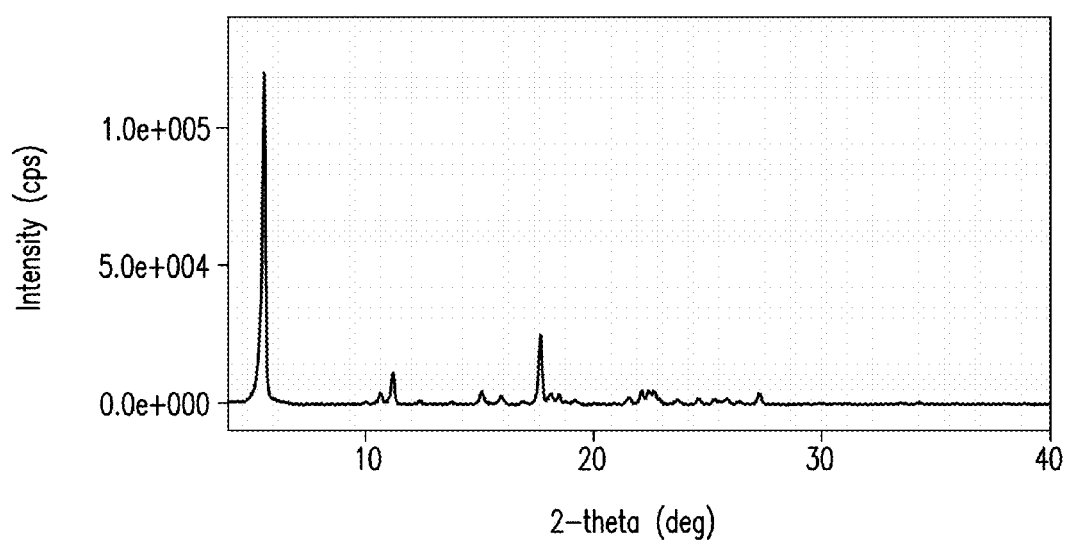
Figure 85:
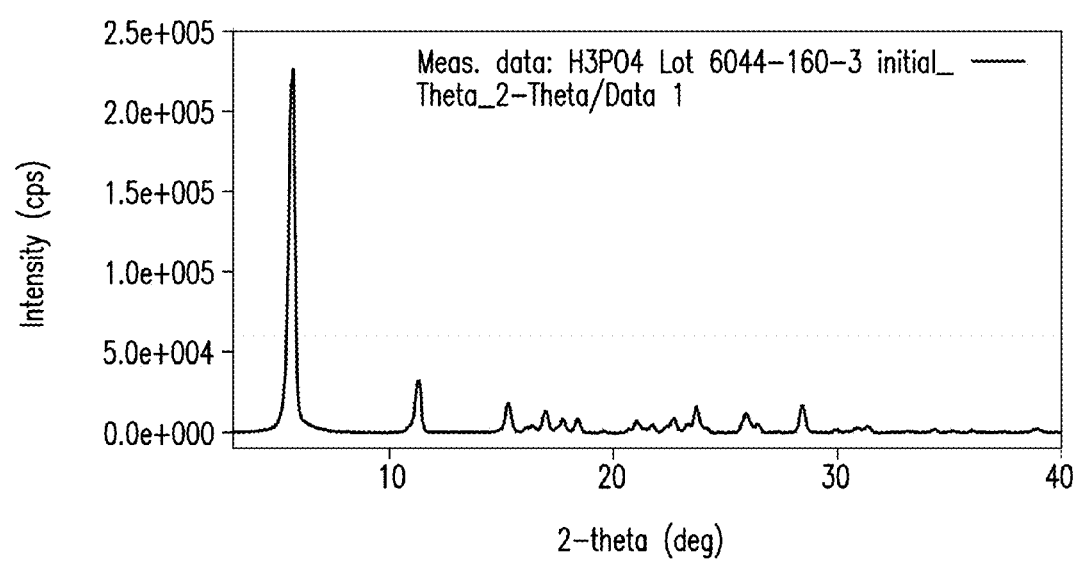
Figure 86:
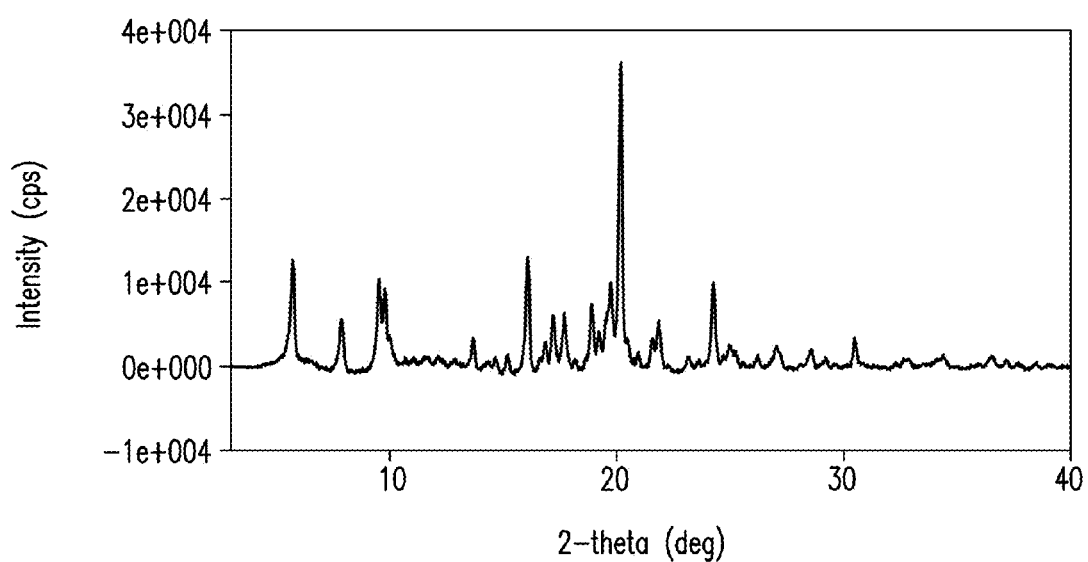
Figure 87:
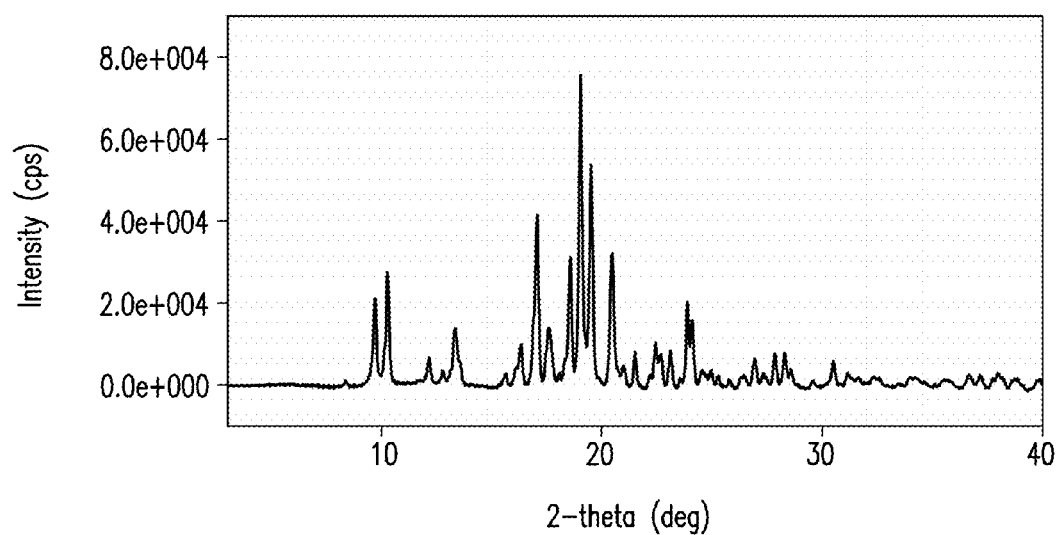
Figure 88:
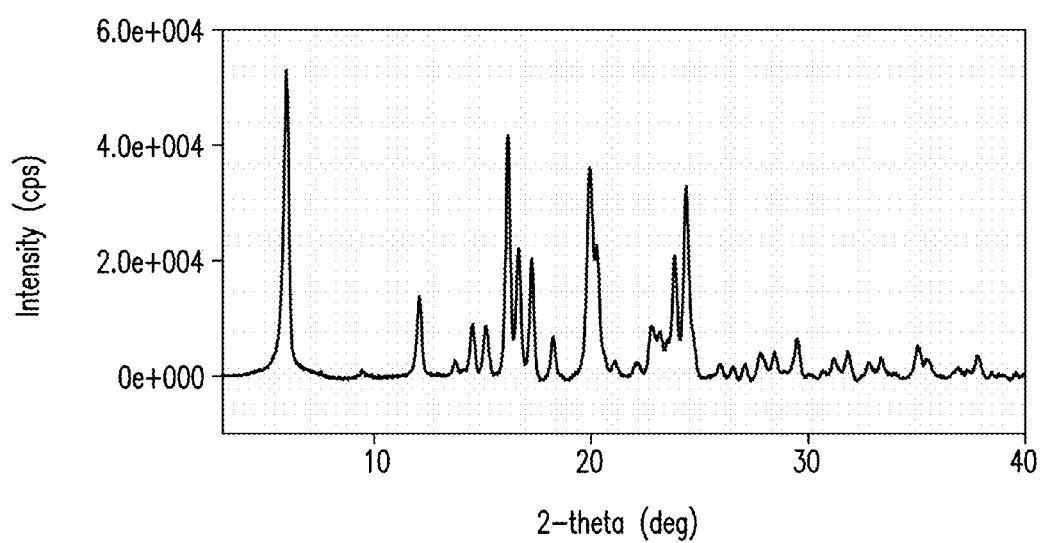
Figure 89:
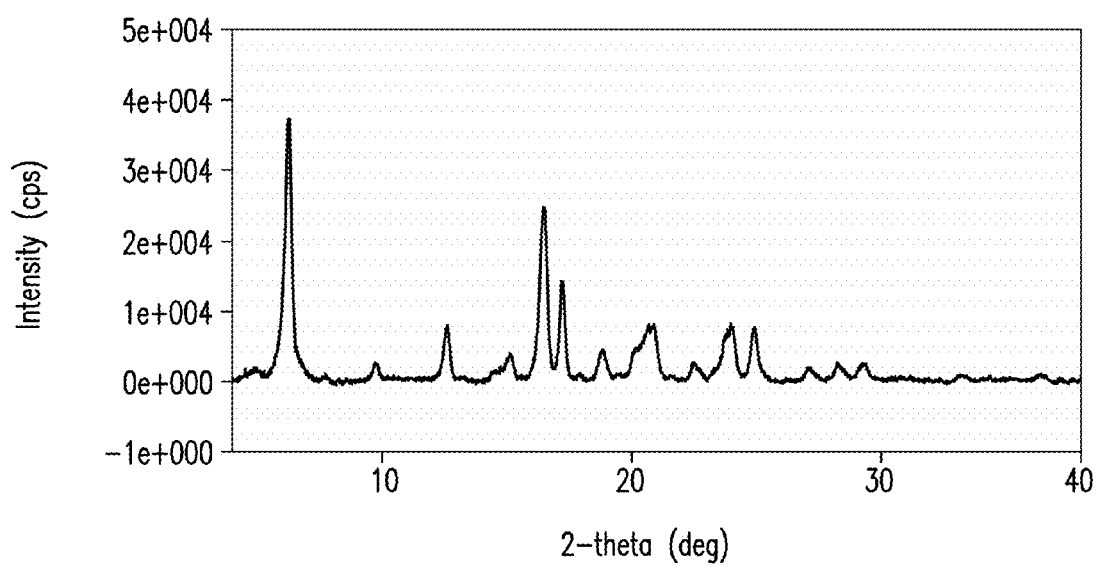
Figure 90:
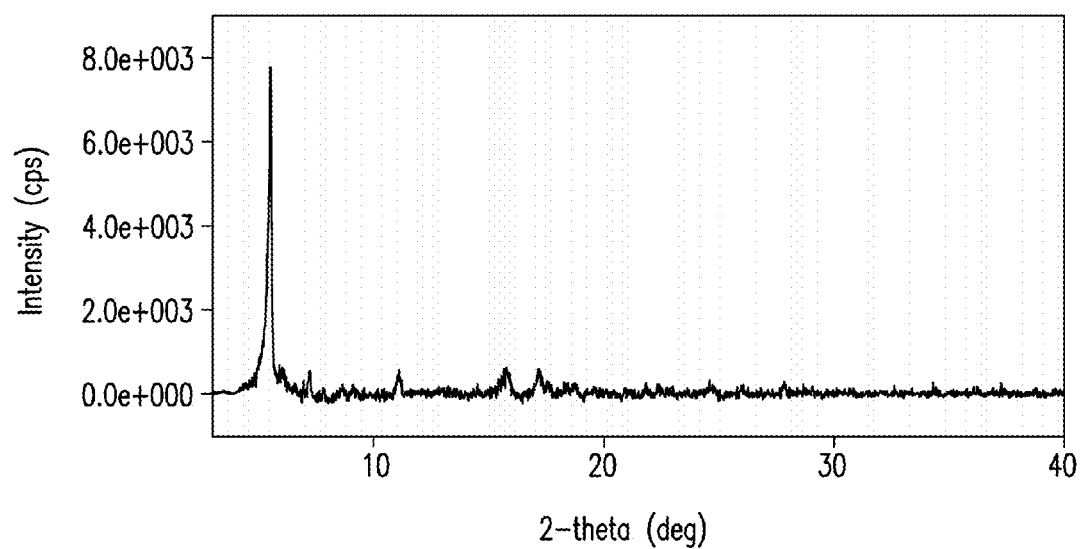
Figure 91:
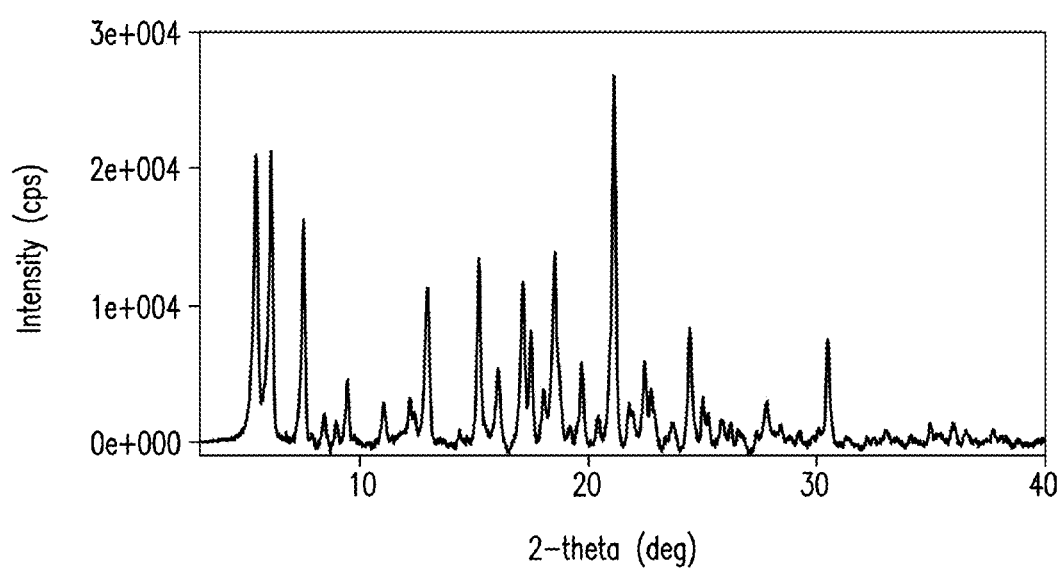
Figure 92:
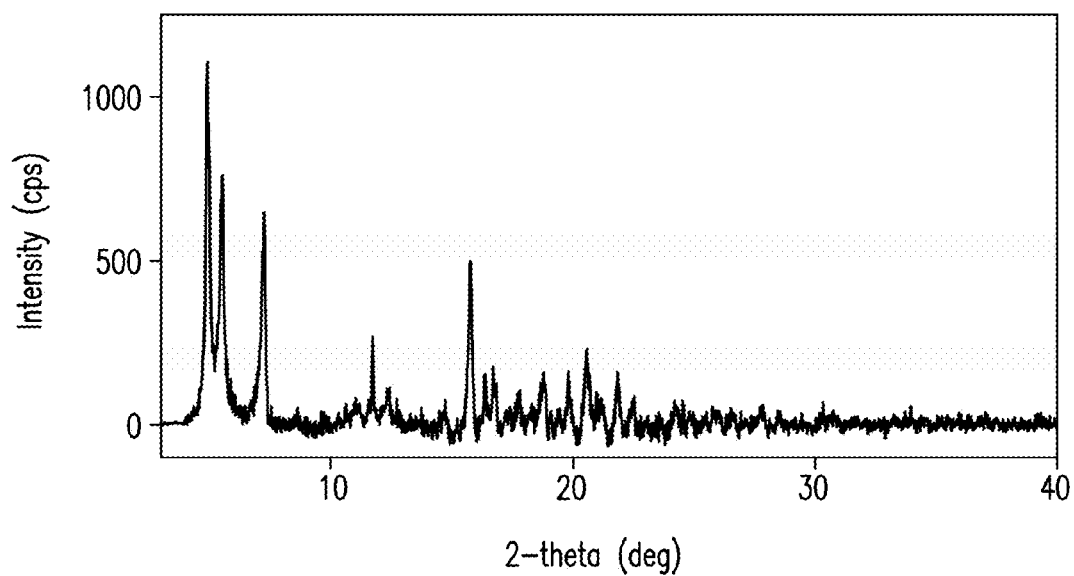
Figure 93:
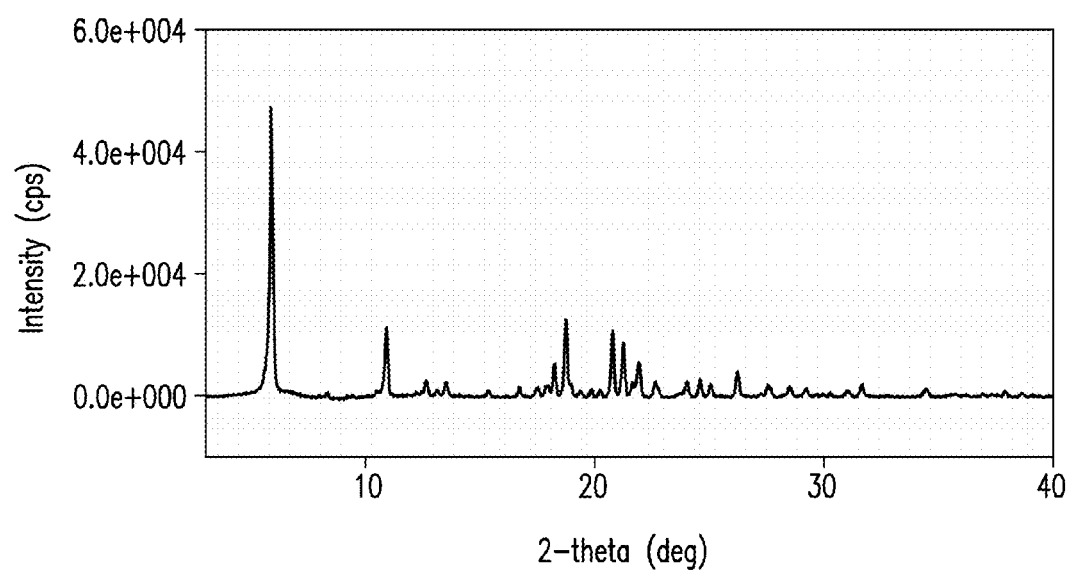
Figure 94:
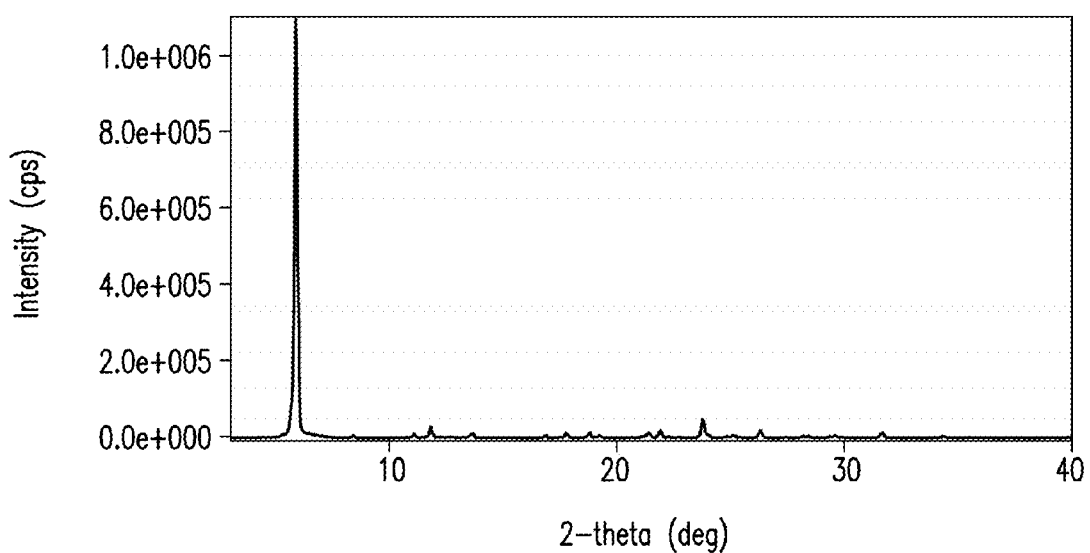
Figure 95:
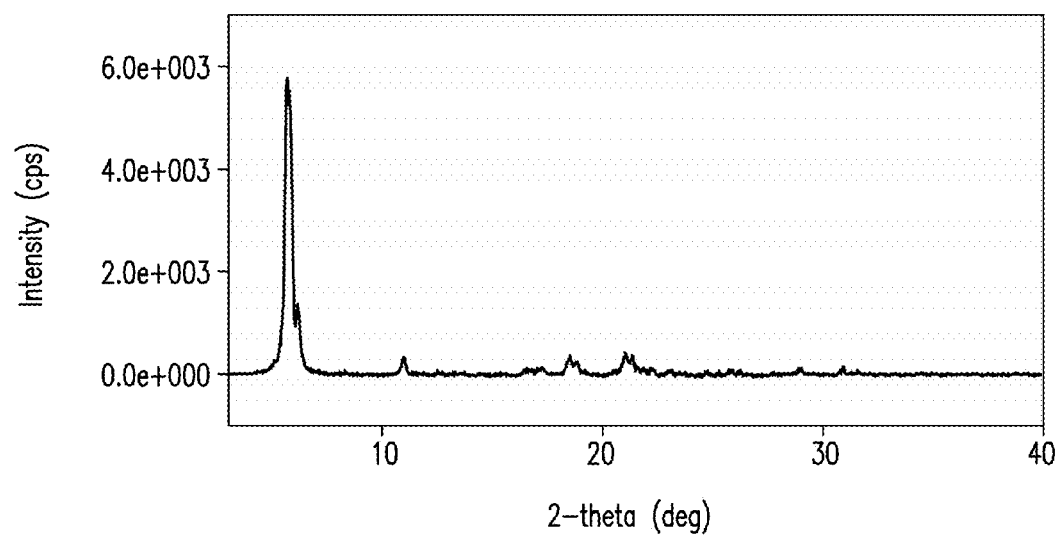
Figure 96:
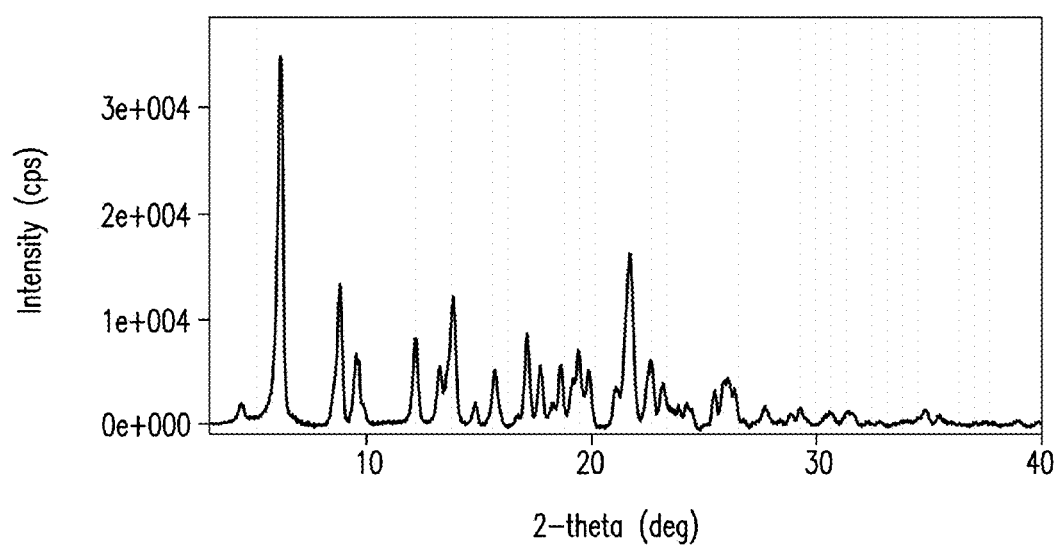
Figure 97:
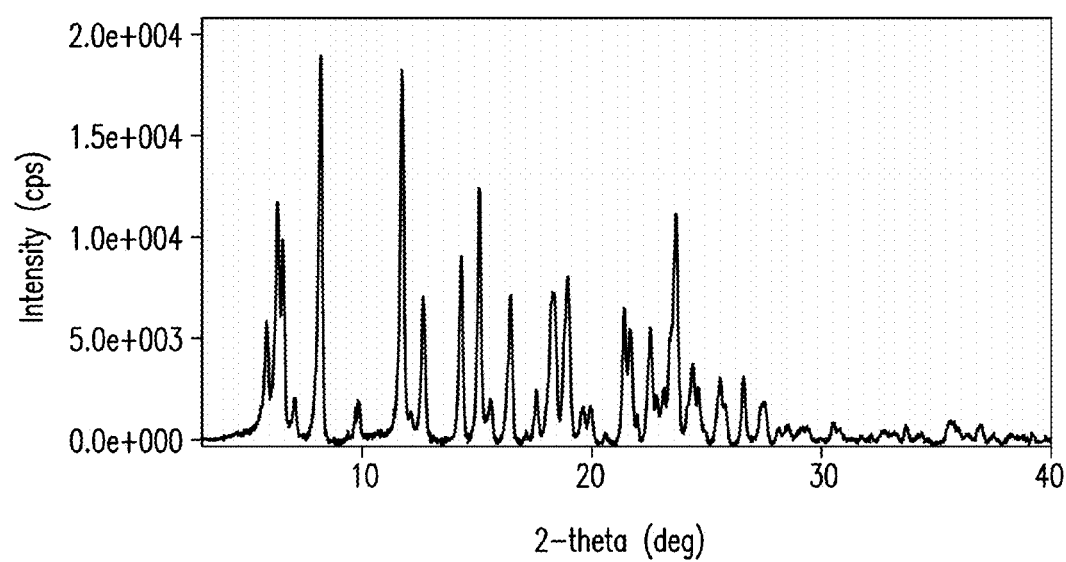
Figure 98:
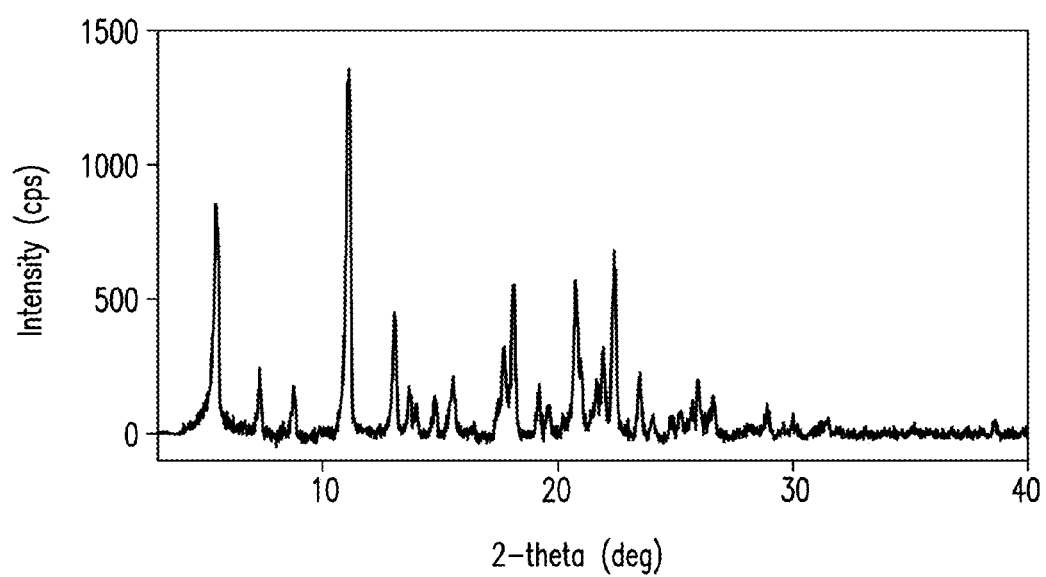
Figure 99:
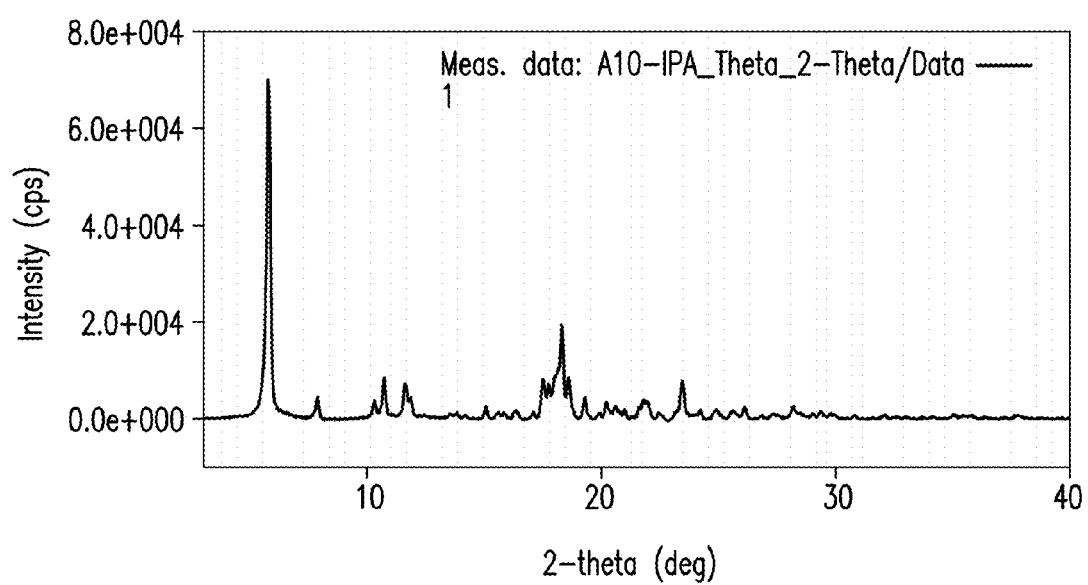
Figure 100:
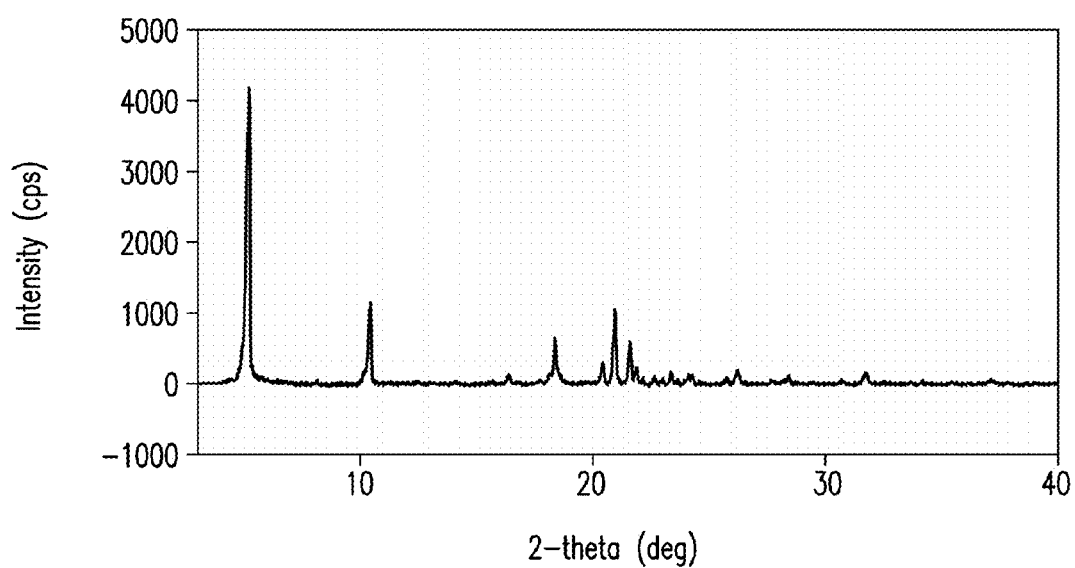
Figure 101:
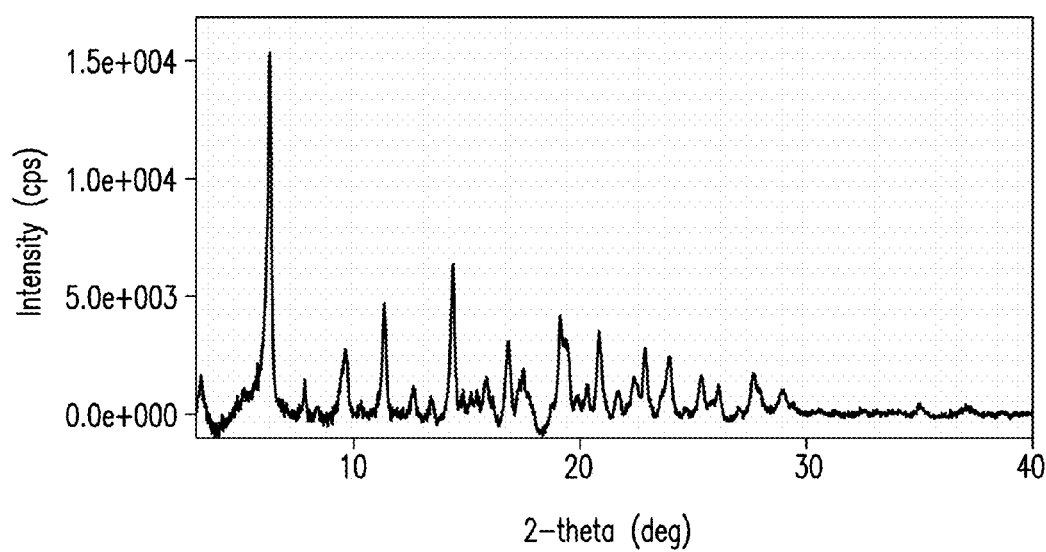
Figure 102:
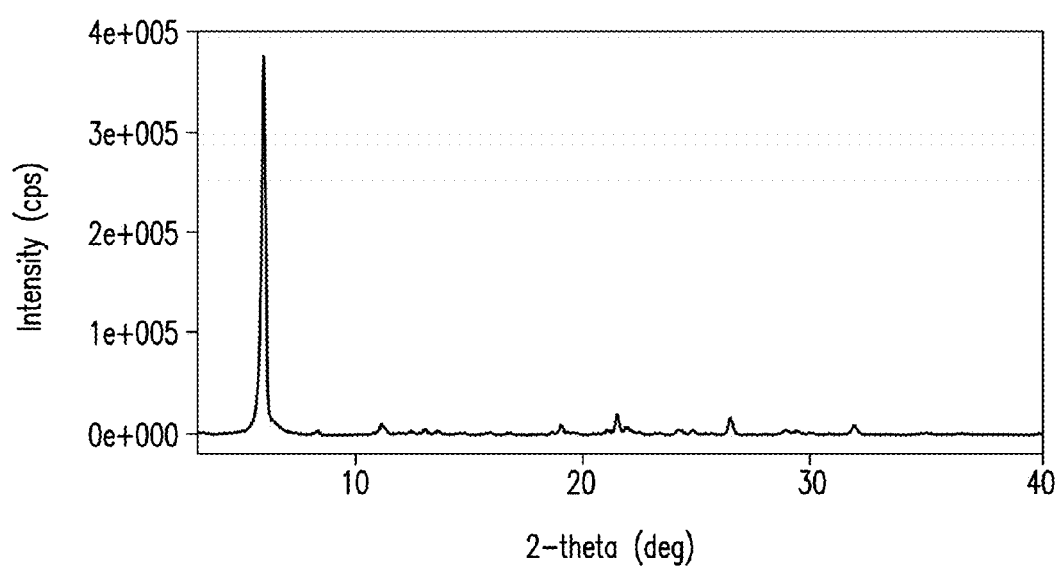
Figure 103:
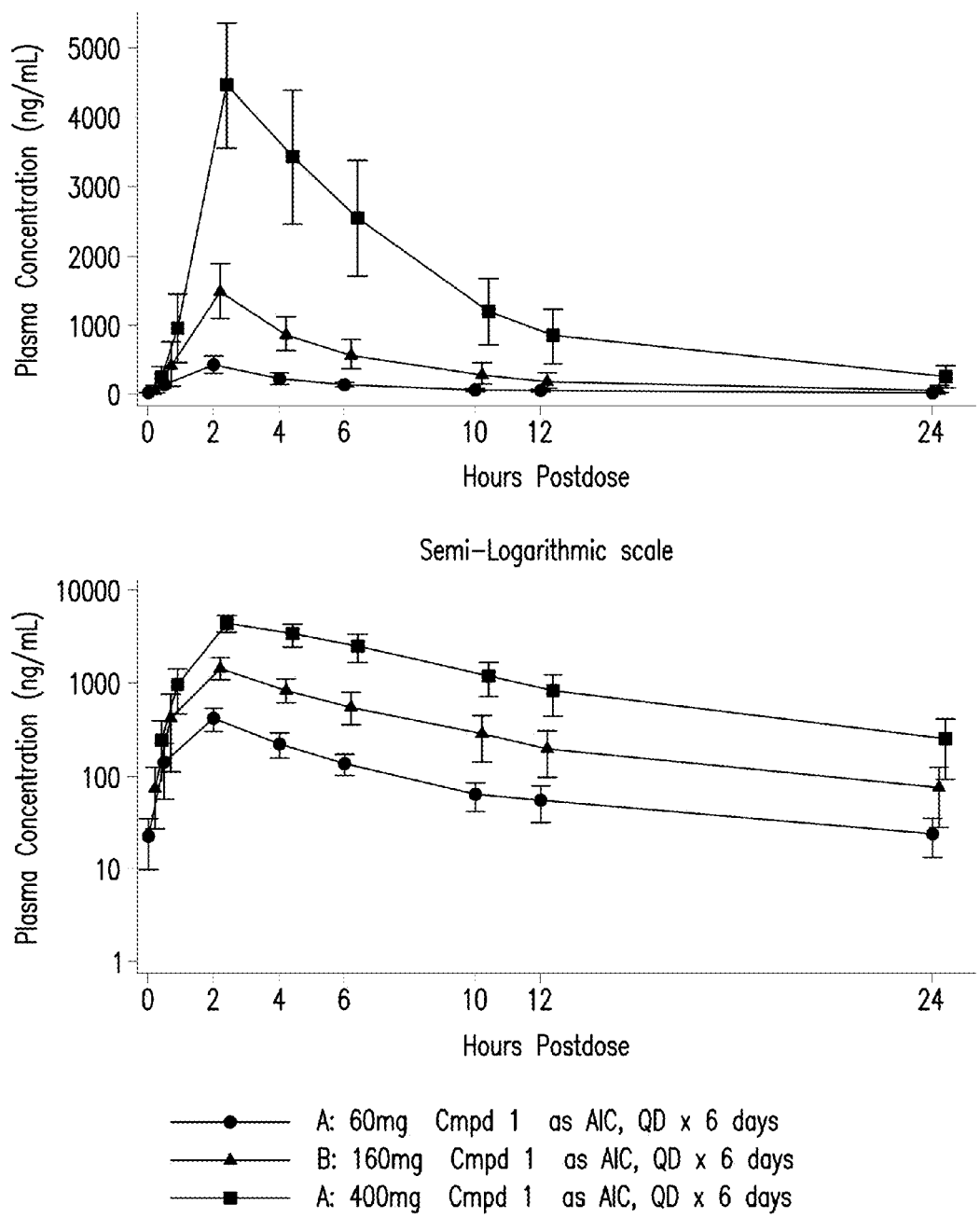

FIG. 75 depicts an XRPD pattern of HCl salt form 1.
FIG. 76 depicts an XRPD pattern of HCl salt form 2.
FIG. 77 depicts an XRPD pattern of HCl salt form 3.
FIG. 78 depicts an XRPD pattern of HCl salt form 4.
FIG. 79 depicts an XRPD pattern of HCl salt form 5.
FIG. 80 depicts an XRPD pattern of HCl salt form 6.
FIG. 81 depicts an XRPD pattern of HCl salt form 7.
FIG. 82 depicts an XRPD pattern of H$_2$SO$_4$ salt form 1.
FIG. 83 depicts an XRPD pattern of H$_2$SO$_4$ salt form 2.
FIG. 84 depicts an XRPD pattern of H$_2$SO$_4$ salt form 3, obtained from H$_2$SO$_4$ salt form 1 when stored under 80° C./75% RH conditions for 2 weeks.
FIG. 85 depicts an XRPD pattern of the H$_3$PO$_4$ salt.
FIG. 86 depicts an XRPD pattern of L-lactate salt form 1.
FIG. 87 depicts an XRPD pattern of L-lactate salt form 2.
FIG. 88 depicts an XRPD pattern of L-tartrate salt form 1.
FIG. 89 depicts an XRPD pattern of L-tartrate salt form 2.
FIG. 90 depicts an XRPD pattern of L-malate salt form 1.
FIG. 91 depicts an XRPD pattern of L-malate salt form 2.
FIG. 92 depicts an XRPD pattern of L-malate salt form 3.
FIG. 93 depicts an XRPD pattern of L-malate salt form 4.
FIG. 94 depicts an XRPD pattern of succinate salt form 1.
FIG. 95 depicts an XRPD pattern of succinate salt form 2.
FIG. 96 depicts an XRPD pattern of tosylate salt form 1.
FIG. 97 depicts an XRPD pattern of tosylate salt form 2.
FIG. 98 depicts an XRPD pattern of tosylate salt form 3.
FIG. 99 depicts an XRPD pattern of mesylate salt form 1.
FIG. 100 depicts an XRPD pattern of mesylate salt form 2.
FIG. 101 depicts an XRPD pattern of the besylate salt.
FIG. 102 depicts an XRPD pattern of the fumarate salt.
FIG. 103 depicts arithmetic mean (±SD) plasma concentrations of Compound 1 in healthy subjects following multiple doses (qd×6 days) of Compound 1 (Part 1).

Figure 104:
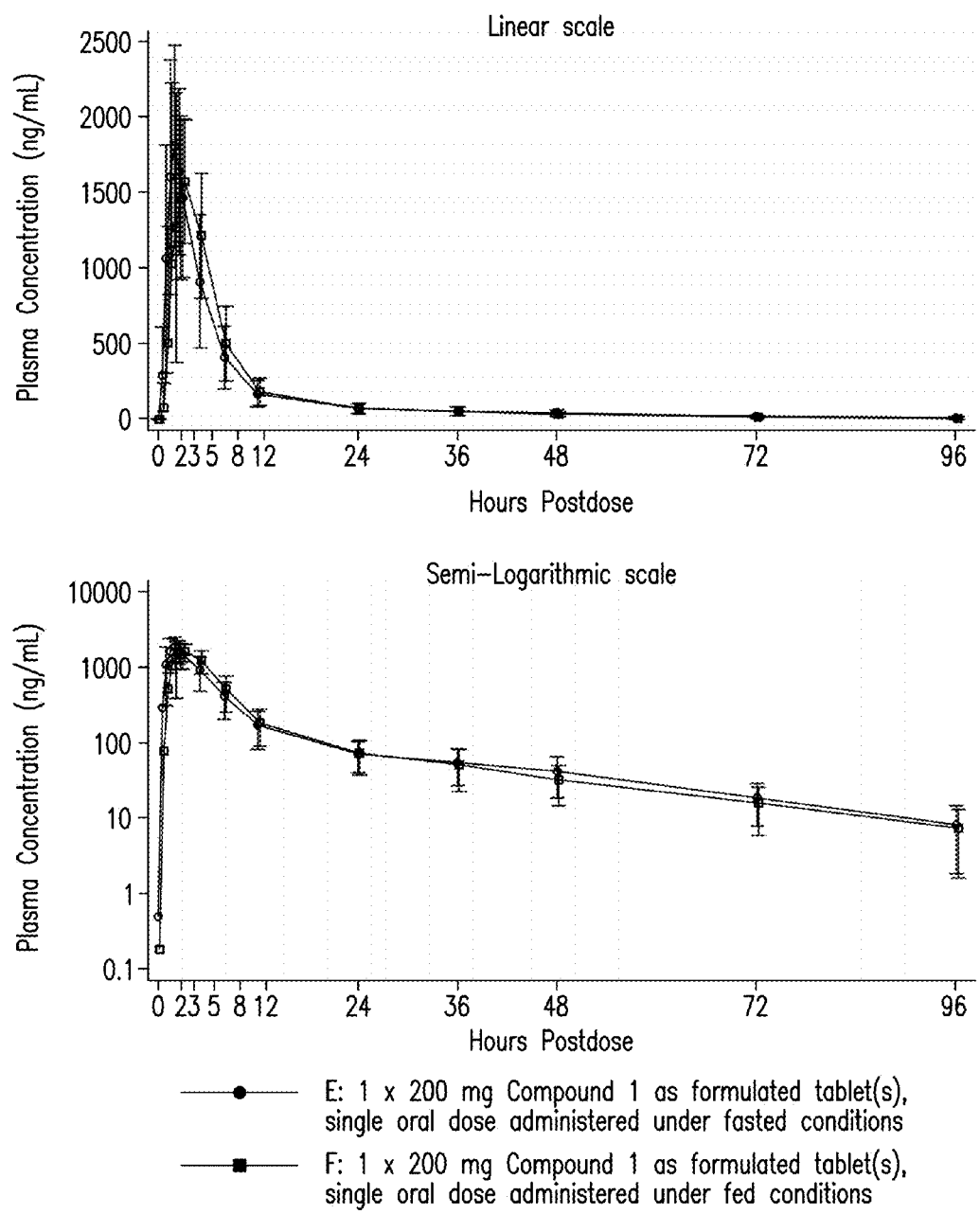

FIG. 104 depicts arithmetic mean (±SD) plasma concentrations of Compound 1 in healthy subjects following a single dose of Compound 1 under fasted and fed conditions in a study of Compound 1 (Part 2).

Figure 105:
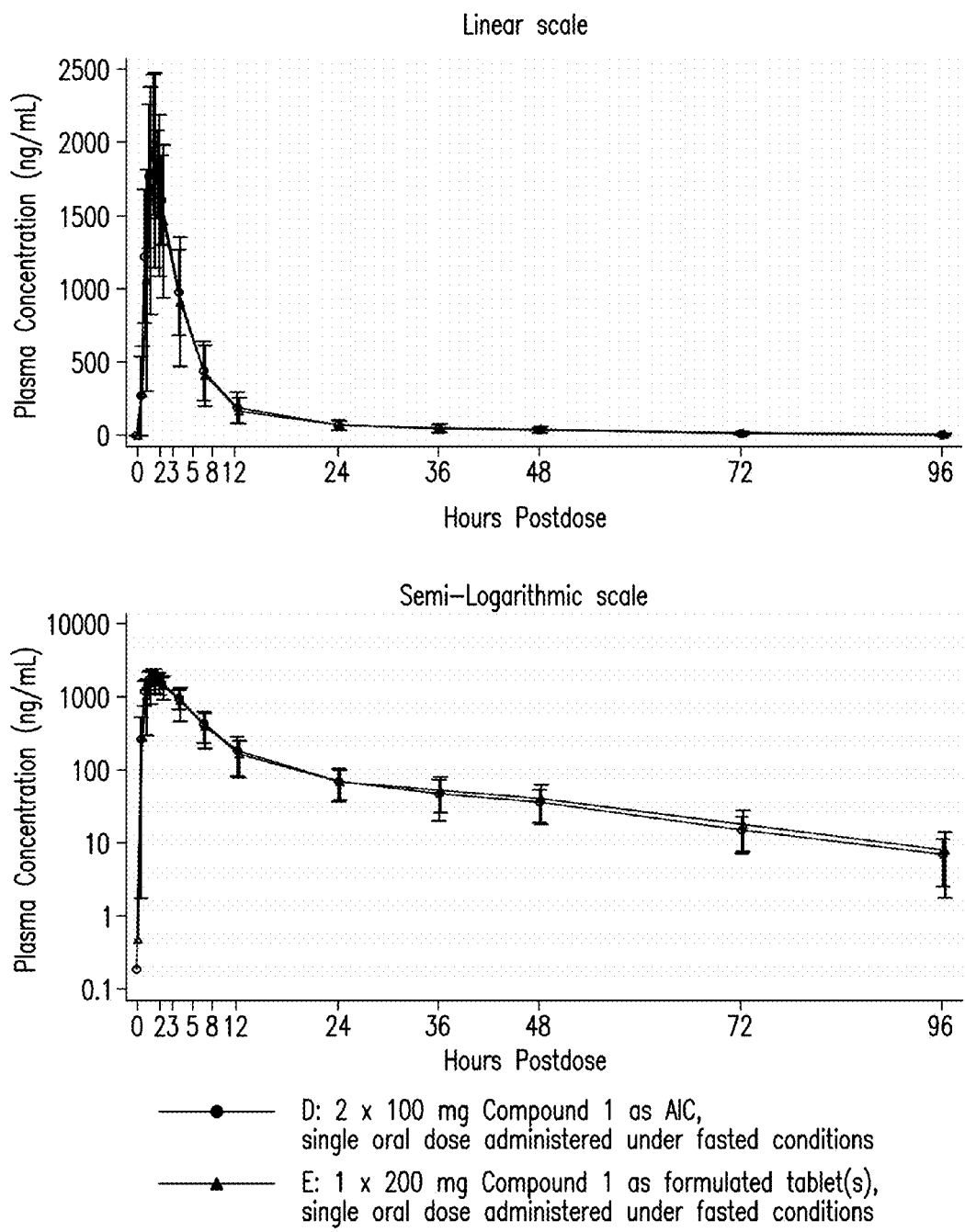

FIG. 105 depicts arithmetic mean (±SD) plasma concentrations of Compound 1 in healthy subjects following a single dose of compound 1 under fasted conditions (Part 2).

Figure 106:
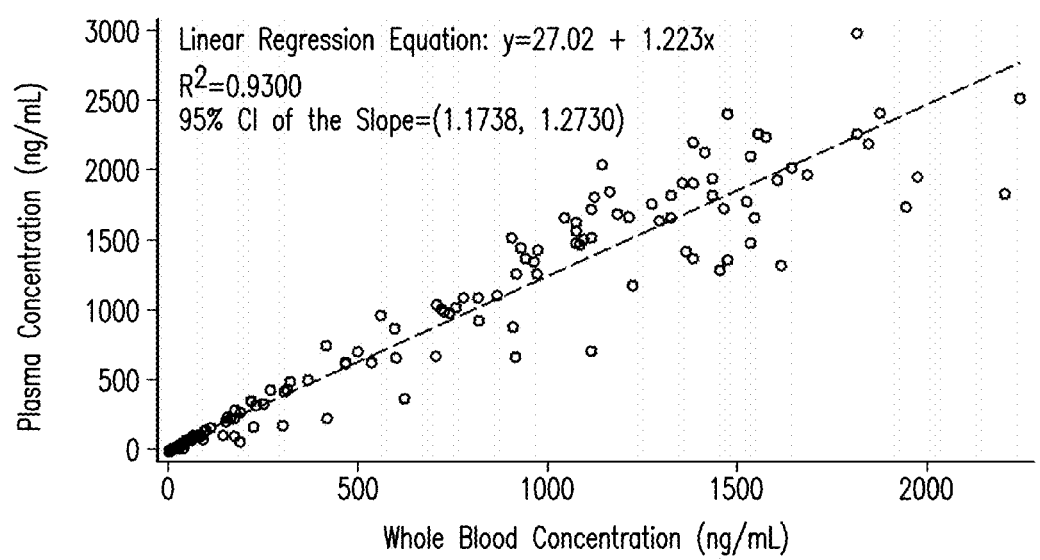

FIG. 106 depicts plasma concentrations versus whole blood concentrations of Compound 1 in healthy subjects following a single 200 mg dose of Compound 1 (Part 2, Treatment D).

Figure 107:
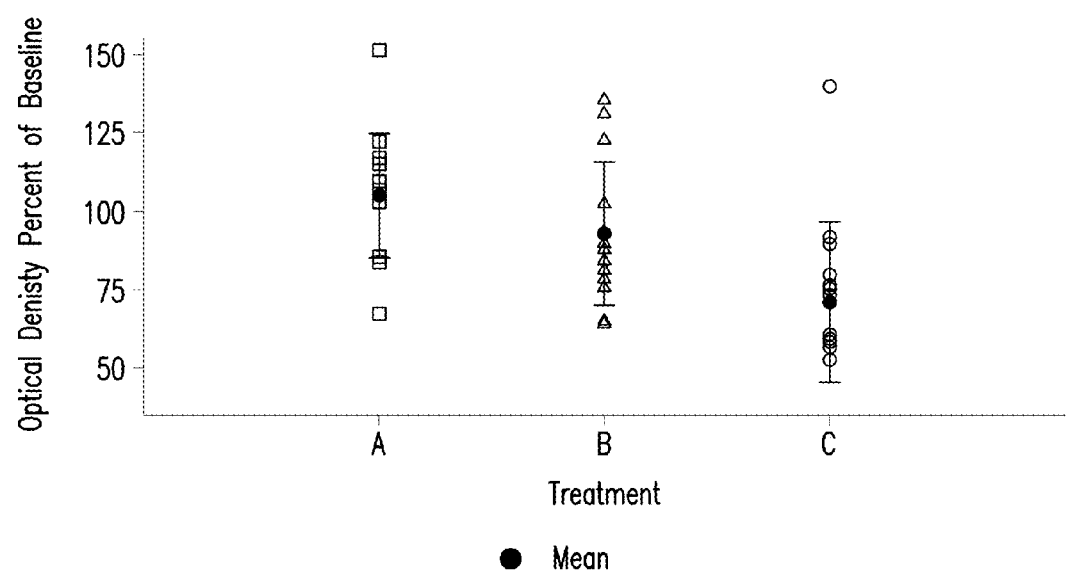

FIG. 107 depicts individual percentages of baseline phospho c-Jun integrated optical density scores.

Figure 108:
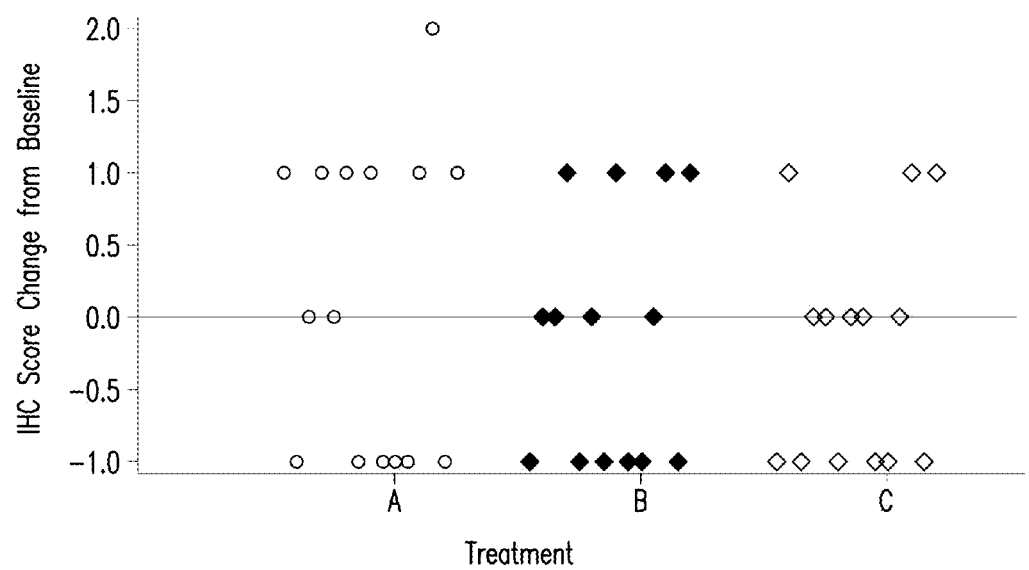

FIG. 108 depicts changes from baseline in individual phospho c-Jun immunohistochemistry histology scores.

5. DETAILED DESCRIPTION

5.1. Definitions

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, L-asparate, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. Compounds can have chiral centers and can occur as racemates, individual enantiomers or diastereomers, and mixtures thereof. All such isomeric forms are included within the embodiments disclosed herein, including mixtures thereof. The use of stereomerically pure forms of such compounds, as well as the use of mixtures of those forms are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the compounds can include E and Z isomers, or a mixture thereof, and cis and trans isomers or a mixture thereof. In certain embodiments, compounds are isolated as either the cis or trans isomer. In other embodiments, compounds are a mixture of the cis and trans isomers.

As used herein, and in the specification and the accompanying claims, the indefinite articles "a" and "an" and the definite article "the" include plural as well as single referents, unless the context clearly indicates otherwise.

As used herein, and unless otherwise specified, the terms "about" and "approximately," when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, a crystalline that is "pure," i.e., substantially free of other crystalline or amorphous solids, contains less than about 10% by weight of one or more other crystalline or amorphous solids, less than about 5% by weight of one or more other crystalline or amorphous solids, less than about 3% by weight of one or more other crystalline or amorphous solids, or less than about 1% by weight of one or more other crystalline or amorphous solids.

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," as used herein, refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

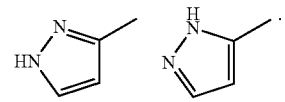

As readily understood by one skilled in the art, a wide variety of functional groups and other structures may exhibit tautomerism and all tautomers of Compound 1 are within the scope of the present invention.

It should also be noted that Compound 1 can contain unnatural proportions of atomic isotopes at one or more of the atoms. For example, Compound 1 may be radiolabeled with radioactive isotopes, such as for example tritium ($^3$H), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of Compound 1 and or Compound A, whether radioactive or not, are intended to be encompassed within the scope of the embodiments provided herein. In some embodiments, there are provided isotopologues of Compound 1, for example, the isotopologues are deuterium, carbon-13, or nitrogen-15 enriched Compound 1 and/or Compound A.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

"JNK" means a protein or an isoform thereof expressed by a JNK1, JNK2, or JNK3 gene (Gupta, S., Barrett, T., Whitmarsh, A. J., Cavanagh, J., Sluss, H. K., Derijard, B. and Davis, R. J. *The EMBO J.* 15:2760-2770 (1996)).

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a condition treatable or preventable by inhibition of a JNK pathway, as described herein. In another embodiment, the disorder is selected from interstitial pulmonary fibrosis, systemic sclerosis, scleroderma, chronic allograft nephropathy, antibody mediated rejection, or lupus. In yet another embodiment, the disorder is a liver fibrotic disorder, or diabetes and/or metabolic syndrome leading to liver fibrotic disorders, as described herein. In some embodiments, the disorder is a liver fibrotic disorder, such as non-alcoholic steatohepatitis, steatosis (i.e. fatty liver), cirrhosis, primary sclerosing cholangitis, primary biliary cirrhosis, hepatitis, hepatocellular carcinoma, or liver fibrosis coincident with chronic or repeated alcohol ingestion (alcoholic hepatitis), with infection (e.g., viral infection such as HCV), with liver transplant, or with drug induced liver injury (e.g., acetaminophen toxicity). In some embodiments, "treating" means an alleviation, in whole or in part, of a disorder, disease or condition, or symptoms associated with diabetes or metabolic syndrome leading to liver fibrotic disorders, such as non-alcoholic steatohepatitis, steatosis (i.e. fatty liver), hepatitis or cirrhosis, or a slowing, or halting of further progression or worsening of those symptoms. In one embodiment, the symptom is jaundice.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a condition treatable or preventable by inhibition of a JNK pathway, as described herein. In another embodiment, the disorder is selected from interstitial pulmonary fibrosis, systemic sclerosis, scleroderma, chronic allograft nephropathy, antibody mediated rejection, or lupus. In one embodiment, the disorder is a liver fibrotic disorder, or diabetes or metabolic syndrome leading to liver fibrotic disorders, as described herein, or symptoms thereof In another embodiment, the disorder is selected from interstitial pulmonary fibrosis, systemic sclerosis, scleroderma, chronic allograft nephropathy, antibody mediated rejection, or lupus. In yet another embodiment, the disorder is a liver fibrotic disorder, or diabetes and/or metabolic syndrome leading to liver fibrotic disorders, as described herein. In some embodiments, the disorder is a liver fibrotic disorder, such as non-alcoholic steatohepatitis, steatosis (i.e. fatty liver), cirrhosis, primary sclerosing cholangitis, primary biliary cirrhosis, hepatitis, hepatocellular carcinoma, or liver fibrosis coincident with chronic or repeated alcohol ingestion (alcoholic hepatitis), with infection (e.g., viral infection such as HCV), with liver transplant, or with drug induced liver injury (e.g., acetaminophen toxicity).

The term "effective amount" in connection with Compound 1 or Compound A means an amount capable of treating or preventing a disorder, disease or condition, or symptoms thereof, disclosed herein.

"Patient" or "subject" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like, in one embodiment a mammal, in another embodiment a human. In one embodiment, a subject is a human having or at risk for having interstitial pulmonary fibrosis, systemic sclerosis, scleroderma, chronic allograft nephropathy, antibody mediated rejection, or lupus. In another, a subject is a human having or at risk for having liver fibrotic disorders or diabetes or metabolic syndrome leading to liver fibrotic disorders, or a condition, treatable or preventable by inhibition of a JNK pathway, or a symptom thereof. In one embodiment, a subject is fasted. In another embodiment, a subject is fed.

5.2. Compound 1

The compositions and methods of use provided herein relate to Compound 1:

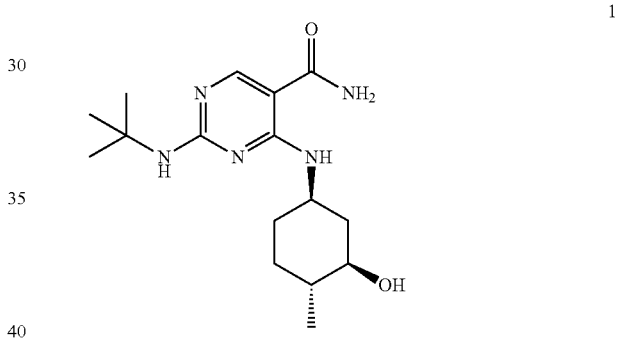

having the alternative names 2-(tert-butylamino)-4-((1R, 3R,4R)-3-hydroxy-4-methylcyclohexylamino)-pyrimidine-5-carboxamide or 2-[(1,1-dimethylethyl)amino]-4-[[(1R, 3R,4R)-3-hydroxy-4-methylcyclohexyl]amino]-5-pyrimidinecarboxamide, or a pharmaceutically acceptable stereoisomer, tautomer, solid form, polymorph, salt, hydrate, clathrate, or solvate thereof (collectively referred to as Compound A).

Compound A and Compound 1 can be prepared using reagents and methods provided herein or known in the art, including the methods provided in U.S. Patent Application Publication No. 2013/0029987, published on Jan. 31, 2013, U.S. Provisional Patent Application No. 61/933,636, filed on Jan. 30, 2014, U.S. Provisional Patent Application No. 62/025,161, filed on Jul. 16, 2014, and International Pub. No. WO2012/145569, the entire contents of each of which are incorporated herein by reference.

Free base forms (Forms A, B, C, D, E, F, G, H, and I) were previously described in U.S. Provisional Patent Application No. 61/933,636, filed on Jan. 30, 2014, U.S. and Provisional Patent Application No. 62/025,161, filed on Jul. 16, 2014.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3. Pharmaceutical Compositions

Provided herein are pharmaceutical compositions and dosage forms of Compound A. In some embodiments, the dosage forms are suitable for oral administration to a patient. In other embodiments, the dosage forms provided herein exhibit advantageous physical and/or pharmacological properties. Such properties include, but are not limited to, ease of assay, content uniformity, flow properties for manufacture, dissolution and bioavailability, and stability.

Provided herein are kits comprising pharmaceutical compositions and dosage forms provided herein. Also provided herein are methods of treating, managing, and/or preventing a disease or condition, which comprises administering to a patient in need thereof a pharmaceutical composition or a dosage form provided herein.

In certain embodiments, the unit dosage forms provided herein are oral dosage forms.

In certain embodiments, the pharmaceutical compositions and dosage forms provided herein are tablets.

5.4. Formulation A

In one embodiment, provided herein is a pharmaceutical composition comprising Compound A, and one or more pharmaceutically acceptable excipients or carriers. In one embodiment, the pharmaceutical composition is Formulation A comprising excipients or carriers described in Table 1.

In one embodiment, provided herein is a pharmaceutical composition comprising Compound A and one or more pharmaceutically acceptable excipients and carriers selected from diluents, surfactants, disintegrants and lubricants. In certain embodiments, the pharmaceutical compositions can be coated.

In certain embodiments, the diluents include, but are not limited to, mannitol (e.g., Mannitol 200), cellulose (e.g., microcrystalline cellulose, such as AVICEL® PH 101 and AVICEL® PH 102). In one embodiment, the diluent is mannitol. In yet another embodiment, the diluent is Mannitol 200. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102.

In certain embodiments, the surfactants include, but are not limited to, hydroxypropyl methylcellulose (HPMC) (e.g., Methocel™ K3). In one embodiment, the surfactant is Methocel™ K3.

In certain embodiments, the disintegrants include, but are not limited to, carboxymethyl cellulose (e.g., croscarmellose sodium, such as AC-DI-SOL®). In one embodiment, the disintegrant is carboxymethyl cellulose. In another embodiment, the disintegrant is croscarmellose sodium. In still another embodiment, the disintegrant is AC-DI-SOL®.

In one embodiment, the lubricant is magnesium stearate.

In certain embodiments, the coating includes, but is not limited to, Opadry (e.g., Opadry yellow, Opadry white and Opadry brown). In one embodiment, the coating is Opadry. In another embodiment, the coating is Opadry yellow. In another embodiment, the coating is Opadry white. In another embodiment, the coating is Opadry brown.

In certain embodiments, provided herein are pharmaceutical compositions comprising Compound A and one or more pharmaceutically acceptable excipients or carriers, each independently selected from mannitol, cellulose, HPMC, carboxymethyl cellulose and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from mannitol, microcrystalline cellulose, HPMC, croscarmellose sodium and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from Mannitol 200, AVICEL® PH 101, AVICEL® PH 102, Methocel™ K3, AC-DI-SOL® and magnesium stearate. In certain embodiments, the pharmaceutical compositions are coated with Opadry white, Opadry yellow or Opadry brown.

In one embodiment, provided herein is a pharmaceutical composition comprising Compound A, a diluent(s)/binder(s), a disintegrant(s), a surfactant(s) and a lubricant(s). In certain embodiments, the pharmaceutical compositions are coated.

In one embodiment, provided herein is a pharmaceutical composition comprising Compound A, mannitol and magnesium stearate.

In one embodiment, provided herein is a pharmaceutical composition comprising Compound A, mannitol, cellulose and magnesium stearate.

In certain embodiments, provided herein are pharmaceutical compositions comprising Compound A, mannitol, microcrystalline cellulose, carboxymethyl cellulose and magnesium stearate.

In certain embodiments, provided herein are pharmaceutical compositions comprising Compound A, mannitol, microcrystalline cellulose, croscarmellose sodium and magnesium stearate.

In certain embodiments, provided herein are pharmaceutical compositions comprising Compound A, Mannitol 200, AVICEL®PH 101, AC-DI-SOL®, Methocel™ K3 and magnesium stearate.

In certain embodiments, provided herein are pharmaceutical compositions comprising Compound A, Mannitol 200, AVICEL®PH 102, AC-DI-SOL®, Methocel™ K3 and magnesium stearate.

In certain embodiments, provided herein are pharmaceutical compositions comprising Compound A, Mannitol 200, AVICEL®PH 101, AVICEL®PH 102, AC-DI-SOL®, Methocel™ K3 and magnesium stearate.

In one embodiment, provided herein is a pharmaceutical composition comprising about 20-40% by weight of Compound A, about 50-70% by weight of diluent(s)/binder(s), about 1-10% by weight of disintegrant(s), about 1-10% by weight of surfactant(s) and about 0.1-2% by weight of lubricant(s).

In one embodiment, provided herein is a pharmaceutical composition comprising about 28.57% by weight of Compound A, about 63.43% by weight of diluent(s)/binder(s), about 4% by weight of disintegrant(s), about 3% by weight of surfactant(s) and about 1% by weight of lubricant(s).

In one embodiment, provided herein is a pharmaceutical composition comprising about 20-40% by weight of Compound A, about 30-50% by weight of cellulose, about 20-40% by weight of mannitol, about 1-10% by weight of carboxymethyl cellulose, about 1-10% by weight of hydroxypropyl methylcellulose (HPMC) and about 0.1-2% by weight of magnesium stearate.

In one embodiment, provided herein is a pharmaceutical composition comprising about 28.57% by weight of Compound A, about 37.43% by weight of cellulose, about 26% by weight of mannitol, about 4% by weight of carboxymethyl cellulose, about 3% by weight of HPMC and about 1% by weight of magnesium stearate.

In one embodiment, provided herein is a pharmaceutical composition comprising about 20-40% by weight of Compound A, about 30-50% by weight of microcrystalline cellulose, about 20-40% by weight of mannitol, about 1-10% by weight of carboxymethyl cellulose, about 1-10% by weight of HPMC and about 0.1-2% by weight of magnesium stearate.

In one embodiment, provided herein is a pharmaceutical composition comprising about 28.57% by weight of Compound A, about 37.43% by weight of microcrystalline cellulose, about 26% by weight of mannitol, about 4% by weight of carboxymethyl cellulose, about 3% by weight of HPMC and about 1% by weight of magnesium stearate.

In one embodiment, provided herein is a pharmaceutical composition comprising about 20-40% by weight of Compound A, about 30-50% by weight of AVICEL® PH 101 or AVICEL® PH 102, about 20-40% by weight of Mannitol 200, about 1-10% by weight of AC-DI-SOL®, about 1-10% by weight of Methocel™ K3 and about 0.1-2% by weight of magnesium stearate.

In one embodiment, provided herein is a pharmaceutical composition comprising about 28.57% by weight of Compound A, about 37.43% by weight of AVICEL® PH 101 or AVICEL® PH 102, about 26% by weight of Mannitol 200, about 4% by weight of AC-DI-SOL®, about 3% by weight of Methocel™ K3 and about 1% by weight of magnesium stearate.

In one embodiment, the pharmaceutical composition further comprises a coating adding about 1-10% weight. In one embodiment, the pharmaceutical composition further comprises a coating adding about 3% weight. In one embodiment, the pharmaceutical composition further comprises a coating comprising Opadry and adding about 1-10% weight. In one embodiment, the pharmaceutical composition further comprises a coating comprising Opadry and adding about 3% weight. In one embodiment, the pharmaceutical composition further comprises a coating comprising Opadry yellow, Opadry white or Opadry brown and adding about 1-10% weight. In one embodiment, the pharmaceutical composition further comprises a coating comprising Opadry yellow, Opadry white or Opadry brown and adding about 3% weight.

In one embodiment, provided herein is a pharmaceutical composition comprising about 50-200 mg Compound A, about 100-400 mg diluent(s)/binder(s), about 7-30 mg disintegrant(s), about 5-20 mg surfactant(s) and about 0.1-10 mg lubricant(s).

In one embodiment, provided herein is a pharmaceutical composition comprising about 100 mg Compound A, about 222 mg diluent(s)/binder(s), about 14 mg disintegrant(s), about 10.5 mg surfactant(s) and about 3.5 mg lubricant(s).

In one embodiment, provided herein is a pharmaceutical composition comprising about 50-200 mg Compound A, about 60-260 mg cellulose, about 40-180 mg mannitol, about 7-30 mg carboxymethyl cellulose, about 5-20 mg hydroxypropyl methylcellulose (HPMC) and about 0.1-10 mg magnesium stearate.

In one embodiment, provided herein is a pharmaceutical composition comprising about 100 mg Compound A, about 131.01 mg cellulose, about 91 mg mannitol, about 14 mg carboxymethyl cellulose, about 10.5 mg HPMC and about 3.5 mg magnesium stearate.

In one embodiment, provided herein is a pharmaceutical composition comprising about 50-200 mg Compound A, about 60-260 mg microcrystalline cellulose, about 40-180 mg mannitol, about 7-30 mg carboxymethyl cellulose, about 5-20 mg HPMC and about 0.1-10 mg magnesium stearate.

In one embodiment, provided herein is a pharmaceutical composition comprising about 100 mg Compound A, about 131.01 mg microcrystalline cellulose, about 91 mg mannitol, about 14 mg carboxymethyl cellulose, about 10.5 mg HPMC and about 3.5 mg magnesium stearate.

In one embodiment, provided herein is a pharmaceutical composition comprising about 50-200 mg Compound A, about 60-260 mg AVICEL® PH 101 or AVICEL® PH 102, about 40-180 mg Mannitol 200, about 7-30 mg AC-DI-SOL®, about 5-20 mg Methocel™ K3 and about 0.1-10 mg magnesium stearate.

In one embodiment, provided herein is a pharmaceutical composition comprising about 100 mg Compound A, about 131.01 mg AVICEL® PH 101 or AVICEL® PH 102, about 91 mg Mannitol 200, about 14 mg AC-DI-SOL®, about 10.5 mg Methocel™ K3 and about 3.5 mg magnesium stearate.

In one embodiment, the pharmaceutical composition further comprises a coating adding about 5-20 mg weight. In one embodiment, the pharmaceutical composition further comprises a coating adding about 10.5 mg weight. In one embodiment, the pharmaceutical composition further comprises a coating comprising Opadry and adding about 5-20 mg weight. In one embodiment, the pharmaceutical composition further comprises a coating comprising Opadry and adding about 10.5 mg weight. In one embodiment, the pharmaceutical composition further comprises a coating comprising Opadry yellow, Opadry white or Opadry brown and adding about 5-20 mg weight. In one embodiment, the pharmaceutical composition further comprises a coating comprising Opadry yellow, Opadry white or Opadry brown and adding about 10.5 mg weight.

In certain embodiments, provided herein are single unit dosage forms of Formulation A. In particular embodiments, the single unit dosage forms are 30 mg, 100 mg or 200 mg tablets.

In one such embodiment, Compound A is Compound 1. In another embodiment, Compound A is a pharmaceutically acceptable salt of Compound 1. In yet another embodiment, Compound A is a solid form of Compound 1.

5.5. Formulation B

In one embodiment, provided herein is a pharmaceutical composition comprising Compound A, and one or more pharmaceutically acceptable excipients or carriers. In one embodiment, the pharmaceutical composition is Formulation B comprising excipients or carriers described in Table 4.

In one embodiment, provided herein is a pharmaceutical composition comprising Compound A and one or more pharmaceutically acceptable excipients and carriers selected from diluents, surfactants, disintegrants and lubricants. In certain embodiments, the pharmaceutical compositions can be coated.

In certain embodiments, the diluents include, but are not limited to, mannitol (e.g., Mannitol 200), cellulose (e.g., microcrystalline cellulose, such as AVICEL® PH 101 and AVICEL® PH 102). In one embodiment, the diluent is mannitol. In yet another embodiment, the diluent is Mannitol 200. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102.

In certain embodiments, the surfactants include, but are not limited to, hydroxypropyl methylcellulose (HPMC) (e.g., Methocel™ K3). In one embodiment, the surfactant is Methocel™ K3.

In certain embodiments, the disintegrants include, but are not limited to, carboxymethyl cellulose (e.g., croscarmellose sodium, such as AC-DI-SOL®). In one embodiment, the disintegrant is carboxymethyl cellulose. In another embodiment, the disintegrant is croscarmellose sodium. In still another embodiment, the disintegrant is AC-DI-SOL®.

In one embodiment, the lubricant is magnesium stearate.

In certain embodiments, the coating includes, but is not limited to, Opadry (e.g., Opadry yellow, Opadry white and Opadry brown). In one embodiment, the coating is Opadry. In another embodiment, the coating is Opadry yellow. In another embodiment, the coating is Opadry white. In another embodiment, the coating is Opadry brown.

In certain embodiments, provided herein are pharmaceutical compositions comprising Compound A and one or more pharmaceutically acceptable excipients or carriers, each independently selected from mannitol, cellulose, HPMC, carboxymethyl cellulose and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from mannitol, microcrystalline cellulose, HPMC, croscarmellose sodium and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from Mannitol 200, AVICEL® PH 101, AVICEL® PH 102, Methocel™ K3, AC-DI-SOL® and magnesium stearate. In certain embodiments, the pharmaceutical compositions are coated with Opadry white, Opadry yellow or Opadry brown.

In one embodiment, provided herein is a pharmaceutical composition comprising Compound A, a diluent(s)/binder(s), a disintegrant(s), a surfactant(s) and a lubricant(s). In certain embodiments, the pharmaceutical compositions can be coated.

In one embodiment, provided herein is a pharmaceutical composition comprising Compound A, mannitol and magnesium stearate.

In one embodiment, provided herein is a pharmaceutical composition comprising Compound A, mannitol, cellulose and magnesium stearate.

In certain embodiments, provided herein are pharmaceutical compositions comprising Compound A, mannitol, microcrystalline cellulose, carboxymethyl cellulose and magnesium stearate.

In certain embodiments, provided herein are pharmaceutical compositions comprising Compound A, mannitol, microcrystalline cellulose, croscarmellose sodium and magnesium stearate.

In certain embodiments, provided herein are pharmaceutical compositions comprising Compound A, Mannitol 200, AVICEL®PH 101, AC-DI-SOL®, Methocel™ K3 and magnesium stearate.

In certain embodiments, provided herein are pharmaceutical compositions comprising Compound A, Mannitol 200, AVICEL®PH 102, AC-DI-SOL®, Methocel™ K3 and magnesium stearate.

In certain embodiments, provided herein are pharmaceutical compositions comprising Compound A, Mannitol 200, AVICEL®PH 101, AVICEL®PH 102, AC-DI-SOL®, Methocel™ K3 and magnesium stearate.

In one embodiment, provided herein is a pharmaceutical composition comprising about 20-40% by weight of Compound A, about 50-70% by weight of diluent(s)/binder(s), about 1-20% by weight of disintegrant(s), about 1-10% by weight of surfactant(s) and about 0.1-2% by weight of lubricant(s).

In one embodiment, provided herein is a pharmaceutical composition comprising about 28.57% by weight of Compound A, about 59.43% by weight of diluent(s)/binder(s), about 8% by weight of disintegrant(s), about 3% by weight of surfactant(s) and about 1% by weight of lubricant(s).

In one embodiment, provided herein is a pharmaceutical composition comprising about 20-40% by weight of Compound A, about 20-40% by weight of cellulose, about 20-40% by weight of mannitol, about 1-20% by weight of carboxymethyl cellulose, about 1-10% by weight of hydroxypropyl methylcellulose (HPMC) and about 0.1-2% by weight of magnesium stearate.

In one embodiment, provided herein is a pharmaceutical composition comprising about 28.57% by weight of Compound A, about 33.43% by weight of cellulose, about 26% by weight of mannitol, about 8% by weight of carboxymethyl cellulose, about 3% by weight of HPMC and about 1% by weight of magnesium stearate.

In one embodiment, provided herein is a pharmaceutical composition comprising about 20-40% by weight of Compound A, about 20-40% by weight of microcrystalline cellulose, about 20-40% by weight of mannitol, about 1-20% by weight of carboxymethyl cellulose, about 1-10% by weight of HPMC and about 0.1-2% by weight of magnesium stearate.

In one embodiment, provided herein is a pharmaceutical composition comprising about 28.57% by weight of Compound A, about 33.43% by weight of microcrystalline cellulose, about 26% by weight of mannitol, about 8% by weight of carboxymethyl cellulose, about 3% by weight of HPMC and about 1% by weight of magnesium stearate.

In one embodiment, provided herein is a pharmaceutical composition comprising about 20-40% by weight of Compound A, about 20-40% by weight of AVICEL® PH 101 or AVICEL® PH 102, about 20-40% by weight of Mannitol 200, about 1-20% by weight of AC-DI-SOL®, about 1-10% by weight of Methocel™ K3 and about 0.1-2% by weight of magnesium stearate.

In one embodiment, provided herein is a pharmaceutical composition comprising about 28.57% by weight of Compound A, about 33.43% by weight of AVICEL® PH 101 or AVICEL® PH 102, about 26% by weight of Mannitol 200, about 8% by weight of AC-DI-SOL®, about 3% by weight of Methocel™ K3 and about 1% by weight of magnesium stearate.

In one embodiment, the pharmaceutical composition further comprises a coating adding about 1-10% weight. In one embodiment, the pharmaceutical composition further comprises a coating adding about 3% weight. In one embodiment, the pharmaceutical composition further comprises a coating comprising Opadry and adding about 1-10% weight. In one embodiment, the pharmaceutical composition further comprises a coating comprising Opadry and adding about 3% weight. In one embodiment, the pharmaceutical composition further comprises a coating comprising Opadry yellow, Opadry white or Opadry brown and adding about 1-10% weight. In one embodiment, the pharmaceutical composition further comprises a coating comprising Opadry yellow, Opadry white or Opadry brown and adding about 3% weight.

In one embodiment, provided herein is a pharmaceutical composition comprising about 50-200 mg Compound A, about 100-400 mg diluent(s)/binder(s), about 10-60 mg disintegrant(s), about 5-20 mg surfactant(s) and about 0.1-10 mg lubricant(s).

In one embodiment, provided herein is a pharmaceutical composition comprising about 100 mg Compound A, about 208.1 mg diluent(s)/binder(s), about 28 mg disintegrant(s), about 10.5 mg surfactant(s) and about 3.5 mg lubricant(s).

In one embodiment, provided herein is a pharmaceutical composition comprising about 50-200 mg Compound A, about 60-240 mg cellulose, about 40-180 mg mannitol, about 10-60 mg carboxymethyl cellulose, about 5-20 mg hydroxypropyl methylcellulose (HPMC) and about 0.1-10 mg magnesium stearate.

In one embodiment, provided herein is a pharmaceutical composition comprising about 100 mg Compound A, about 117.1 mg cellulose, about 91 mg mannitol, about 28 mg carboxymethyl cellulose, about 10.5 mg HPMC and about 3.5 mg magnesium stearate.

In one embodiment, provided herein is a pharmaceutical composition comprising about 50-200 mg Compound A, about 60-240 mg microcrystalline cellulose, about 40-180 mg mannitol, about 10-60 mg carboxymethyl cellulose, about 5-20 mg HPMC and about 0.1-10 mg magnesium stearate.

In one embodiment, provided herein is a pharmaceutical composition comprising about 100 mg Compound A, about 117.1 mg microcrystalline cellulose, about 91 mg mannitol, about 28 mg carboxymethyl cellulose, about 10.5 mg HPMC and about 3.5 mg magnesium stearate.

In one embodiment, provided herein is a pharmaceutical composition comprising about 50-200 mg Compound A, about 60-240 mg AVICEL® PH 101 or AVICEL® PH 102, about 40-180 mg Mannitol 200, about 10-60 mg AC-DI-SOL®, about 5-20 mg Methocel™ K3 and about 0.1-10 mg magnesium stearate.

In one embodiment, provided herein is a pharmaceutical composition comprising about 100 mg Compound A, about 117.1 mg AVICEL® PH 101 or AVICEL® PH 102, about 91 mg Mannitol 200, about 28 mg AC-DI-SOL®, about 10.5 mg Methocel™ K3 and about 3.5 mg magnesium stearate.

In one embodiment, the pharmaceutical composition further comprises a coating adding about 5-20 mg weight. In one embodiment, the pharmaceutical composition further comprises a coating adding about 10.5 mg weight. In one embodiment, the pharmaceutical composition further comprises a coating comprising Opadry and adding about 5-20 mg weight. In one embodiment, the pharmaceutical composition further comprises a coating comprising Opadry and adding about 10.5 mg weight. In one embodiment, the pharmaceutical composition further comprises a coating comprising Opadry yellow, Opadry white or Opadry brown and adding about 5-20 mg weight. In one embodiment, the pharmaceutical composition further comprises a coating comprising Opadry yellow, Opadry white or Opadry brown and adding about 10.5 mg weight.

In certain embodiments, provided herein are single unit dosage forms of Formulation B. In particular embodiments, the single unit dosage forms are 30 mg, 100 mg or 200 mg tablets.

In one such embodiment, Compound A is Compound 1. In another embodiment, Compound A is a pharmaceutically acceptable salt of Compound 1. In yet another embodiment, Compound A is a solid form of Compound 1.

5.6. Formulation C

In one embodiment, provided herein is a pharmaceutical composition comprising Compound A, and one or more pharmaceutically acceptable excipients or carriers. In one embodiment, the pharmaceutical composition is Formulation C comprising excipients or carriers described in Table 5.

In one embodiment, provided herein is a pharmaceutical composition comprising Compound A and one or more pharmaceutically acceptable excipients and carriers selected from diluents, surfactants, disintegrants and lubricants. In certain embodiments, the pharmaceutical compositions can be coated.

In certain embodiments, the diluents include, but are not limited to, mannitol (e.g., Mannitol 200), cellulose (e.g., microcrystalline cellulose, such as AVICEL® PH 101 and AVICEL® PH 102). In one embodiment, the diluent is mannitol. In yet another embodiment, the diluent is Mannitol 200. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102.

In certain embodiments, the surfactants include, but are not limited to, hydroxypropyl methylcellulose (HPMC) (e.g., Methocel™ K3). In one embodiment, the surfactant is Methocel™ K3.

In certain embodiments, the disintegrants include, but are not limited to, carboxymethyl cellulose (e.g., croscarmellose sodium, such as AC-DI-SOL®). In one embodiment, the disintegrant is carboxymethyl cellulose. In another embodiment, the disintegrant is croscarmellose sodium. In still another embodiment, the disintegrant is AC-DI-SOL®.

In one embodiment, the lubricant is magnesium stearate.

In certain embodiments, the coating includes, but is not limited to, Opadry (e.g., Opadry yellow, Opadry white and Opadry brown). In one embodiment, the coat is Opadry. In another embodiment, the coat is Opadry yellow. In another embodiment, the coat is Opadry white. In another embodiment, the coat is Opadry brown.

In certain embodiments, provided herein are pharmaceutical compositions comprising Compound A and one or more pharmaceutically acceptable excipients or carriers, each independently selected from mannitol, cellulose, HPMC, carboxymethyl cellulose and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from mannitol, microcrystalline cellulose, HPMC, croscarmellose sodium and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from Mannitol 200, AVICEL® PH 101, AVICEL® PH 102, Methocel™ K3, AC-DI-SOL® and magnesium stearate. In certain embodiments, the pharmaceutical compositions are coated with Opadry white, Opadry yellow or Opadry brown.

In one embodiment, provided herein is a pharmaceutical composition comprising Compound A, a diluent(s)/binder(s), a disintegrant(s), a surfactant(s) and a lubricant(s). In certain embodiments, the pharmaceutical compositions can be coated.

In one embodiment, provided herein is a pharmaceutical composition comprising Compound A, mannitol and magnesium stearate.

In one embodiment, provided herein is a pharmaceutical composition comprising Compound A, mannitol, cellulose and magnesium stearate.

In certain embodiments, provided herein are pharmaceutical compositions comprising Compound A, mannitol, microcrystalline cellulose, carboxymethyl cellulose and magnesium stearate.

In certain embodiments, provided herein are pharmaceutical compositions comprising Compound A, mannitol, microcrystalline cellulose, croscarmellose sodium and magnesium stearate.

In certain embodiments, provided herein are pharmaceutical compositions comprising Compound A, Mannitol 200, AVICEL®PH 101, AC-DI-SOL®, Methocel™ K3 and magnesium stearate.

In certain embodiments, provided herein are pharmaceutical compositions comprising Compound A, Mannitol 200, AVICEL®PH 102, AC-DI-SOL®, Methocel™ K3 and magnesium stearate.

In certain embodiments, provided herein are pharmaceutical compositions comprising Compound A, Mannitol 200, AVICEL®PH 101, AVICEL®PH 102, AC-DI-SOL®, Methocel™ K3 and magnesium stearate.

In one embodiment, provided herein is a pharmaceutical composition comprising about 20-40% by weight of Compound A, about 50-70% by weight of diluent(s)/binder(s), about 1-20% by weight of disintegrant(s), about 1-10% by weight of surfactant(s) and about 0.1-2% by weight of lubricant(s).

In one embodiment, provided herein is a pharmaceutical composition comprising about 28.57% by weight of Compound A, about 57.93% by weight of diluent(s)/binder(s), about 8% by weight of disintegrant(s), about 4.5% by weight of surfactant(s) and about 1% by weight of lubricant(s).

In one embodiment, provided herein is a pharmaceutical composition comprising about 20-40% by weight of Compound A, about 20-40% by weight of cellulose, about 20-40% by weight of mannitol, about 1-20% by weight of carboxymethyl cellulose, about 1-10% by weight of hydroxypropyl methylcellulose (HPMC) and about 0.1-2% by weight of magnesium stearate.

In one embodiment, provided herein is a pharmaceutical composition comprising about 28.57% by weight of Compound A, about 31.93% by weight of cellulose, about 26% by weight of mannitol, about 8% by weight of carboxymethyl cellulose, about 4.5% by weight of HPMC and about 1% by weight of magnesium stearate.

In one embodiment, provided herein is a pharmaceutical composition comprising about 20-40% by weight of Compound A, about 20-40% by weight of microcrystalline cellulose, about 20-40% by weight of mannitol, about 1-20% by weight of carboxymethyl cellulose, about 1-10% by weight of HPMC and about 0.1-2% by weight of magnesium stearate.

In one embodiment, provided herein is a pharmaceutical composition comprising about 28.57% by weight of Compound A, about 31.93% by weight of microcrystalline cellulose, about 26% by weight of mannitol, about 8% by weight of carboxymethyl cellulose, about 4.5% by weight of HPMC and about 1% by weight of magnesium stearate.

In one embodiment, provided herein is a pharmaceutical composition comprising about 20-40% by weight of Compound A, about 20-40% by weight of AVICEL® PH 101 or AVICEL® PH 102, about 20-40% by weight of Mannitol 200, about 1-20% by weight of AC-DI-SOL®, about 1-10% by weight of Methocel™ K3 and about 0.1-2% by weight of magnesium stearate.

In one embodiment, provided herein is a pharmaceutical composition comprising about 28.57% by weight of Compound A, about 31.93% by weight of AVICEL® PH 101 or AVICEL® PH 102, about 26% by weight of Mannitol 200, about 8% by weight of AC-DI-SOL®, about 4.5% by weight of Methocel™ K3 and about 1% by weight of magnesium stearate.

In one embodiment, the pharmaceutical composition further comprises a coating adding about 1-10% weight. In one embodiment, the pharmaceutical composition further comprises a coating adding about 3% weight. In one embodiment, the pharmaceutical composition further comprises a coating comprising Opadry and adding about 1-10% weight. In one embodiment, the pharmaceutical composition further comprises a coating comprising Opadry and adding about 3% weight. In one embodiment, the pharmaceutical composition further comprises a coating comprising Opadry yellow, Opadry white or Opadry brown and adding about 1-10% weight. In one embodiment, the pharmaceutical composition further comprises a coating comprising Opadry yellow, Opadry white or Opadry brown and adding about 3% weight.

In one embodiment, provided herein is a pharmaceutical composition comprising about 50-200 mg Compound A, about 100-400 mg diluent(s)/binder(s), about 10-60 mg disintegrant(s), about 5-30 mg surfactant(s) and about 0.1-10 mg lubricant(s).

In one embodiment, provided herein is a pharmaceutical composition comprising about 100 mg Compound A, about 202.76 mg diluent(s)/binder(s), about 28 mg disintegrant(s), about 15.75 mg surfactant(s) and about 3.5 mg lubricant(s).

In one embodiment, provided herein is a pharmaceutical composition comprising about 50-200 mg Compound A, about 50-220 mg cellulose, about 40-180 mg mannitol, about 10-60 mg carboxymethyl cellulose, about 5-30 mg hydroxypropyl methylcellulose (HPMC) and about 0.1-10 mg magnesium stearate.

In one embodiment, provided herein is a pharmaceutical composition comprising about 100 mg Compound A, about 111.76 mg cellulose, about 91 mg mannitol, about 28 mg carboxymethyl cellulose, about 15.75 mg HPMC and about 3.5 mg magnesium stearate.

In one embodiment, provided herein is a pharmaceutical composition comprising about 50-200 mg Compound A, about 50-220 mg microcrystalline cellulose, about 40-180 mg mannitol, about 10-60 mg carboxymethyl cellulose, about 5-30 mg HPMC and about 0.1-10 mg magnesium stearate.

In one embodiment, provided herein is a pharmaceutical composition comprising about 100 mg Compound A, about 111.76 mg microcrystalline cellulose, about 91 mg mannitol, about 28 mg carboxymethyl cellulose, about 15.75 mg HPMC and about 3.5 mg magnesium stearate.

In one embodiment, provided herein is a pharmaceutical composition comprising about 50-200 mg Compound A, about 50-220 mg AVICEL® PH 101 or AVICEL® PH 102, about 40-180 mg Mannitol 200, about 10-60 mg AC-DI-SOL®, about 5-30 mg Methocel™ K3 and about 0.1-10 mg magnesium stearate.

In one embodiment, provided herein is a pharmaceutical composition comprising about 100 mg Compound A, about 111.76 mg AVICEL® PH 101 or AVICEL® PH 102, about 91 mg Mannitol 200, about 28 mg AC-DI-SOL®, about 15.75 mg Methocel™ K3 and about 3.5 mg magnesium stearate.

In one embodiment, the pharmaceutical composition further comprises a coating adding about 5-20 mg weight. In one embodiment, the pharmaceutical composition further comprises a coating adding about 10.5 mg weight. In one embodiment, the pharmaceutical composition further comprises a coating comprising Opadry and adding about 5-20 mg weight. In one embodiment, the pharmaceutical composition further comprises a coating comprising Opadry and adding about 10.5 mg weight. In one embodiment, the pharmaceutical composition further comprises a coating comprising Opadry yellow, Opadry white or Opadry brown and adding about 5-20 mg weight. In one embodiment, the pharmaceutical composition further comprises a coating comprising Opadry yellow, Opadry white or Opadry brown and adding about 10.5 mg weight.

In certain embodiments, provided herein are single unit dosage forms of Formulation C. In particular embodiments, the single unit dosage forms are 30 mg, 100 mg or 200 mg tablets.

In one such embodiment, Compound A is Compound 1. In another embodiment, Compound A is a pharmaceutically acceptable salt of Compound 1. In yet another embodiment, Compound A is a solid form of Compound 1.

5.7. Formulation D

In one embodiment, provided herein is a pharmaceutical composition comprising Compound A, and one or more pharmaceutically acceptable excipients or carriers. In one embodiment, the pharmaceutical composition is Formulation C comprising excipients or carriers described in Table 6.

In one embodiment, provided herein is a pharmaceutical composition comprising Compound A and one or more pharmaceutically acceptable excipients and carriers selected from diluents, surfactants, disintegrants and lubricants. In certain embodiments, the pharmaceutical compositions can be coated.

In certain embodiments, the diluents include, but are not limited to, mannitol (e.g., Mannitol 200), cellulose (e.g., microcrystalline cellulose, such as AVICEL® PH 101 and AVICEL® PH 102). In one embodiment, the diluent is mannitol. In yet another embodiment, the diluent is Mannitol 200. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102.

In certain embodiments, the surfactants include, but are not limited to, hydroxypropyl methylcellulose (HPMC) (e.g., Methocel™ K3). In one embodiment, the surfactant is Methocel™ K3.

In certain embodiments, the disintegrants include, but are not limited to, carboxymethyl cellulose (e.g., croscarmellose sodium, such as AC-DI-SOL®). In one embodiment, the disintegrant is carboxymethyl cellulose. In another embodiment, the disintegrant is croscarmellose sodium. In still another embodiment, the disintegrant is AC-DI-SOL®.

In one embodiment, the lubricant is magnesium stearate.

In certain embodiments, the coating includes, but is not limited to, Opadry (e.g., Opadry yellow, Opadry white and Opadry brown). In one embodiment, the coat is Opadry. In another embodiment, the coat is Opadry yellow. In another embodiment, the coat is Opadry white. In another embodiment, the coat is Opadry brown.

In certain embodiments, provided herein are pharmaceutical compositions comprising Compound A and one or more pharmaceutically acceptable excipients or carriers, each independently selected from mannitol, cellulose, HPMC, carboxymethyl cellulose and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from mannitol, microcrystalline cellulose, HPMC, croscarmellose sodium and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from Mannitol 200, AVICEL® PH 101, AVICEL® PH 102, Methocel™ K3, AC-DI-SOL® and magnesium stearate. In certain embodiments, the pharmaceutical compositions are coated with Opadry white, Opadry yellow or Opadry brown.

In one embodiment, provided herein is a pharmaceutical composition comprising Compound A, a diluent(s)/binder(s), a disintegrant(s), a surfactant(s) and a lubricant(s). In certain embodiments, the pharmaceutical compositions can be coated.

In one embodiment, provided herein is a pharmaceutical composition comprising Compound A, mannitol and magnesium stearate.

In one embodiment, provided herein is a pharmaceutical composition comprising Compound A, mannitol, cellulose and magnesium stearate.

In certain embodiments, provided herein are pharmaceutical compositions comprising Compound A, mannitol, microcrystalline cellulose, carboxymethyl cellulose and magnesium stearate.

In certain embodiments, provided herein are pharmaceutical compositions comprising Compound A, mannitol, microcrystalline cellulose, croscarmellose sodium and magnesium stearate.

In certain embodiments, provided herein are pharmaceutical compositions comprising Compound A, Mannitol 200, AVICEL®PH 101, AC-DI-SOL®, Methocel™ K3 and magnesium stearate.

In certain embodiments, provided herein are pharmaceutical compositions comprising Compound A, Mannitol 200, AVICEL®PH 102, AC-DI-SOL®, Methocel™ K3 and magnesium stearate.

In certain embodiments, provided herein are pharmaceutical compositions comprising Compound A, Mannitol 200, AVICEL®PH 101, AVICEL®PH 102, AC-DI-SOL®, Methocel™ K3 and magnesium stearate.

In one embodiment, provided herein is a pharmaceutical composition comprising about 20-40% by weight of Compound A, about 50-70% by weight of diluent(s)/binder(s), about 1-10% by weight of disintegrant(s), about 1-10% by weight of surfactant(s) and about 0.1-2% by weight of lubricant(s).

In one embodiment, provided herein is a pharmaceutical composition comprising about 28.57% by weight of Compound A, about 61.93% by weight of diluent(s)/binder(s), about 4% by weight of disintegrant(s), about 4.5% by weight of surfactant(s) and about 1% by weight of lubricant(s).

In one embodiment, provided herein is a pharmaceutical composition comprising about 20-40% by weight of Compound A, about 20-50% by weight of cellulose, about 20-40% by weight of mannitol, about 1-10% by weight of carboxymethyl cellulose, about 1-10% by weight of hydroxypropyl methylcellulose (HPMC) and about 0.1-2% by weight of magnesium stearate.

In one embodiment, provided herein is a pharmaceutical composition comprising about 28.57% by weight of Compound A, about 35.93% by weight of cellulose, about 26% by weight of mannitol, about 4% by weight of carboxymethyl cellulose, about 4.5% by weight of HPMC and about 1% by weight of magnesium stearate.

In one embodiment, provided herein is a pharmaceutical composition comprising about 20-40% by weight of Compound A, about 20-50% by weight of microcrystalline cellulose, about 20-40% by weight of mannitol, about 1-10% by weight of carboxymethyl cellulose, about 1-10% by weight of HPMC and about 0.1-2% by weight of magnesium stearate.

In one embodiment, provided herein is a pharmaceutical composition comprising about 28.57% by weight of Compound A, about 35.93% by weight of microcrystalline cellulose, about 26% by weight of mannitol, about 4% by weight of carboxymethyl cellulose, about 4.5% by weight of HPMC and about 1% by weight of magnesium stearate.

In one embodiment, provided herein is a pharmaceutical composition comprising about 20-40% by weight of Compound A, about 20-50% by weight of AVICEL® PH 101 or AVICEL® PH 102, about 20-40% by weight of Mannitol 200, about 1-10% by weight of AC-DI-SOL®, about 1-10% by weight of Methocel™ K3 and about 0.1-2% by weight of magnesium stearate.

In one embodiment, provided herein is a pharmaceutical composition comprising about 28.57% by weight of Compound A, about 35.93% by weight of AVICEL® PH 101 or AVICEL® PH 102, about 26% by weight of Mannitol 200, about 4% by weight of AC-DI-SOL®, about 4.5% by weight of Methocel™ K3 and about 1% by weight of magnesium stearate.

In one embodiment, the pharmaceutical composition further comprises a coating adding about 1-10% weight. In one embodiment, the pharmaceutical composition further comprises a coating adding about 3% weight. In one embodiment, the pharmaceutical composition further comprises a coating comprising Opadry and adding about 1-10% weight. In one embodiment, the pharmaceutical composition further comprises a coating comprising Opadry and adding about 3% weight. In one embodiment, the pharmaceutical composition further comprises a coating comprising Opadry yellow, Opadry white or Opadry brown and adding about 1-10% weight. In one embodiment, the pharmaceutical composition further comprises a coating comprising Opadry yellow, Opadry white or Opadry brown and adding about 3% weight.

In one embodiment, provided herein is a pharmaceutical composition comprising about 50-200 mg Compound A, about 100-400 mg diluent(s)/binder(s), about 7-30 mg disintegrant(s), about 5-30 mg surfactant(s) and about 0.1-10 mg lubricant(s).

In one embodiment, provided herein is a pharmaceutical composition comprising about 100 mg Compound A, about 216.76 mg diluent(s)/binder(s), about 14 mg disintegrant(s), about 15.75 mg surfactant(s) and about 3.5 mg lubricant(s).

In one embodiment, provided herein is a pharmaceutical composition comprising about 50-200 mg Compound A, about 60-240 mg cellulose, about 40-180 mg mannitol, about 7-30 mg carboxymethyl cellulose, about 5-30 mg hydroxypropyl methylcellulose (HPMC) and about 0.1-10 mg magnesium stearate.

In one embodiment, provided herein is a pharmaceutical composition comprising about 100 mg Compound A, about 125.76 mg cellulose, about 91 mg mannitol, about 14 mg carboxymethyl cellulose, about 15.75 mg HPMC and about 3.5 mg magnesium stearate.

In one embodiment, provided herein is a pharmaceutical composition comprising about 50-200 mg Compound A, about 60-240 mg microcrystalline cellulose, about 40-180 mg mannitol, about 7-30 mg carboxymethyl cellulose, about 5-30 mg HPMC and about 0.1-10 mg magnesium stearate.

In one embodiment, provided herein is a pharmaceutical composition comprising about 100 mg Compound A, about 125.76 mg microcrystalline cellulose, about 91 mg mannitol, about 14 mg carboxymethyl cellulose, about 15.75 mg HPMC and about 3.5 mg magnesium stearate.

In one embodiment, provided herein is a pharmaceutical composition comprising about 50-200 mg Compound A, about 60-240 mg AVICEL® PH 101 or AVICEL® PH 102, about 40-180 mg Mannitol 200, about 7-30 mg AC-DI-SOL®, about 5-30 mg Methocel™ K3 and about 0.1-10 mg magnesium stearate.

In one embodiment, provided herein is a pharmaceutical composition comprising about 100 mg Compound A, about 125.76 mg AVICEL® PH 101 or AVICEL® PH 102, about 91 mg Mannitol 200, about 14 mg AC-DI-SOL®, about 15.75 mg Methocel™ K3 and about 3.5 mg magnesium stearate.

In one embodiment, the pharmaceutical composition further comprises a coating adding about 5-20 mg weight. In one embodiment, the pharmaceutical composition further comprises a coating adding about 10.5 mg weight. In one embodiment, the pharmaceutical composition further comprises a coating comprising Opadry and adding about 5-20 mg weight. In one embodiment, the pharmaceutical composition further comprises a coating comprising Opadry and adding about 10.5 mg weight. In one embodiment, the pharmaceutical composition further comprises a coating comprising Opadry yellow, Opadry white or Opadry brown and adding about 5-20 mg weight. In one embodiment, the pharmaceutical composition further comprises a coating comprising Opadry yellow, Opadry white or Opadry brown and adding about 10.5 mg weight.

In certain embodiments, provided herein are single unit dosage forms of Formulation D. In particular embodiments, the single unit dosage forms are 30 mg, 100 mg or 200 mg tablets.

In one such embodiment, Compound A is Compound 1. In another embodiment, Compound A is a pharmaceutically acceptable salt of Compound 1. In yet another embodiment, Compound A is a solid form of Compound 1.

5.8. Methods of Use

Pharmaceutical compositions, and dosage forms of Compound A have utility as pharmaceuticals to treat, prevent or improve conditions in animals or humans. Compound A is active against protein kinases, particularly JNK1 and/or JNK2. Accordingly, provided herein are many uses of pharmaceutical compositions, dosage forms and salts of Compound A, including the treatment or prevention of those diseases set forth below. The methods provided herein comprise the administration of a pharmaceutical composition, and dosage form of Compound A to a subject in need thereof. In one aspect, provided herein are methods of inhibiting a kinase in a cell expressing said kinase, comprising contacting said cell with an effective amount of a pharmaceutical composition, and dosage form of Compound A. In one embodiment, the kinase is JNK1, JNK2, or a mutant or isoform thereof, or a combination thereof.

In another aspect, provided herein are methods for treating or preventing one or more disorders selected from interstitial pulmonary fibrosis, systemic sclerosis, scleroderma, chronic allograft nephropathy, antibody mediated rejection, or lupus, comprising administering to a subject in need thereof an effective amount of a pharmaceutical composition, or dosage form of Compound A. In some such embodiments, the lupus is lupus erythematosus (such as discoid lupus erythematosus, or cutaneous lupus erythematosus) or systemic lupus. In some embodiments, the disorder is pulmonary fibrosis. In some embodiments, the pulmonary fibrosis is a documented usual interstitial pneumonia (UIP) pattern or nonspecific interstitial pneumonia (NSIP) pattern, for example, based on computed tomography or a documented fibrotic NSIP or documented UIP pattern, for example, based on surgical lung biopsy. In some embodiments, the underlying disease of the pulmonary fibrosis is connective tissue disease-associated interstitial lung disease, interstitial pulmonary fibrosis, idiopathic pulmonary fibrosis (IPF), environmental- or chemical-related pulmonary fibrosis, or Hermansky-Pudlak syndrome.

In another aspect, provided herein are methods for treating or preventing liver fibrotic disorders, such as non-alcoholic steatohepatitis, steatosis (i.e. fatty liver), cirrhosis, primary sclerosing cholangitis, primary biliary cirrhosis, hepatitis, hepatocellular carcinoma, and liver fibrosis coincident with chronic or repeated alcohol ingestion (alcoholic hepatitis), with infection (e.g., viral infection such as HCV), with liver transplant, or with drug induced liver injury (e.g., acetaminophen toxicity), comprising administering to a subject in need thereof an effective amount of a pharmaceutical composition, or dosage form of Compound A. In some such aspects, provided herein are methods for treating or preventing diabetes or metabolic syndrome leading to liver fibrotic disorders, such as non-alcoholic steatohepatitis, steatosis (i.e. fatty liver), cirrhosis, primary sclerosing cholangitis, primary biliary cirrhosis, and hepatitis, comprising administering to a subject in need thereof an effective amount of a pharmaceutical composition, or dosage form of Compound A.

In another aspect, provided herein are methods for treating or preventing conditions treatable or preventable by inhibition of JNK1 and/or JNK2, the method comprising administering to a subject in need thereof an effective amount of a pharmaceutical composition, or dosage form of Compound A. Examples of such conditions include rheumatoid arthritis, rheumatoid spondylitis, osteoarthritis, asthma, bronchitis, allergic rhinitis, chronic obstructive pulmonary disease, cystic fibrosis, inflammatory bowel disease, irritable bowel syndrome, mucous colitis, ulcerative colitis, Crohn's disease, Huntington's disease, hepatitis, pancreatitis, nephritis, multiple sclerosis, lupus erythematosus, Type II diabetes, obesity, atherosclerosis, restenosis following angioplasty, left ventricular hypertrophy, myocardial infarction, stroke, ischemic damages of heart, lung, gut, kidney, liver, pancreas, spleen and brain, acute or chronic organ transplant rejection, preservation of the organ for transplantation, organ failure or loss of limb (e.g., including, but not limited to, that resulting from ischemia-reperfusion injury, trauma, gross bodily injury, car accident, crush injury or transplant failure), graft versus host disease, endotoxin shock, multiple organ failure, psoriasis, burn from exposure to fire, chemicals or radiation, eczema, dermatitis, skin graft, ischemia, ischemic conditions associated with surgery or traumatic injury (e.g., vehicle accident, gunshot wound or limb crush), epilepsy, Alzheimer's disease, Parkinson's disease, immunological response to bacterial or viral infection, cachexia, angiogenic and proliferative diseases, solid tumor, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

In one embodiment, provided herein are methods for modulating the levels of a disease marker in a subject having a JNK1 and/or JNK2-mediated disorder, comprising administering an effective amount of Compound A or a pharmaceutical composition provided herein, to said subject. In some embodiments, the JNK1 and/or JNK2-mediated disorder is pulmonary fibrosis. In some embodiments, the modulation of the disease marker is assessed in a biological sample of the subject, such as in circulating blood, skin biopsies, colon biopsies, synovial tissue, and/or urine. In such embodiments, the amount of disease marker modulation is assessed by comparison of the amount of disease marker before and after administration of Compound A. In some embodiments, the modulation in disease biomarker is a reduction about 5%, 10%, 20%, 25%, 30%, 40%, 50%, 60%, 70%, 75%, 80%, 90%, 95%, 99%, or about 100% compared to baseline levels. In some embodiments, the disease marker is mRNA or protein levels of one or more of matrix metalloproteinase-7, Tenascin C, or Surfactant Protein-D.

In one such embodiment, Compound A is Compound 1. In another embodiment, Compound A is a pharmaceutically acceptable salt of Compound 1. In yet another embodiment, Compound A is a solid form of Compound 1.

5.9. Routes of Administration and Dosage

Pharmaceutical compositions, and dosage forms of Compound A can be administered to a subject orally, topically or parenterally in the conventional form of preparations, such as tablets, granules, powder, troches, pills, suppositories, injections, suspensions, syrups, patches, creams, lotions, ointments, gels, sprays, solutions and emulsions. The effective amount of Compound A in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of Compound A to be administered to a subject is rather widely variable and can be subject to the judgment of a healthcare practitioner. In general, Compound A can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of Compound A administered will depend on such factors as the solubility of the active component, the formulation used and the route of administration. In one embodiment, application of a topical concentration provides intracellular exposures or concentrations of about 0.01-10 μM.

In another embodiment, provided herein are methods for the treatment or prevention of a disease or disorder comprising the administration of a pharmaceutical composition, or dosage form comprising about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of Compound A to a subject in need thereof.

In another embodiment, provided herein are methods for the treatment or prevention of a disease or disorder comprising the administration of a pharmaceutical composition, or dosage form comprising about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day, about 60 mg/day to about 720 mg/day, about 240 mg/day to about 720 mg/day or about 600 mg/day to about 800 mg/day of Compound A to a subject in need thereof. In a particular embodiment, the methods disclosed herein comprise the administration of a pharmaceutical composition, or dosage form comprising about 400 mg/day, about 600 mg/day or about 800 mg/day of Compound A to a subject in need thereof.

In another embodiment, provided herein are methods for the treatment or prevention of a disease or disorder comprising the administration of a pharmaceutical composition, or dosage form comprising about 10 mg/day to about 720 mg/day, about 10 mg/day to about 480 mg/day, about 60 mg/day to about 720 mg/day or about 240 mg/day to about 720 mg/day of Compound A to a subject in need thereof.

In one embodiment, provided herein are methods for the treatment or prevention of a disease or disorder comprising the administration of a pharmaceutical composition, or dosage form comprising about 10 mg/day, about 30 mg/day, about 60 mg/day, about 100 mg/day, about 120 mg/day, about 240 mg/day, about 480 mg/day, or about 720 mg/day of Compound A to a subject in need thereof. In one embodiment, provided herein are methods for the treatment or prevention of a disease or disorder comprising the administration of a pharmaceutical composition, or dosage form comprising about 60 mg/day, about 160 mg/day, or about 400 mg/day of Compound A to a subject in need thereof. In one embodiment, provided herein are methods for the treatment or prevention of a disease or disorder comprising the administration of a pharmaceutical composition, or dosage form comprising about 100 mg/day, or about 200 mg/day of Compound A to a subject in need thereof. In another embodiment, provided herein are methods for the treatment or prevention of a disease or disorder comprising the administration of a pharmaceutical composition, or dosage form comprising about 100 mg/day of Compound A to a subject in need thereof. In another embodiment, provided herein are methods for the treatment or prevention of a disease or disorder comprising the administration of a pharmaceutical composition, or dosage form comprising about 200 mg/day of Compound A to a subject in need thereof. In one embodiment, provided herein are methods for the treatment or prevention of a disease or disorder comprising the administration of a pharmaceutical composition, or dosage form comprising about 10 mg/day, about 30 mg/day, about 60 mg/day, about 120 mg/day, about 160 mg/day, about 200 mg/day, about 240 mg/day, about 400 mg/day, about 480 mg/day, or about 720 mg/day of Compound A to a subject in need thereof.

In another embodiment, provided herein are unit dosage formulations that comprise between about 10 mg and about 100 mg, about 1 mg and about 200 mg, about 30 mg and about 200 mg, about 35 mg and about 1400 mg, about 125 mg and about 1000 mg, about 250 mg and about 1000 mg, or about 500 mg and about 1000 mg of Compound A.

In another embodiment, provided herein are unit dosage formulations that comprise about 1 mg, about 5 mg, about 10 mg, about 15 mg, about 20 mg, about 30 mg, about 35 mg, about 50 mg, about 60 mg, about 70 mg, about 100 mg, about 120 mg, about 125 mg, about 140 mg, about 175 mg, about 200 mg, about 240 mg, about 250 mg, about 280 mg, about 350 mg, about 480 mg, about 500 mg, about 560 mg, about 700 mg, about 720 mg, about 750 mg, about 1000 mg or about 1400 mg of Compound A.

In another embodiment, provided herein are unit dosage forms that comprise about 30 mg, about 100 mg or about 200 mg of Compound A.

Pharmaceutical compositions, and dosage forms of Compound A can be administered once, twice, three, four or more times daily. In one embodiment, pharmaceutical compositions, and dosage forms of Compound A can be administered once daily for 14 days.

Pharmaceutical compositions, and dosage forms of Compound A can be administered orally for reasons of convenience. In one embodiment, when administered orally, pharmaceutical compositions, and dosage forms of Compound A are administered with a meal and water. In another embodiment, pharmaceutical compositions, and dosage forms of Compound A (e.g., granules or dispersible tablets) are dispersed in water or juice (e.g., apple juice or orange juice) and administered orally as a suspension.

Pharmaceutical compositions, and dosage forms of Compound A can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one such embodiment, Compound A is Compound 1. In another embodiment, Compound A is a pharmaceutically acceptable salt of Compound 1. In yet another embodiment, Compound A is a solid form of Compound 1.

5.10. Process for Making Dosage Forms

Dosage forms provided herein can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent.

In some embodiments, the active ingredients and excipients are directly blended and compressed directly into tablets. A direct-blended dosage form may be more advantageous than a compacted (e.g., roller-compacted) dosage form in certain instances, since direct-blending can reduce or eliminate the harmful health effects that may be caused by airborne particles of ingredients during the manufacture using compaction process.

Direct blend formulations may be advantageous in certain instances because they require only one blending step, that of the active and excipients, before being processed into the final dosage form, e.g., tablet. This can reduce the production of airborne particle or dust to a minimum, while roller-compaction processes may be prone to produce dust. In roller-compaction process, the compacted material is often milled into smaller particles for further processing. The milling operation can produce significant amounts of airborne particles, since the purpose for this step in manufacturing is to reduce the materials particle size. The milled material is then blended with other ingredients prior to manufacturing the final dosage form.

For certain active ingredients, in particular for a compound with a low solubility, the active ingredient's particle size is reduced to a fine powder in order to help increase the active ingredient's rate of solubilization. The increase in the rate of solubilization is often necessary for the active ingredient to be effectively absorbed in the gastrointestinal tract. However for fine powders to be directly-blended and compressed to tablets, the excipients should preferably provide certain characteristics which render the ingredients suitable for the direct-blend process. Examples of such characteristics include, but are not limited to, acceptable flow characteristics. In one embodiment, therefore, provided herein is the use of, and compositions comprising, excipients which may provide characteristics, which render the resulting mixture suitable for direct-blend process, e.g., good flow characteristics.

In certain embodiments, provided herein are methods for preparing a composition provided herein, comprising: (i) weighing out the desired amount of Compound A and the desired amount of a first portion of excipients; (ii) preparing an aqueous solution of surfactant(s); (iii) passing the mixture of Compound A and the first portion of the excipients without the surfactant(s) through a screen; (iv) mixing or blending Compound A, the aqueous solution of surfactant(s) and the first portion of the excipients; (v) drying the mixture; (vi) passing a second portion of the excipients through a screen; (vii) mixing or blending the mixture of step (v) and the second portion of the excipients; (viii) weighing out the desired amount of lubricating agents; (ix) passing the lubricating agents through a screen; (x) mixing or blending the mixture of step (vii) and the lubricating agents; (xi) compressing the mixture of step (x); and (ix) coating the compressed mixture with a coating agent. In one embodiment, the mixture of Compound A, the excipients and the lubricating agents is compressed into a tablet form. In one embodiment, the screen is 18 mesh screen. In another embodiment, the screen is 1000 µm screen. In one embodiment, the screen is 20 mesh screen. In another embodiment, the screen is 841 µm screen. In one embodiment, the screen is 30 mesh screen. In another embodiment, the screen is 595 µm screen.

In one such embodiment, Compound A is Compound 1. In another embodiment, Compound A is a pharmaceutically acceptable salt of Compound 1. In yet another embodiment, Compound A is a solid form of Compound 1.

5.11. Dissolution Profiles

In certain embodiments, the tablets comprising Compound A provided herein have a dissolution profile wherein about A00% of Compound A is released in about 10-20 minutes, about 30-40 minutes, about 50-60 minutes, about 70-80 minutes, about 90-100 minutes or about 110-120 minutes in a 0.1N HCl aqueous solution, a 0.01N HCl aqueous solution or an aqueous buffer solution of about pH 4.5.

In certain embodiments, the tablets comprising Compound A provided herein have a dissolution profile wherein about 50% of Compound A is released in about 5-10 minutes in a 0.1N HCl aqueous solution.

In certain embodiments, the tablets comprising Compound A provided herein have a dissolution profile wherein about 50% of Compound A is released in about 8 minutes in a 0.1N HCl aqueous solution.

In certain embodiments, the tablets comprising Compound A provided herein have a dissolution profile wherein about 50% of Compound A is released in about 1-5 minutes in a 0.01N HCl aqueous solution.

In certain embodiments, the tablets comprising Compound A provided herein have a dissolution profile wherein about 50% of Compound A is released in about 3 minutes in a 0.01N HCl aqueous solution.

In certain embodiments, the tablets comprising Compound A provided herein have a dissolution profile wherein about 50% of Compound A is released in about 10-15 minutes in an aqueous buffer solutions of about pH 4.5.

In certain embodiments, the tablets comprising Compound A provided herein have a dissolution profile wherein about 50% of Compound A is released in about 12 minutes in an aqueous buffer solutions of about pH 4.5.

In one such embodiment, Compound A is Compound 1. In another embodiment, Compound A is a pharmaceutically acceptable salt of Compound 1. In yet another embodiment, Compound A is a solid form of Compound 1.

5.12. Salts of Compound 1

Further provided herein are pharmaceutically acceptable salts of Compound 1, including hydrochloride, sulfate, phosphate, L-tartrate, L-malate, L-lactate, succinate, p-toluenesulfate (tosylate), methanesulfate (mesylate), benzensulfate (besylate), fumarate and citrate salts.

In certain embodiments, the pharmaceutical compositions and dosage forms of Compound A comprise one or more pharmaceutically acceptable salts of Compound 1, including hydrochloride, sulfate, phosphate, L-tartrate, L-malate, L-lactate, succinate, p-toluenesulfate (tosylate), methanesulfate (mesylate), benzensulfate (besylate), fumarate and citrate salts.

In certain embodiments, the methods of use provided herein comprise the administration of one or more pharmaceutically acceptable salts of Compound 1, including hydrochloride, sulfate, phosphate, L-tartrate, L-malate, L-lactate, succinate, p-toluenesulfate (tosylate), methanesulfate (mesylate), benzensulfate (besylate), fumarate and citrate salts.

The salts provided herein (e.g., the HCl salt, $H_2SO_4$ salt, $H_3PO_4$ salt, L-tartrate salt, L-lactate salt, L-malate salt, citrate salt, succinate salt, tosylate salt, mesylate salt, besylate salt and fumarate salt of Compound 1) may be characterized using a number of methods known to a person skilled in the art, including, but not limited to, single crystal X-ray diffraction, X-ray powder diffraction (XRPD), microscopy (e.g., scanning electron microscopy (SEM), polarized light microscopy (PLM) and hot-stage microscopy)), thermal analysis (e.g., differential scanning calorimetry (DSC)), dynamic vapor sorption (DVS), thermal gravimetric analysis (TGA), spectroscopy (e.g., infrared, Raman, and solid-state nuclear magnetic resonance), ultra-high performance liquid chromatography (UHPLC), and proton nuclear magnetic resonance ($^1$H NMR) spectrum. The particle size and size distribution of the salt provided herein may be determined by conventional methods, such as laser light scattering technique.

It should be understood that the numerical values of the peaks of an X-ray powder diffraction pattern may vary slightly from one machine to another or from one sample to another, and so the values quoted are not to be construed as absolute, but with an allowable variability, such as ±0.2° 2θ (see United State Pharmacopoeia, page 2228 (2003)).

In certain embodiments, provided herein are evaporation methods for making a salt of Compound 1, comprising 1) dissolving Compound 1 in a solvent to yield a solution; 2) adding an acidic counter-ion; 3) evaporating the solution to yield a solid; and 4) collecting the solid. In certain embodiments, the solvent is ACN, EtOH, EtOAc, Hexane, IPA MeOAc, MTBE, $MeNO_2$ or acetone. In certain embodiments, the acidic counter-ion is provided by HCl, $H_2SO_4$, $H_3PO_4$, L-tartaric acid, L-lactic acid, L-malic acid, citric acid, succinic acid, p-toluenesulfonic acid, methanesulfonic acid, benzenesulfonic acid or fumaric acid.

5.13. HCl Salt of Compound 1

In one embodiment, provided herein is an HCl salt of Compound 1. In certain embodiments, the HCl salt has 7 different forms.

In certain embodiments, the HCl salt is prepared by evaporation of a solution comprising Compound 1 and HCl. In certain embodiments, the HCl salt is prepared by evaporation of a solution comprising Compound 1 and HCl in EtOH/IPA, IPA, EtOAc, acetone or water.

In one embodiment, HCl salt form 1 is a hydrate prepared by evaporation of a solution comprising Compound 1 and HCl in ACN, suspension in SGF or exposure to moisture.

In one embodiment, HCl salt form 2 contains water and is prepared by evaporation of a solution comprising Compound 1 and HCl in EtOH/IPA or IPA. In one embodiment, HCl salt form 2 is converted to a hydrate when exposed to moisture (to HCl salt form 1) or suspended in water (to HCl salt form 7).

In one embodiment, HCl salt form 3 is prepared by evaporation of a solution comprising Compound 1 and HCl in EtOAc.

In one embodiment, HCl salt form 4 is prepared by evaporation of a solution comprising Compound 1 and HCl in acetone.

In one embodiment, HCl salt form 5 is prepared through heating HCl salt form 2 to 180° C. In one embodiment, HCl salt form 5 is converted to a hydrate (HCl salt form 1) when exposed to moisture.

In one embodiment, HCl salt form 6 is a dehydrated hydrate. In one embodiment, HCl salt form 6 is prepared by heating HCl salt form 2 to 220° C. In one embodiment, HCl salt form 6 is converted to a hydrate (HCl salt form 1) when exposed to moisture.

In one embodiment, HCl salt form 7 is a hydrate. In one embodiment, HCl salt form 7 is prepared by suspending HCl salt form 1 in water at ambient temperature.

In one embodiment, the HCl salt is a solid. In one embodiment, the HCl salt is crystalline. In one embodiment, the HCl salt is anhydrous. In one embodiment, the HCl salt is hygroscopic. In another embodiment, the HCl salt is a hydrate. In another embodiment, the HCl salt form 1 is a monohydrate.

In one embodiment, HCl salt form 2 has a TGA thermogram corresponding substantially to the representative TGA thermogram as depicted in FIG. 34. In certain embodiments, HCl salt form 2 exhibits a TGA thermogram comprising a total mass loss of approximately 2.82% of the total mass of the sample between approximately 25° C. and approximately 119.9° C. when heated from approximately 25° C. to approximately 300° C. Thus, in certain embodiments, HCl salt form 2 loses about 2.82% of its total mass when heated from about ambient temperature to about 300° C.

In one embodiment, HCl salt form 2 has a DSC thermogram as depicted in FIG. 34 comprising an endothermic event at 163.0° C. when heated from approximately 25° C. to approximately 300° C. In one embodiment, the DSC thermogram further comprises a melt and decomposition event with an onset temperature of about 220° C. when heated from approximately 25° C. to approximately 300° C.

In one embodiment, HCl salt form 2 has a DVS isotherm plot substantially as depicted in FIG. 41.

In certain embodiments, solid forms provided herein, e.g., HCl salt forms 1-4, are substantially crystalline, as indicated by, e.g., X-ray powder diffraction measurements. In one embodiment, HCl salt forms 1-4 have X-ray powder diffraction patterns substantially as shown in FIG. 6.

In one embodiment, HCl salt forms 1-4 have Raman spectra substantially as depicted in FIG. 7.

In certain embodiments, a solid form provided herein, e.g., HCl salt form 1, is substantially crystalline, as indicated by, e.g., X-ray powder diffraction measurements. In one embodiment, HCl salt form 1 has an X-ray powder diffraction pattern substantially as shown in FIG. 75. In one embodiment, HCl salt form 1 has one or more characteristic X-ray powder diffraction peaks at approximately 5.5, 7.5, 9.0, 9.7, 11.2, 13.1, 13.9, 15.9, 16.5, 17.2, 17.3, 18.3, 19.6, 19.8, 21.7, 22.0, 22.9, 23.7, 24.6, 24.9, 25.9, 26.4, 27.3, 27.7, 28.2, 28.5, 29.9, 30.6, 31.0, 31.2, 31.7, 32.0, 32.6, 33.0, 33.4, 33.7, 34.2, 36.3, 37.8 or 38.8° 2θ as depicted in FIG. 75. In a specific embodiment, HCl salt form 1 has one, two, three, four, five, six, seven or eight characteristic X-ray powder diffraction peaks at approximately 5.5, 11.2, 17.2, 17.3, 18.3, 19.6, 21.7 or 23.7° 2θ. In another embodiment, HCl salt form 1 has one, two, three, four or five characteristic X-ray powder diffraction peaks at approximately 5.5, 13.1, 18.3, 19.6 or 21.7° 2θ. In another embodiment, HCl salt form 1 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine or forty characteristic X-ray powder diffraction peaks as set forth in Table 32.

In certain embodiments, a solid form provided herein, e.g., HCl salt form 2, is substantially crystalline, as indicated by, e.g., X-ray powder diffraction measurements. In one embodiment, HCl salt form 2 has an X-ray powder diffraction pattern substantially as shown in FIG. 76. In one embodiment, HCl salt form 2 has one or more characteristic X-ray powder diffraction peaks at approximately 5.37, 7.92, 9.23, 9.53, 11.95, 12.40, 12.61, 13.09, 14.90, 15.69, 16.52, 17.92, 18.17, 18.64, 18.94, 20.54, 20.69, 20.93, 21.36, 21.69, 22.05, 22.80, 23.55, 24.28, 24.71, 25.09, 25.25, 25.78, 25.99, 27.02, 28.42, 28.87, 29.63, 30.74, 31.58, 31.87, 32.33, 32.76, 33.35, 34.02, 35.10, 36.06, 36.61, 37.00, 37.86, 38.10, 39.16 or 39.92° 2θ as depicted in FIG. 76. In a specific embodiment, HCl salt form 2 has one, two, three, four, five, six, seven or eight characteristic X-ray powder diffraction peaks at approximately 7.92, 9.23, 18.64, 18.94, 20.69, 25.25, 27.02 or 29.63° 2θ. In another embodiment, HCl salt form 2 has one, two, three, four or five characteristic X-ray powder diffraction peaks at approximately 7.92, 9.23, 18.94, 20.69 or 29.63° 2θ. In another embodiment, HCl salt form 2 has one, two, three, four or five characteristic X-ray powder diffraction peaks at approximately 7.92, 9.23, 11.95, 12.40 or 18.94° 2θ. In another embodiment, HCl salt form 2 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven or forty-eight characteristic X-ray powder diffraction peaks as set forth in Table 33.

In certain embodiments, a solid form provided herein, e.g., HCl salt form 3, is substantially crystalline, as indicated by, e.g., X-ray powder diffraction measurements. In one embodiment, HCl salt form 3 has an X-ray powder diffraction pattern substantially as shown in FIG. 77. In one embodiment, HCl salt form 3 has one or more characteristic X-ray powder diffraction peaks at approximately 5.71, 9.48, 9.85, 11.34, 13.24, 14.10, 16.75, 17.86, 18.44, 19.67, 21.82, 23.10, 23.84, 25.03, 26.04, 27.81, 30.65, 31.83 or 38.91° 2θ as depicted in FIG. 77. In a specific embodiment, HCl salt form 3 has one, two, three, four, five, six, seven or eight characteristic X-ray powder diffraction peaks at approximately 5.71, 9.85, 11.34, 13.24, 16.75, 18.44, 19.67 or 21.82° 2θ. In another embodiment, HCl salt form 3 has one, two, three, four or five characteristic X-ray powder diffraction peaks at approximately 5.71, 11.34, 13.24, 16.75 or 18.44° 2θ. In another embodiment, HCl salt form 3 has one, two, three, four or five characteristic X-ray powder diffraction peaks at approximately 5.71, 9.48, 11.34, 13.24 or 18.44° 2θ. In another embodiment, HCl salt form 3 has one, two, three, four, five, six, seven, eight, nine, ten, eleven, twelve, thirteen, fourteen, fifteen, sixteen, seventeen, eighteen or nineteen characteristic X-ray powder diffraction peaks as set forth in Table 34.

In certain embodiments, a solid form provided herein, e.g., HCl salt form 4, is substantially crystalline, as indicated by, e.g., X-ray powder diffraction measurements. In one embodiment, HCl salt form 4 has an X-ray powder diffraction pattern substantially as shown in FIG. 78. In one embodiment, HCl salt form 4 has one or more characteristic X-ray powder diffraction peaks at approximately 5.65, 5.73, 7.50, 9.31, 9.77, 11.38, 13.77, 14.23, 16.20, 17.16, 17.54, 18.16, 18.69, 19.06, 20.56, 21.65, 21.75, 22.10, 22.65, 23.05, 24.04, 26.18, 28.30, 28.45, 28.70, 29.59, 30.90, 32.47 or 35.63° 2θ as depicted in FIG. 78. In a specific embodiment, HCl salt form 4 has one, two, three, four, five, six, seven or eight characteristic X-ray powder diffraction peaks at approximately 5.65, 5.73, 9.77, 11.38, 13.77, 17.16, 21.65 or 29.59° 2θ. In another embodiment, HCl salt form 4 has one, two, three, four or five characteristic X-ray powder diffraction peaks at approximately 5.65, 5.73, 9.77, 11.38 or 13.77° 2θ. In another embodiment, HCl salt form 4 has one, two, three, four or five characteristic X-ray powder diffraction peaks at approximately 5.65, 9.77, 11.38, 13.77 or 21.65° 2θ. In another embodiment, HCl salt form 4 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight or twenty-nine characteristic X-ray powder diffraction peaks as set forth in Table 35.

In certain embodiments, a solid form provided herein, e.g., HCl salt form 5, is substantially crystalline, as indicated by, e.g., X-ray powder diffraction measurements. In one embodiment, HCl salt form 5 has an X-ray powder diffraction pattern substantially as shown in FIG. 79. In one embodiment, HCl salt form 5 has one or more characteristic X-ray powder diffraction peaks at approximately 5.63, 6.29, 7.61, 8.45, 9.74, 10.76, 11.27, 12.23, 12.59, 13.16, 14.02, 14.63, 15.97, 16.63, 16.92, 17.35, 17.74, 18.40, 18.69, 19.10, 19.66, 21.80, 22.63, 23.05, 23.80, 24.58, 24.98, 25.94, 26.51, 27.78, 28.25, 28.57, 30.62, 31.38, 31.78, 32.61, 33.01, 33.40, 35.40, 37.88 or 38.82° 2θ as depicted in FIG. 79. In a specific embodiment, HCl salt form 5 has one, two, three, four, five, six, seven or eight characteristic X-ray powder diffraction peaks at approximately 5.63, 17.35, 18.40, 18.69, 19.66, 21.80, 23.80 or 25.94° 2θ. In another embodiment, HCl salt form 5 has one, two, three, four or five characteristic X-ray powder diffraction peaks at approximately 5.63, 18.69, 19.66, 21.80 or 23.80° 2θ. In another embodiment, HCl salt form 5 has one, two, three, four or five characteristic X-ray powder diffraction peaks at approximately 5.63, 8.45, 10.76, 14.63 or 21.80° 2θ. In another embodiment, HCl salt form 5 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty or forty-one characteristic X-ray powder diffraction peaks as set forth in Table 36.

In certain embodiments, a solid form provided herein, e.g., HCl salt form 6, is substantially crystalline, as indicated by, e.g., X-ray powder diffraction measurements. In one embodiment, HCl salt form 6 has an X-ray powder diffraction pattern substantially as shown in FIG. 80. In one embodiment, HCl salt form 6 has one or more characteristic X-ray powder diffraction peaks at approximately 5.58, 7.61, 8.27, 9.13, 9.74, 11.19, 13.14, 13.99, 15.91, 16.65, 16.87, 17.33, 18.38, 19.67, 19.92, 21.79, 21.99, 23.03, 23.32, 23.77, 24.66, 24.97, 25.33, 25.92, 26.52, 27.38, 27.76, 28.24, 28.54, 30.62, 31.34, 31.74, 32.63, 33.04, 33.47, 36.38, 37.83 or 38.79° 2θ as depicted in FIG. 80. In a specific embodiment, HCl salt form 6 has one, two, three, four, five, six, seven or eight characteristic X-ray powder diffraction peaks at approximately 5.58, 11.19, 13.14, 17.33, 18.38, 19.67, 21.79 or 23.77° 2θ. In another embodiment, HCl salt form 6 has one, two, three, four or five characteristic X-ray powder diffraction peaks at approximately 5.58, 17.33, 18.38, 19.67 or 21.79° 2θ. In another embodiment, HCl salt form 6 has one, two, three, four or five characteristic X-ray powder diffraction peaks at approximately 5.58, 8.27, 18.38, 19.67 or 21.79° 2θ. In another embodiment, HCl salt form 6 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven or thirty-eight characteristic X-ray powder diffraction peaks as set forth in Table 37.

In certain embodiments, a solid form provided herein, e.g., HCl salt form 7, is substantially crystalline, as indicated by, e.g., X-ray powder diffraction measurements. In one embodiment, HCl salt form 7 has an X-ray powder diffraction pattern substantially as shown in FIG. 81. In one embodiment, HCl salt form 7 has one or more characteristic X-ray powder diffraction peaks at approximately 5.54, 7.61, 8.95, 9.85, 11.14, 12.86, 14.14, 15.77, 16.83, 17.29, 17.51, 18.04, 18.33, 18.69, 19.82, 21.94, 23.05, 23.90, 28.28, 30.66, 32.02 or 38.98° 2θ as depicted in FIG. 81. In a specific embodiment, HCl salt form 7 has one, two, three, four, five, six, seven or eight characteristic X-ray powder diffraction peaks at approximately 5.54, 7.61, 11.14, 18.04, 19.82, 21.94, 23.05 or 38.98° 2θ. In another embodiment, HCl salt form 7 has one, two, three, four or five characteristic X-ray powder diffraction peaks at approximately 5.54, 7.61, 18.04, 19.82 or 23.05° 2θ. In another embodiment, HCl salt form 7 has one, two, three, four or five characteristic X-ray powder diffraction peaks at approximately 5.54, 7.61, 8.95, 12.86 or 18.04° 2θ. In another embodiment, HCl salt form 7 has one, two, three, four, five, six, seven, eight, nine, ten, eleven, twelve, thirteen, fourteen, fifteen, sixteen, seventeen, eighteen, nineteen, twenty, twenty-one or twenty-two characteristic X-ray powder diffraction peaks as set forth in Table 38.

5.14. $H_2SO_4$ Salt of Compound 1

In one embodiment, provided herein is an $H_2SO_4$ salt of Compound 1. In certain embodiments, the $H_2SO_4$ salt has 3 different forms.

In one embodiment, $H_2SO_4$ salt form 1 is prepared by evaporation of a solution comprising Compound 1 and $H_2SO_4$ in ACN, IPA or EtOAc.

In one embodiment, $H_2SO_4$ salt form 2 is prepared by evaporation of a solution comprising Compound 1 and $H_2SO_4$ in acetone.

In one embodiment, $H_2SO_4$ salt form 3 is prepared by storing form 1 at 80° C. and 75% relative humidity. In one embodiment, $H_2SO_4$ salt form 3 is prepared by storing form 1 at 80° C. and 75% relative humidity for 2 weeks.

In one embodiment, the $H_2SO_4$ salt is a solid. In one embodiment, the $H_2SO_4$ salt is crystalline. In one embodiment, the $H_2SO_4$ salt is anhydrous. In one embodiment, the $H_2SO_4$ salt is hygroscopic. In another embodiment, the $H_2SO_4$ salt is a hydrate.

In certain embodiments, the $H_2SO_4$ salt is prepared by evaporation. In one embodiment, the $H_2SO_4$ salt is prepared by evaporation of a solution comprising Compound 1 and $H_2SO_4$ in ACN, IPA, EtOAc or acetone.

In one embodiment, $H_2SO_4$ salt form 1 has a TGA thermogram corresponding substantially to the representative TGA thermogram as depicted in FIG. 35. In certain embodiments, $H_2SO_4$ form 1 salt exhibits a TGA thermogram comprising a total mass loss of approximately 0.28% of the total mass of the sample between approximately 25° C. and approximately 119.9° C. when heated from approximately 25° C. to approximately 300° C. Thus, in certain embodiments, $H_2SO_4$ salt form 1 loses about 0.28% of its total mass when heated from about ambient temperature to about 300° C.

In one embodiment, $H_2SO_4$ salt form 1 has a DSC thermogram as depicted in FIG. 35 comprising an $T_g$-like event between about 86.0° C. and 88.4° C. when heated from approximately 25° C. to approximately 300° C. In one embodiment, the DSC thermogram further comprises a melting and decomposition event with an onset temperature of about 235° C. when heated from approximately 25° C. to approximately 300° C.

In one embodiment, $H_2SO_4$ salt form 1 has a DVS isotherm plot substantially as depicted in FIG. 43.

In certain embodiments, solid forms provided herein, e.g., $H_2SO_4$ salt forms 1-3, are substantially crystalline, as indicated by, e.g., X-ray powder diffraction measurements. In one embodiment, $H_2SO_4$ salt forms 1-2 have X-ray powder diffraction patterns substantially as shown in FIG. 8. In another embodiment, the $H_2SO_4$ salt form 3 has an X-ray powder diffraction pattern substantially as shown in FIG. 84.

In one embodiment, $H_2SO_4$ salt forms 1-2 have Raman spectra substantially as depicted in FIG. 9.

In certain embodiments, a solid form provided herein, e.g., $H_2SO_4$ salt form 1, is substantially crystalline, as indicated by, e.g., X-ray powder diffraction measurements. In one embodiment, $H_2SO_4$ salt form 1 has an X-ray powder diffraction pattern substantially as shown in FIG. 82. In one embodiment, $H_2SO_4$ salt form 1 has one or more characteristic X-ray powder diffraction peaks at approximately 5.40, 5.66, 9.02, 10.74, 14.78, 16.16, 16.65, 17.65, 18.18, 18.69, 19.67, 20.50, 21.62, 22.28, 22.75, 24.13, 24.57, 24.88, 25.42, 26.55, 28.49, 29.17, 29.88, 31.29, 32.15, 32.66, 33.21, 34.02, 35.78, 36.86, 37.43, 38.27 or 39.64° 2θ as depicted in FIG. 82. In a specific embodiment, $H_2SO_4$ salt form 1 has one, two, three, four, five, six, seven or eight characteristic X-ray powder diffraction peaks at approximately 5.40, 10.74, 18.18, 18.69, 21.62, 22.28, 22.75 or 26.55° 2θ. In another embodiment, $H_2SO_4$ salt form 1 has one, two, three, four or five characteristic X-ray powder diffraction peaks at approximately 5.40, 18.18, 18.69, 21.62 or 22.28° 2θ. In another embodiment, $H_2SO_4$ salt form 1 has one, two, three, four or five characteristic X-ray powder diffraction peaks at approximately 5.40, 10.74, 18.18, 18.69 or 22.28° 2θ. In another embodiment, $H_2SO_4$ salt form 1 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine or forty characteristic X-ray powder diffraction peaks as set forth in Table 39.

In certain embodiments, a solid form provided herein, e.g., $H_2SO_4$ salt form 2, is substantially crystalline, as indicated by, e.g., X-ray powder diffraction measurements. In one embodiment, $H_2SO_4$ salt form 2 has an X-ray powder diffraction pattern substantially as shown in FIG. 83. In one embodiment, $H_2SO_4$ salt form 2 has one or more characteristic X-ray powder diffraction peaks at approximately 5.63, 5.67, 15.25, 16.08, 17.87, 18.57, 21.83, 22.24, 22.75, 25.90, 26.53 or 27.18° 2θ as depicted in FIG. 83. In a specific embodiment, $H_2SO_4$ salt form 2 has one, two, three, four, five, six, seven or eight characteristic X-ray powder diffraction peaks at approximately 5.63, 5.67, 15.25, 16.08, 17.87, 18.57, 22.24 or 22.75° 2θ. In another embodiment, $H_2SO_4$ salt form 2 has one, two, three, four or five characteristic X-ray powder diffraction peaks at approximately 5.63, 5.67, 17.87, 18.57 or 22.75° 2θ. In another embodiment, $H_2SO_4$ salt form 2 has one, two, three, four or five characteristic X-ray powder diffraction peaks at approximately 5.63, 11.30, 15.25, 17.87 or 18.57° 2θ. In another embodiment, $H_2SO_4$ salt form 2 has one, two, three, four, five, six, seven, eight, nine, ten, eleven or twelve characteristic X-ray powder diffraction peaks as set forth in Table 40.

In certain embodiments, a solid form provided herein, e.g., $H_2SO_4$ salt form 3, is substantially crystalline, as indicated by, e.g., X-ray powder diffraction measurements. In one embodiment, $H_2SO_4$ salt form 3 has an X-ray powder diffraction pattern substantially as shown in FIG. 84. In one embodiment, $H_2SO_4$ salt form 3 has one or more characteristic X-ray powder diffraction peaks at approximately 5.60, 10.68, 11.22, 12.41, 13.81, 15.11, 15.96, 16.86, 17.67, 18.10, 18.48, 18.78, 19.15, 21.53, 22.10, 22.38, 22.61, 23.65, 24.56, 25.22, 25.85, 26.27, 27.24, 33.38, 34.20 or 37.96° 2θ as depicted in FIG. 84. In a specific embodiment, $H_2SO_4$ salt form 3 has one, two, three, four, five, six, seven or eight characteristic X-ray powder diffraction peaks at approximately 5.60, 17.67, 11.22, 22.38, 15.11, 18.10, 22.61, 22.10, 27.24, 10.68, 18.48, or 15.96° 2θ. In another embodiment, $H_2SO_4$ salt form 3 has one, two, three, four or five characteristic X-ray powder diffraction peaks at approximately 5.60, 17.67, 11.22, 22.38, or 15.11° 2θ. In another embodiment, $H_2SO_4$ salt form 2 has one, two, three, four or five characteristic X-ray powder diffraction peaks at approximately 5.60, 11.22, 15.11, 15.96, 17.67 or 19.15° 2θ. In another embodiment, $H_2SO_4$ salt form 3 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five or twenty-six characteristic X-ray powder diffraction peaks as set forth in Table 41.

5.15. $H_3PO_4$ Salt of Compound 1

In one embodiment, provided herein is an $H_3PO_4$ salt.

In one embodiment, the $H_3PO_4$ salt is a solid. In one embodiment, the $H_3PO_4$ salt is crystalline. In one embodiment, the $H_3PO_4$ salt is anhydrous. In one embodiment, the $H_3PO_4$ salt is not hygroscopic.

In certain embodiments, the $H_3PO_4$ salt provided herein is prepared by evaporation of a solution comprising Compound 1 and $H_3PO_4$. In one embodiment, the $H_3PO_4$ salt is prepared by evaporation of a solution comprising Compound 1 and $H_3PO_4$ in ACN, IPA, EtOAc or acetone.

In one embodiment, the $H_3PO_4$ salt has a TGA thermogram corresponding substantially to the representative TGA thermogram as depicted in FIG. 36. In certain embodiments, the $H_3PO_4$ salt exhibits a TGA thermogram comprising a total mass loss of approximately 0.25% of the total mass of the sample between approximately 25° C. and approximately 119.9° C. when heated from approximately 25° C. to approximately 300° C. Thus, in certain embodiments, the $H_3PO_4$ salt loses about 0.25% of its total mass when heated from about ambient temperature to about 300° C.

In one embodiment, the $H_3PO_4$ salt has a DSC thermogram as depicted in FIG. 36 comprising a dehydration event with an onset temperature of about 169.9° C. when heated from approximately 25° C. to approximately 300° C. In one embodiment, the DSC thermogram further comprises a melting and decomposition event with an onset temperature of about 238.3° C. when heated from approximately 25° C. to approximately 300° C.

In one embodiment, the $H_3PO_4$ salt has a DVS isotherm plot substantially as depicted in FIG. 45.

In certain embodiments, a solid form provided herein, e.g., a $H_3PO_4$ salt, is substantially crystalline, as indicated by, e.g., X-ray powder diffraction measurements. In one embodiment, the $H_3PO_4$ salt has an X-ray powder diffraction pattern substantially as shown in FIG. 10.

In one embodiment, the $H_3PO_4$ salt has a Raman spectrum substantially as depicted in FIG. 11.

In certain embodiments, a solid form provided herein, e.g., $H_3PO_4$ salt, is substantially crystalline, as indicated by, e.g., X-ray powder diffraction measurements. In one embodiment, $H_3PO_4$ salt has an X-ray powder diffraction pattern substantially as shown in FIG. 85. In one embodiment, $H_3PO_4$ salt has one or more characteristic X-ray powder diffraction peaks at approximately 5.58, 5.73, 11.30, 15.27, 16.07, 16.37, 16.95, 17.46, 17.72, 18.37, 20.64, 20.98, 21.73, 22.34, 22.66, 23.31, 23.65, 24.14, 25.88, 26.42, 28.10, 28.39, 29.89, 30.38, 30.88, 31.35, 33.13, 34.32, 35.08, 35.91, 37.43 or 38.89° 2θ as depicted in FIG. 85. In a specific embodiment, $H_3PO_4$ salt has one, two, three, four, five, six, seven or eight characteristic X-ray powder diffraction peaks at approximately 5.58, 5.73, 11.30, 15.27, 16.95, 23.65, 25.88 or 28.39° 2θ. In another embodiment, $H_3PO_4$ salt has one, two, three, four or five characteristic X-ray powder diffraction peaks at approximately 5.58, 5.73, 11.30, 15.27 or 28.39° 2θ. In another embodiment, $H_3PO_4$ salt has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one or thirty-two characteristic X-ray powder diffraction peaks as set forth in Table 50.

5.16. L-Tartrate Salt of Compound 1

In one embodiment, provided herein is an L-tartrate salt of Compound 1.

In one embodiment, the L-tartrate salt is a solid. In one embodiment, the L-tartrate salt is crystalline. In one embodiment, the L-tartrate salt is slightly hygroscopic. In another embodiment, the L-tartrate salt is a hydrate. In another embodiment, the L-tartrate salt is a dihydrate. In another embodiment, the L-tartrate salt is a hemi-tartrate dihydrate.

In certain embodiments, the L-tartrate salt is prepared by evaporation of a solution comprising Compound 1 and L-tartaric acid. In one embodiment, the L-tartrate salt is prepared by evaporation of a solution comprising Compound 1 and L-tartaric acid in ACN, IPA, EtOAc or acetone.

In one embodiment, the stoichiometric ratio for Compound 1 to L-tartaric acid is about 2:1 in the L-tartrate salt.

In one embodiment, the L-tartrate salt has a TGA thermogram corresponding substantially to the representative TGA thermogram as depicted in FIG. 37. In certain embodiments, the L-tartrate salt exhibits a TGA thermogram comprising a total mass loss of approximately 3.97% of the total mass of the sample between approximately 25° C. and approximately 119.9° C. when heated from approximately 25° C. to approximately 300° C. Thus, in certain embodiments, the L-tartrate salt loses about 3.97% of its total mass when heated from about ambient temperature to about 300° C.

In one embodiment, the L-tartrate salt has a DSC thermogram as depicted in FIG. 37 comprising a dehydration event with an onset temperature of about 89.5° C. when heated from approximately 25° C. to approximately 300° C. In one embodiment, the DSC thermogram further comprises a melt and decomposition event with an onset temperature of about 201.5° C. when heated from approximately 25° C. to approximately 300° C.

In one embodiment, the L-tartrate salt has a DVS isotherm plot substantially as depicted in FIG. 47.

In certain embodiments, a solid form provided herein, e.g., a L-tartrate salt, is substantially crystalline, as indicated by, e.g., X-ray powder diffraction measurements. In one embodiment, the L-tartrate salt has an X-ray powder diffraction pattern substantially as shown in FIG. 12.

In one embodiment, the L-tartrate salt has a Raman spectrum substantially as depicted in FIG. 13.

In certain embodiments, a solid form provided herein, e.g., L-tartrate salt form 1, is substantially crystalline, as indicated by, e.g., X-ray powder diffraction measurements. In one embodiment, L-tartrate salt form 1 has an X-ray powder diffraction pattern substantially as shown in FIG. 88. In one embodiment, L-tartrate salt form 1 has one or more characteristic X-ray powder diffraction peaks at approximately 6.04, 9.47, 12.14, 13.73, 14.57, 15.19, 16.19, 16.68, 17.30, 18.27, 19.98, 20.31, 21.14, 22.08, 22.75, 23.21, 23.84, 24.33, 25.92, 26.51, 27.09, 27.75, 28.44, 29.52, 31.15, 31.83, 32.73, 33.31, 34.99, 35.55, 36.80, 37.25, 37.77 or 38.41° 2θ as depicted in FIG. 88. In a specific embodiment, L-tartrate salt form 1 has one, two, three, four, five, six, seven or eight characteristic X-ray powder diffraction peaks at approximately 6.04, 16.19, 16.68, 17.30, 19.98, 20.31, 23.21 or 24.33° 2θ. In another embodiment, L-tartrate salt form 1 has one, two, three, four or five characteristic X-ray powder diffraction peaks at approximately 6.04, 16.19, 16.68, 19.98 or 24.33° 2θ. In another embodiment, L-tartrate salt form 1 has one, two, three, four or five characteristic X-ray powder diffraction peaks at approximately 6.04, 12.14, 16.19, 18.27 or 24.33° 2θ. In another embodiment, L-tartrate salt form 1 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three or thirty-four characteristic X-ray powder diffraction peaks as set forth in Table 51.

In certain embodiments, a solid form provided herein, e.g., L-tartrate salt form 2, is substantially crystalline, as indicated by, e.g., X-ray powder diffraction measurements. In one embodiment, L-tartrate salt form 2 has an X-ray powder diffraction pattern substantially as shown in FIG. 89. In one embodiment, L-tartrate salt form 2 has one or more characteristic X-ray powder diffraction peaks at approximately 5.02, 6.29, 6.46, 9.71, 12.47, 12.63, 15.21, 16.51, 16.56, 17.23, 18.82, 20.72, 22.49, 22.71, 24.04, 24.86, 24.95, 27.08, 28.25, 29.30, 30.78, 31.16, 31.30, 33.13, 33.96, 34.36, 34.87, 35.03, 35.14, 35.29, 36.36 or 36.58° 2θ as depicted in FIG. 89. In a specific embodiment, L-tartrate salt form 2 has one, two, three, four, five, six, seven or eight characteristic X-ray powder diffraction peaks at approximately 6.29, 6.46, 12.63, 16.51, 17.23, 20.72, 24.04 or 24.95° 2θ. In another embodiment, L-tartrate salt form 2 has one, two, three, four or five characteristic X-ray powder diffraction peaks at approximately 6.29, 6.46, 16.51, 20.72 or 24.04° 2θ. In another embodiment, L-tartrate salt form 2 has one, two, three, four or five characteristic X-ray powder diffraction peaks at approximately 6.29, 12.63, 16.51, 18.82 or 24.95° 2θ. In another embodiment, L-tartrate salt form 2 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one or thirty-two characteristic X-ray powder diffraction peaks as set forth in Table 52.

5.17. L-Lactate Salt of Compound 1

In one embodiment, provided herein is an L-lactate salt of Compound 1. In certain embodiments, the L-lactate salt has 2 different forms.

In certain embodiments, the L-lactate salt is prepared by evaporation of a solution comprising Compound 1 and L-lactic acid. In one embodiment, the L-lactate salt is prepared by evaporation of a solution comprising Compound 1 and L-lactic acid in hexane or EtOAc.

In one embodiment, L-lactate salt form 1 is prepared by evaporation of a solution comprising Compound 1 and L-lactic acid in hexane. In one embodiment, L-lactate salt form 2 is prepared by evaporation of a solution comprising Compound 1 and L-lactic acid in EtOAc.

In one embodiment, the L-lactate salt is a solid. In one embodiment, the L-lactate salt is crystalline. In one embodiment, the L-lactate salt is moderately hygroscopic. In another embodiment, the L-lactate salt is a hydrate.

In one embodiment, L-lactate salt form 2 has a TGA thermogram corresponding substantially to the representative TGA thermogram as depicted in FIG. 39. In certain embodiments, L-lactate salt form 1 exhibits a TGA thermogram comprising a total mass loss of approximately 1.74% of the total mass of the sample between approximately 25° C. and approximately 119.9° C. when heated from approximately 25° C. to approximately 300° C. Thus, in certain embodiments, L-lactate salt form 1 loses about 1.74% of its total mass when heated from about ambient temperature to about 300° C.

In one embodiment, L-tartrate salt form 2 has a DSC thermogram as depicted in FIG. 39 comprising a dehydration event with an onset temperature of about 76.5° C. when heated from approximately 25° C. to approximately 300° C. In one embodiment, the DSC thermogram further comprises a melt and decomposition event with an onset temperature of about 145.3° C. when heated from approximately 25° C. to approximately 300° C.

In one embodiment, L-lactate salt form 2 has a DVS isotherm plot substantially as depicted in FIG. 52.

In certain embodiments, solid forms provided herein, e.g., L-lactate salt forms 1-2, are substantially crystalline, as indicated by, e.g., X-ray powder diffraction measurements. In one embodiment, L-lactate salt forms 1-2 have X-ray powder diffraction patterns substantially as shown in FIG. 16.

In one embodiment, L-lactate salt forms 1-2 have Raman spectra substantially as depicted in FIG. 17.

In certain embodiments, a solid form provided herein, e.g., L-lactate salt form 1, is substantially crystalline, as indicated by, e.g., X-ray powder diffraction measurements. In one embodiment, L-lactate salt form 1 has an X-ray powder diffraction pattern substantially as shown in FIG. 86. In one embodiment, L-lactate salt form 1 has one or more characteristic X-ray powder diffraction peaks at approximately 5.77, 7.93, 9.57, 9.81, 10.01, 11.69, 12.09, 12.81, 13.72, 14.39, 14.66, 16.10, 16.89, 17.19, 17.70, 18.89, 19.20, 19.54, 19.72, 20.16, 20.43, 20.96, 21.55, 21.84, 23.12, 24.22, 24.67, 24.92, 25.21, 26.19, 27.06, 28.55, 29.20, 30.43, 32.82, 34.36 or 36.29° 2θ as depicted in FIG. 86. In a specific embodiment, L-lactate salt form 1 has one, two, three, four, five, six, seven or eight characteristic X-ray powder diffraction peaks at approximately 5.77, 9.57, 9.81, 16.10, 18.89, 19.54, 20.16 or 24.22° 2θ. In another embodiment, L-lactate salt form 1 has one, two, three, four or five characteristic X-ray powder diffraction peaks at approximately 5.77, 9.57, 16.10, 19.54 or 20.16° 2θ. In another embodiment, L-lactate salt form 1 has one, two, three, four or five characteristic X-ray powder diffraction peaks at approximately 5.77, 7.93, 16.10, 20.16 or 24.22° 2θ. In another embodiment, L-lactate salt form 1 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six or thirty-seven characteristic X-ray powder diffraction peaks as set forth in Table 53.

In certain embodiments, a solid form provided herein, e.g., L-lactate salt form 2, is substantially crystalline, as indicated by, e.g., X-ray powder diffraction measurements. In one embodiment, L-lactate salt form 2 has an X-ray powder diffraction pattern substantially as shown in FIG. 87. In one embodiment, L-lactate salt form 2 has one or more characteristic X-ray powder diffraction peaks at approximately 9.69, 10.23, 12.14, 12.74, 13.29, 13.51, 15.62, 16.05, 16.29, 16.87, 17.02, 17.55, 18.00, 18.51, 18.97, 19.47, 20.41, 20.98, 21.45, 22.39, 22.64, 23.08, 23.50, 23.84, 24.03, 24.46, 24.88, 25.21, 26.42, 26.86, 27.24, 27.77, 28.23, 28.53, 30.47, 31.04, 31.58, 32.44, 33.93, 35.53, 36.58, 37.11 or 38.68° 2θ as depicted in FIG. 87. In a specific embodiment, L-lactate salt form 2 has one, two, three, four, five, six, seven or eight characteristic X-ray powder diffraction peaks at approximately 9.69, 10.23, 13.29, 17.02, 18.51, 18.97, 19.47 or 20.41° 2θ. In another embodiment, L-lactate salt form 2 has one, two, three, four or five characteristic X-ray powder diffraction peaks at approximately 10.23, 17.02, 18.97, 19.47 or 20.41° 2θ. In another embodiment, L-lactate salt form 2 has one, two, three, four or five characteristic X-ray powder diffraction peaks at approximately 9.69, 10.23, 13.29, 17.02 or 18.97° 2θ. In another embodiment, L-lactate salt form 2 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two or forty-three characteristic X-ray powder diffraction peaks as set forth in Table 54.

5.18. L-Malate Salt of Compound 1

In one embodiment, provided herein is an L-malate salt of Compound 1. In certain embodiments, the L-malate salt has 4 different forms.

In one embodiment, the L-malate salt is a solid. In one embodiment, the L-malate salt is crystalline. In one embodiment, the L-malate salt is hygroscopic. In another embodiment, the L-malate salt is a hydrate.

In certain embodiments, the L-malate salt is prepared by evaporation of a solution comprising Compound 1 and L-malic acid. In one embodiment, the L-malate salt is prepared by evaporation of a solution comprising Compound 1 and L-malic acid in ACN, IPA, EtOAc or acetone.

In one embodiment, L-malate salt form 1 is prepared by evaporation of a solution comprising Compound 1 and L-malic acid in ACN.

In one embodiment, L-malate salt form 2 is prepared by evaporation of a solution comprising Compound 1 and L-malic acid in MeNO$_2$.

In one embodiment, L-malate salt form 3 is prepared by evaporation of a solution comprising Compound 1 and L-malic acid in EtOAc.

In one embodiment, L-malate salt form 4 is prepared by evaporation of a solution comprising Compound 1 and L-malic acid in IPA.

In one embodiment, the stoichiometric ratio for Compound 1 to L-malic acid is about 1:1 in the L-malic salt.

In one embodiment, the L-malate salt form 2 has a TGA thermogram corresponding substantially to the representative TGA thermogram as depicted in FIG. 38. In certain embodiments, the L-malate salt exhibits a TGA thermogram comprising a total mass loss of approximately 1.21% of the total mass of the sample between approximately 25° C. and approximately 94.8° C. when heated from approximately 25° C. to approximately 300° C. Thus, in certain embodiments, the L-malate salt loses about 1.21% of its total mass when heated from about ambient temperature to about 300° C.

In one embodiment, the L-malate salt form 2 has a DSC thermogram as depicted in FIG. 38 comprising a dehydration event with an onset temperature of about 94.8° C. when heated from approximately 25° C. to approximately 300° C. In one embodiment, the DSC thermogram further comprises a solid-solid transition event with an onset temperature of about 100.8° C. when heated from approximately 25° C. to approximately 300° C.

In one embodiment, the L-malate salt form 2 has a DVS isotherm plot substantially as depicted in FIG. 50.

In certain embodiments, solid forms provided herein, e.g., L-malate salt forms 1-4, are substantially crystalline, as indicated by, e.g., X-ray powder diffraction measurements. In one embodiment, L-malate salt forms 1-4 have an X-ray powder diffraction pattern substantially as shown in FIG. 18.

In one embodiment, L-malate forms 1-4 salt have Raman spectra substantially as depicted in FIG. 19.

In certain embodiments, a solid form provided herein, e.g., L-malate salt form 1, is substantially crystalline, as indicated by, e.g., X-ray powder diffraction measurements. In one embodiment, L-malate salt form 1 has an X-ray powder diffraction pattern substantially as shown in FIG. 90. In one embodiment, L-malate salt form 1 has one or more characteristic X-ray powder diffraction peaks at approximately 5.52, 11.12, 15.86 or 17.18° 2θ as depicted in FIG. 90. In another embodiment, L-malate salt form 1 has one, two, three or four characteristic X-ray powder diffraction peaks at approximately 5.52, 11.12, 15.86 or 17.18° 2θ. In another embodiment, L-malate salt form 1 has one, two, three or four characteristic X-ray powder diffraction peaks as set forth in Table 55.

In certain embodiments, a solid form provided herein, e.g., L-malate salt form 2, is substantially crystalline, as indicated by, e.g., X-ray powder diffraction measurements. In one embodiment, L-malate salt form 2 has an X-ray powder diffraction pattern substantially as shown in FIG. 91. In one embodiment, L-malate salt form 2 has one or more characteristic X-ray powder diffraction peaks at approximately 5.48, 6.15, 7.56, 8.50, 8.99, 9.50, 11.08, 12.21, 12.97, 15.23, 16.09, 17.16, 17.50, 18.01, 18.48, 19.21, 19.69, 20.38, 21.09, 21.75, 22.47, 22.72, 23.70, 24.44, 24.96, 25.23, 25.80, 26.20, 26.51, 27.78, 28.41, 30.01, 30.41, 32.95, 34.90, 35.28, 35.91, 36.41 or 37.63° 2θ as depicted in FIG. 91. In a specific embodiment, L-malate salt form 2 has one, two, three, four, five, six, seven or eight characteristic X-ray powder diffraction peaks at approximately 5.48, 6.15, 7.56, 12.97, 15.23, 17.16, 18.48 or 21.09° 2θ. In another embodiment, L-malate salt form 2 has one, two, three, four or five characteristic X-ray powder diffraction peaks at approximately 5.48, 6.15, 7.56, 18.48 or 21.09° 2θ. In another embodiment, L-malate salt form 2 has one, two, three, four or five characteristic X-ray powder diffraction peaks at approximately 5.48, 6.15, 7.56, 15.23 or 21.09° 2θ. In another embodiment, L-malate salt form 2 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight or thirty-nine characteristic X-ray powder diffraction peaks as set forth in Table 56.

In certain embodiments, a solid form provided herein, e.g., L-malate salt form 3, is substantially crystalline, as indicated by, e.g., X-ray powder diffraction measurements. In one embodiment, L-malate salt form 3 has an X-ray powder diffraction pattern substantially as shown in FIG. 92. In one embodiment, L-malate salt form 3 has one or more characteristic X-ray powder diffraction peaks at approximately 4.89, 5.49, 7.25, 11.74, 12.39, 15.76, 16.34, 16.73, 19.79, 20.54 or 21.23° 2θ as depicted in FIG. 92. In a specific embodiment, L-malate salt form 3 has one, two, three, four, five, six, seven or eight characteristic X-ray powder diffraction peaks at approximately 4.89, 5.49, 7.25, 11.74, 12.39, 15.76, 16.73 or 20.54° 2θ. In another embodiment, L-malate salt form 3 has one, two, three, four or five characteristic X-ray powder diffraction peaks at approximately 4.89, 5.49, 7.25, 15.76 or 20.54° 2θ. In another embodiment, L-malate salt form 3 has one, two, three, four or five characteristic X-ray powder diffraction peaks at approximately 4.89, 5.49, 7.25, 11.74 or 15.76° 2θ. In another embodiment, L-malate salt form 3 has one, two, three, four, five, six, seven, eight, nine, ten or eleven characteristic X-ray powder diffraction peaks as set forth in Table 57.

In certain embodiments, a solid form provided herein, e.g., L-malate salt form 4, is substantially crystalline, as indicated by, e.g., X-ray powder diffraction measurements. In one embodiment, L-malate salt form 4 has an X-ray powder diffraction pattern substantially as shown in FIG. 93. In one embodiment, L-malate salt form 4 has one or more characteristic X-ray powder diffraction peaks at approximately 5.91, 8.34, 10.45, 10.91, 12.67, 13.10, 13.48, 15.34, 16.71, 17.49, 17.89, 18.22, 18.72, 18.95, 19.41, 19.84, 20.21, 20.77, 21.22, 21.62, 21.91, 22.60, 23.99, 24.56, 25.03, 26.20, 27.19, 27.52, 28.45, 29.19, 29.60, 29.96, 30.24, 30.99, 31.61, 34.44, 35.66, 36.10, 36.86, 37.19, 37.83, 38.58 or 39.05° 2θ as depicted in FIG. 93. In a specific embodiment, L-malate salt form 4 has one, two, three, four, five, six, seven or eight characteristic X-ray powder diffraction peaks at approximately 5.91, 10.91, 18.22, 18.72, 20.77, 21.22, 21.91 or 26.20° 2θ. In another embodiment, L-malate salt form 4 has one, two, three, four or five characteristic X-ray powder diffraction peaks at approximately 5.91, 10.91, 18.72, 20.77 or 21.22° 2θ. In another embodiment, L-malate salt form 4 has one, two, three, four or five characteristic X-ray powder diffraction peaks at approximately 5.91, 10.91, 12.67, 18.72 or 20.77° 2θ. In another embodiment, L-malate salt form 4 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two or forty-three characteristic X-ray powder diffraction peaks as set forth in Table 58.

5.19. Citrate Salt of Compound 1

In one embodiment, provided herein is a citrate salt of Compound 1.

In one embodiment, the citrate salt is a solid. In one embodiment, the citrate salt is amorphous.

In certain embodiments, the citrate salt is prepared by evaporation of a solution comprising Compound 1 and citric acid in MTBE, MeNO$_2$, hexane or MeOAc.

In one embodiment, the stoichiometric ratio for Compound 1 to citric acid is about 1:1 in the citrate salt.

In certain embodiments, a solid form provided herein, e.g., a citrate salt, is substantially crystalline, as indicated by, e.g., X-ray powder diffraction measurements. In one embodiment, the citrate salt has an X-ray powder diffraction pattern substantially as shown in FIG. 20.

In one embodiment, the citrate salt has a Raman spectrum substantially as depicted in FIG. 21.

5.20. Succinate Salt of Compound 1

In one embodiment, provided herein is a succinate salt of Compound 1. In certain embodiments, the succinate salt has 3 different forms.

In one embodiment, the succinate salt is a solid. In one embodiment, the succinate salt is crystalline.

In certain embodiments, the succinate salt is prepared by evaporation of a solution comprising Compound 1 and succinic acid. In one embodiment, the succinate salt is prepared by evaporation of a solution comprising Compound 1 and succinic acid in ACN, IPA, EtOAc or acetone.

In one embodiment, succinate salt form 1 is prepared by evaporation of a solution comprising Compound 1 and succinic acid in ACN or EtOH. In one embodiment, succinate salt form 2 is prepared by evaporation of a solution comprising Compound 1 and succinic acid in EtOAc.

In certain embodiments, solid forms, e.g., succinate salt forms 1-2, are substantially crystalline, as indicated by, e.g., X-ray powder diffraction measurements. In one embodiment, succinate salt forms 1-2 have X-ray powder diffraction patterns substantially as shown in FIG. 22.

In one embodiment, succinate salt forms 1-2 have Raman spectra substantially as depicted in FIG. 23.

In certain embodiments, a solid form provided herein, e.g., succinate salt form 1, is substantially crystalline, as indicated by, e.g., X-ray powder diffraction measurements. In one embodiment, succinate salt form 1 has an X-ray powder diffraction pattern substantially as shown in FIG. 94. In one embodiment, succinate salt form 1 has one or more characteristic X-ray powder diffraction peaks at approximately 5.86, 8.43, 11.07, 11.79, 12.67, 13.55, 13.69, 14.47, 16.84, 17.38, 17.74, 18.77, 18.97, 19.22, 20.59, 21.11, 21.33, 21.43, 21.83, 21.90, 22.23, 22.78, 23.74, 23.97, 24.84, 25.12, 26.29, 27.42, 28.10, 28.20, 28.39, 28.88, 29.35, 29.57, 29.82, 30.88, 31.61, 33.87, 34.33, 35.36, 39.11 or 39.85° 2θ as depicted in FIG. 94. In a specific embodiment, succinate salt form 1 has one, two, three, four, five, six, seven or eight characteristic X-ray powder diffraction peaks at approximately 5.86, 11.79, 17.74, 18.77, 21.90, 23.74, 26.29 or 31.61° 2θ. In another embodiment, succinate salt form 1 has one, two, three, four or five characteristic X-ray powder diffraction peaks at approximately 5.86, 11.79, 23.74, 26.29 or 31.61° 2θ. In another embodiment, succinate salt form 1 has one, two, three, four or five characteristic X-ray powder diffraction peaks at approximately 5.86, 11.79, 13.69, 21.33 or 23.74° 2θ. In another embodiment, succinate salt form 1 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one or forty-two characteristic X-ray powder diffraction peaks as set forth in Table 59.

In certain embodiments, a solid form provided herein, e.g., succinate salt form 2, is substantially crystalline, as indicated by, e.g., X-ray powder diffraction measurements. In one embodiment, succinate salt form 2 has an X-ray powder diffraction pattern substantially as shown in FIG. 95. In one embodiment, succinate salt form 2 has one or more characteristic X-ray powder diffraction peaks at approximately 5.69, 5.90, 6.18, 11.02, 16.48, 17.31, 18.49, 20.99, 22.30, 23.16, 29.01 or 30.85° 2θ as depicted in FIG. 95. In a specific embodiment, succinate salt form 2 has one, two, three, four, five, six, seven or eight characteristic X-ray powder diffraction peaks at approximately 5.69, 5.90, 6.18, 11.02, 16.48, 18.49, 20.99 or 30.85° 2θ. In another embodiment, succinate salt form 2 has one, two, three, four or five characteristic X-ray powder diffraction peaks at approximately 5.69, 5.90, 6.18, 18.49 or 20.99° 2θ. In another embodiment, succinate salt form 2 has one, two, three, four or five characteristic X-ray powder diffraction peaks at approximately 5.69, 6.18, 11.02, 18.49 or 20.99° 2θ. In another embodiment, succinate salt form 2 has one, two, three, four, five, six, seven, eight, nine, ten, eleven or twelve characteristic X-ray powder diffraction peaks as set forth in Table 60.

5.21. Tosylate Salt of Compound 1

In one embodiment, provided herein is a tosylate salt of Compound 1. In certain embodiments, the tosylate salt has 3 different forms.

In one embodiment, the tosylate salt is a solid. In one embodiment, the tosylate salt is crystalline.

In certain embodiments, the tosylate salt is prepared by evaporation of a solution comprising Compound 1 and p-toluenesulfonic acid. In one embodiment, the tosylate salt is prepared by evaporation of a solution comprising Compound 1 and p-toluenesulfonic acid in ACN, IPA, EtOAc or acetone.

In one embodiment, tosylate salt form 1 is prepared by evaporation of a solution comprising Compound 1 and p-toluenesulfonic acid in ACN. In one embodiment, tosylate salt form 2 is prepared by evaporation of a solution comprising Compound 1 and p-toluenesulfonic acid in MeNO$_2$ or acetone. In one embodiment, tosylate salt form 3 is prepared by evaporation of a solution comprising Compound 1 and p-toluenesulfonic acid in EtOAc.

In certain embodiments, solid forms provided herein, e.g., tosylate salt forms 1-3, are substantially crystalline, as indicated by, e.g., X-ray powder diffraction measurements. In one embodiment, tosylate salt forms 1-3 have X-ray powder diffraction patterns substantially as shown in FIG. 24.

In one embodiment, tosylate salt forms 1-3 have Raman spectra substantially as depicted in FIG. 25.

In certain embodiments, a solid form provided herein, e.g., tosylate salt form 1, is substantially crystalline, as indicated by, e.g., X-ray powder diffraction measurements. In one embodiment, tosylate salt form 1 has an X-ray powder diffraction pattern substantially as shown in FIG. 96. In one embodiment, tosylate salt form 1 has one or more characteristic X-ray powder diffraction peaks at approximately 4.50, 6.22, 8.88, 9.55, 9.67, 12.19, 13.25, 13.89, 14.86, 15.71, 17.14, 17.73, 18.29, 18.63, 19.45, 19.90, 21.06, 21.71, 22.64, 23.12, 23.88, 24.27, 25.43, 25.84, 26.06, 26.37, 27.71, 28.45, 28.82, 29.20, 30.62, 31.45, 33.81, 34.89 or 35.38° 2θ as depicted in FIG. 96. In a specific embodiment, tosylate salt form 1 has one, two, three, four, five, six, seven or eight characteristic X-ray powder diffraction peaks at approximately 6.22, 8.88, 12.19, 13.89, 17.14, 19.45, 21.71 or 22.64° 2θ. In another embodiment, tosylate salt form 1 has one, two, three, four or five characteristic X-ray powder diffraction peaks at approximately 6.22, 8.88, 13.89, 19.45 or 21.71° 2θ. In another embodiment, tosylate salt form 1 has one, two, three, four or five characteristic X-ray powder diffraction peaks at approximately 6.22, 8.88, 12.19, 13.89 or 21.71° 2θ. In another embodiment, tosylate salt form 1 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four or thirty-five characteristic X-ray powder diffraction peaks as set forth in Table 61.

In certain embodiments, a solid form provided herein, e.g., tosylate salt form 2, is substantially crystalline, as indicated by, e.g., X-ray powder diffraction measurements. In one embodiment, tosylate salt form 2 has an X-ray powder diffraction pattern substantially as shown in FIG. 97. In one embodiment, tosylate salt form 2 has one or more characteristic X-ray powder diffraction peaks at approximately 5.78, 6.24, 6.48, 7.01, 8.13, 9.79, 11.67, 12.04, 12.60, 14.25, 15.04, 15.57, 16.42, 17.53, 18.13, 18.31, 18.89, 19.55, 19.90, 21.36, 21.61, 21.94, 22.49, 22.74, 23.05, 23.35, 23.59, 24.36, 24.55, 25.53, 25.78, 26.54, 27.40, 28.07, 28.49, 29.32, 30.44, 32.58, 33.16, 33.62, 35.52 or 36.88° 2θ as depicted in FIG. 97. In a specific embodiment, tosylate salt form 2 has one, two, three, four, five, six, seven or eight characteristic X-ray powder diffraction peaks at approximately 6.24, 6.48, 8.13, 11.67, 15.04, 18.31, 18.89 or 23.59° 2θ. In another embodiment, tosylate salt form 2 has one, two, three, four or five characteristic X-ray powder diffraction peaks at approximately 6.24, 8.13, 11.67, 15.04 or 18.31° 2θ. In another embodiment, tosylate salt form 2 has one, two, three, four or five characteristic X-ray powder diffraction peaks at approximately 5.78, 6.24, 6.48, 8.13 or 21.36° 2θ. In another embodiment, tosylate salt form 2 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one or forty-two characteristic X-ray powder diffraction peaks as set forth in Table 62.

In certain embodiments, a solid form provided herein, e.g., tosylate salt form 3, is substantially crystalline, as indicated by, e.g., X-ray powder diffraction measurements. In one embodiment, tosylate salt form 3 has an X-ray powder diffraction pattern substantially as shown in FIG. 98. In one embodiment, tosylate salt form 3 has one or more characteristic X-ray powder diffraction peaks at approximately 5.59, 7.44, 8.91, 11.22, 13.13, 13.78, 14.05, 14.89, 15.62, 17.78, 18.15, 19.24, 19.70, 20.77, 21.72, 21.96, 22.40, 23.49, 24.97, 25.97, 26.66, 28.92 or 31.46° 2θ as depicted in FIG. 98. In a specific embodiment, tosylate salt form 3 has one, two, three, four, five, six, seven or eight characteristic X-ray powder diffraction peaks at approximately 5.59, 11.22, 13.13, 17.78, 18.15, 20.77, 21.96 or 22.40° 2θ. In another embodiment, tosylate salt form 3 has one, two, three, four or five characteristic X-ray powder diffraction peaks at approximately 5.59, 11.22, 18.15, 20.77 or 22.40° 2θ. In another embodiment, tosylate salt form 3 has one, two, three, four or five characteristic X-ray powder diffraction peaks at approximately 5.59, 7.44, 11.22, 18.15 or 20.77° 2θ. In another embodiment, tosylate salt form 3 has one, two, three, four, five, six, seven, eight, nine, ten, eleven, twelve, thirteen, fourteen, fifteen, sixteen, seventeen, eighteen, nineteen, twenty, twenty-one, twenty-two or twenty-three characteristic X-ray powder diffraction peaks as set forth in Table 63.

5.22. Mesylate Salt of Compound 1

In one embodiment, provided herein is a mesylate salt of Compound 1. In certain embodiments, the mesylate salt has 2 different forms.

In one embodiment, the mesylate salt is a solid. In one embodiment, the mesylate salt is crystalline.

In certain embodiments, the mesylate salt provided herein is prepared by evaporation of a solution comprising Compound 1 and methanesulfonic acid. In one embodiment, the mesylate salt is prepared by evaporation of a solution comprising Compound 1 and methanesulfonic acid in ACN/IPA, EtOH/IPA, EtOAc or acetone.

In one embodiment, mesylate salt form 1 is prepared by evaporation of a solution comprising Compound 1 and methanesulfonic acid in ACN/IPA, EtOH/IPA or acetone. In one embodiment, mesylate salt form 2 is prepared by evaporation of a solution comprising Compound 1 and methanesulfonic acid in EtOAc.

In certain embodiments, solid forms provided herein, e.g., mesylate salt forms 1-2, are substantially crystalline, as indicated by, e.g., X-ray powder diffraction measurements. In one embodiment, mesylate salt forms 1-2 have X-ray powder diffraction patterns substantially as shown in FIG. 26.

In one embodiment, mesylate salt forms 1-2 have Raman spectra substantially as depicted in FIG. 27.

In certain embodiments, a solid form provided herein, e.g., mesylate salt form 1, is substantially crystalline, as indicated by, e.g., X-ray powder diffraction measurements. In one embodiment, mesylate salt form 1 has an X-ray powder diffraction pattern substantially as shown in FIG. 99. In one embodiment, mesylate salt form 1 has one or more characteristic X-ray powder diffraction peaks at approximately 5.78, 7.87, 10.30, 10.71, 11.61, 11.86, 12.39, 13.50, 13.83, 14.17, 15.05, 15.56, 15.80, 16.29, 17.06, 17.49, 17.74, 18.10, 18.30, 18.54, 19.25, 19.89, 20.18, 20.58, 20.98, 21.56, 21.95, 23.41, 24.22, 24.82, 25.53, 26.08, 26.77, 27.27, 28.17, 28.38, 29.03, 29.31, 29.87, 30.81, 32.02, 32.99, 34.03, 35.01, 35.45, 35.72, 36.33 or 37.65° 2θ as depicted in FIG. 99. In a specific embodiment, mesylate salt form 1 has one, two, three, four, five, six, seven or eight characteristic X-ray powder diffraction peaks at approximately 5.78, 10.71, 11.61, 17.49, 18.10, 18.30, 18.54 or 23.41° 2θ. In another embodiment, mesylate salt form 1 has one, two, three, four or five characteristic X-ray powder diffraction peaks at approximately 5.78, 10.71, 11.61, 18.10 or 23.41° 2θ. In another embodiment, mesylate salt form 1 has one, two, three, four or five characteristic X-ray powder diffraction peaks at approximately 5.78, 7.87, 10.71, 18.10 or 19.25° 2θ. In another embodiment, mesylate salt form 1 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five thirty-six, thirty-seven, thirty-eight, thirty-nine, forty, forty-one, forty-two, forty-three, forty-four, forty-five, forty-six, forty-seven or forty-eight characteristic X-ray powder diffraction peaks as set forth in Table 64.

In certain embodiments, a solid form provided herein, e.g., mesylate salt form 2, is substantially crystalline, as indicated by, e.g., X-ray powder diffraction measurements. In one embodiment, mesylate salt form 2 has an X-ray powder diffraction pattern substantially as shown in FIG. 100. In one embodiment, mesylate salt form 2 has one or more characteristic X-ray powder diffraction peaks at approximately 5.14, 5.26, 10.45, 16.37, 18.36, 20.41, 20.95, 21.59, 21.86, 22.14, 22.63, 23.33, 24.24, 25.76, 26.16, 28.41 or 31.70° 2θ as depicted in FIG. 100. In a specific embodiment, mesylate salt form 2 has one, two, three, four, five, six, seven or eight characteristic X-ray powder diffraction peaks at approximately 5.14, 5.26, 10.45, 18.36, 20.41, 20.95, 21.59 or 26.16° 2θ. In another embodiment, mesylate salt form 2 has one, two, three, four or five characteristic X-ray powder diffraction peaks at approximately 5.14, 5.26, 10.45, 18.36 or 20.95° 2θ. In another embodiment, mesylate salt form 2 has one, two, three, four or five characteristic X-ray powder diffraction peaks at approximately 5.14, 10.45, 18.36, 20.41 or 20.95° 2θ. In another embodiment, mesylate salt form 2 has one, two, three, four, five, six, seven, eight, nine, ten, eleven, twelve, thirteen, fourteen, fifteen, sixteen or seventeen characteristic X-ray powder diffraction peaks as set forth in Table 65.

5.23. Besylate Salt of Compound 1

In one embodiment, provided herein is a besylate salt of Compound 1.

In one embodiment, the besylate salt is a solid. In one embodiment, the besylate salt is crystalline.

In certain embodiments, the besylate salt provided herein is prepared by evaporation of a solution comprising Compound 1 and benzenesulfonic acid. In one embodiment, the besylate salt is prepared by evaporation of a solution comprising Compound 1 and benzenesulfonic acid in MeNO$_2$.

In certain embodiments, a solid form provided herein, e.g., a besylate salt, is substantially crystalline, as indicated by, e.g., X-ray powder diffraction measurements. In one embodiment, the besylate salt has an X-ray powder diffraction pattern substantially as shown in FIG. 28.

In one embodiment, a besylate salt has a Raman spectrum substantially as depicted in FIG. 29.

In certain embodiments, a solid form provided herein, e.g., besylate salt, is substantially crystalline, as indicated by, e.g., X-ray powder diffraction measurements. In one embodiment, besylate salt has an X-ray powder diffraction pattern substantially as shown in FIG. 101. In one embodiment, besylate salt has one or more characteristic X-ray powder diffraction peaks at approximately 6.29, 7.84, 9.64, 11.32, 12.63, 14.38, 15.89, 16.81, 17.44, 19.09, 19.39, 19.82, 20.31, 20.79, 21.63, 22.35, 22.82, 23.87, 25.30, 26.12, 27.64, 28.94 or 34.90° 2θ as depicted in FIG. 101. In a specific embodiment, besylate salt has one, two, three, four, five, six, seven or eight characteristic X-ray powder diffraction peaks at approximately 6.29, 9.64, 11.32, 14.38, 19.39, 20.79, 23.87 or 27.64° 2θ. In another embodiment, besylate salt has one, two, three, four or five characteristic X-ray powder diffraction peaks at approximately 6.29, 11.32, 14.38, 19.39 or 23.87° 2θ. In another embodiment, besylate salt has one, two, three, four or five characteristic X-ray powder diffraction peaks at approximately 6.29, 7.84, 11.32, 14.38 or 20.79° 2θ. In another embodiment, besylate salt has one, two, three, four, five, six, seven, eight, nine, ten, eleven, twelve, thirteen, fourteen, fifteen, sixteen, seventeen, eighteen, nineteen, twenty, twenty-one, twenty-two or twenty-three characteristic X-ray powder diffraction peaks as set forth in Table 66.

5.24. Fumarate Salt of Compound 1

In one embodiment, provided herein is a fumarate salt of Compound 1.

In one embodiment, the fumarate salt is a solid. In one embodiment, the fumarate salt is crystalline. In one embodiment, the fumarate salt is a hemi-fumarate salt.

In certain embodiments, the fumarate salt is prepared by evaporation of a solution comprising Compound 1 and fumaric acid. In one embodiment, the fumarate salt is prepared by evaporation of a solution comprising Compound 1 and fumaric acid in ACN.

In one embodiment, the stoichiometric ratio for Compound 1 to fumaric acid is about 2:1 in the fumarate salt.

In certain embodiments, a solid form provided herein, e.g., a fumarate salt, is substantially crystalline, as indicated by, e.g., X-ray powder diffraction measurements. In one embodiment, the fumarate salt has an X-ray powder diffraction pattern substantially as shown in FIG. 28.

In one embodiment, a fumarate salt has a Raman spectrum substantially as depicted in FIG. 29.

In certain embodiments, a solid form provided herein, e.g., fumarate salt, is substantially crystalline, as indicated by, e.g., X-ray powder diffraction measurements. In one embodiment, fumarate salt has an X-ray powder diffraction pattern substantially as shown in FIG. 102. In one embodiment, fumarate salt has one or more characteristic X-ray powder diffraction peaks at approximately 5.97, 8.31, 11.09, 11.92, 12.38, 12.97, 13.53, 14.72, 15.81, 16.66, 18.51, 18.92, 20.94, 21.36, 21.76, 22.34, 23.33, 24.08, 24.65, 25.58, 26.31, 28.74, 29.20, 29.83, 30.96, 31.72, 34.86 or 36.34° 2θ as depicted in FIG. 102. In a specific embodiment, fumarate salt has one, two, three, four, five, six, seven or eight characteristic X-ray powder diffraction peaks at approximately 5.97, 11.09, 18.92, 21.36, 21.76, 26.31, 28.74 or 31.72° 2θ. In another embodiment, fumarate salt has one, two, three, four or five characteristic X-ray powder diffraction peaks at approximately 5.97, 11.09, 21.36, 21.76 or 26.31° 2θ. In another embodiment, fumarate salt has one, two, three, four or five characteristic X-ray powder diffraction peaks at approximately 5.97, 8.31, 11.09, 20.94 or 24.08° 2θ. In another embodiment, fumarate salt has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven or twenty-eight characteristic X-ray powder diffraction peaks as set forth in Table 67.

6. EXAMPLES

The following Examples are presented by way of illustration, not limitation. The following abbreviations are used in descriptions and examples:
ACN: Acetonitrile
DSC: Differential Scanning calorimetry
DVS: Dynamic Vapor Sorption
EtOAc: Ethyl acetate
EtOH: Ethanol
HPLC: High performance liquid chromatography
IPA: Isopropanol
MeNO$_2$: Nitromethane
MeOH: Methanol
mp: Melting point
MTBE: tert-Butyl methyl ether
NMR: Nuclear magnetic resonance
RH: Relative Humidity
SGF: Simulated Gastric Fluid (without Pepsin)
XRPD: X-Ray Powder Diffraction Certain compositions comprising Compound A were prepared and tested for a number of physical and chemical properties. Modifications were then made and subsequent formulations were also tested, until formulations possessing desirable physical and chemical properties were found. The following example describes these formulations and their testing.

6.1. Formulation A

Table 1 provides a dosage formulation for a 100 mg strength Compound 1 single unit dose (Formulation A).

TABLE 1

| Ingredients | Percent Per Tablet (%) | Amount Per Tablet (mg) | Amount Per Batch (g) |
|---|---|---|---|
| *Formulation A* | | | |
| *Intragranular* | | | |
| Compound 1 | 28.57 | 100.0 | 285.71 |
| Microcrystalline Cellulose (Avicel PH101) | 29.43 | 103.01 | 294.3 |
| Mannitol (Mannitol 200) | 26 | 91.00 | 260.0 |
| Ac-Di-Sol (Portion 1) | 2 | 7.00 | 20.00 |
| HPMC 3 cps (Methocel K3) | 3 | 10.50 | 30.00 |
| Water, USP, | 0 | NA | 0 *(570.0) |
| *Extragranular* | | | |
| Microcrystalline Cellulose (Avicel PH102) | 8 | 28.00 | 80.00 |
| Ac-Di-Sol (Portion 2) | 2 | 7.00 | 20.00 |
| Magnesium Stearate | 1 | 3.5 | 10.00 |
| Total Core Tablet | 100 | 350.0 | 1000 |

*Amount of purified water, USP, dispensed, based on 5% granulation solution.

The process for preparation of Formulation A comprised the steps of:

a) Weighing out excipients.
b) Weighing out API.
c) Preparing granulation binder solution (5%).
d) Preparing 570 g of purified water, USP, by heating it to ~70° C.
e) Slowly dispersing 30 g of HPMC into the water while mixing and continued mixing until material was fully dissolved.
f) Passing the Compound 1, Avicel 101, Mannitol 200 and Ac-Di-Sol (Portion 1) through an 18/20 mesh Screen.
g) Loading Compound 1, Avicel 101, Mannitol 200 and Ac-Di-Sol (Portion 1) into the KG5 Granulator, equipped with an appropriate sized bowl and dry mix for 10 minutes.
h) Equipping the KG5 with a spray tip and peristaltic tubing sufficient to produce an adequate spray rate that allowed for consistent application of the granulation binder solution. Adding additional water as needed.
i) Wetting mass material sufficiently to ensure that granulation appeared visually consistent throughout the bowl.
j) Discharging the wet mass from the granulator and transferring to the expansion chamber of the GPCG-1 Fluid Bed Granulator. Dry until an endpoint of <2 Loss on Drying was achieved.

TABLE 2

DRYING PROCESS
Start Up Parameters*

| | |
|---|---|
| Initial Inlet Air-Volume 20-35 CFM | Inlet Temp. Set Point 70° C. |
| Inlet Temp. Target 60-80° C. | Product Temp Target 40-60° C. |
| Initial Inlet Air-Volume 20-35 CFM | Inlet Temp. Set Point 70° C. |

*May be changed as needed to achieve proper bed characteristics.

k) Milling the dried granules using the Comil®, fitted with an appropriate screen (0.075R).
l) Performing bulk/tap density tests and particle size distribution analysis. After the tests were complete, returning the test materials to milled granulation.
m) Obtaining a net weight for the milled granule.
n) Calculating yield percentage through milling.
o) Re-calculating and re-weighing the extra-granular excipients according to the yield in Step n.
p) Passing the Avicel 102 and Ac-Di-Sol (Portion 2) through an 18/20 mesh Screen.
q) Combining the milled granulation with the screened Avicel 102 and Ac-Di-Sol into an appropriate sized V-shell blender and blending for 100 revolutions (adjusting blender speed to achieve desired blend time).
r) Passing the magnesium stearate through a 30 mesh screen.
s) Adding the screened magnesium stearate to the blender and blending for 50 revolutions (adjusting blender speed to achieve desired blend time).
t) Discharging the blend into a suitable container and labeling appropriately. Performing bulk/tap density tests and particle size distribution analysis. After the tests were completed, returning the test materials to final blend material.
u) Setting up compress stations of the Compacta tablet press using selected tooling.
v) Adjusting the tablet press until the following specifications in Table 3 for tablet weights were met. Ensuring that initial tablet physicals were acceptable, (i.e., friability less than 0.3% without capping), before proceeding with compressing. Hardness, tablet thickness and disintegration times were measured and documented.
w) Compressing tablets and collect acceptable core tablets in a tinted container, double lined with polyethylene bags.

TABLE 3

| Individual Tablet Weights | | Mean Tablet Weights | |
|---|---|---|---|
| Upper Limit (+7%) | 374.5 mg | Upper Limit (+5%) | 367.5 mg |
| Upper Control Limit (+5%) | 367.5 mg | Upper Control Limit (+2%) | 357.0 mg |
| Target | 350.0 mg | Target | 350.0 mg |
| Lower Control Limit (−5%) | 332.5 mg | Lower Control Limit (−2%) | 343.0 mg |
| Lower Limit (−7%) | 325.5 mg | Lower Limit (−5%) | 332.5 mg |

Friability tests were performed on 10 tablets at the beginning of the compression run and on a 10 tablet composite sample after the batch was completed. The apparatus and method were defined in the USP/NF <1216> and in SOP PHARM 0008. Specification—weight loss was less than 0.3% without capping.

Disintegration time tests were performed on 6 samples at the beginning of the compression run, and on a 6 tablet composite sample after the batch was completed. The apparatus and method were defined in the USP/NF <701> with one disk.

Hardness tests were performed on 10 samples taken at the beginning, middle, and end of the compression run. The hardness of 10 tablets was measured and the average was calculated.

Thickness tests were performed on a 10 tablet sample taken at the Beginning of the run and on 10 tablets of a composite sample after the run is completed. The thickness of 10 tablets was measured and an average was calculated.

Weighing 10 tablets individually at the beginning, middle, and end of run. Recording weights to 0.1 mg. Acceptance Criteria: +/−7% of theoretical tablet weight (350.0 mg). Acceptance limit: 325.5-374.5 mg.

10 tablets were sampled and weighed together at the beginning, middle, and end of run, and an average tablet weight (ATW) was calculated. Record ATW to 0.1 mg. Acceptance Criteria: Mean weight of 10 tablets must be within +/−5% of theoretical. Average tablet weight (350.0 mg). Acceptance limit: 332.5-367.5 mg.

6.2. Formulation B

Table 4 provides a dosage formulation for a 100 mg strength Compound 1 single unit dose (Formulation B).

The process for preparation of Formulation B comprises the same steps in the preparation of Formulation A.

TABLE 4

Formulation B

| Ingredients | Percent Per Tablet (%) | Amount Per Tablet (mg) | Amount Per Batch (g) |
|---|---|---|---|
| Intragranular | | | |
| Compound 1 | 28.57 | 100.0 | 285.71 |
| Microcrystalline Cellulose (Avicel PH101) | 25.43 | 89.01 | 254.3 |
| Mannitol (Mannitol 200) | 26 | 91.00 | 260.0 |
| Ac-Di-Sol (Portion 1) | 4 | 14.00 | 40.00 |
| HPMC 3 cps (Methocel K3) | 3 | 10.50 | 30.00 |
| Water, USP, | 0 | NA | 0 |

TABLE 4-continued

Formulation B

| Ingredients | Percent Per Tablet (%) | Amount Per Tablet (mg) | Amount Per Batch (g) |
|---|---|---|---|
| | | | *(570.0) |
| Extragranular | | | |
| Microcrystalline Cellulose (Avicel PH102) | 8 | 28.00 | 80.00 |
| Ac-Di-Sol (Portion 2) | 4 | 14.00 | 40.00 |
| Magnesium Stearate | 1 | 3.5 | 10.00 |
| Total Core Tablet | 100 | 350.0 | 1000 |

*Amount of purified water, USP, dispensed, based on 5% granulation solution.

6.3. Formulation C

Table 5 provides a dosage formulation for a 100 mg strength Compound 1 single unit dose (Formulation C).

The process for preparation of Formulation C comprises the same steps in the preparation of Formulation A.

TABLE 5

Formulation C

| Ingredients | Percent Per Tablet (%) | Amount Per Tablet (mg) | Amount Per Batch (g) |
|---|---|---|---|
| Intragranular | | | |
| Compound 1 | 28.57 | 100.0 | 285.71 |
| Microcrystalline Cellulose (Avicel PH101) | 23.93 | 83.76 | 239.3 |
| Mannitol (Mannitol 200) | 26 | 91.00 | 260.0 |
| Ac-Di-Sol (Portion 1) | 4 | 14.00 | 40.00 |
| HPMC 3 cps (Methocel K3) | 4.5 | 15.75 | 45.00 |
| Water, USP, | 0 | NA | 0 *(570.0) |
| Extragranular | | | |
| Microcrystalline Cellulose (Avicel PH102) | 8 | 28.00 | 80.00 |
| Ac-Di-Sol (Portion 2) | 4 | 14.00 | 40.00 |
| Magnesium Stearate | 1 | 3.5 | 10.00 |
| Total Core Tablet | 100 | 350.0 | 1000 |

*Amount of purified water, USP, dispensed, based on 5% granulation solution.

6.4. Formulation D

Table 6 provides a dosage formulation for a 100 mg strength Compound 1 single unit dose (Formulation D).

The process for preparation of Formulation D comprises the same steps in the preparation of Formulation A.

TABLE 6

Formulation D

| Ingredients | Percent Per Tablet (%) | Amount Per Tablet (mg) | Amount Per Batch (g) |
|---|---|---|---|
| Intragranular | | | |
| Compound 1 | 28.57 | 100.0 | 285.71 |
| Microcrystalline Cellulose (Avicel PH101) | 27.93 | 97.76 | 279.3 |
| Mannitol (Mannitol 200) | 26 | 91.00 | 260.0 |
| Ac-Di-Sol (Portion 1) | 2 | 7.00 | 20.00 |
| HPMC 3 cps (Methocel K3) | 4.5 | 15.75 | 45.00 |
| Water, USP, | 0 | NA | 0 *(570.0) |
| Extragranular | | | |
| Microcrystalline Cellulose (Avicel PH102) | 8 | 28.00 | 80.00 |
| Ac-Di-Sol (Portion 2) | 2 | 7.00 | 20.00 |
| Magnesium Stearate | 1 | 3.5 | 10.00 |
| Total Core Tablet | 100 | 350.0 | 1000 |

*Amount of purified water, USP, dispensed, based on 5% granulation solution.

6.5. Formulation Development

Objective: The objective of this exercise was to provide confirmation of scalability of the Compound 1 common blend granulation process, previously used for the 100 mg dosage form development and to evaluate the 30 mg and 200 mg dosage form compression and coating processes. The primary purposes, of these experiments, were to acquire technical knowledge, in preparation for the subsequent CTM manufacturing, of all three strengths.

Development: In order to allow for a range of 30 mg-200 mg dosage forms, while producing a common granulation, the following formulation in Table 7 was selected as the basis for this exercise.

TABLE 7

| Ingredients | Percent Per Batch (%) | Amount Per Batch (g) |
|---|---|---|
| Compound 1 Drug Substance | 28.57 | 1428.5 |
| Microcrystalline Cellulose (Avicel PH101) | 25.43 | 1271.5 |
| Mannitol Pearlitol (200) | 26 | 1300 |
| Ac-Di-Sol (Portion 1) | 4 | 200.0 |
| HPMC 3 cps (Methocel K3) | 3 | 150.0 |
| Microcrystalline Cellulose (Avicel PH102) | 8 | 400.0 |
| Ac-Di-Sol (Portion 2) | 4 | 200.0 |
| Magnesium Stearate | 1 | 50.00 |
| Total Core Tablet | 100 | 5000 |

Based on this 28.57% Compound 1 loading within a common granulation, three discreet dosage forms were prepared, to meet the following specifications in Table 8.

TABLE 8

| Product | Tablet Weight | Dimensions | Shape | Color | Embossing |
|---|---|---|---|---|---|
| Compound 1, 30 mg Tablet | 105.0 mg | 0.25" | Round/Standard Concave | Yellow | None |
| Compound 1, 100 mg Tablet | 350.0 mg | 0.2220" × 0.5720" | Modified Capsule/Standard Concave | White | None |
| Compound 1, 200 mg Tablet | 700.0 mg | 0.6693" × 0.3937" | Oval/Standard Concave | Brown | None |

Figure 1:
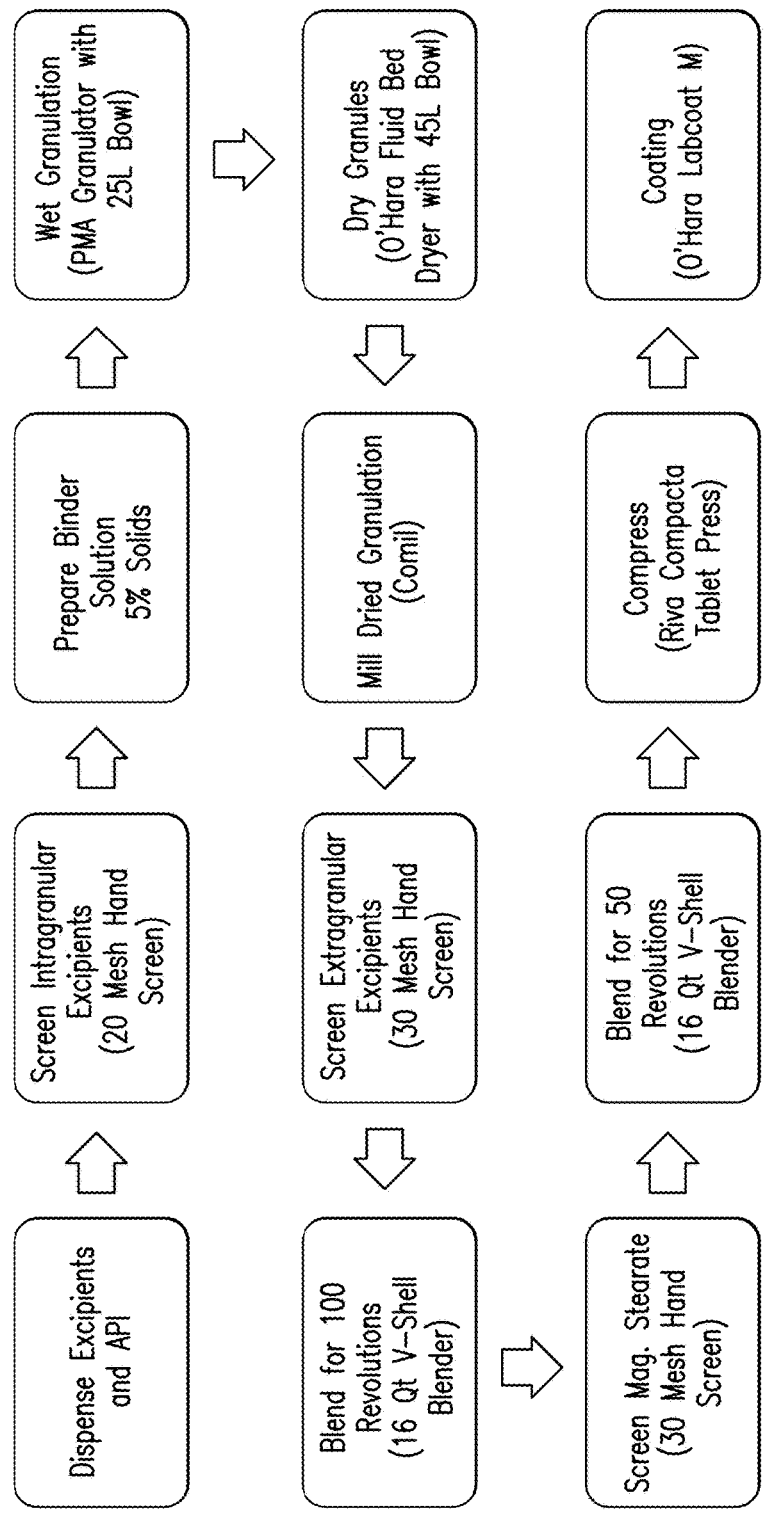
FIG. 1 depicts the process and equipment for wet granulation processes of Compound 1 compositions.

The processes and equipments for wet granulation process are provided in FIG. 1.

Granulation: First, 5% binder solution was prepared comprising 1) heating 2850 g of purified water, USP to 70° C.; 2) dispersing 150 g of Hypromelose 3 cps (Methocel K3) into the water; and 3) mixing until dissolved. Second, intragranular material was screened by 20 mesh screen, which includes Compound 1, microcrystalline cellulose (Avicel 101), mannitol (pearlitol 200) and croscarmellose sodium (Ac-Di-Sol) portion 1. Third, granulation process was performed in PMA Granulator 25 Liter bowl according to the parameters in Table 9 and Table 10.

TABLE 9

Granulation Parameters for Lot 1

| Step | Amount (g) | Elapsed Time (mm:ss) | Impeller Speed (RPM) | Chopper Speed (RPM) | ~Spray Rate (gpm) | Power Consumption |
|---|---|---|---|---|---|---|
| Mix | N/A | 10:00 | Low | *Low/Off | N/A | 9 |
| Binder Addition | 3000 | 36:00 | Low | Low | 83 | 9 |
| Mix | N/A | 1:00 | Low | Off | N/A | 9 |
| Mix | N/A | 1:00 | Low | Low | N/A | 9 |

*Stopped chopper approx. 15 minutes into binder addition.

TABLE 10

Granulation Parameters for Lot 2

| Solution | Amount (g) | Elapsed Time (mm:ss) | Impeller Speed (RPM) | Chopper Speed (RPM) | ~Spray Rate (gpm) | Power Consumption |
|---|---|---|---|---|---|---|
| Mix | N/A | 10:00 | Low | Off | N/A | 9 |
| Binder Addition | 3000 | 36:00 | Low | Low | 83 | 9 |
| Mix | N/A | 1:00 | Low | Off | N/A | 9 |
| Mix | N/A | 1:00 | Low | Low | N/A | 9 |

The drying process was performed in O'Hara FBD with 45 L bowl according to the parameters in Table 11, Table 12 and Table 13.

TABLE 11

Start Up Parameters

| Initial Inlet Air-Volume | TBD |
|---|---|
| Inlet Temp. Set Point | 70° C. |
| Inlet Temp. Target | 60-80° C. |
| Product Temp Target | 40-60° C. |

TABLE 12

Drying Parameters for Lot 1

| Step | Time Elapsed (hh:min) | Inlet Air Vol CFM | Inlet Temp. Set Point (° C.) | Inlet Temp. Actual (° C.) | Product Temp (° C.) | Comments |
|---|---|---|---|---|---|---|
| Dry | 00:00 | 700 | 70 | 27 | 22 | 37.50% Initial LOD |
| Dry | 15:00 | 800 | 60 | 55 | 30 | 14.05% LOD |
| Dry | 30:00 | 1000 | 70 | 67 | 49 | 1:00% LOD (0.95% From Bowl) |

TABLE 13

Drying Parameters for Lot 2

| Step | Time Elapsed (hh:min) | Inlet Air Vol CFM | Inlet Temp. Set Point (° C.) | Inlet Temp. Actual (° C.) | Product Temp (° C.) | Comments |
|---|---|---|---|---|---|---|
| Dry | 00:00 | 1000 | 70 | 32 | 34 | 36.50% Initial LOD |
| Dry | 15:00 | 1000 | 70 | 70 | 40 | 3.05% LOD |
| Dry | 22:00 | 1000 | 70 | 70 | 40 | 0.95% LOD (0.95% From Bowl) |

After the mixture was screened with Screen 075R050 (0.075"), the mixture was milled at 1400 RPM.

The amount of the extragranular excipients including microcrystalline cellulose (Avicel 102) and croscarmellose sodium (Ac-Di-Sol) portion 2 was adjusted in proportion to milled granule yield. Then the extragranular excipients were screened with 20 mesh screen.

The milled material and extragranular excipients were blended in a 16 Qt V-Shell Blender for 4 minutes at 30 RPM (120 revolutions).

The magnesium stearate was screened with 30 mesh screen and then was blended with the milled material and extragranular excipients in a 16 Qt V-Shell blender for 2 minutes at 30 RPM (60 revolutions).

The analytical data for the granulated material is provided below in Table 14, Table 15 and Table 16.

TABLE 14

Milled Granule Bulk & Tapped Density

| BATCH | TEST | MILLED GRANULE | FINAL BLEND |
|---|---|---|---|
| Lot 1 | Average Bulk Density | 0.53 | 0.56 |
|  | Average | 0.60 | 0.65 |

TABLE 14-continued

Milled Granule Bulk & Tapped Density

| BATCH | TEST | MILLED GRANULE | FINAL BLEND |
|---|---|---|---|
| Lot 2 | Tapped Density Average Carr Index | 13 | 15 |
| | Average Bulk Density | 0.56 | 0.59 |
| | Average Tapped Density | 0.65 | 0.68 |
| | Average Carr Index | 15 | 14 |

TABLE 15

Milled Granule Particle Size Analysis - Lot 1

| Screen size | Milled Granule % Retained | Final Blend % Retained |
|---|---|---|
| 30 mesh | 33.7 | 10.0 |
| 40 mesh | 12.5 | 12.5 |
| 60 mesh | 37.6 | 48.7 |
| 80 mesh | 9.1 | 13.0 |
| 100 mesh | 1.7 | 3.6 |
| 200 mesh | 3.0 | 6.2 |
| Fines | 2.4 | 5.7 |

TABLE 16

Milled Granule Particle Size Analysis - Lot 2

| Screen size | Milled Granule % Retained | Final Blend % Retained |
|---|---|---|
| 30 mesh | 8.3 | 7.4 |
| 40 mesh | 6.9 | 7.4 |
| 60 mesh | 46.0 | 42.0 |
| 80 mesh | 22.5 | 20.2 |
| 100 mesh | 5.1 | 5.0 |
| 200 mesh | 9.2 | 10.2 |
| Fines | 0.6 | 7.7 |

Prior each compression event, a minimum of three compression forces were evaluated to determine which would provide optimal tablet physical characteristics on the Compacta tablet press. Results of this evaluation are provided below in Table 17.

TABLE 17

| Batch | Force | Compression Force (kN) | Friability (% Loss) | Average Disintegration (mm:ss) | Average Tablet Thickness (mm) | Average Hardness (kP) | Min. Individual Tablet Weight (mg) | Max. Individual Tablet Weight (mg) |
|---|---|---|---|---|---|---|---|---|
| Lot 1 | A | 8 | 0.17 | 06:13 | 3.56 | 5.7 | 107.2 | 110.0 |
| (30 mg | B | 11 | 0.15 | 06:32 | 3.51 | 6.0 | 106.8 | 111.2 |
| tablets) | C | 16 | 0.39 | 02:23 | 3.63 | 3.9 | 105.0 | 107.2 |
| Lot 2 | A | 11 | 0.22 | 04:58 | 4.86 | 11.7 | 344.5 | 351.6 |
| (100 mg | B | 13 | 0.18 | 07:13 | 4.74 | 13.7 | 342.7 | 346.0 |
| tablets) | C | 8 | 0.30 | 02:43 | 5.11 | 6.9 | 344.8 | 349.5 |
| | D | 15 | 0.12 | 08:52 | 4.75 | 14.3 | 352.1 | 353.3 |
| Lot 2 | A | 20 | 0.19 | 04:03 | 5.69 | 9.5 | 695.0 | 702.6 |
| (200 mg | B | 25 | 0.17 | 05:20 | 5.62 | 10.5 | 695.2 | 702.4 |
| tablets) | C | 30 | 0.12 | 07:46 | 5.54 | 10.2 | 695.1 | 704.8 |
| | D | 35 | 0.12 | 08:32 | 5.51 | 12.3 | 694.8 | 703.3 |

Compound 1 30 mg tablets were prepared on Compacta B-D tablet press with 0.25" standard round concave plain/plain tooling, 7 stations and target friability <0.3% without capping. The target tablet weights are provided in Table 18.

TABLE 18

| Individual Tablet Weights | | Mean Tablet Weights | |
|---|---|---|---|
| Upper Limit (+7%) | 115.5 mg | Upper Limit (+5%) | 110.3 mg |
| Upper Control Limit (+5%) | 110.3 mg | Upper Control Limit (+2%) | 107.1 mg |
| Target | 105.0 mg | Target | 105.0 mg |
| Lower Control Limit (−5%) | 99.7 mg | Lower Control Limit (−2%) | 102.9 mg |
| Lower Limit (−7%) | 94.5 mg | Lower Limit (−5%) | 99.7 mg |

Compound 1 100 mg Tablets were prepared on Compacta B-D tablet press with 0.2220"×0.5720" modified standard concave plain/plain tooling, 4 stations, and target friability <0.3% without capping. The target tablet weights are provided in Table 19.

TABLE 19

| Individual Tablet Weights | | Mean Tablet Weights | |
|---|---|---|---|
| Upper Limit (+7%) | 374.5 mg | Upper Limit (+5%) | 367.5 mg |
| Upper Control Limit (+5%) | 367.5 mg | Upper Control Limit (+2%) | 357.0 mg |
| Target | 350.0 mg | Target | 350.0 mg |
| Lower Control Limit (−5%) | 332.5 mg | Lower Control Limit (−2%) | 343.0 mg |
| Lower Limit (−7%) | 325.5 mg | Lower Limit (−5%) | 332.5 mg |

Compound 1 200 mg tablets were prepared on Compacta B-D tablet press with 0.6693"×0.3937" standard concave plain/plain tooling, 4 stations and target friability <0.3% without capping. The target tablet weights are provided in Table 20.

TABLE 20

| Individual Tablet Weights | | Mean Tablet Weights | |
|---|---|---|---|
| Upper Limit (+7%) | 749.0 mg | Upper Limit (+5%) | 735.0 mg |
| Upper Control Limit (+5%) | 735.0 mg | Upper Control Limit (+2%) | 714.0 mg |
| Target | 700.0 mg | Target | 700.0 mg |
| Lower Control Limit (−5%) | 665.0 mg | Lower Control Limit (−2%) | 686.0 mg |
| Lower Limit (−7%) | 651.0 mg | Lower Limit (−5%) | 665.0 mg |

In-process compression test results are provided in Table 21.

TABLE 21

| Interval | | Avg Hardness (kP) | Avg Thickness (mm) | Avg Friability (% Loss) | Avg Disintegration (mm:ss) | Min. Individual Tablet Weight (mg) | Max. Individual Tablet Weight (mg) | Avg Weight of 10 Tablets (mg) |
|---|---|---|---|---|---|---|---|---|
| Lot 1 (30 mg tablets) | Initial | 5.4 | 3.50 | 0.16 | 06:05: | 104.3 | 109.2 | 109.7 |
| | Mid | 4.8 | N/A | N/A | N/A | 102.3 | 104.9 | 103.2 |
| | End/Composite | 4.2 | 3.41 | 0.11 | 05:19 | 101.6 | 106.6 | 104.0 |
| Lot 2 (100 mg tablets) | Initial | 12.5 | 4.81 | 0.14 | 07:40 | 347.5 | 353.3 | 345.8 |
| | Mid | 11.7 | N/A | N/A | N/A | 354.0 | 359.6 | 350.8 |
| | End/Composite | 11.2 | 4.77 | 0.17 | 06:29 | 352.4 | 357.9 | 347.4 |
| Lot 2 (200 mg tablets) | Initial | 10.5 | 5.55 | 0.16 | 07:15 | 699.0 | 705.8 | 701.6 |
| | Mid | 9.7 | N/A | N/A | N/A | 697.3 | 705.4 | 699.6 |
| | End/Composite | 9.9 | 5.56 | 0.10 | 07:00 | 695.8 | 705.1 | 698.6 |

Film Coating:

Compound 1 30 mg tablets were coated with Opadry yellow (03B12885) in 15% solids coating suspension. The minimum suspension mix time was 45 minutes. The tablets had about 3% weight gain after coating. Coating pan load was 1358 g. Coater used was O'Hara Labcoat II w/12" Pan.

The film-coat was applied to the pre-warmed core tablets in the O'Hara coating pan to a weight gain of approximately 3% as follows (record in-process data in table below at least every 15 minutes):

a) Mean pre-warmed tablet weight (from step 5)=104.4 mg b) Desired target weight (3% weight gain)=6a*1.03=107.5 mg c) Target supply temp=60° C. (may be adjusted to maintain nominal exhaust temp.)

d) Target air flow (cfm)=60-120

Atomization air psi: 19; pattern air psi: 19; gun distance: 4"

TABLE 22

| Time (hh:mm) | Supply Temp Set/actual (° C.) | Exhaust Temp (° C.) | Air Flow (cfm) | Spray Rate (g/min) | Pan Speed (RPM) | Mean Tab Wt. (n = 100) (mg) |
|---|---|---|---|---|---|---|
| 15:30 | 60/60 | 39.6 | 110 | 5 | 20 | 104.4 |
| 15:44 | 60/60 | 41.4 | 120 | 15 | 20 | 105.6 |
| 16:00 | 60/60 | 40.0 | 120 | 13 | 20 | 107 |
| 16:10 | 60/60 | 41.0 | 120 | 14 | 20 | 107.6 | e) Record the final mean Opadry coated tablet weight: 107.6 mg.

Compound 1 100 mg tablets were coated with Opadry white (YS-1-18202-A) in 15% solids coating suspension. The minimum suspension mix time was 45 minutes. The tablets had about 3% weight gain after coating. Coating pan load was 2487 g. Coater used was O'Hara labcoat II w/15" pan.

The film-coat was applied to the pre-warmed core tablets in the O'Hara coating pan to a weight gain of approximately 3% as follows (record in-process data in table below at least every 15 minutes):

a) Mean pre-warmed tablet weight (from step 5)=349.9 mg b) Desired target weight (3% weight gain)=6a*1.03=360.4 mg c) Target supply temp=60° C. (may be adjusted to maintain nominal exhaust temp.)

d) Target Air flow (cfm)=60-120

Atomization air psi: 20; pattern air psi: 20; gun distance: 5"

TABLE 23

| Time (hh:mm) | Supply Temp Set/actual (° C.) | Exhaust Temp (° C.) | Air Flow (cfm) | Spray Rate (g/min) | Pan Speed (RPM) | Mean Tab Wt. (n = 100) (mg) |
|---|---|---|---|---|---|---|
| 00:00 | 60/59.7 | 35 | 140 | 14 | 13 | 349.9 |
| 00:15 | 68/68 | 42 | 170 | 15 | 18 | 353.5 |
| 00:30 | 60/60 | 42 | 175 | 14 | 18 | 358.4 |
| 00:35 | 60/60 | 42 | 175 | 14 | 18 | 360.5 | e) Record the final mean Opadry coated tablet weight: 360.5 mg.

Compound 1 200 mg tablets were coated with Opadry brown (03B16878) in 15% solids coating suspension. The minimum suspension mix time was 45 minutes. The tablets had about 3% weight gain after coating. Coating pan load was 4252 g. Coater used was O'Hara labcoat II w/19" pan.

The film-coat was applied to the pre-warmed core tablets in the O'Hara coating pan to a weight gain of approximately 3% as follows (record in-process data in table below at least every 15 minutes):

a) Mean pre-warmed tablet weight (from step 5)=698.9 mg b) Desired target weight (3% weight gain)=6a*1.03=719.9 mg c) Target supply temp=60° C. (may be adjusted to maintain nominal exhaust temp.)

d) Target air flow (cfm)=60-120

Atomization air psi: 20; pattern air psi: 20; gun distance: 5"

TABLE 24

| Time (hh:mm) | Supply Temp Set/actual (° C.) | Exhaust Temp (° C.) | Air Flow (cfm) | Spray Rate (g/min) | Pan Speed (RPM) | Mean Tab Wt. (n = 100) (mg) |
|---|---|---|---|---|---|---|
| 00:00 | 60/59 | 39 | 175 | 20 | 15 | 698.9 |
| 00:15 | 67/67 | 42 | 175 | 20 | 15 | 706.5 |

TABLE 24-continued

| Time (hh:mm) | Supply Temp Set/actual (° C.) | Exhaust Temp (° C.) | Air Flow (cfm) | Spray Rate (g/min) | Pan Speed (RPM) | Mean Tab Wt. (n = 100) (mg) |
|---|---|---|---|---|---|---|
| 00:30 | 67/67 | 43 | 175 | 20 | 15 | 709.6 |
| 00:45 | 63/63 | 43 | 175 | 20 | 15 | 717.4 |
| 00:55 | 63/63 | 43 | 175 | 20 | 15 | 720.0 | e) Record the final mean Opadry coated tablet weight: 360.5 mg.

Figure 2:
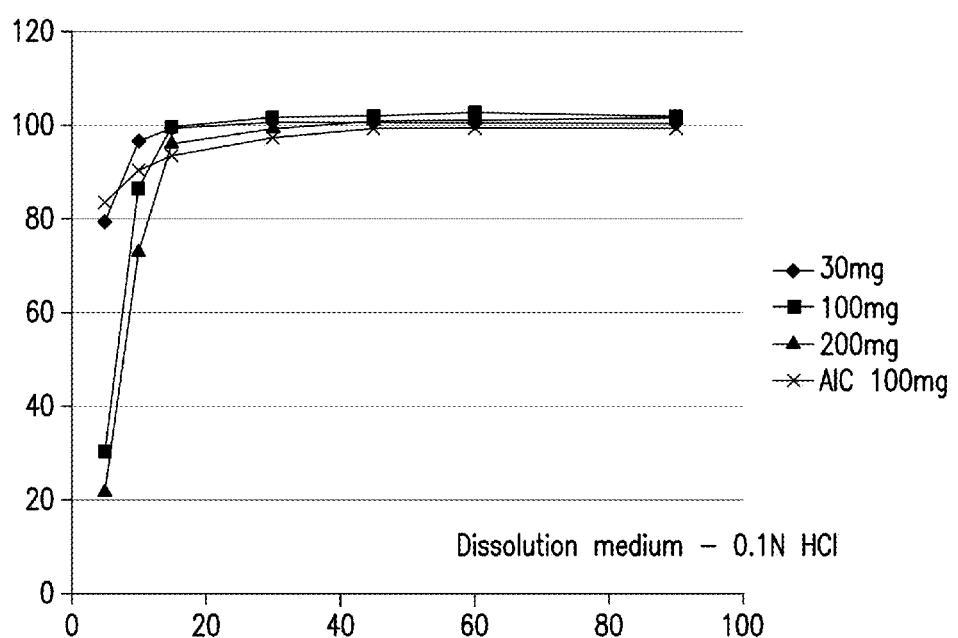
FIG. 2 depicts dissolution profiles of Compound 1 tablets in 0.1 N HCl.

FIG. 2 depicts dissolution profiles of Compound 1 tablets in 0.1 N HCl.

Figure 3:
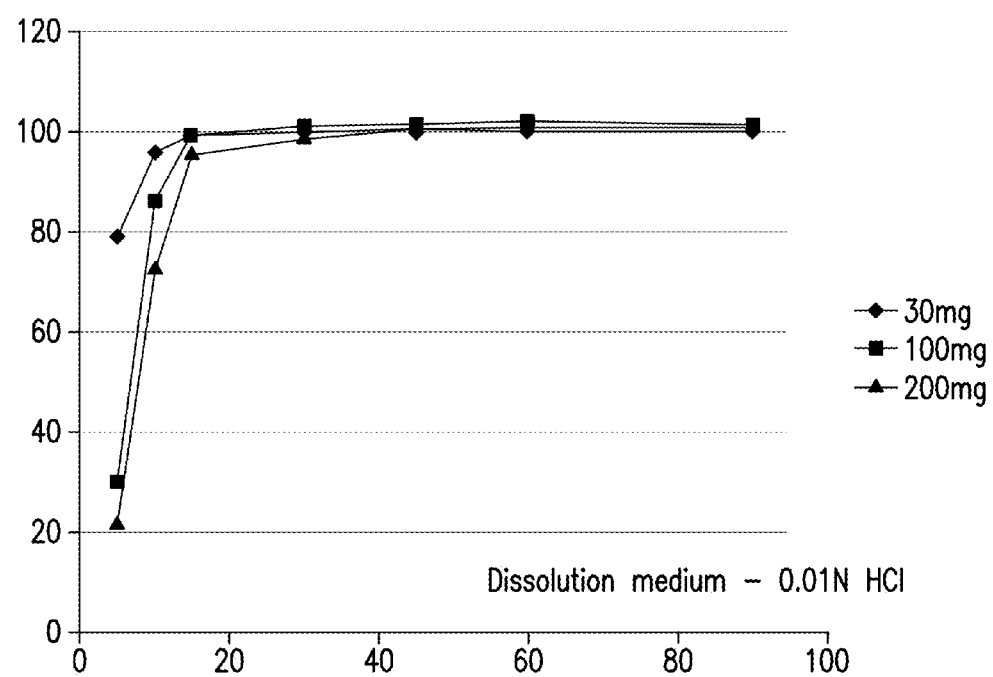
FIG. 3 depicts dissolution profiles of Compound 1 tablets in 0.01 N HCl.

FIG. 3 depicts dissolution profiles of Compound 1 tablets in 0.01 N HCl.

Figure 4:
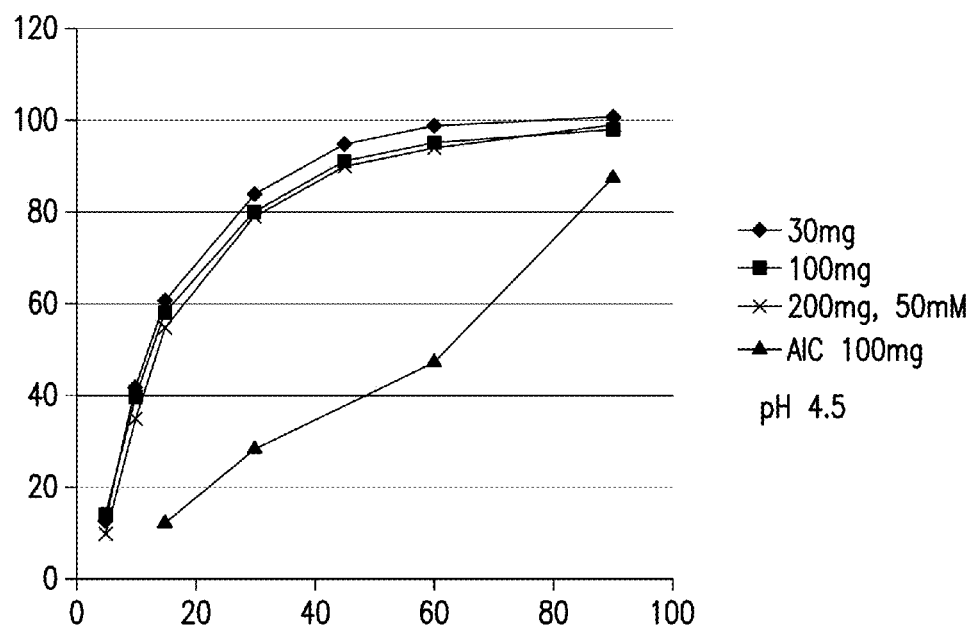
FIG. 4 depicts dissolution profiles of Compound 1 tablets in an aqueous solution at pH 4.5.

FIG. 4 depicts dissolution profiles of Compound 1 tablets in an aqueous solution with pH 4.5.

6.6. Protocol of Dog Pharmacokinetic Studies

A total of 4 male beagle dogs (as close to 10 kg as possible) were assigned to study. For each phase, all animals were fasted for at least 8 hours prior to dosing and through the first 4 hours of blood sample collection (food was returned within 30 minutes following collection of the last blood sample at the 4 hour collection interval, where applicable). Total fasting time did exceed 24 hours.

Phase 1: Each animal in Group 1 received a single capsule dose of Compound 1 as outlined in the table below.

Phase 2: Following a washout of approximately 5 days, each animal in Group 1 received a single tablet dose of Compound 1 as outlined in the table below.

TABLE 25

| Group | Test Article | Number of Males | Dose Route | Vehicle | Dose Level (mg/kg) | Dose Volume | Collection Intervals |
|---|---|---|---|---|---|---|---|
| Phase 1 |  |  |  |  |  |  |  |
| 1 | Cmpd 1 | 4 | Oral capsule | Capsule[A] | 100 | 1 capsule per animal | Blood[B] |
| Phase 2 |  |  |  |  |  |  |  |
| 1 | Cmpd 1 | 4 | Oral tablet | Tablet[A] | 100 | 1 tablet per animal | Blood[B] |

[A]All capsule/tablet formulations were provided pre-formulated and were used as received.
[B]Blood samples were collected predose and at 0.5 (30 min.), 1, 2, 4, 8, 12, and 24 hours postdose, and processed for plasma.

TABLE 26

Pharmacokinetic Blood Collection

| Blood Collection | Volume: 1 mL/sample |
|---|---|
| Anticoagulant | K$_2$EDTA |
| Site of Collection | Jugular |
| Sample Storage | Plasma samples were stored frozen at −60 to −90° C. until shipment. |

TABLE 27

Antemortem Evaluations

| Cageside Observations | All animals were observed at least twice a day for morbidity, mortality, injury, and availability of food and water. Any animals in poor health were identified for further monitoring and possible euthanasia. |
|---|---|

TABLE 27-continued

Antemortem Evaluations

| Body Weights | For each dose, bodyweights were measured and recorded on the day of dosing or the day prior to dosing. |
|---|---|
| Detailed Observations | A detailed clinical examination for each animal were performed pretest and at approximately 1-2 hours postdose. In addition, any positive clinical signs were recorded if observed. |

Figure 5:
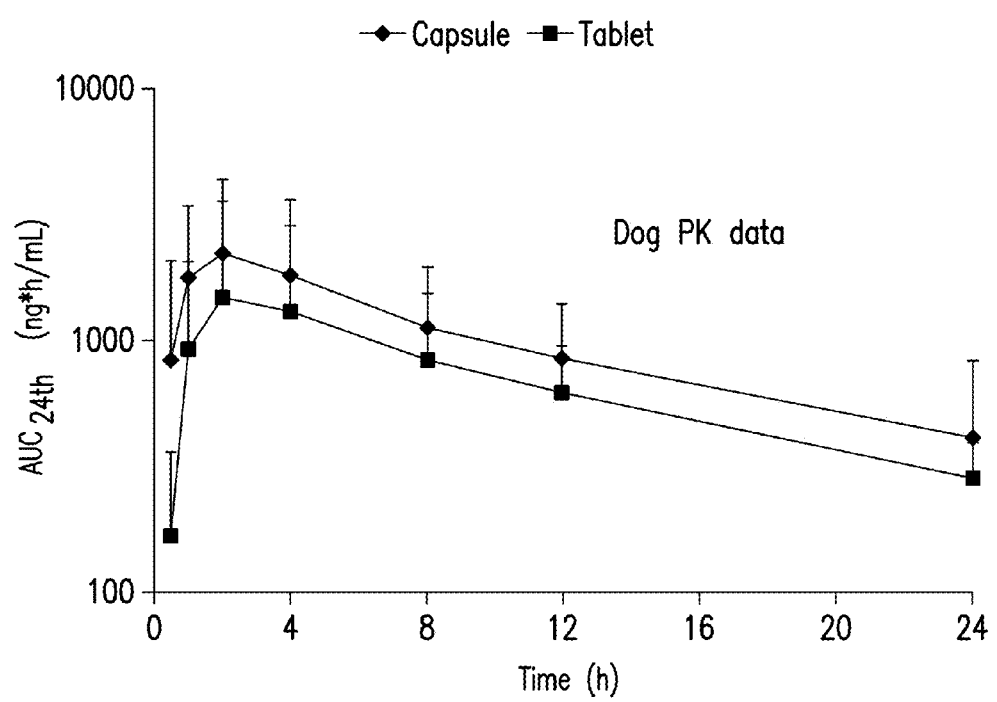
FIG. 5 depicts pharmacokinetic (PK) data of Compound 1 capsules and tablets in a dog.

FIG. 5 depicts pK data of Compound 1 capsule and tablets in a dog.

6.7. Clinical Protocol: A Two-Part, Phase 1 Study to Evaluate the Pharmacokinetics and Pharmacodynamics of Multiple Dose Compound 1 and the Effects of Food and Formulation on the Pharmacokinetics of Single Dose Compound 1 in Healthy Subjects Primary Objectives:

Part 1: To evaluate the effect of multiple oral doses of Compound 1 on JNK activity following ultraviolet (UV) irradiation of human skin Part 2: To evaluate pharmacokinetics of formulated Compound 1 tablets in the presence of food, and the relative bioavailability of formulated Compound 1 tablets compared to the active-ingredient-in capsule (AIC) formulation following a single oral dose.

Secondary Objectives:

Part 1: To evaluate the safety of single and multiple oral doses of Compound 1.

Part 2: To evaluate the safety and tolerability of formulated Compound 1 tablets when administered with food.

Study Design:

This is a two-part, Phase 1 study to evaluate the pharmacokinetics and pharmacodynamics of multiple doses of Compound 1 and the effects of food and formulation on the pharmacokinetics of single dose Compound 1 in healthy subjects.

Part 1:

This is an open-label, multiple-dose, 3-period, fixed sequence study, to evaluate the effect of Compound 1 on JNK activity following UV irradiation.

The study will consist of a screening phase (Day −21 to −2), minimum erythema dose (MED) determination prior to dosing, baseline (Day −1), 3 treatment/assessment periods during which increasing doses of Compound 1 are administered, and a follow-up visit. There will be no washout in between periods.

On the first day prior to dosing (baseline), and on the 6th day of each dosing period (Days 6, 12, and 18), twice the MED intensity of UV light will be administered to delineated sites on the subjects' buttocks. The irradiation at baseline (Day −1) should be administered at approximately the same time that irradiation is scheduled on Days 6, 12, and 18, which is at 2 hours post dose. Eight hours after UV irradiation, a skin punch biopsy will be taken from the UV exposure site. The end of confinement will be Day 19. The follow-up visit will occur 7-10 days (i.e. Day 25 to Day 28) following the last dose in Period 3. An early termination (ET) visit will occur within 10 days of the day of discontinuation.

The MED will be determined within 10 days of dosing in Period 1. It is recommended that MED be done earlier than Day −2 in case MED is unsuccessful on the first attempt. Confinement is not required for MED assessment.

Sixteen healthy qualified screened subjects with valid MEDs should report to the study center on Day −1 of Period 1 for baseline assessments (including 2×MED irradiation with biopsy), and to begin confinement.

Following scheduled check-in procedures, a skin test site will be delineated on the subject's upper buttock between the beltline and the natal cleft on right side. The test site will be minimum of 3 cm×3 cm, and will be outlined in ink (using a skin marker) with the subject lying prone. Subjects will receive 2×MED UV irradiation to one site on the buttock. One baseline skin punch biopsy will be taken from the UV-exposed site 8 hours (+/−10 minutes) after the UV-irradiation.

On Day 1, after a minimum 8 hours fast, subjects will receive the first dose of study drug at approximately 8 AM:

All subjects will receive the following doses of Compound 1 in the fixed sequence below:

Treatment A: 60 mg Compound 1 as active in capsule (AIC), QD×6 days, followed by Treatment B: 160 mg Compound 1 AIC, QD×6 days, followed by Treatment C: 400 mg of Compound 1 AIC, QD×6 days.

During each period, subjects may be domiciled at the study site starting on Day −1 (or as early as Day 2, if Baseline 2×MED is scheduled early in the day of Day −1), and will be discharged on Day 19 upon satisfactory safety review and after the completion of study-related procedures.

The study drug (as AIC) will be given orally with approximately 240 mL of noncarbonated water (at room temperature). The first meal following the morning dose on the 6th day of each dosing period will be 4 hours post dose. On all other dosing days, the next meal/snack can be served after a minimum 2 hours fast after dosing.

On Baseline (Day −1), Days 6, 12, and 18, the skin test sites will be delineated on the subject's upper buttock between the beltline and the natal cleft on right side. The right side of the buttock will be divided into three (3) different test sites, one positioned site for 2×MED irradiation at Baseline and at each of the 3 periods (Day 6, Day 12, and Day 18). Each test site will be as large as possible (minimum of 3 cm×3 cm). The test site areas will be outlined in ink (using a skin marker) with the subject lying prone.

Subjects will receive 2×MED UV irradiation to one site on the buttock 2 hours (+/−10 minutes) after administration of the study drug on Days 6, 12, and 18. Ultraviolet irradiation at Baseline should be scheduled approximately 2 hours after the planned dosing time for Day 1. It is suggested that the UV exposure sites be in sequential order starting with the extreme left and moving across to the extreme right (i.e. exposure site 1 for Baseline; and exposure site 4 for Period 3).

One skin punch biopsy will be taken from the UV-exposed site 8 hours (+/−10 minutes) after the UV-irradiation. Four biopsies will be taken throughout the study; ie. baseline and one biopsy per period. The biopsies will be processed into tissue slides by a third party to be designated by Celgene and analyzed by immunohistochemistry (ICH). This third party will be blinded to the treatment periods (Baseline and doses).

Subjects will be discharged from the clinical site on Day 19 after all scheduled procedures have been completed.

Adverse event (AE) monitoring, physical examinations, vital signs, electrocardiograms (ECGs), safety laboratory evaluation, and evaluation of wound healing will be performed at specified time points for safety assessments.

Serial blood samples will be collected at pre-defined time points (Days 6, 12, and 18: predose, 0.5, 2, 4, 6, 10, 12, and 24 hr postdose) for analysis of Compound 1 levels. All evaluations will be performed in accordance with the Table of Events and Procedures.

Procedures (except for the change in treatment) will be consistent across all 3 periods.

Activities, environment, food, procedures, and schedule between treatment periods should be kept as consistent as possible.

Part 2:

Part 2 will be an open label, randomized, cross-over study with 3 periods. The study will consist of a screening phase (Day −21 to −2), baseline (Day −1), 3 treatment/assessment periods, and a follow-up phone call.

Twelve eligible subjects will check into the study center on Day −1 of Period 1 for baseline assessments. On Day 1 of Period 1, subjects who continue to be qualified for participation in the study will be randomly assigned to one of three dosing sequences during which they will receive one of the following dosing regimens:

Treatment D: 2×100 mg Compound 1 as AIC, single oral dose administered under fasted conditions.

Treatment E: 1×200 mg Compound 1 (formulated tablet(s)) single oral dose administered under fasted conditions.

Treatment F: 1×200 mg Compound 1 (formulated tablet(s)) single oral dose administered under fed conditions (standard high fat breakfast).

TABLE 28

Food Effect Treatment Sequences

| Sequence | Period 1 | Period 2 | Period 3 |
| --- | --- | --- | --- |
| Sequence 1 | D | E | F |
| Sequence 2 | E | F | D |
| Sequence 3 | F | D | E |

All subjects will fast overnight for at least 10 hours prior to dosing. Subjects receiving Treatment D and E (fasted) will continue to fast for at least 4 hours after dosing.

For Treatment F, subjects will receive a standard high fat (approximately 50% of the total caloric content of the meal), high-calorie (approximately 800 to 1000 calories) breakfast within 30 minutes before dosing (based on FDA Center for Drug Evaluation and Research Food Effect Guidance, (FDA, 2002)). The meal should derive approximately 150, 250, and 500 to 600 calories from protein, carbohydrates, and fat, respectively. Subjects must consume the entire meal within 30 minutes of serving. Dosing must occur 30 minutes (±5 minutes) after serving the meal.

During each study period, subjects will be housed at the study center starting on Day −1. Subjects will be discharged from the study center on Day 5 of the last period upon completion of study procedures. Each treatment period will be separated by a washout period of at least 7 but no more than 10 days from the last Compound 1 dose to the next scheduled dose. Serial blood samples will be collected during each period at predose, 0.5, 1, 1.5, 2, 2.5, 3, 5, 8, 12, 24, 36, 48, 72, and 96 hours post dose to determine the levels of Compound 1 in plasma.

If necessary, subjects may leave the clinic following scheduled procedures on the morning of Day 5 of Periods 1 and/or 2, and return for the following period. In certain instances, a longer washout may be acceptable if mutually agreed upon.

Study Population.

Healthy male and female subjects. Sixteen subjects will be enrolled in Part 1. Twelve volunteers will be enrolled in Part 2. Subjects may only participate in either Part 1 or Part 2.

Length of Study.

Part 1: approximately 7 weeks (including screening). Part 2: approximately 6 weeks (including screening).

The End of Trial is defined as either the date of the last visit of the last subject to complete the study, or the date of receipt of the last data point from the last subject that is required for primary, secondary and/or exploratory analysis, as pre-specified in the protocol and/or the Statistical Analysis Plan, whichever is the later date.

Study Treatments.

Compound 1 as AIC (30 mg and 100 mg dose strengths) and formulated tablets (200 mg) will be supplied in bulk containers by Celgene.

Part 1:

Treatment A (60 mg): 2×30 mg Compound 1 as AIC, QD×6 days; Treatment B (160 mg): 2×30 mg+1×100 mg Compound 1 as AIC, QD×6 days; Treatment C (400 mg): 4×100 mg Compound 1 as AIC, QD×6 days Part 2:

Treatment D: Compound 1 2×100 mg as AIC (200 mg), given QD in the fasted state; Treatment E: Compound 1 as formulated tablets (1×200 mg), given QD in the fasted state; Treatment F: Compound 1, as formulated tablets (1×200 mg), given QD in the fed state Overview of Safety Assessments:

Safety will be monitored throughout the study. Safety evaluations will include adverse event (AE) reporting, PEs, vital signs, 12-lead ECGs, clinical laboratory safety tests (including liver function tests (LFTs), total cholesterol, triglycerides, high-density lipoprotein (HDL), and low-density lipoprotein (LDL)) in addition to standard clinical chemistry, hematology, and urinalysis tests), review of concomitant medications/procedures, evaluation of wound healing, and pregnancy tests for female subjects.

All AEs will be monitored and recorded throughout the study from the time the informed consent form (ICF) is signed until study completion, and when made known to the Investigator within 28 days after the last dose of Compound 1 (and those serious adverse events (SAEs) made known to the Investigator at any time thereafter that are suspected of being related to IP). All concomitant medications and procedures will be reviewed and recorded from the time the subject signs the ICF until study completion. A follow-up visit (Part 1) or a follow-up phone call (Part 2) will be scheduled for all subjects. If a subject is discontinued from the study for any reason, an ET visit will be performed.

Overview of Pharmacokinetic Assessments:

In both parts of the study, blood samples will be collected at specified times to determine plasma levels of Compound 1.

Part 1:

Collect blood/plasma on Day 6, 12, and 18: predose, 0.5, 2, 4, 6, 10, 12, and 24 hour post dose;

Plasma PK parameters at steady state including but not limited to the following: $AUC_\tau$ (Area under the plasma concentration-time curve from time zero to tau, where tau is the dosing interval); $C_{max}$ (Maximum observed plasma concentration), $C_{min}$ (Minimum observed plasma concentration), $T_{max}$ (Time to $C_{max}$).

Part 2: Collect blood/plasma at each period: predose, 0.5, 1, 1.5, 2, 2.5, 3, 5, 8, 12, 24, 36, 48, 72, and 96 hours post dose.

PK parameters at steady state including but limited to the following: $AUC_{0-t}$, (Area under the plasma concentration-time curve from time zero to the last quantifiable concentration); $AUC_\infty$ (Area under the plasma concentration-time curve from time zero extrapolated to infinity); CL/F (Apparent total plasma clearance when dosed orally); $V_z/F$ (Apparent total volume of distribution when dosed orally, based on the terminal phase); $t_{1/2}$ (Terminal-phase elimination half-life); $C_{max}$ (Maximum observed plasma concentration); and $T_{max}$ (Time to $C_{max}$).

Overview of Pharmacodynamic Assessments:

Individual ultraviolet B (UVB) exposure for MED determination:

UVB exposure within 10 days of first dosing in Period 1 consisting of UVB exposure to 6 sites on the left buttock with incrementally increasing UV intensity MED determination approximately 24 hours after UVB exposure Individual UVB exposure (2×MED):

At Baseline (Day −1) and on Days 6, 12, and 18: 2×MED UVB exposure to single site on upper buttock at 2 hours post Compound 1 dose.

Collection of biopsies: One punch biopsy (approximately 3 mm in diameter by approximately 0.8 mm in depth) from each test site will be collected at baseline (Day −1), and on Days 6, 12, and 18: eight (8) hours post UVB irradiation (a total of 4 punch biopsies).

Analysis of biopsy samples: Biopsies will be analyzed and phospho-cJun expression will be analyzed by Immunohistochemistry (IHC) assays. Other biomarkers such as, but not limited to, c-Jun, may be explored using the same skin biopsies and may be reported separately.

Phospho-cJun IHC data may be analyzed by either an analog scoring system or by an automated measurement of integrated optical density by trained individuals who are blinded to the treatments. For Part 1 only the Phospho-c-Jun IHC data will be subjectively scored on a scale of 0 to 4 based on the intensity and number of epidermal keratinocyte nuclei stained within the tissue section by trained individuals blinded to treatment.

6.8. A Two-Part, Phase 1 Study to Evaluate the Pharmacokinetics and Pharmacodynamics of Multiple Dose Compound 1 and the Effects of Food and Formulation on the Pharmacokinetics of Single Dose Compound 1 in Healthy Subjects Primary Objectives:

Part 1: To evaluate the effect of multiple oral doses of Compound 1 on JNK activity following ultraviolet (UV) irradiation of human skin; and Part 2: To evaluate the PK of formulated Compound 1 tablets in the presence of food and the relative bioavailability of formulated Compound 1 tablets compared to the active ingredient in capsule (AIC) formulation following a single oral dose.

Secondary Objectives:

Part 1: To evaluate the safety of single and multiple oral doses of Compound 1; and Part 2: To evaluate the safety and tolerability of the formulated Compound 1 tablets when administered with food.

Investigational Plan

Overall Study Design and Plan:

This was a two-part, two-site, Phase 1 study to evaluate the PK and pharmacodynamics (PD) of multiple doses of Compound 1 and the effects of food and formulation on the PK of a single dose of Compound 1 in healthy subjects. Part 1 and Part 2 of the study were conducted at two different sites.

Part 1:

Part 1 was an open label, multiple dose, three period, fixed sequence study to evaluate the effect of Compound 1 on JNK activity following UV irradiation.

The study consisted of a screening phase (Days −21 to −2), minimum erythema dose (MED) determination prior to dosing, baseline (Day −1), three treatment/assessment periods during which increasing doses of Compound 1 were administered, and a follow up visit. There was no washout in between the dosing periods.

The MED was determined no later than Day −2 in case MED determination was unsuccessful on the first attempt. Confinement was not required for MED assessment. Sixteen healthy subjects with valid MEDs reported to the study center on Day −1 for baseline assessments (including 2×MED irradiation with biopsy) and to begin confinement. On Day 1, after a minimum of an 8-hour fast, subjects received the first dose of Compound 1. All subjects received the following oral doses of Compound 1 in the fixed sequence below:

Treatment A: 60 mg Compound 1 as AIC, QD×6 days;
Treatment B: 160 mg Compound 1 as AIC, QD×6 days; and
Treatment C: 400 mg Compound 1 as AIC, QD×6 days.

There was no washout between treatments. The end of confinement was Day 19. The follow up visit occurred 7 to 10 days (i.e., Days 25 to 28) following the last dose in the third treatment period. An early termination (ET) visit occurred within 10 days of the day of discontinuation.

Part 2:

Part 2 was an open label, randomized, crossover study with three periods. The study consisted of a screening phase (Days −21 to −2), baseline (Day −1), three treatment/assessment periods, and a follow up phone call.

Twelve eligible subjects reported to the study center on Day −1 of Period 1 for confinement and baseline assessments. On Day 1 of Period 1, subjects who continued to be qualified for participation in the study were randomly assigned to one of three dosing sequences (Table 29) during which they received one of the following dosing regimens:

Treatment D: 2×100 mg Compound 1 as AIC, single oral dose administered under fasted conditions;
Treatment E: 1×200-mg Compound 1 formulated tablet, single oral dose administered under fasted conditions; and
Treatment F: 1×200-mg Compound 1 formulated tablet, single oral dose administered under fed conditions (standard high-fat breakfast).

TABLE 29

Treatment Sequences-Part 2

| Sequence | Period 1 | Period 2 | Period 3 |
|---|---|---|---|
| Sequence 1 | D | E | F |
| Sequence 2 | E | F | D |
| Sequence 3 | F | D | E |

All subjects fasted overnight for at least 10 hours prior to dosing. For Treatment F, subjects received a standard high-fat breakfast 30 minutes before dosing. Dosing occurred 30 minutes (±5 minutes) after serving the meal.

Each treatment period was separated by a washout period of 7 to 8 days. Subjects were discharged from the study center on Day 5 of the last period upon completion of study procedures. An end-of-study (EOS) phone call occurred 7 days following the last dose in the third period.

Discussion of the Study Design, Including Choice of Control Groups

Part 1:

This was a fixed sequence, multiple-treatment (from low to high doses) design to evaluate the effect of Compound 1 on JNK inhibition in human skin. Three Compound 1 dose levels were explored to obtain an exposure response relationship. A fixed sequence allowed for efficient conduct of the trial. Although there was no washout between treatments, PD and PK carry-over effects were not anticipated at Day 6 of each treatment period when Compound 1 concentrations were expected to reach steady state and PK and PD were assessed. The confounding factor of time with the fixed sequence design was limited from both PK and PD perspectives. As such, this fixed sequence design allowed for adequate assessment of the study objectives.

The study was open label for the investigators, subjects, and sponsor; however, it was blinded for the third party processing and analyzing of skin biopsy samples.

Each treatment was QD for 6 days. It was anticipated that the steady state of exposure would be reached by Day 6.

Ultraviolet exposure occurred at baseline and at 2 hours postdose on Day 6 of each treatment, which was the anticipated Compound 1 $T_{max}$ at steady state. The dose of UV was 2×MED UVB, which has been demonstrated to activate JNK. A skin biopsy was taken 8 hours post UV exposure, as this is the time c Jun phosphorylation reaches plateau. A total of four skin biopsies were taken, one at baseline and one each on the sixth day of each treatment period.

The 2×MED UV exposure and skin biopsy procedures were well tolerated by healthy subjects.

Part 2:

This was a randomized, single dose, three way crossover design to evaluate the relative bioavailability and food effect of Compound 1. A single 200-mg Compound 1 formulated tablet administered under fasted conditions (Treatment E) was assessed for bioavailability relative to 2×100 mg Compound 1 as AIC (Treatment D). Food effect was explored by comparing 200-mg Compound 1 formulated tablet administered under fasted conditions (Treatment E) to 200-mg Compound 1 formulated tablet administered under fed conditions (Treatment F).

Selection of Study Population

Inclusion Criteria

Subjects must have satisfied all of the following criteria to be eligible for enrollment in the study:

1. Must have understood and voluntarily signed a written informed consent document (ICD) prior to any study-related assessments/procedures being performed.

2. Must have been able to communicate with the investigator and to understand and adhere to the study visit schedule and other protocol requirements.

3. Must have been a male or female*, aged 18 to 65 years (inclusive) at the time of signing the ICD.

* A woman of childbearing potential (WCBP) must have agreed to ongoing pregnancy testing during the course of the study and at the end of the study. This applied even if the subject practiced true abstinence from heterosexual contact. A WCBP was a sexually mature woman who had not undergone a hysterectomy or who had not been naturally postmenopausal for at least 24 consecutive months (i.e., who had had menses at any time in the preceding 24 consecutive months).

a. Females must have either committed to true abstinence** from heterosexual contact (which must have been reviewed on a monthly basis) or agreed to use, and been able to comply with, two highly effective contraception methods without interruption 28 days prior to starting study drug, during the study therapy (including dose interruptions), and for at least 28 days after discontinuation of study drug.

b. Females not of child-bearing potential should have been either surgically sterilized at least 6 months prior to screening (hysterectomy or bilateral tubal ligation) or been postmenopausal (defined as 24 months with no menses prior to screening and with a plasma follicle-stimulating hormone >40 IU/L at screening). Documentation was required in cases of tubal ligation.

4. Males must have practiced true abstinence** or agreed to use a condom (a latex condom was recommended) during sexual contact with a pregnant female or WCBP while on study drug, or while participating in this study, during dose interruptions, and for at least 28 days following study drug discontinuation, even if he had undergone a successful vasectomy.

** True abstinence was acceptable when this was in line with the preferred and usual lifestyle of the subject (periodic abstinence (e.g., calendar, ovulation, symptothermal, postovulation methods) and withdrawal were not acceptable methods of contraception).

5. Must have had a body mass index (BMI=weight (kg)/(height (m)$^2$) between 18 and 33 kg/m$^2$ (inclusive).

6. Must have been healthy as determined by the investigator based on medical history, PE, clinical laboratory test results, vital signs, and 12 lead ECGs.

a. Must have been afebrile (febrile was defined as ≥38° C. or 100.3° F.).

b. Must have had systolic blood pressure in the range of 80 to 140 mmHg, diastolic blood pressure in the range of 40 to 90 mmHg, and pulse rate in the range of 40 to 110 beats per minute.

c. Must have had QT interval corrected for heart rate using Fridericia's formula value ≤430 msec for male subjects and ≤450 msec for female subjects. An ECG could have been repeated up to three times to determine subject eligibility.

7. Additional criteria for Part 1 only:

a. Must have been Fitzpatrick skin type I or II.

b. Must have had a valid MED obtained within 10 days prior to dosing.

Exclusion Criteria

The presence of any of the following excluded a subject from enrollment in the study:

1. Had a history (i.e., within 3 years) of any clinically significant neurological, gastrointestinal, hepatic, renal, respiratory, cardiovascular, metabolic, endocrine, hematological, dermatological, psychological, or other major disorders.

2. Had any condition, including the presence of laboratory abnormalities, that would have placed the subject at unacceptable risk if he/she were to have participated in the study or confounded the ability to interpret data from the study.

3. Used any prescribed systemic or topical medication, including vaccines, within 30 days of the first dose.

4. Used any nonprescribed systemic or topical medication (including herbal medicines) within 14 days of the first dose administration (with the exception of vitamin/mineral supplements).

5. Used any metabolic enzyme inhibitors or inducers (i.e., cytochrome P450 [CYP] 3A inducers and inhibitors or St. John's wort) within 30 days of the first dose administration.

a. The University of Indiana "Cytochrome P450 Drug Interaction Table" was used to determine inhibitors and/or inducers of CYP3A4.

6. Had any surgical or medical conditions possibly affecting drug absorption, distribution, metabolism, and excretion (e.g., bariatric procedure).

a. Appendectomy and cholecystectomy were acceptable.

7. Donated blood or plasma within 8 weeks before the first dose administration.

8. Had a history of drug abuse (as defined by the current version of the Diagnostic and Statistical Manual (DSM)) within 2 years before dosing or positive drug screening test reflecting consumption of illicit drugs.

9. Had a history of alcohol abuse (as defined by the current version of the DSM) within 2 years before dosing or positive alcohol screen.

10. Known to have serum hepatitis, known to be a carrier of the hepatitis B surface antigen or hepatitis C antibody, or had a positive result to the test for human immunodeficiency virus antibodies at screening.

11. Exposed to an investigational drug (new chemical entity) within 30 days preceding the first dose administration or five half-lives of that investigational drug, if known (whichever was longer).

12. Smoked more than 10 cigarettes per day or the equivalent in other tobacco products (self reported).

13. Had a history of multiple drug allergies (i.e., two or more).

Additional Exclusion Criteria for Subjects in Part 1 Only:

1. Were unable to evaluate the skin in and around the test sites due to sunburn, tans, uneven skin tones, tattoos, scars, excessive hair, numerous freckles, or any other disfiguration.

2. Used any creams or lotions (i.e., containing sun protection factor (SPF)) in the test area (i.e., buttocks) within 7 days of study start (Day 1).

3. Participated in any test for irritation or sensitization or any test involving UV exposures on the test area within 4 weeks of study start.

4. Participated in another study requiring biopsy (on the planned test area) within the past 2 months.

5. Had a history of wound healing or blood clotting abnormality.

6. Had a history of keloid formation or hypertrophic scarring following skin injury.

7. Had a history of severe reactions from exposure to sunlight.

8. Had a history of allergy to lidocaine or other similar local anesthetics.

9. Had a history of allergy to epinephrine.

Removal of Subjects from Therapy or Assessment

The following events were considered sufficient reasons for discontinuing a subject from the investigational product and/or from the study:

Adverse event;
Withdrawal by subject;
Death;
Lost to follow-up; and
Protocol violation.

The reason for discontinuation was recorded in the source documents and case report form (CRF).

The decision to discontinue a subject remained the responsibility of the treating physician, which was not delayed or refused by the sponsor. However, prior to discontinuing a subject, the investigator could have contacted the medical monitor and forwarded appropriate supporting documents for review and discussion.

In the event that a subject was discontinued from the study for any reason, an ET visit was performed. Every effort was made to ensure that procedures scheduled for the follow-up visit were performed at the ET visit.

Treatments
Treatments Administered
Part 1:
All subjects received the following oral doses of Compound 1 as AIC:

Days 1 through 6: Treatment A: 60 mg Compound 1 AIC, QD×6 days;

Days 7 through 12: Treatment B: 160 mg Compound 1 AIC, QD×6 days; and

Days 13 through 18: Treatment C: 400 mg Compound 1 AIC, QD×6 days.

The treatments were administered in the morning following an overnight fast of at least 8 hours. All doses were administered with 240 mL of noncarbonated, room temperature water. Water was allowed as desired except for 1 hour before and 1 hour after drug administration. The first meal following the morning dose on the sixth day of each dosing period was 4 hours postdose. On all other dosing days, the next meal/snack was served after a minimum 2 hours after dosing.

TABLE 30

Dosage Regimen-Part 1

| Treatment | Compound 1 Capsules 30 mg | 100 mg | Total Number of Capsules per Dosing Day |
|---|---|---|---|
| 60 mg Compound 1 | 2 | 0 | 2 |
| 160 mg Compound 1 | 2 | 1 | 3 |
| 400 mg Compound 1 | 0 | 4 | 4 |

Subjects remained semi-recumbent for at least 2 hours postdose.

Part 2:
On Day 1 of each period, subjects were administered each treatment (D, E, or F):

Treatment D: 2×100 mg Compound 1 as AIC, single oral dose administered under fasted conditions;

Treatment E: 1×200 mg Compound 1 (formulated tablet), single oral dose administered under fasted conditions; and Treatment F: 1×200 mg Compound 1 (formulated tablet), single oral dose administered under fed conditions (standard high-fat breakfast).

Treatments D and E were administered in the morning following an overnight fast of at least 10 hours. Subjects who received Treatments D and E (fasted) continued to fast for at least 4 hours after dosing. For Treatment F, subjects received a standard high fat (approximately 50% of the total caloric content of the meal), high calorie (approximately 800 to 1000 calories) breakfast 30 minutes before dosing. The meal derived approximately 150, 250, and 500 to 600 calories from protein, carbohydrates, and fat, respectively. Subjects consumed the entire meal within 30 minutes of serving. Dosing occurred 30 minutes (±5 minutes) after serving the meal.

Subjects received two 100 mg Compound 1 as AIC or one 200-mg tablet depending on the assigned treatment. All doses were administered with 240 mL of noncarbonated, room temperature water. Water was allowed as desired except for 1 hour before and 1 hour after drug administration.

Identity of Investigational Products

TABLE 31

Test Materials

| Information | Compound 1 | Compound 1 | Compound 1 |
|---|---|---|---|
| Formulation | AIC | AIC | Tablet |
| Strength | 30 mg | 100 mg | 200 mg |

Method of Assigning Subjects to Treatment Groups

Prior to dosing, subjects were identified by their initials and unique screening number assigned by the clinical site. On the morning of Day 1, Period 1 and prior to dosing, each subject was assigned a unique subject number.

For Part 2, subjects were randomly assigned to one of three treatment sequences prior to dosing on the morning of Day 1, Period 1 according to a computer-generated randomization code.

Selection of Doses in the Study
Part 1:
Compound 1 doses were 60, 160, and 400 mg QD×6 days. Based upon available human PK and preclinical pharmacology data, the doses were anticipated to provide a range of PD effects including both minimum and maximum JNK inhibition. The dose range also covered the dose (240 mg QD) that yielded AUC comparable to the AUC (23400 ng·h/mL) in rats at which anti fibrotic activity was observed.

In addition, Compound 1 doses selected were supported by toxicology studies and human experience. Compound 1 has been tested in GLP repeating dose toxicology studies in rats and dogs for 28 days. The AUC at the dog no observed adverse effect level was 81200 ng·h/mL. This was higher than the AUC observed in humans receiving 480 mg QD at steady state, and Compound 1 doses up to 480 mg QD×14 days were well tolerated by healthy subjects.

Part 2:
The highest unit strength of the formulated tablet was 200 mg Compound 1. Tablets with other unit strengths are of the same formulation. The available strengths for the AIC were 10, 30, and 100 mg. Therefore, the bioavailability of a single 200 mg tablet (Treatment E) was tested in comparison to 2×100 mg AIC reference (Treatment D).

The formulated tablets were planned to be used in future clinical trials; therefore, the food effect evaluated the PK of 200-mg Compound 1 formulated tablet administered under fasted conditions (Treatment E) in comparison to 200-mg Compound 1 formulated tablet administered under fed conditions (Treatment F).

Pharmacokinetic, Pharmacodynamic, and Safety Variables

Pharmacokinetic Parameters

Method and Timing of Pharmacokinetic Sample Collection

Part 1:

Blood samples for Compound 1 plasma PK analysis were collected at the following time points on Days 6, 12, and 18: predose and 0.5, 2, 4, 6, 10, 12, and 24 hours postdose.

Part 2:

Blood samples for Compound 1 plasma PK analysis were collected at the following time points in all periods: predose and 0.5, 1, 1.5, 2, 2.5, 3, 5, 8, 12, 24, 36, 48, 72, and 96 hours postdose.

During Treatment D (Compound 1 AIC, fasted), DBS specimens (by lancet to the finger) were collected from subjects at each PK time point and were used to measure concentrations of Compound 1 in whole blood.

Determination of Drug Concentration

Concentrations of Compound 1 in plasma were measured using a validated liquid chromatography tandem mass spectrometry (LC-MS/MS) assay. In Part 2, concentrations of Compound 1 in whole blood were measured using a validated LC-MS/MS method.

Calculation of Pharmacokinetic Parameters

Plasma and whole blood PK parameters were derived for Compound 1 by noncompartmental analysis. Actual sampling times were used in the calculation of PK parameters.

Part 1:

$AUC_\tau$: AUC from time zero to tau, where tau is the dosing interval.

$C_{max}$: Maximum observed plasma concentration.

$C_{min}$: Minimum observed plasma concentration.

$T_{max}$: Time to $C_{max}$.

Part 2:

$AUC_t$: AUC from time zero to the last quantifiable concentration.

$AUC_\infty$: AUC from time zero extrapolated to infinity.

$C_{max}$: Maximum observed plasma concentration.

$T_{max}$: Time to $C_{max}$.

CL/F: Apparent total plasma clearance when dosed orally.

$V_z/F$: Apparent total volume of distribution when dosed orally.

$t_{1/2}$: Terminal phase elimination half-life.

Pharmacodynamic Parameters

Method and Timing of Pharmacodynamic Sample Collection

For Part 1, no later than 2 days prior to enrollment in Period 1 (i.e., Day −2), six unprotected sites on the left buttock were exposed to UVB in incrementally increasing UV intensity, and the MED was determined approximately 24 hours (±1 hour) after UVB exposure.

On baseline (Day −1) and on the sixth day of each dosing period (Days 6, 12, and 18), the skin test sites were delineated on the subject's upper buttock between the beltline and the natal cleft on the right side. The right side of the buttock was divided into four different test sites, one site for 2×MED irradiation at baseline and each of the three dosing periods. Each test site was a minimum of 3 cm×3 cm. Subjects received 2×MED UV irradiation at baseline (Day −1) at approximately the same time that irradiation was scheduled on Days 6, 12, and 18, which was 2 hours postdose. Eight hours after UV irradiation (±10 minutes), a skin punch biopsy was taken from the UV exposure site. The biopsies were processed into tissue slides by a third party and analyzed by immunohistochemistry (IHC). This third party was blinded to the treatment periods (baseline and doses).

Determination of Pharmacodynamic Parameters

Phospho-c-Jun expression in biopsies was analyzed by IHC. Phospho-c-Jun IHC data were subjectively scored on a scale of 0 to 4 based on the intensity and number of epidermal keratinocyte nuclei stained within the tissue section by trained individuals blinded to treatment. The IHC was also analyzed by automated measurement of integrated optical density.

Study Subjects

Disposition of Subjects

Overall, 28 subjects were enrolled in this study and 27 subjects completed the study. In Part 1, 15 of 16 subjects completed the study. All 12 subjects enrolled and randomized in Part 2 completed the study. In Part 1, one subject experienced a treatment-emergent adverse event (TEAE) of viral infection that was assessed by the Investigator as not suspected to be related to Compound 1. The viral infection began on Day 10 and resulted in discontinuation of study procedures on Day 11. The subject remained at the site for monitoring until he was discharged on Day 13 at his request. A summary of subject disposition is presented in Table 32.

TABLE 32

Subject Disposition and Analysis Populations

| | Part 1 | Part 2 | Total |
|---|---|---|---|
| Number of Subjects Enrolled (N) | 16 | 12 | 28 |
| Number of Subjects Completed (N (%)) | 15 (93.8) | 12 (100) | 27 (96.4) |
| Number of Subjects Discontinued (N (%)) | 1 (6.3) | — | 1 (3.6) |
| Number of Subjects in Safety Population (N (%)) | 16 (100) | 12 (100) | 28 (100) |
| Number of Subjects in PK Population (N (%)) | 16 (100) | 12 (100) | 28 (100) |
| Number of Subjects in PD Population (N (%)) | 15 (93.8) | — | 15 (53.6) |
| Primary Reason for Discontinuation from the Study | | | |
| Adverse Event | 1 (100) | — | 1 (100) |

N = total number of subjects;
PD = pharmacodynamic;
PK = pharmacokinetic.
Note:
Percentages for the reasons for discontinuation are based on the number of subjects who prematurely withdrew from the study. All other percentages are based on the number of subjects enrolled.

Pharmacokinetic/Pharmacodynamic Evaluation

Analysis Population

Pharmacokinetic Population:

The PK population included all 28 subjects (16 in Part 1 and 12 in Part 2) in this study who were administered at least one dose of Compound 1. One subject in Part 1 was discontinued from study procedures on Day 11. Therefore, the PK samples were not collected on Days 12 or 18 for this subject.

Pharmacodynamic Population:

The PD population included 15 of the 16 subjects in Part 1 of this study who received all required doses of Compound 1 within a given period, were exposed to 2×MED, and had evaluable biopsies for at least one treatment period (excluding the baseline biopsy). One subject was excluded from the PD population because his baseline phospho-c-Jun optical density score was more than four standard deviations (SDs) lower than the mean of the other subjects' baseline scores. Another subject was discontinued from the study on Day 11 and therefore has no evaluable biopsies for Days 12 or 18. He was included in the PD population because he had biopsy data from Day 6.

Pharmacokinetic/Pharmacodynamic Results

Pharmacokinetic Results

Plasma and Whole Blood Concentrations for Compound 1

Mean (±SD) plasma concentrations versus time profiles for Compound 1 (Part 1 and Part 2) are displayed in FIG. 103, FIG. 104 and FIG. 105, respectively.

Review of the individual concentration-time data indicated that vast majority of the subjects at all dose levels showed quantifiable Compound 1 plasma concentrations up to 96 hours post-dose. Plasma concentrations were highly correlated with whole blood concentration for Compound 1 as shown in FIG. 106.

Summary statistics of plasma pharmacokinetic parameters for Part 1 and Part 2 are presented in Table 33 and Table 34, respectively.

Part 1:

Compound 1 was rapidly absorbed following single or multiple oral doses at the dose levels evaluated with a median $T_{max}$ of approximately 1.0 to 4 hours postdose. After achieving $C_{max}$, Compound 1 started to decline from plasma in a bi-exponential manner. The mean terminal half life of Compound 1 was estimated to be between approximately 14 and 21 hours following multiple doses. The systemic exposure of Compound 1 ($AUC_\infty$, $AUC_t$, and $C_{max}$) appeared to increase in a more than dose-proportional manner as the dose increased from 60 mg to 400 mg following multiple oral doses.

TABLE 33

Summary of Pharmacokinetic Parameters of Compound 1 Following Multiple Oral Doses of 60, 160, and 400 mg (QD × 6 days), Part 1

| Parameter | Geometric Mean (Geometric CV %) Treatment (Dose) | | |
|---|---|---|---|
| | A (60 mg) (N = 15) | B (160 mg) (N = 15) | C (400 mg) (N = 15) |
| $C_{max}$ (ng/mL) | 419 (24.7) | 1460 (25.1) | 4460 (19.5) |
| $C_{min}$ (ng/mL) | 22 (44.6) | 65 (67.5) | 212 (69.7) |
| $T_{max}$[a] (hr) | 1.95 (1.92, 4.00) | 1.95 (1.92, 2.00) | 1.97 (1.92, 5.93) |
| $AUC_{0-\tau}$ (ng·h/mL) | 2290 (24.6) | 8560 (32.6) | 31300 (31.4) |

$AUC_{0-\tau}$ = area under the plasma concentration versus time curve from time 0 to τ (tau), where τ is 24 hours (the length of the dosing interval);
$C_{max}$ = maximum observed plasma concentration;
$C_{min}$ = observed plasma concentration at 24 hours postdose;
CV = coefficient of variation; N = total number of subjects;
$T_{max}$ = time to maximum observed plasma concentration.
[a]$T_{max}$ is presented as median (minimum, maximum).

Treatment A: 60 mg Compound 1 as AIC, QD×6 days.

Treatment B: 160 mg Compound 1 as AIC, QD×6 days.

Treatment C: 400 mg Compound 1 as AIC, QD×6 days.

TABLE 34

Summary of Pharmacokinetic Parameters of Compund 1 Following a Single Oral Dose of 2 × 100 mg capsules or a 200 mg Tablet under Fed or Fasted Conditions, Part 2

| Parameter | Geometric Mean (Geometric CV %) Treatment (Dose) | | |
|---|---|---|---|
| | D (200 mg) (N = 12) | E (200 mg) (N = 12) | F (200 mg) (N = 12) |
| $AUC_t$ (ng·h/mL) | 12900 (21.3) | 11900 (32.2) | 12000 (27.4) |
| $AUC_\infty$ (ng·h/mL) | 13100 (21.7) | 12200 (32.5) | 12300 (27.00) |
| $C_{max}$ (ng/mL) | 2080 (17.5) | 1730 (70.7) | 1840 (33.1) |
| $T_{max}$[a] (hr) | 2 (1.00, 3.00) | 2 (1.50, 3.00) | 3.00 (1.50, 5.00) |
| $t_{1/2}$ (hr) | 20.3 (28.9) | 20.1 (21.5) | 21.7 (29.7) |
| CL/F (mL/min) | 15.2 (21.7) | 16.4 (32.5) | 16.3 (27.0) |
| Vz/F (L) | 447 (33.4) | 477 (30.5) | 510 (35.5) |

$AUC_\infty$ = area under the plasma concentration versus time curve from time zero to infinity;
$AUC_t$ = area under the plasma concentration versus time curve from time 0 to the last quantifiable concentration;
$C_{max}$ = maximum observed plasma concentration;
CL/F = apparent total plasma clearance;
N = total number of subjects;
$t_{1/2}$ = terminal elimination half-life;
$T_{max}$ = time to maximum observed plasma concentration;
Vz/F = apparent total volume of distribution.
[a]$T_{max}$ is presented as median (minimum, maximum).

Treatment D: 2×100 mg Compound 1 as AIC, single oral dose administered under fasted conditions.

Treatment E: 1×200 mg Compound 1 as formulated tablet(s), single oral dose administered under fasted conditions.

Treatment F: 1×200 mg Compound 1 as formulated tablet(s), single oral dose administered under fed conditions.

In Part 2, Compound 1 was administered as a single oral dose of 2×100 mg capsules or 200 mg tablet. Under fasted conditions, the tablet achieved an equivalent $AUC_t$ and $AUC_\infty$ compared to the capsules, but a lower $C_{max}$ (~17%) relative to the capsule formulation (Table 34). $T_{max}$ was similar following either formulation.

As shown in Table 33 and Table 35, Compound 1 administered as a single oral dose of 200 mg tablet under fasted or fed conditions resulted in equivalent $AUC_t$ and $AUC_\infty$ with a slightly higher $C_{max}$ (by ~6%) in the fed state compared to the fasted state. The median $T_{max}$ of Compound 1 was delayed by 0.87 hours after administration of a single 200 mg Compound 1 tablet under fed conditions compared with fasted conditions (Table 36).

Statistical Analysis of Pharmacokinetic Parameters

As shown in Table 35, the 90% CIs of the geometric mean ratios between treatments for $AUC_t$ and $AUC_\infty$ were fully contained within the range of 80% to 125%, but the 90% CIs of the geometric mean ratios between treatments for $C_{max}$ were outside of the range of 80% to 125%. The statistical analysis further supports that the 200 mg tablet provides equivalent extent of exposure though the peak concentration ($C_{max}$) is ~17% lower. The results also demonstrate that the presence of food has no effect on the PK of the tablet formulation of Compound 1.

When Compound 1 was administered as a 200 mg tablet or 2×100 mg capsules, there was no statistically significant change (p>0.05) noted.

When Compound 1 was administered as a tablet with food, a statistically significant (p<0.05) increase (by 0.87 hours) in the median $t_{max}$ was observed when compared with fasted conditions (90% CI of median difference does not contain zero), but this change (a 0.87 hour-delay in absorption) is considered not clinically meaningful.

The median, median difference (fed-fasted), and 90% confidence interval of the median difference were from the Hodges-Lehmann estimate.

The p-value was from the Wilcoxon signed-rank test.

Pharmacodynamic Results

Phospho c-Jun Immunohistochemistry: Quantitative Analysis

Phospho c-Jun IHC images were analyzed at Quintiles for integrated optical density of positive nuclear staining using

TABLE 35

Statistical Analysis of Plasma Pharmacokinetic Parameters of Compound 1 (Pharmacokinetic Population)

| Parameter | Treatment | N | Geometric Mean | Comparison | Ratio (%) of Geometric Means | 90% CI of Ratio of Geometric Means | Intra-subject CV % |
|---|---|---|---|---|---|---|---|
| $AUC_t$ | D | 12 | 12889 | E/D | 92.6 | (82.7, 103.6) | 16.1 |
| (ng · hr/mL) | E | 12 | 11933 | F/E | 100.6 | (89.8, 112.6) | |
| | F | 12 | 12002 | | | | |
| $AUC_\infty$ | D | 12 | 13123 | E/D | 92.9 | (82.9, 104.0) | 16.2 |
| (ng · hr/mL) | E | 12 | 12187 | F/E | 100.8 | (90.0, 112.9) | |
| | F | 12 | 12285 | | | | |
| $C_{max}$ | D | 12 | 2082 | E/D | 82.9 | (64.3, 106.8) | 37.2 |
| (ng/mL) | E | 12 | 1726 | F/E | 106.4 | (82.6, 137.1) | |
| | F | 12 | 1836 | | | | |

$AUC_{0-\infty}$ = area under the plasma concentration-time curve from time 0 extrapolated to infinity; $AUC_{0-t}$ = AUC from time 0 to time t where t is the last measurable time point; $C_{max}$ = maximum observed plasma concentration; LS = least squares.

Treatment D: 2×100 mg Compound 1 as AIC, single oral dose administered under fasted conditions.

Treatment E: 1×200 mg Compound 1 as formulated tablet(s), single oral dose administered under fasted conditions Treatment F: 1×200 mg Compound 1 as formulated tablet(s), single oral dose administered under fed conditions.

Geometric least squares (LS) means, ratio (fed/fasted) and 90% confidence intervals (CIs) of the ratio of geometric LS means were from an analysis of variance (ANOVA) model with treatment, period, and sequence as fixed effects, and subject nested within sequence as a random effect on the natural log-transformed pharmacokinetics.

The ratio and 90% CI of the ratio were presented as a percentage.

Intrasubject coefficient of variation=square root of (exp(mean square error of ANOVA)−1)×100.

Aperio imaging software (Leica Biosystems). The Phospho c-jun score (Optical Density Scale) reflects the percentage of nuclei with '3+' staining intensity (the cutoff for determining positive staining) as determined by the Aperio nuclear phospho c-jun quantitative image analysis algorithm. The percent of baseline of the individual integrated optical density by treatment is presented in FIG. 107. While the phospho c-jun staining is not decreased from baseline in the 60 mg dose group, there is a 7.5% decrease in the 160 mg dose group (p=0.18), and a 29.5% decrease in the 400 mg group (p<0.0001).

The following are the percentages of subjects with a decrease in optical density score compared to baseline values:

60 mg dose: 4/14=29%
160 mg dose: 11/13=85%
400 mg dose: 13/13=100%

TABLE 36

Statistical Analysis of $T_{max}$ (Pharmacokinetic Population)

| Parameter | Treatment | N | Median | Comparison | Median Difference | 90% Confidence Interval of Median Difference | P-Value |
|---|---|---|---|---|---|---|---|
| $t_{max}$ (hr) | D | 12 | 2.00 | E/D | 0.01 | (0.00, 0.25) | 0.3438 |
| | E | 12 | 2.00 | F/E | 0.87 | (0.25, 1.50) | 0.0234 |
| | F | 12 | 3.00 | | | | |

$t_{max}$ = time to maximum observed plasma concentration.

Treatment D: 2×100 mg Compound 1 as AIC, single oral dose administered under fasted conditions.

Treatment E: 1×200 mg Compound 1 as formulated tablet(s), single oral dose administered under fasted conditions Treatment F: 1×200 mg Compound 1 as formulated tablet(s), single oral dose administered under fed conditions.

Phospho c-Jun Immunohistochemistry: Histopathology Scores

Phospho c-Jun immunohistochemistry (IHC) images were scored by 2 independent pathologists from Quintiles using a scoring scale of 0-4. The percentage of epithelial c-Jun positive nuclei was scored as follows:

0=0% to 19%
1=20% to 39%
2=40% to 59%

3=60% to 79%
4=80% to 100%.

The individual median histopathology scores by treatment are presented in FIG. 107, and the absolute change from baseline is presented in FIG. 108. The change from baseline in median histopathology scores is not significantly affected by treatment. There are nominally more decreases in score (18), than increases (14), across all three treatment groups, and the percentage of individuals showing either no change or a decrease in score increases in a dose-dependent manner: 8/15=53% in the 60 mg dose group; 10/14=71% in the 160 mg dose group, and 11/14=79% in the 400 mg dose group.

Pharmacokinetic and Pharmacodynamic Summary and Conclusions

Pharmacokinetic Summary and Conclusions

The PK of Compound 1 was well characterized in healthy subjects following administration of a single oral dose of 200 mg under fasted or fed conditions and multiple oral doses of Compound 1 at 60 mg, 160 mg and 400 mg QD.

The systemic exposure of Compound 1 ($AUC_t$ and $C_{max}$) appeared to increase in a more than dose-proportional manner as the dose was increased from 60 mg to 400 mg following multiple doses.

Compound 1 was rapidly absorbed and slowly eliminated from plasma with a terminal elimination $t_{1/2}$ of approximately 20 hours following a single oral dose of 200 mg.

Under fasted conditions, the 200 mg tablet administration resulted in an equivalent $AUC_t$ and $AUC_\infty$ compared to the 2×100 mg capsule administration, but a lower $C_{max}$ (~17%) relative to the capsule formulation.

Food had no effect on the PK of a single oral 200 mg tablet of Compound 1 in healthy subjects.

Compound 1 plasma concentrations correlated well with whole blood concentrations.

Pharmacodynamic Summary and Conclusions

Compound 1 inhibited UVB-induced phospho c-jun expression in skin in a dose-dependent manner. At the highest tested Compound 1 dose of 400 mg the decrease in UVB-induced phospho c-jun was 29.5%, at the intermediate 160 mg dose-7.5%, and there was no change at the lowest 60 mg dose (measured by automated quantitative image analysis of integrated optical density).

The Compound 1-associated inhibition of UVB-induced phospho c-jun expression in skin did not reach significance using the histopathologist scoring system. This may be due to the limitations of the assay, which utilizes subjective scoring of the intensity and number of stained epidermal keratinocyte nuclei by trained individuals (on a scale of 0 to 4).

Safety Summary and Conclusions

Overall, 11 of 28 subjects (39.3%) reported 17 TEAEs.

No subjects experienced an SAE or severe TEAE. The majority of the TEAEs were mild in severity. One subject discontinued from the study due to a TEAE of viral infection that was judged by the investigator as not suspected of being related to Compound 1. Overall in this study, 11 of 28 subjects (39.3%) reported 17 TEAEs. The most common TEAEs on the study were gastrointestinal in nature and included nausea (observed in 4 subjects) and diarrhea (observed in 2 subjects) that were judged by the investigator as suspected of being related to Compound 1. No clinically significant changes or findings were noted in clinical laboratory evaluations, vital sign measurements, or ECGs. Overall, there were no remarkable clinical safety findings during the study as nausea and diarrhea were previously reported in Compound 1 SAD/MAD study and are manageable with standard of care.

Multiple doses of Compound 1 were safe and well tolerated when administered as 60, 160, and 400 mg AIC QD for 6 days in healthy male subjects. Single doses of 200 mg as formulated tablets in both fed and fasted states and AIC in the fasted state were safe and well tolerated in healthy subjects.

Discussion And Overall Conclusions

Discussion

The primary objectives of the study were:

to evaluate the effect of multiple oral doses of Compound 1 on JNK activity following UV irradiation of human skin;

to evaluate the PK of formulated Compound 1 tablets in the presence of food; and to evaluate the relative bioavailability of formulated Compound 1 tablets compared to the AIC formulation following a single oral dose.

Secondary objective was to evaluate the safety and tolerability of single and multiple oral doses of Compound 1 and formulated Compound 1 tablets when administered with food.

In Part 1, Compound 1 was administered as multiple oral doses of 60 mg, 160 mg, and 400 mg QD for 6 days to determine steady-state exposure of Compound 1. Steady state exposure of Compound 1 ($AUC_t$ and $C_{max}$) appeared to increase in a more than dose-proportional manner as the dose was increased from 60 mg to 400 mg following multiple doses. Based on the coefficient of variance, inter-subject variability for the PK parameters was generally in a moderate range.

In Part 2, Compound 1 was administered as a single oral dose of 200 mg capsule or 200 mg tablet under fasted and fed conditions to determine whether or not the 200 mg tablet achieves a comparable exposure to the 200 mg capsule and whether or not food affects the PK of Compound 1.

The PK of Compound 1 was characterized by rapid absorption with a median $T_{max}$ of approximately between 1.95 to 3 hours postdose for all doses. After achieving $C_{max}$ Compound 1 started to decline from plasma in a bi-exponential manner. The mean terminal elimination half-life of Compound 1 was estimated to be approximately 20 hours.

Under fasted conditions, a single 200 mg tablet administration achieved an equivalent $AUC_t$ and $AUC_\infty$ to the 2×100 mg capsule administration, but a lower $C_{max}$ (~17%) relative to the capsule formulation. $T_{max}$ was similar following dosing with either formulation. The results demonstrate that the 200 mg tablet is equivalent in extent of exposure with ~17% lower peak exposure; this lowering of peak exposure if expected as food often extends the time to $T_{max}$.

Compound 1 administered as a single oral dose of 200 mg tablet under fasted or fed conditions resulted in equivalent $AUC_t$ and $AUC_\infty$ with a slightly higher $C_{max}$ (by ~6%) in the fed state compared to the fasted state. The median tmax of Compound 1 was delayed by 0.87 hours after administration of a single 200 mg Compound 1 tablet under fed conditions compared with fasted conditions. As a result of the small differences in $C_{max}$ and no change in AUC exposure, food is not considered to meaningfully affect the PK of Compound 1.

Compound 1 inhibited UVB-induced phospho c-jun in the skin in a dose-dependent manner as measured by quantitative image analysis of phospho c-jun IHC optical density. The percentage of subjects with a decrease from baseline in optical density score increased from 29% in the 60 mg dose group to 85% in the 160 mg dose group and 100% in the 400 mg dose group. Measured as percent change from baseline in optical density score, Compound 1 significantly decreased UVB-induced phospho c-jun by 29.5% in the skin at a dose of 400 mg, with a non-significant decrease of 7.5% at a dose of 160 mg.

Compound 1 was safe and well tolerated when administered to healthy subjects as multiple oral doses of 60, 160, or 400 mg AIC QD for 6 days. A single oral dose of 200 mg Compound 1 was safe and well tolerated when administered to healthy subjects in the fasted state as AIC or a formulated tablet and in the fed state as a formulated tablet.

No subjects experienced an SAE or severe TEAE. The majority of the TEAEs were mild in severity. One subject discontinued from the study due to a TEAE of viral infection that was judged by the investigator as not suspected of being related to Compound 1. Overall in this study, 11 of 28 subjects (39.3%) reported 17 TEAEs. The most common TEAEs on the study were gastrointestinal in nature and included nausea (observed in 4 subjects) and diarrhea (observed in 2 subjects) that were judged by the investigator as suspected of being related to Compound 1. No clinically significant changes or findings were noted in clinical laboratory evaluations, vital sign measurements, or ECGs.

Conclusions

Pharmacokinetic Conclusions

The systemic exposure of Compound 1 ($AUC_t$ and $C_{max}$) appeared to increase in a more than dose-proportional manner as the dose was increased from 60 mg to 400 mg following multiple doses.

Under fasted conditions, 200 mg tablet administration resulted in an equivalent $AUC_t$ and $AUC_\infty$ to the 200 mg capsule administration though a lower $C_{max}$ (~17%) was noted.

Food had no effect on the PK of a single oral 200 mg tablet of Compound 1 in healthy subjects.

Compound 1 plasma concentrations correlated well with Compound 1 whole blood concentrations.

Pharmacodynamic Conclusions

Compound 1 inhibited UVB-induced phospho c-jun expression in skin in a dose-dependent manner. At the highest tested Compound 1 dose of 400 mg the decrease in UVB-induced phospho c-jun was 29.5%, at the intermediate 160 mg dose-7.5%, and there was no change at the lowest 60 mg dose (measured by automated quantitative image analysis of integrated optical density).

The Compound 1-associated inhibition of UVB-induced phospho c-jun expression in skin did not reach significance using the histopathologist scoring system. This may be due to the limitations of the assay, which utilizes subjective scoring of the intensity and number of stained epidermal keratinocyte nuclei by trained individuals (on a scale of 0 to 4).

Safety Conclusions

Compound 1 was safe and well tolerated in healthy male subjects when administered as multiple oral doses of 60, 160, and 400 mg AIC QD for 6 days.

A single oral dose of 200 mg Compound 1 was safe and well tolerated in healthy subjects when administered in the fasted state as AIC or a formulated tablet and in the fed state as a formulated tablet.

6.9. A Phase 1B, Multicenter, Open-Label, Staggered-Dose Study to Assess the Safety, Tolerability, Pharmacokinetics, and Pharmacodynamics of Multiple Doses of Compound 1 for 12 Weeks in Subjects with Pulmonary Fibrosis Primary Objectives:

To evaluate the safety and tolerability of Compound 1 in subjects with pulmonary fibrosis.

Secondary Objectives:

To evaluate the pharmacokinetic (PK) profile of Compound 1 from plasma samples in subjects with pulmonary fibrosis.

Study Design.

This is an open-label, staggered dose-escalation, cohort expansion study that will enroll subjects at multiple study sites in the United States of America (USA) and Australia. The study will consist of two treatment arms:

Low dose (100 mg) Compound 1 administered orally once daily (QD) for 12 continuous weeks.

High dose (200 mg) Compound 1 administered orally QD for 12 continuous weeks.

The high dose Compound 1 arm will not start until at least three subjects complete a minimum of 2 weeks of low dose Compound 1 and the low dose treatment arm is determined not to meet the study dose escalation stopping criteria.

Each subject will participate in a Screening Period (up to 4 weeks prior to treatment), a 12-week Treatment Phase, and a 4-week Follow-up visit. Subjects will be screened for eligibility. Subjects who meet all of the inclusion criteria and none of the exclusion criteria at Screening will return to the study site on Day 1 for assessments and to begin administration of a QD dose of Compound 1, according to the dose level in which the subject is enrolled. Three subjects will initially be enrolled to receive low dose Compound 1, 100 mg QD, and will be evaluated for all scheduled assessments through 2 weeks of treatment. Once a total of three subjects have completed the Week 2 visit, a decision to continue the study at the high dose level (200 mg QD) will be determined.

If the criteria for escalation to the high dose are met, the low dose (100 mg QD) subjects will remain on low dose and three additional subjects will be enrolled at the high dose level (200 mg QD). A predefined dose-escalation decision tree will be utilized to determine the subsequent treatment arm if criteria for escalation to the high dose is not met. If one of the three subjects at the low dose (100 mg QD) experiences an event that meets the individual subject dose stopping criteria, another three subjects will be enrolled in the low dose arm. Dose escalation will not occur if two or more of the three subjects meet the individual subject dose stopping criteria. All subjects (low and high dose) will remain on Compound 1 for a total of 12 weeks unless an individual subject experiences an event that meets any of the individual subject stopping criteria. In addition, the dose of Compound 1 may be reduced to the low dose level (100 mg QD) for any individual subject at the high dose level (200 mg QD) who meets any of the individual subject dose reduction criteria. If two or more subjects in the high dose arm experience an event that meets the individual stopping criteria, the 200 mg QD dose arm may be repeated in three additional subjects, or three additional subjects will be enrolled in the high dose level, or the study may be stopped.

Study visits will occur at Screening, Day 1, and Weeks 1, 2, 3, 4, 6, 8, 10, 12, and 16. Blood and urine samples will be collected at specified times for clinical safety laboratory assessments, PK assessments, and PD analyses. Safety will be monitored throughout the study.

In the event that a subject discontinues from the study, an early termination visit will be performed.

Study Population.

The study population will consist of approximately nine to 18 adult male or female subjects at least 18 years of age with pulmonary fibrosis. Specifically, subjects will have a documented usual interstitial pneumonia (UIP) pattern or nonspecific interstitial pneumonia (NSIP) pattern based on computed tomography OR a documented fibrotic NSIP or documented UIP pattern on surgical lung biopsy. The underlying disease may include, but is not limited to, connective tissue disease-associated interstitial lung disease, interstitial pulmonary fibrosis, idiopathic pulmonary fibrosis (IPF), environmental- or chemical-related pulmonary fibrosis, or Hermansky-Pudlak syndrome.

Length of Study.

The study duration for each subject will be up to 20 weeks and includes a 4-week Screening period, a 12-week Treatment Phase, and a 4-week Follow-up. The total duration of the study, from first subject's first visit to last subject's last visit, is expected to be approximately 12 months.

End of Study.

The end of study is defined as either the date of the last visit of the last subject to complete the study, or the date of receipt of the last data point from the last subject that is required for primary, secondary, and/or exploratory analysis, as prespecified in the protocol or the statistical analysis plan, whichever is the later date.

Study Treatments.

Study treatment arms include:

Low dose (100 mg) Compound 1, administered orally QD for 12 weeks.

High dose (200 mg) Compound 1, administered orally QD for 12 weeks.

The high dose Compound 1 arm will start after at least three subjects complete a minimum of 2 weeks of low dose Compound 1 and the low dose treatment arm is determined not to meet the study dose escalation stopping criteria.

Individual Subject Stopping Criteria.

Compound 1 dosing should be stopped for a subject if any of the following individual subject stopping criteria occur:

Nausea, vomiting, or diarrhea that results in electrolyte (sodium, chloride, potassium, and/or creatinine) abnormalities and/or that requires intravenous hydration.

Intestinal intussusception, bowel obstruction, or moderate/severe gastrointestinal bleed as determined by the Investigator.

Any serious adverse event (SAE) considered by the Investigator to be related to Compound 1.

Alanine aminotransferase (ALT) or aspartate aminotransferase (AST)>8× upper limit of normal (ULN).

ALT or AST>5×ULN for more than 2 weeks.

ALT or AST>3×ULN and total bilirubin>2×ULN.

ALT or AST>3×ULN and with the appearance of fatigue, nausea, vomiting, right upper quadrant pain or tenderness, fever, rash and/or eosinophilia (>5%).

Any other event that is deemed to pose an unacceptable risk to the subject.

Subjects who meet individual subject dose stopping criteria due to an aminotransferase AST or ALT or bilirubin elevation should not be re-challenged. Rechallenge for any event other than an AST, ALT, or bilirubin elevation may occur at the discretion of the Investigator. Subjects should be rechallenged at the same dose being administered prior to meeting the individual subject stopping criterion. However, a subject in the high dose group may be dose-reduced to 100 mg should the Investigator and Sponsor elect that it is in the best interest of the subject.

Any subject experiencing an event meeting the individual subject dose stopping criteria which is considered by the Investigator to be related to Compound 1 administration will be accounted for during the dose escalation decision, even if that subject has not completed a total of 2 weeks of dosing.

Individual Subject Dose Reduction Criteria.

The individual subject dose reduction criteria apply to subjects receiving high dose Compound 1 only. Since there is no dose reduction for subjects receiving low dose Compound 1, low dose subjects meeting these criteria should be closely monitored, considered for dose interruption prior to rechallenge at 100 mg QD (at the discretion of the Investigator), considered for dose discontinuation, or discontinued from study when and if the event worsens to the point of meeting individual subject stopping criteria.

In the event that a subject at the 200 mg QD dose experiences an event that meets the individual subject dose reduction criteria, the dose may be reduced to 100 mg QD after the subject has recovered from the event. Subject dosing should be reduced if any one of the following individual subject dose reduction criteria occur:

ALT or AST>3×ULN which is confirmed by repeat analysis AND does not meet individual subject stopping criteria AND has no sign of severe liver toxicity. The Investigator should also consider discontinuing confounding medical products and monitoring the subject closely.

Any subject experiencing moderate or severe gastrointestinal adverse events (AEs) such as abdominal discomfort, nausea or vomiting may be treated symptomatically (ondansetron, bismuth subsalicylate, 5-HT$_3$, etc) at the discretion of the Investigator. If the event is not improved after 5 days, the dose will be held until the event is improved, at which time Compound 1 will be resumed at the reduced dose.

Any other condition that is considered by the Investigator to be related to Compound 1 and is considered by the Investigator to improve with a dose reduction. The Investigator is to notify Celgene in a timely manner of any such dose reductions.

Study Dose Escalation Stopping Criteria.

The criteria for stopping the escalation from the low dose treatment arm of 100 mg to the high dose arm of 200 mg QD will be evaluated after at least three subjects complete a minimum of 2 weeks of low dose Compound 1. The high dose (200 mg QD) Compound 1 arm will only be enrolled if the predefined dose escalation criteria are met.

Safety parameters reviewed prior to each dose escalation will include review of relevant AEs, physical examination findings, vital signs, 12 lead electrocardiograms, clinical laboratory safety tests, and concomitant medications/procedures.

Overview of Pharmacokinetic Assessments.

Pharmacokinetic endpoints by

Compound 1 plasma sample concentrations sparsely collected

Compound 1 dry blood spot sample concentrations sparsely collected

Population-based PK approach as appropriate for the following (but not limited to) parameters:

Apparent clearance.

Apparent central volume of distribution.

First-order rate of absorption.

Disease as a covariate may be explored in the population PK analysis. The derived PK parameters such as the maximum plasma concentration of the drug and the area under the plasma concentration-time curve may be also determined based on the population PK model as appropriate.

Overview of Pharmacodynamic Assessments.

Blood draw for PD biomarkers may include but are not limited to:

Matrix metalloproteinase-7

Tenascin C

Overview of Efficacy Assessments.

Exploratory efficacy assessments include:
Pulmonary function tests which, at a minimum, are to include forced vital capacity, forced expiratory volume in 1 second, and lung diffusion capacity.
Oxygen saturation by pulse oximetry.
Overview of Safety Assessments.
Safety will be monitored throughout the study. The safety of Compound 1 will be evaluated based on the following assessments:
Complete physical examination.
Clinical laboratory assessments (chemistry, hematology, urinalysis with microscopy).
Urine pregnancy tests.
miR-122 levels. Prompt reflex assessments of miR-122 levels will be performed for clinical signs of liver toxicity or liver function test abnormality (AST or ALT>2.5×ULN) or at Investigator discretion.
Serology (hepatitis B surface antigen, hepatitis C virus antibody, and human immunodeficiency virus)
Hepatic ultrasound.
INR.
Vital signs including heart rate, blood pressure, respiratory rate, and temperature.
12-lead electrocardiogram.
Adverse Events. All AEs will be monitored and recorded throughout the study from the time the informed consent form is signed until 28 days after the last dose of Compound 1. Any SAEs made known to the Investigator at any time thereafter that are suspected of being related to Compound 1 administration must also be reported.
Concomitant medications and procedures will be reviewed and recorded from the time the subject signs the informed consent form until the end of the study.
Prompt reflex assessments will be performed for clinical signs of liver toxicity or liver function test abnormality (AST or ALT>2.5×ULN) or at the Investigator's discretion. Reflex assessments of liver toxicity include repeat clinical laboratory assessments, miR-122, a hepatic ultrasound, a serology test for hepatitis B surface antigen, hepatitis C virus antibody, and human immunodeficiency virus, and an international normalized ratio. Additional evaluations should be performed at the investigator's discretion based upon the subject's signs and symptoms. The Investigator should also consider discontinuing confounding medical products and monitoring the subject closely.
Safety review meetings will occur:
Every 4 weeks subsequent to the first subject dosed.
After three subjects complete the initial 2 weeks of treatment with low dose Compound 1.
In the event that a significant toxicity is observed in any subject as determined by the Investigator.
Inclusion Criteria.
Potential subjects must satisfy all of the following criteria to be enrolled into the study: 1. Subject ≥18 years of age; 2. Documented clinical diagnosis of a fibrotic lung disease supported by at least one of the following: a. Usual interstitial pneumonia (UIP) pattern based on computed tomography (CT scan); or b. Nonspecific interstitial pneumonia (NSIP) pattern based on CT scan; or c. A documented fibrotic NSIP on surgical lung biopsy; or d. A documented UIP pattern on surgical lung biopsy. The underlying etiology of the fibrotic lung disease may be of any cause, including, but NOT LIMITED TO any of the following: Connective tissue disease-associated interstitial lung disease, idiopathic pulmonary fibrosis (IPF), environmental or chemical-related pulmonary fibrosis, other forms of interstitial pulmonary fibrosis, Hermansky-Pudlak syndrome; 3. Must understand and voluntarily sign a written ICF prior to any study-related procedures being performed; 4. Must be able to communicate with the Investigator, understand and comply with the requirements of the study, and agree to adhere to restrictions and examination schedules; 5. AST or serum glutamic-oxaloacetic transaminase within limits of normal; 6. ALT or serum glutamic pyruvic transaminase within limits of normal; 7. Total bilirubin and INR within limits of normal; 8. No clinically significant laboratory test results as determined by the Investigator; 9. Male subjects agree to use barrier contraception NOT made of natural (animal) membrane (e.g., latex or polyurethane condoms are acceptable) when engaging in sexual activity with a female of childbearing potential (FCBP) while on Compound 1 and for at least 28 days after the last dose of study medication. A FCBP is defined as a sexually mature female who has not undergone a hysterectomy or bilateral oophorectomy or who has not been naturally postmenopausal for at least 24 consecutive months (i.e., who has had menses at any time in the preceding 24 consecutive months); 10. All FCBPs must have a negative pregnancy test at Screening and Day 1. Any FCBP who engages in activity in which conception is possible must use two forms of contraception simultaneously while on Compound 1 and for at least 28 days after taking the last dose of Compound 1: one highly effective form (i.e., hormonal, intrauterine device, tubal ligation, vasectomized partner) and one additional form (latex condom or any nonlatex condom NOT made of natural [animal] membrane [e.g., polyurethane], diaphragm, sponge). If one highly effective form of contraception cannot be used, then two forms of barrier contraception must be used, i.e., latex condom or any nonlatex condom NOT made out of natural (animal) membrane [e.g., polyurethane] with either of the following: sponge with spermicide or diaphragm with spermicide; 11. Female subjects that are postmenopausal (defined as 24 months without menses before Screening, with an estradiol level of <30 pg/mL and FSH level of >40 IU/L at Screening).
Exclusion Criteria.
Potential subjects will be excluded from enrollment if any of the following occur: 1. Exposed to an investigational drug (new chemical entity) within 30 days preceding the first dose of Compound 1 administration, or five half-lives of that investigational drug, if known (whichever is longer); 2. Subjects who are part of the clinical staff personnel or family members of the study site staff; 3. Screening FVC<40% predicted; 4. Screening DLco<20% predicted; 5. Any condition other than pulmonary fibrosis that is likely to result in the subject's death or increases the risk of death within a year from signing the ICF; 6. Known clinical diagnosis of pulmonary arterial hypertension that currently requires treatment; 7. Subjects with cystic fibrosis, active aspergillosis, active tuberculosis, or other serious concomitant respiratory disorder other than pulmonary fibrosis, as determined by the Investigator. Subjects with reactive airway disease, chronic obstructive pulmonary disease, and asthma may be included as long as, in the opinion of the Investigator, fibrosis is the major contributing factor to the subject's respiratory disorder; 8. Use of any cytotoxic agents within 4 weeks of dosing. 9. Currently being administered any targeted therapy for pulmonary fibrosis and not on a stable dose for ≥6 weeks duration prior to first study dosing (potential subjects should be excluded if a dose increase is planned during the study period); 10. Use of Esbriet® (pirfenidone) or Ofev® (nintedanib) within 30 day prior to first dose; 11. Currently being administered statins (HMG-CoA reductase inhibitors) and not on a stable dose for ≥6 weeks duration prior to first study dosing (potential subjects should be excluded if a dose increase is planned during the study period); 12. Taking medications that are substrates of the transporters P-gp, BCRP, OAT3, OATP1B1, OATP1B3, and OCT2 and have a narrow therapeutics index (e.g., P-gp substrate digoxin); 13. Use of acetaminophen (paracetamol) at a dosage >3 grams per day within 2 weeks of first study dosing; 14. Use of niacin at a dosage >2 grams/day within 2 weeks prior to first study dosing; 15. Any significant medical condition, laboratory abnormality, or psychiatric illness that would prevent the subject from participating in the study; 16. History of recurrent bacterial infections (at least three major infections resulting in hospitalization and/or requiring intravenous antibiotic treatment within the past 2 years); 17. History of HIV, HBV, or HCV. Subjects treated for HCV who have a sustained virologic response of 6 months following final HCV treatment can be included; 18. History of active malignancy within 5 years prior to signing the ICF, excluding nonmelanoma skin cancer.

6.10. Salt Screening

6.10.1. Solid State Characterization of Salts

The physicochemical properties of Compound 1 free base and salts are summarized in The physicochemical property assessment included crystallinity, melting point, solubility in water and simulated gastric fluid (SGF, without Pepsin), hygroscopicity, accelerated physical and chemical stability in the solid state under stress conditions. The physicochemical properties for the free base and salts of Compound 1 are summarized in Table 38. Among salts and free base evaluated, the phosphate salt showed better physicochemical properties.

The details were presented in the following sections.

$^1$H NMR:

A portion of the sample was dissolved in dimethyl sulfoxide (DMSO-$d_6$) (containing TMS) and tested using the NMR spectrometer with 32 or 64 scans.

Elemental Analysis:

Elemental analyses on the salts were performed by Intertek Pharmaceutical Services/QTI.

Raman:

A portion of the sample was placed on a Rigaku zero-background XRPD sample holder and analyzed using Raman in reflection mode. The conditions were indicated as follows:

exposure time: 2 seconds;
accumulations: 2;
magnitude: 10×; and
laser power: 300 mW.

XRPD:

A portion of the sample was placed on a Rigaku zero-background XRPD sample holder and analyzed using XRPD from 3-40 degree 2 theta angle at a speed of 5 degree/min with 40 kV and 44 mA.

Simultaneous TGA/DSC:

A portion of the sample was loaded into an aluminum (Al) crucible and tested using the TGA/DSC system at a heating rate of 10° C./min. An empty Al pan was used as blank.

DSC:

A portion of the sample was weighed into an Al sample pan, crimped with a pin-holed Al lid and tested using the DSC Q1000 system at a heating rate of 10° C./min. An empty Al pan with lid was used as reference.

TGA:

A portion of the sample was loaded to an Al sample pan and tested using the TGA Q500 system at a heating rate of 10° C./min.

DVS:

A portion of the sample was loaded into a quartz sample holder and tested using DVS-Advantage system in two continuous adsorption/desorption cycles. The settings are described as follows:

Solvent: water;
Temperature: 25° C.;
Adsorption/desorption cycle 1: 50 to 95 to 0% RH;
Adsorption/desorption cycle 2: 0 to 95 to 0% RH;
Step size: 10% RH; and
dm/dt (%/min): 0.001 in 15 min with a minimum of 10 min and a maximum of 180 min.

PLM:

A portion of the sample was placed on a clear glass slide, dispersed with silicon oil and examined under the microscope with 10× subject and transmitted light.

Solubility in Water and SGF:

A portion of the sample was weighed into a 2 mL clear HPLC vial. After added with water of 1 mL, the vial was capped and shaken on an orbital shaker at 300 RPM at ambient temperature for 24 hours. The sample was removed from the shaker and pH measurement was performed using a calibrated pH meter. Then a portion of the sample was filtered using 0.2 μm Nylon-membraned centrifuge tube filter at 14000 RPM for 5 min. The filtrate was analyzed using HPLC/UV with appropriate dilution. The filtered solid residues were analyzed using XRPD.

For solubility in SGF, the samples were prepared and assayed in the same procedures as mentioned above.

6.10.2. Summary of Salts

Salt screening was performed on Compound 1 using 13 acidic counter-ions and a variety of solvents. The crystalline salts obtained were hydrochloride (HCl), sulfate ($H_2SO_4$), phosphate ($H_3PO_4$), L-tartrate, L-malate, L-lactate, succinate, p-toluenesulfate (tosylate), methanesulfate (mesylate), benzensulfate (besylate) and fumarate. An amorphous salt was obtained when citric acid was used as the counter-ion. Multiple forms or polymorphs were observed for most of the crystalline salts. The results of the salt screen are summarized in Table 37.

TABLE 37

Summary of Salt Screening Results for Compound 1.

| Sample | 01 HCl | 02 $H_2SO_4$ | 03 $H_3PO_4$ | 04 L-lactic | 05 L-tartaric | 06 L-malic |
|---|---|---|---|---|---|---|
| A | salt, form 1, hydrate | salt, form 1 | salt, form 1 | free base, form C | salt, form 1, hydrate | salt, form 1 |
| B | salt, form 2, anhydrate | salt, form 1 | salt, salt form 1 | salt, form 1 | salt, form 1, hydrate | salt, form 2, w/MeNO$_2$ |
| C | salt, form 3, w/trace EtOAc | salt, form 1 | salt, form 1 | salt, form 2 | salt, form 1, hydrate | salt, form 3, w/EtOAc |

TABLE 37-continued

Summary of Salt Screening Results for Compound 1.

| D | salt, form 4, w/trace Acetone | salt, form 2 | salt, form 1 | free base, form B, w/Acetone | salt, form 1, hydrate, w/trace Acetone | salt, form 4, w/IPA |
|---|---|---|---|---|---|---|
| Sample | 07 Citric | 08 Succinic | 09 PsOH | 10 MsOH | 11 L-aspartic | 12 Free base |
| A | salt, w/trace ACN | salt, form 1, w/ACN | salt, form 1 | salt, form 1, w/IPA | free base, form C, w/ACN | form C, w/ACN |
| B | salt, w/trace MeNO$_2$ | salt, form 1, w/EtOH | salt, form 2 | salt, form 1, w/IPA | mix of free base form B (trace), form C (trace) and acid, not stoichiometric | form C, w/EtOH & IPA |
| C | salt | salt, form 2, w/EtOAc | salt, form 3 | salt, form 2 | mix of free base form C, form G and acid, not stoichiometric | form G, w/EtOAc |
| D | salt, w/MeOAc | mix of succinic salt form 1 and free base form B | salt, form 2 | salt, form 1, w/Acetone | free base, form C, w/Acetone | form B, w/Acetone |

Notes:
Citrate salts are amorphous.
Initial re-crystallization solvents: A = ACN, B = EtOH, C = EtOAc, D = Acetone.

Free base: form A (initial material), form D (MeOH solvate). The free base Forms A, Form B, Form C and Form G were previously described in U.S. Provisional Patent Application No. 61/933,636, filed on Jan. 30, 2014, and U.S. Provisional Patent Application No. 62/025,161, filed on Jul. 16, 2014.

MeOAc=methyl acetate, EtOAc=ethyl acetate, ACN=acetonitrile, EtOH=ethanol, MeOH=methanol, MeNO$_2$=nitromethane, IPA=isopropanol, PsOH=p-toluenesulfonic acid, MsOH=methanesulfonic acid.

Additional crystalline salts obtained: besylate and fumarate.

The physicochemical property assessment included crystallinity, melting point, solubility in water and simulated gastric fluid (SGF, without Pepsin), hygroscopicity, accelerated physical and chemical stability in the solid state under stress conditions. The physicochemical properties for the free base and salts of Compound 1 are summarized in Table 38. Among salts and free base evaluated, the phosphate salt showed better physicochemical properties.

TABLE 38

Summary of Physicochemical Properties for Compound 1 Free Base and Salts.

| Property | | Free base | HCl | H$_2$SO$_4$ | H$_3$PO$_4$ |
|---|---|---|---|---|---|
| Number of forms observed | | 5 | 7 | 3 | 1 |
| Form evaluated | | form A | form 2 | form 1 | form 1 |
| Water/Solvent (%) | | 0.22 (TGA to 119.9° C.) | 2.82 (TGA to 119.9° C.) | 0.28 (TGA to 119.9° C.) | 0.25 (TGA to 119.9° C.) |
| Melting Point (° C., DSC onset temperature) | | 223.1 (melting) | Endothermic peak at 163.0; melting & decomp at 264.0 | 235.0 (melting & decomp.) | 238.3 (melting & decomp.) |
| Solubility (mg/mL, equiv. to free base) | In water | 0.018 (pH 8.96) | 10.761 (pH 3.87) | 2.647 (pH 1.69) | 5.433 (pH 4.50) |
| | In SGF | 7.167 (pH 2.20) | 6.058 (pH 1.19) | 3.187 (pH 1.03) | 9.157 (pH 1.44) |
| Hygroscopicity (80% RH, 25° C., cycle 1 sorption) | | 0.17 | 5.21 | 6.13 | 0.48 |
| Physical stability (open vial, 2 weeks) | 80° C. | no change | no change | no change | no change |
| | 80° C./75% RH | no change | form change | form change | no change |
| Chemical stability (open vial, 2 weeks) | 80° C. | no change | no change | no change | no change |
| | 80° C./75% RH | no change | no change | no change | no change |
| Property | | L-tartrate | | L-malate | L-lactate |
| Number of forms observed | | 2 | | 4 | 2 |
| Form evaluated | | form 1 | | form 2 | form 2 |

TABLE 38-continued

Summary of Physicochemical Properties for Compound 1 Free Base and Salts.

| Water/Solvent (%) | | 3.97 (water, TGA to 119.9° C.) | 1.25 (TGA to 119.9° C.) | 1.74 (TGA to 119.9° C.) |
|---|---|---|---|---|
| Melting Point (° C., DSC onset temperature) | | Dehydration at 89.5; melting & decomp at 219.9 | Multiple events at 100.8 and 163.2 | 145.3 (decomp.) |
| Solubility (mg/mL, equiv. to free base) | In water | 0.405 (pH 5.35) | 4.496 (pH 4.07) | 4.220 (pH 4.52) |
| | In SGF | 9.223 (pH 1.59) | 8.922 (pH 1.54) | 9.529 (pH 1.67) |
| Hygroscopicity (80% RH, 25° C., cycle 1 sorption) | | 0.81 (hydrate) | 5.60 | 2.65 |
| Physical stability (open vial, 2 weeks) | 80° C. | no change | form change | form change |
| | 80° C./75% RH | no change | form change | form change |
| Chemical stability (open vial, 2 weeks) | 80° C. | no change | ~12% degradation | no change |
| | 80° C./75% RH | no change | ~7% degradation | no change |

6.10.3. Preparation of the Salts

The concentration of 0.12 mol/L was used for all acids except for L-aspartic acid. HCl, $H_2SO_4$, $H_3PO_4$, L-lactic acid, methanesulfonic acid and benzenesulfonic acid were prepared in ACN, L-tartaric acid, L-malic acid, citric acid, succinic acid, p-toluenesulfonic acid and fumaric acid were prepared in MeOH. L-aspartic acid (0.03 mol/L) was prepared in water. Compound 1 (free base) of 604.8 mg was dissolved in methanol/dichloromethane (MeOH/DCM, 1/1 v/v pre-mixed) of 50 mL, resulting in a clear solution with concentration of 12.1 mg/mL after sonicated for 5 min. This was used for the salt preparations except for besylate and fumarate samples.

The salt samples were prepared based on a stoichiometric ratio of 1:1.05 for free base to acid. An aliquot of 1.04 mL of free base solution (i.e., 0.039 mmole of free base) was mixed with 0.342 mL of acid (i.e., 0.041 mmole of acid) to obtain one salt sample in a 2 mL or 4 mL clear glass vial. Four salt samples for each acid were prepared in the same procedure.

As to the besylate and fumarate samples, Compound 1 (free base) of 33.3 mg was dissolved in 2 mL of MeOH/dichloromethane to generate a solution of 16.7 mg/mL. One mL of free base solution was mixed with 0.453 mL of acid to obtain a salt sample, resulting in only one sample for each acid.

The preparation of the salt samples comprised the steps of:

1) covering (for 2 mL vials) or capping (for 4 mL vials) the sample vial containing the solution of Compound 1 and shaking on an orbital shaker at 150 RPM at ambient temperature for 2 hours;
2) removing cover or caps;
3) evaporating the solvent in the sample vials under nitrogen purge in a fume hood;
4) adding ACN, EtOH, EtOAc or acetone to 4 sample vials, respectively, corresponding to each acidic counter-ion based on the one-solvent for one-sample fashion;
5) adding an acidic counter-ion;
6) covering or capping and shaking the samples vial at 200 RPM at ambient temperature for 24 hours;
7) removing cover and caps;
8) evaporating the solvent in the sample vials under nitrogen purge in a fume hood;
9) adding additional solvent in attempt to generate powder-like solids if no powder-like solids were visually observed upon dried;
10) filtering the sample using 0.45 μm Nylon-membraned centrifuge tube filter at 14000 RPM for 5 min if powder-like solids were visually observed during drying;
11) collecting and drying the solids in a closed chamber connected to house vacuum for 2 hours; and
12) harvesting the solids at the end.

The solids were subjected to analysis using Raman, XRPD, proton NMR NMR), TGA/DSC and/or PLM.

6.10.4. Elemental Analysis

Elemental analysis results are presented in Table 39. They are in agreement with the theoretical values for the tested elements.

TABLE 39

Elemental Analysis Results of Compound 1 Salts

| Sample | Element | | | |
|---|---|---|---|---|
| HCl Salt Form 2 | % C | % H | % N | % Cl |
| Theoretical | 53.70 | 7.89 | 19.57 | 9.91 |
| Experimental | 51.72 | 8.15 | 18.74 | 9.24 |
| Difference | −1.98 | 0.26 | −0.83 | −0.67 |
| $H_2SO_4$ Salt Form 1 | % C | % H | % N | % S |
| Theoretical | 45.81 | 6.97 | 16.69 | 7.64 |
| Experimental | 45.39 | 6.94 | 16.44 | 8.38 |
| Difference | −0.42 | −0.03 | −0.25 | 0.74 |
| $H_3PO_4$ Salt Form 1 | % C | % H | % N | % P |
| Theoretical | 45.82 | 7.21 | 16.70 | 7.39 |
| Experimental | 45.80 | 7.24 | 16.54 | 7.59 |
| Difference | −0.02 | 0.03 | −0.16 | 0.20 |
| L-tartrate Salt Form 2 | % C | % H | % N | |
| Theoretical | 52.16 | 7.78 | 16.90 | |
| Experimental | 50.95 | 7.65 | 16.40 | |
| Difference | −1.21 | −0.13 | −0.50 | |
| L-malate Salt Form 2 | % C | % H | % N | |
| Theoretical | 52.74 | 7.30 | 15.37 | |
| Experimental | 52.07 | 7.37 | 15.71 | |
| Difference | −0.67 | 0.07 | 0.34 | |

TABLE 39-continued

Elemental Analysis Results of Compound 1 Salts

| Sample | Element | | |
|---|---|---|---|
| L-lactate Salt Form 2 | % C | % H | % N |
| Theoretical | 55.46 | 8.08 | 17.02 |
| Experimental | 55.36 | 8.22 | 16.69 |
| Difference | −0.10 | 0.14 | −0.33 |

Note:
Theoretical calculations for L-tartrate were based on hemi-tartrate dihydrate.

6.10.5. Salt Screening Results

As presented in Table 37, crystalline salts were obtained for the acids, HCl, $H_2SO_4$, $H_3PO_4$, L-tartaric acid, L-lactic acid, L-malic acid, succinic acid, p-toluenesulfonic acid and methanesulfonic acid. An amorphous salt was obtained for citric acid.

Based on XRPD and Raman data, multiple forms were observed for the salts except that the $H_3PO_4$ salt and L-tartrate salt. $^1$H NMR and simultaneous TGA/DSC indicated some forms contained water or organic solvents.

6.10.5.1. HCl Salt of Compound 1

Totally 7 different forms of the HCl salt were prepared.

In summary, seven forms of HCl salt were prepared as follows:

HCl salt form 1: hydrate, obtained through crystallization in ACN, or suspended in SGF or exposed to moisture;

HCl salt form 2: contained water, obtained through crystallization in EtOH/IPA or IPA, converted to hydrate when exposed to moisture (to form 1) or suspended in water (to form 7);

HCl salt form 3: obtained through crystallization in EtOAc;

HCl salt form 4: obtained through crystallization in acetone;

HCl salt form 5: obtained though heating form 2 to 180° C., converted to hydrate form 1 when exposed to moisture;

HCl salt form 6: dehydrate hydrate, obtained though heating form 2 to 220° C., converted to hydrate form 1 when exposed to moisture; and HCl salt form 7: hydrate, obtained though suspending form 1 in water at ambient temperature.

The XRPD patterns and Raman spectra of HCl salt forms 1-4 of Compound 1 are provided in FIG. 6 and FIG. 7, respectively.

HCl salt form 1 had a crystalline XRPD pattern as shown in FIG. 75.

A list of X-Ray Diffraction Peaks for HCl salt form 1 is provided below in Table 40.

TABLE 40

X-Ray Diffraction Peaks for HCl salt form 1

| Two-theta angle (°) | d Space (Å) | Height (cps) | Integrated Intensity (cps deg) |
|---|---|---|---|
| 5.5 | 16.0 | 12969.1 | 2068.1 |
| 7.5 | 11.7 | 1916.6 | 177.6 |
| 9.0 | 9.8 | 1288.7 | 164.0 |
| 9.7 | 9.1 | 4706.0 | 846.5 |
| 11.2 | 7.9 | 7392.3 | 1379.4 |
| 13.1 | 6.8 | 6097.3 | 1064.5 |
| 13.9 | 6.3 | 2629.6 | 396.9 |
| 15.9 | 5.6 | 1838.4 | 262.7 |
| 16.5 | 5.4 | 2214.5 | 355.6 |
| 17.2 | 5.2 | 5130.2 | 1766.5 |
| 17.3 | 5.1 | 5855.7 | 1237.4 |
| 18.3 | 4.8 | 17932.2 | 3594.4 |
| 19.6 | 4.5 | 15494.7 | 3471.5 |
| 19.8 | 4.5 | 2868.8 | 806.8 |
| 21.7 | 4.1 | 14631.1 | 3058.6 |
| 22.0 | 4.0 | 2354.4 | 290.7 |
| 22.9 | 3.9 | 3438.0 | 1080.1 |
| 23.7 | 3.7 | 7449.4 | 1796.7 |
| 24.6 | 3.6 | 687.9 | 124.3 |
| 24.9 | 3.6 | 2183.3 | 439.3 |
| 25.9 | 3.4 | 5740.1 | 927.3 |
| 26.4 | 3.4 | 758.8 | 192.3 |
| 27.3 | 3.3 | 709.7 | 52.8 |
| 27.7 | 3.2 | 3379.1 | 765.1 |
| 28.2 | 3.2 | 4483.6 | 1063.5 |
| 28.5 | 3.1 | 1718.2 | 451.3 |
| 29.9 | 3.0 | 1186.0 | 187.7 |
| 30.6 | 2.9 | 4778.8 | 849.3 |
| 31.0 | 2.9 | 579.1 | 142.9 |
| 31.2 | 2.9 | 1004.1 | 293.2 |
| 31.7 | 2.8 | 3247.0 | 607.3 |
| 32.0 | 2.8 | 490.8 | 40.2 |
| 32.6 | 2.7 | 1788.3 | 320.3 |
| 33.0 | 2.7 | 2215.9 | 521.6 |
| 33.4 | 2.7 | 1783.0 | 343.1 |
| 33.7 | 2.7 | 905.0 | 191.9 |
| 34.2 | 2.6 | 459.8 | 77.8 |
| 36.3 | 2.5 | 1031.8 | 281.1 |
| 37.8 | 2.4 | 938.8 | 168.8 |
| 38.8 | 2.3 | 1982.7 | 408.2 |

HCl salt form 2 had a crystalline XRPD pattern as shown in FIG. 76. A list of X-Ray Diffraction Peaks for HCl salt form 2 is provided below in Table 41.

TABLE 41

X-Ray Diffraction Peaks for HCl salt form 2

| Two-theta angle (°) | d Space (Å) | Height (cps) | Integrated Intensity (cps deg) |
|---|---|---|---|
| 5.37 | 16.45 | 592.55 | 653.57 |
| 7.92 | 11.15 | 35976.02 | 7129.51 |
| 9.23 | 9.57 | 12118.24 | 2899.30 |
| 9.53 | 9.27 | 1421.61 | 374.75 |
| 11.95 | 7.40 | 3305.19 | 604.45 |
| 12.40 | 7.13 | 3829.96 | 761.05 |
| 12.61 | 7.01 | 3151.61 | 620.59 |
| 13.09 | 6.76 | 2672.35 | 447.18 |
| 14.90 | 5.94 | 1349.67 | 281.34 |
| 15.69 | 5.64 | 453.74 | 255.32 |
| 16.52 | 5.36 | 959.65 | 359.23 |
| 17.92 | 4.94 | 3894.23 | 592.00 |
| 18.17 | 4.88 | 1435.64 | 287.43 |
| 18.64 | 4.76 | 3595.38 | 1089.65 |
| 18.94 | 4.68 | 7474.81 | 1966.00 |
| 20.54 | 4.32 | 2348.09 | 486.82 |
| 20.69 | 4.29 | 9741.77 | 2458.87 |
| 20.93 | 4.24 | 2316.35 | 485.29 |
| 21.36 | 4.16 | 1483.99 | 326.24 |
| 21.69 | 4.09 | 2744.34 | 547.92 |
| 22.05 | 4.03 | 2192.50 | 487.17 |
| 22.80 | 3.90 | 4442.54 | 937.81 |
| 23.55 | 3.77 | 642.11 | 115.13 |
| 24.28 | 3.66 | 4273.40 | 950.29 |
| 24.71 | 3.60 | 2550.28 | 426.18 |
| 25.09 | 3.55 | 2388.93 | 360.05 |
| 25.25 | 3.52 | 1805.08 | 1004.78 |
| 25.78 | 3.45 | 2459.67 | 564.50 |
| 25.99 | 3.43 | 599.00 | 135.04 |

TABLE 41-continued

X-Ray Diffraction Peaks for HCl salt form 2

| Two-theta angle (°) | d Space (Å) | Height (cps) | Integrated Intensity (cps deg) |
|---|---|---|---|
| 27.02 | 3.30 | 3349.83 | 968.94 |
| 28.42 | 3.14 | 399.55 | 113.91 |
| 28.87 | 3.09 | 435.96 | 108.32 |
| 29.63 | 3.01 | 3577.77 | 1098.93 |
| 30.74 | 2.91 | 1588.78 | 574.33 |
| 31.58 | 2.83 | 605.09 | 156.91 |
| 31.87 | 2.81 | 848.03 | 124.95 |
| 32.33 | 2.77 | 377.17 | 63.59 |
| 32.76 | 2.73 | 502.69 | 59.45 |
| 33.35 | 2.68 | 875.09 | 200.67 |
| 34.02 | 2.63 | 558.64 | 122.35 |
| 35.10 | 2.55 | 350.60 | 235.04 |
| 36.06 | 2.49 | 586.34 | 82.05 |
| 36.61 | 2.45 | 1109.37 | 368.63 |
| 37.00 | 2.43 | 510.30 | 107.25 |
| 37.86 | 2.37 | 782.15 | 154.15 |
| 38.10 | 2.36 | 325.09 | 23.66 |
| 39.16 | 2.30 | 726.50 | 203.98 |
| 39.92 | 2.26 | 269.71 | 34.45 |

HCl salt form 3 had a crystalline XRPD pattern as shown in FIG. 77.

A list of X-Ray Diffraction Peaks for HCl salt form 3 is provided below in Table 42.

TABLE 42

X-Ray Diffraction Peaks for HCl salt form 3

| Two-theta angle (°) | d Space (Å) | Height (cps) | Integrated Intensity (cps deg) |
|---|---|---|---|
| 5.71 | 15.47 | 1872.85 | 491.40 |
| 9.48 | 9.32 | 158.22 | 16.75 |
| 9.85 | 8.98 | 161.51 | 41.55 |
| 11.34 | 7.80 | 420.89 | 84.75 |
| 13.24 | 6.68 | 238.55 | 53.54 |
| 14.10 | 6.28 | 127.25 | 26.40 |
| 16.75 | 5.29 | 66.83 | 49.71 |
| 17.86 | 4.96 | 41.98 | 4.90 |
| 18.44 | 4.81 | 399.82 | 83.45 |
| 19.67 | 4.51 | 187.75 | 49.56 |
| 21.82 | 4.07 | 138.69 | 41.10 |
| 23.10 | 3.85 | 106.66 | 26.29 |
| 23.84 | 3.73 | 105.12 | 24.30 |
| 25.03 | 3.55 | 79.21 | 9.11 |
| 26.04 | 3.42 | 76.81 | 13.09 |
| 27.81 | 3.21 | 35.67 | 26.16 |
| 30.65 | 2.91 | 24.89 | 9.32 |
| 31.83 | 2.81 | 47.28 | 6.83 |
| 38.91 | 2.31 | 82.80 | 16.42 |

HCl salt form 4 had a crystalline XRPD pattern as shown in FIG. 78.

A list of X-Ray Diffraction Peaks for HCl salt form 4 is provided below in Table 43.

TABLE 43

X-Ray Diffraction Peaks for HCl salt form 4

| Two-theta angle (°) | d Space (Å) | Height (cps) | Integrated Intensity (cps deg) |
|---|---|---|---|
| 5.65 | 15.63 | 4924.84 | 825.47 |
| 5.73 | 15.41 | 5498.85 | 591.99 |
| 7.50 | 11.77 | 279.33 | 45.50 |
| 9.31 | 9.49 | 277.38 | 51.20 |

TABLE 43-continued

X-Ray Diffraction Peaks for HCl salt form 4

| Two-theta angle (°) | d Space (Å) | Height (cps) | Integrated Intensity (cps deg) |
|---|---|---|---|
| 9.77 | 9.05 | 764.25 | 137.09 |
| 11.38 | 7.77 | 1245.36 | 192.73 |
| 13.77 | 6.43 | 1857.08 | 316.92 |
| 14.23 | 6.22 | 225.80 | 41.68 |
| 16.20 | 5.47 | 114.71 | 39.23 |
| 17.16 | 5.16 | 304.94 | 111.55 |
| 17.54 | 5.05 | 177.51 | 14.77 |
| 18.16 | 4.88 | 127.71 | 20.78 |
| 18.69 | 4.74 | 347.52 | 64.84 |
| 19.06 | 4.65 | 202.42 | 29.94 |
| 20.56 | 4.32 | 90.65 | 21.84 |
| 21.65 | 4.10 | 1074.30 | 88.67 |
| 21.75 | 4.08 | 477.54 | 24.35 |
| 22.10 | 4.02 | 92.97 | 17.23 |
| 22.65 | 3.92 | 68.46 | 7.91 |
| 23.05 | 3.86 | 129.05 | 14.51 |
| 24.04 | 3.70 | 198.45 | 40.76 |
| 26.18 | 3.40 | 83.26 | 32.14 |
| 28.30 | 3.15 | 92.13 | 14.64 |
| 28.45 | 3.13 | 128.73 | 16.20 |
| 28.70 | 3.11 | 100.53 | 13.07 |
| 29.59 | 3.02 | 606.36 | 75.13 |
| 30.90 | 2.89 | 53.64 | 28.04 |
| 32.47 | 2.76 | 60.31 | 13.68 |
| 35.63 | 2.52 | 137.84 | 16.16 |

HCl salt form 5 had a crystalline XRPD pattern as shown in FIG. 79.

A list of X-Ray Diffraction Peaks for HCl salt form 5 is provided below in Table 44.

TABLE 44

X-Ray Diffraction Peaks for HCl salt form 5

| Two-theta angle (°) | d Space (Å) | Height (cps) | Integrated Intensity (cps deg) |
|---|---|---|---|
| 5.63 | 15.69 | 8757.84 | 2202.44 |
| 6.29 | 14.03 | 966.00 | 355.83 |
| 7.61 | 11.60 | 877.18 | 137.61 |
| 8.45 | 10.46 | 2316.04 | 443.76 |
| 9.74 | 9.08 | 2656.26 | 542.46 |
| 10.76 | 8.22 | 1049.40 | 386.31 |
| 11.27 | 7.85 | 3658.20 | 726.37 |
| 12.23 | 7.23 | 846.40 | 176.62 |
| 12.59 | 7.02 | 283.48 | 81.70 |
| 13.16 | 6.72 | 3704.71 | 860.85 |
| 14.02 | 6.31 | 1508.74 | 362.71 |
| 14.63 | 6.05 | 2066.39 | 566.49 |
| 15.97 | 5.54 | 237.35 | 56.74 |
| 16.63 | 5.33 | 878.65 | 150.23 |
| 16.92 | 5.24 | 699.58 | 83.76 |
| 17.35 | 5.11 | 4030.83 | 1382.01 |
| 17.74 | 5.00 | 2443.62 | 348.59 |
| 18.40 | 4.82 | 6073.33 | 1172.14 |
| 18.69 | 4.74 | 4103.82 | 2582.57 |
| 19.10 | 4.64 | 2293.83 | 529.63 |
| 19.66 | 4.51 | 7592.14 | 2574.56 |
| 21.80 | 4.07 | 7719.16 | 2045.12 |
| 22.63 | 3.93 | 792.18 | 132.23 |
| 23.05 | 3.86 | 3608.05 | 701.52 |
| 23.80 | 3.74 | 6333.67 | 1485.01 |
| 24.58 | 3.62 | 855.84 | 285.38 |
| 24.98 | 3.56 | 1705.94 | 288.11 |
| 25.94 | 3.43 | 4528.66 | 1061.43 |
| 26.51 | 3.36 | 1115.02 | 242.90 |
| 27.78 | 3.21 | 2251.91 | 555.95 |
| 28.25 | 3.16 | 2814.48 | 672.69 |
| 28.57 | 3.12 | 1083.07 | 420.02 |
| 30.62 | 2.92 | 3510.29 | 896.26 |

TABLE 44-continued

X-Ray Diffraction Peaks for HCl salt form 5

| Two-theta angle (°) | d Space (Å) | Height (cps) | Integrated Intensity (cps deg) |
|---|---|---|---|
| 31.38 | 2.85 | 650.63 | 288.80 |
| 31.78 | 2.81 | 1924.51 | 446.62 |
| 32.61 | 2.74 | 1419.18 | 422.36 |
| 33.01 | 2.71 | 1024.52 | 282.57 |
| 33.40 | 2.68 | 675.21 | 391.50 |
| 35.40 | 2.53 | 566.07 | 145.81 |
| 37.88 | 2.37 | 731.57 | 141.30 |
| 38.82 | 2.32 | 986.44 | 438.18 |

HCl salt form 6 had a crystalline XRPD pattern as shown in FIG. 80.

A list of X-Ray Diffraction Peaks for HCl salt form 6 is provided below in Table 45.

TABLE 45

X-Ray Diffraction Peaks for HCl salt form 6

| Two-theta angle (°) | d Space (Å) | Height (cps) | Integrated Intensity (cps deg) |
|---|---|---|---|
| 5.58 | 15.81 | 31929.40 | 7867.13 |
| 7.61 | 11.61 | 2354.93 | 399.68 |
| 8.27 | 10.68 | 942.70 | 156.02 |
| 9.13 | 9.67 | 1041.26 | 178.68 |
| 9.74 | 9.08 | 5902.42 | 1316.22 |
| 11.19 | 7.90 | 8964.42 | 1880.17 |
| 13.14 | 6.73 | 7139.88 | 1488.68 |
| 13.99 | 6.32 | 3397.71 | 771.69 |
| 15.91 | 5.57 | 1911.79 | 311.33 |
| 16.65 | 5.32 | 2298.21 | 475.14 |
| 16.87 | 5.25 | 1228.29 | 312.19 |
| 17.33 | 5.11 | 9891.46 | 3506.94 |
| 18.38 | 4.82 | 17540.88 | 4446.97 |
| 19.67 | 4.51 | 16386.83 | 4653.87 |
| 19.92 | 4.45 | 3596.19 | 952.42 |
| 21.79 | 4.07 | 15553.47 | 3148.95 |
| 21.99 | 4.04 | 2610.38 | 1456.90 |
| 23.03 | 3.86 | 7569.93 | 1479.04 |
| 23.32 | 3.81 | 988.39 | 480.26 |
| 23.77 | 3.74 | 11655.19 | 2269.32 |
| 24.66 | 3.61 | 809.20 | 131.82 |
| 24.97 | 3.56 | 3705.27 | 646.97 |
| 25.33 | 3.51 | 824.98 | 151.05 |
| 25.92 | 3.43 | 7418.01 | 1432.81 |
| 26.52 | 3.36 | 1905.31 | 385.66 |
| 27.38 | 3.25 | 407.44 | 102.52 |
| 27.76 | 3.21 | 4154.50 | 956.34 |
| 28.24 | 3.16 | 6007.39 | 1332.17 |
| 28.54 | 3.13 | 2152.95 | 564.23 |
| 30.62 | 2.92 | 5038.25 | 963.05 |
| 31.34 | 2.85 | 824.03 | 518.33 |
| 31.74 | 2.82 | 2993.10 | 591.44 |
| 32.63 | 2.74 | 2078.78 | 362.73 |
| 33.04 | 2.71 | 1869.26 | 488.45 |
| 33.47 | 2.68 | 1096.36 | 626.44 |
| 36.38 | 2.47 | 1154.33 | 301.56 |
| 37.83 | 2.38 | 967.95 | 193.48 |
| 38.79 | 2.32 | 1459.86 | 469.44 |

HCl salt form 7 had a crystalline XRPD pattern as shown in FIG. 81.

A list of X-Ray Diffraction Peaks for HCl salt form 7 is provided below in Table 46.

TABLE 46

X-Ray Diffraction Peaks for HCl salt form 7

| Two-theta angle (°) | d Space (Å) | Height (cps) | Integrated Intensity (cps deg) |
|---|---|---|---|
| 5.54 | 15.95 | 6246.28 | 1256.69 |
| 7.61 | 11.61 | 7037.98 | 595.99 |
| 8.95 | 9.87 | 1033.78 | 121.16 |
| 9.85 | 8.97 | 1288.63 | 176.25 |
| 11.14 | 7.94 | 2359.79 | 283.51 |
| 12.86 | 6.88 | 1130.30 | 176.10 |
| 14.14 | 6.26 | 351.89 | 124.94 |
| 15.77 | 5.62 | 665.95 | 92.06 |
| 16.83 | 5.27 | 844.94 | 132.97 |
| 17.29 | 5.13 | 469.56 | 63.63 |
| 17.51 | 5.06 | 732.33 | 101.81 |
| 18.04 | 4.91 | 3457.16 | 535.82 |
| 18.33 | 4.84 | 533.06 | 58.91 |
| 18.69 | 4.74 | 195.55 | 23.23 |
| 19.82 | 4.48 | 1843.83 | 457.27 |
| 21.94 | 4.05 | 1075.92 | 247.17 |
| 23.05 | 3.85 | 2919.74 | 372.20 |
| 23.90 | 3.72 | 986.64 | 157.89 |
| 28.28 | 3.15 | 610.86 | 102.24 |
| 30.66 | 2.91 | 247.39 | 102.03 |
| 32.02 | 2.79 | 481.59 | 79.64 |
| 38.98 | 2.31 | 1528.36 | 239.71 |

In the TGA/DSC thermogram of the HCl salt form 2 (FIG. 34), 2.82% weight loss upon heating to 119.9° C. on TGA is attributed to the water content in the material. A small endothermic peak at 163.0° C. in DSC thermogram is likely a solid-solid transition followed by melting and decomposition around 220° C.

The sorption/desorption of HCl salt form 2 is presented in FIG. 41. It demonstrated that the current HCl salt (form 2) was hygroscopic in nature, and likely formed a monohydrate upon uptaking water. The water uptake is 4.89% at 40% RH from Cycle 2 sorption isotherm. This is close to the theoretical value of water content (4.79%) for the HCl salt monohydrate. It appears that the hydrate is not hygroscopic, but water departures quickly when RH is below 20% even at 25° C. As shown in FIG. 42, the XRPD pattern of the post-DVS sample is different from that of the initial material.

The XRPD patterns of Compound 1 HCl salt under stress conditions are presented in FIG. 55. Compared to that of the initial material, the XRPD pattern of HCl salt form 2 stored under 80° C. for 2 weeks remained unchanged, but the XRPD pattern of HCl salt stored under 80° C./75% RH is different. The results indicated that the current HCl salt is physically stable under 80° C. dry condition, but not stable under wet condition.

The HCl salt form 2 was heated in DSC to 180° C. at 10° C./min. Raman and XRPD were immediately run for the solid residues at the end of DSC run when the sample pan was unloaded between 35-45° C. Afterwards, the solid residues were stored at 40° C./75% RH up to 6 days and tested using XRPD.

The HCl salt form 2 was heated in DSC to 220° C. at 10° C./min. Raman and XRPD were immediately run for the solid residues at the end of DSC run when the sample pan was unloaded between 35-45° C. Afterwards, the solid residues were stored at 40° C./75% RH up to 64 hours and tested using XRPD.

As indicated by Raman in FIG. 56 and XRPD in FIG. 57, two new forms of HCl salts were obtained when HCl salt form 2 was heated to 180° C. and 220° C., respectively. They were designated as form 5 for the material heated to 180° C.

and form 6 for the material heated to 220° C. After being stored at 40° C./75% RH, the two forms showed the same XRPD patterns as that of unheated HCl salt (initial material) stored in the same condition for 2 weeks. This demonstrated that form 5 and form 6 tended to become hydrates when exposed to moisture at 40° C. It was confirmed by TGA/DSC (FIG. 58) that the sample of the HCl salt stored at 40° C./75% RH for the physical stability test was an hydrate. As indicated by XRPD in FIG. 57, the hydrate is different from the solid residue (tentatively assigned as form 7) obtained from solubility test of the HCl salt in water.

Simultaneous TGA/DSC was also conducted on HCl salt (form 2) by heating it to 220° C., cooling back to 25° C. and then heating to 280° C. The heating/cooling rate was 10° C./min. The TGA/DSC thermograms were presented in FIG. 59. From the first heating process, a weight loss of 2.91% was observed from TGA up to 131.2° C. No weight loss or other thermal events were observed during second heating up to 210° C., showing that form 6 (HCl salt heated to 220° C.) did not contain water. Form 1 of HCl salt was first obtained through crystallization using ACN (no ACN contained in the sample based on $^1$H NMR), and it was likely the same material as HCl salt suspended in SGF or exposed to moisture. As shown in FIG. 60, form 1 appeared to be a hydrate. Since form 6 did not contain water but converted to a hydrate when exposed to moisture, it was likely a dehydrate hydrate.

6.10.5.2. $H_2SO_4$ Salt of Compound 1

$H_2SO_4$ salt form 1 was prepared by evaporation of a solution comprising Compound 1 and $H_2SO_4$ in ACN, IPA or EtOAc. $H_2SO_4$ salt form 2 was prepared by evaporation of a solution comprising Compound 1 and $H_2SO_4$ in acetone.

The XRPD patterns and Raman spectra of $H_2SO_4$ salt forms 1-2 of Compound 1 are provided in FIG. 8 and FIG. 9, respectively.

$H_2SO_4$ salt form 1 had a crystalline XRPD pattern as shown in FIG. 82.

A list of X-Ray Diffraction Peaks for $H_2SO_4$ salt form 1 is provided below in Table 47.

TABLE 47

X-Ray Diffraction Peaks for $H_2SO_4$ salt form 1

| Two-theta angle (°) | d Space (Å) | Height (cps) | Integrated Intensity (cps deg) |
|---|---|---|---|
| 5.40 | 16.35 | 22092.62 | 7232.95 |
| 5.66 | 15.61 | 1917.86 | 1455.52 |
| 9.02 | 9.79 | 528.92 | 86.33 |
| 10.74 | 8.23 | 6630.92 | 1762.86 |
| 14.78 | 5.99 | 1863.07 | 506.47 |
| 16.16 | 5.48 | 3763.67 | 955.60 |
| 16.65 | 5.32 | 843.38 | 287.69 |
| 17.65 | 5.02 | 1373.47 | 1338.01 |
| 18.18 | 4.88 | 18989.96 | 3922.05 |
| 18.69 | 4.74 | 10432.71 | 2885.01 |
| 19.67 | 4.51 | 2121.35 | 450.50 |
| 20.50 | 4.33 | 930.91 | 322.41 |
| 21.62 | 4.11 | 8852.02 | 2582.96 |
| 22.28 | 3.99 | 12575.42 | 2783.45 |
| 22.75 | 3.91 | 8651.16 | 2341.78 |
| 24.13 | 3.69 | 5109.83 | 1395.18 |
| 24.57 | 3.62 | 930.19 | 210.07 |
| 24.88 | 3.58 | 3420.54 | 811.66 |
| 25.42 | 3.50 | 1458.25 | 964.96 |
| 26.55 | 3.35 | 9457.08 | 2103.26 |
| 28.49 | 3.13 | 1137.23 | 182.53 |
| 29.17 | 3.06 | 982.32 | 358.95 |
| 29.88 | 2.99 | 1812.40 | 495.30 |
| 31.29 | 2.86 | 693.51 | 325.31 |

TABLE 47-continued

X-Ray Diffraction Peaks for $H_2SO_4$ salt form 1

| Two-theta angle (°) | d Space (Å) | Height (cps) | Integrated Intensity (cps deg) |
|---|---|---|---|
| 32.15 | 2.78 | 1179.11 | 251.18 |
| 32.66 | 2.74 | 871.43 | 185.29 |
| 33.21 | 2.70 | 717.07 | 238.85 |
| 34.02 | 2.63 | 736.56 | 453.03 |
| 35.78 | 2.51 | 444.20 | 64.31 |
| 36.86 | 2.44 | 435.04 | 57.67 |
| 37.43 | 2.40 | 497.72 | 81.14 |
| 38.27 | 2.35 | 1574.41 | 354.26 |
| 39.64 | 2.27 | 568.60 | 217.43 |

$H_2SO_4$ salt form 2 had a crystalline XRPD pattern as shown in FIG. 83.

A list of X-Ray Diffraction Peaks for $H_2SO_4$ salt form 2 is provided below in Table 48.

TABLE 48

X-Ray Diffraction Peaks for $H_2SO_4$ salt form 2

| Two-theta angle (°) | d Space (Å) | Height (cps) | Integrated Intensity (cps deg) |
|---|---|---|---|
| 5.63 | 15.68 | 1997.46 | 493.57 |
| 5.67 | 15.57 | 487.80 | 287.88 |
| 15.25 | 5.80 | 131.71 | 29.70 |
| 16.08 | 5.51 | 58.35 | 31.09 |
| 17.87 | 4.96 | 504.85 | 129.56 |
| 18.57 | 4.77 | 165.17 | 65.89 |
| 21.83 | 4.07 | 55.13 | 16.10 |
| 22.24 | 3.99 | 154.81 | 35.67 |
| 22.75 | 3.91 | 92.30 | 47.78 |
| 25.90 | 3.44 | 69.67 | 14.82 |
| 26.53 | 3.36 | 29.58 | 6.94 |
| 27.18 | 3.28 | 104.25 | 20.42 |
| 11.30 | N/A | N/A | N/A |

In the TGA/DSC thermogram of the $H_2SO_4$ salt form 1 (FIG. 35), 0.28% weight loss upon heating to 119.9° C. on TGA is attributed to the trace amount of water in the material. A small $T_g$-like event between 86.0° C. and 88.4° C. in DSC thermogram was noticed and no further investigation was carried out in this study. TGA thermogram indicated a continuous weight loss starting from 119.9° C., while DSC indicated significant melting and decomposition started around 220° C.

The sorption/desorption of $H_2SO_4$ salt form 1 is presented in FIG. 43. It demonstrated that the current $H_2SO_4$ salt (form 1) was hygroscopic in nature. As shown in FIG. 44, the XRPD pattern of the solid residues after DVS test is different from that of the initial material.

The XRPD patterns of Compound 1 $H_2SO_4$ salt under stress conditions are presented in FIG. 61. Compared to that of the initial material, the XRPD pattern of $H_2SO_4$ salt stored under 80° C. for 2 weeks remained unchanged, but the XRPD pattern of $H_2SO_4$ salt stored under 80° C./75% RH is different. The results indicated that the current $H_2SO_4$ salt is physically stable under 80° C. dry condition, but not stable under wet condition. Chemical stability indicated that $H_2SO_4$ salt was stable under stress conditions, therefore a new form (form 3) of $H_2SO_4$ salt was obtained when it was stored under 80° C./75% RH conditions for 2 weeks.

$H_2SO_4$ salt form 3 had a crystalline XRPD pattern as shown in FIG. 84.

A list of X-Ray Diffraction Peaks for $H_2SO_4$ salt form 3 is provided below in Table 49.

TABLE 49

X-Ray Diffraction Peaks for $H_2SO_4$ salt form 3

| Two-theta angle (°) | d Space (Å) | Height (cps) | Integrated Intensity (cps deg) |
|---|---|---|---|
| 5.60 | 15.76 | 84043.67 | 19286.01 |
| 17.67 | 5.01 | 16887.29 | 3444.96 |
| 11.22 | 7.88 | 7847.26 | 1712.69 |
| 22.38 | 3.97 | 3043.71 | 979.78 |
| 15.11 | 5.86 | 3007.89 | 721.89 |
| 18.10 | 4.90 | 2286.45 | 650.14 |
| 22.61 | 3.93 | 2056.14 | 616.97 |
| 22.10 | 4.02 | 3141.47 | 606.73 |
| 27.24 | 3.27 | 2752.01 | 581.93 |
| 10.68 | 8.28 | 2639.54 | 568.81 |
| 18.48 | 4.80 | 2269.44 | 418.76 |
| 15.96 | 5.55 | 1726.73 | 404.85 |
| 21.53 | 4.12 | 1594.47 | 390.21 |
| 25.85 | 3.44 | 1080.69 | 359.32 |
| 25.22 | 3.53 | 1119.71 | 331.14 |
| 24.56 | 3.62 | 1385.37 | 299.12 |
| 23.65 | 3.76 | 1005.15 | 268.82 |
| 19.15 | 4.63 | 901.20 | 225.40 |
| 12.41 | 7.13 | 1028.08 | 166.69 |
| 26.27 | 3.39 | 588.43 | 121.97 |
| 18.78 | 4.72 | 422.19 | 99.28 |
| 13.81 | 6.41 | 429.52 | 84.84 |
| 34.20 | 2.62 | 382.23 | 81.71 |
| 16.86 | 5.26 | 185.84 | 79.25 |
| 33.38 | 2.68 | 305.57 | 71.79 |
| 37.96 | 2.37 | 174.37 | 40.85 |

6.10.5.3. $H_3PO_4$ Salt of Compound 1

The $H_3PO_4$ salt of Compound 1 was prepared by evaporation of a solution comprising Compound 1 and $H_3PO_4$ in ACN, EtOH, EtOAc or acetone.

The XRPD pattern and Raman spectrum of $H_3PO_4$ salt of Compound 1 are provided in FIG. 10 and FIG. 11, respectively.

$H_3PO_4$ salt had a crystalline XRPD pattern as shown in FIG. 85.

A list of X-Ray Diffraction Peaks for $H_3PO_4$ salt is provided below in Table 50.

TABLE 50

X-Ray Diffraction Peaks for $H_3PO_4$ salt

| Two-theta angle (°) | d Space (Å) | Height (cps) | Integrated Intensity (cps deg) |
|---|---|---|---|
| 5.58 | 15.82 | 113896.47 | 43662.53 |
| 5.73 | 15.42 | 83115.98 | 17172.19 |
| 11.30 | 7.83 | 22604.94 | 8264.42 |
| 15.27 | 5.80 | 12217.79 | 4303.97 |
| 16.07 | 5.51 | 1220.72 | 227.74 |
| 16.37 | 5.41 | 2410.31 | 1008.88 |
| 16.95 | 5.23 | 9098.15 | 3097.79 |
| 17.46 | 5.08 | 1398.63 | 350.32 |
| 17.72 | 5.00 | 5630.55 | 1749.92 |
| 18.37 | 4.82 | 5749.42 | 1742.60 |
| 20.64 | 4.30 | 1222.06 | 517.32 |
| 20.98 | 4.23 | 4045.16 | 1304.81 |
| 21.73 | 4.09 | 2784.49 | 975.76 |
| 22.34 | 3.98 | 2069.88 | 521.03 |
| 22.66 | 3.92 | 5785.47 | 1825.70 |
| 23.31 | 3.81 | 3257.99 | 950.98 |
| 23.65 | 3.76 | 9545.98 | 2616.01 |
| 24.14 | 3.68 | 1799.94 | 1196.49 |
| 25.88 | 3.44 | 7708.99 | 3286.84 |

TABLE 50-continued

X-Ray Diffraction Peaks for $H_3PO_4$ salt

| Two-theta angle (°) | d Space (Å) | Height (cps) | Integrated Intensity (cps deg) |
|---|---|---|---|
| 26.42 | 3.37 | 3658.44 | 972.03 |
| 28.10 | 3.17 | 444.85 | 279.86 |
| 28.39 | 3.14 | 11434.58 | 3320.53 |
| 29.89 | 2.99 | 1225.03 | 328.89 |
| 30.38 | 2.94 | 615.58 | 136.38 |
| 30.88 | 2.89 | 1948.99 | 689.16 |
| 31.35 | 2.85 | 2657.30 | 881.21 |
| 33.13 | 2.70 | 586.48 | 275.45 |
| 34.32 | 2.61 | 1351.06 | 388.17 |
| 35.08 | 2.56 | 685.02 | 252.22 |
| 35.91 | 2.50 | 804.38 | 245.10 |
| 37.43 | 2.40 | 449.17 | 119.67 |
| 38.89 | 2.31 | 1307.87 | 709.00 |

In the TGA/DSC thermogram of the $H_3PO_4$ salt (FIG. 36), 0.25% weight loss upon heating to 119.9° C. in TGA is attributed to the trace amount of water in the material. TGA results indicated a continuous weight loss starting from around 169.9° C., while DSC indicated melting and decomposition with an onset temperature of 238.3° C.

The sorption/desorption of $H_3PO_4$ salt is presented in FIG. 45, indicating that $H_3PO_4$ salt is not hygroscopic. As shown in FIG. 46, the XRPD pattern of the solid residues after DVS test remained unchanged from that of the initial material.

The XRPD patterns of Compound 1 $H_3PO_4$ salt under stress conditions are presented in FIG. 62. Compared to that of the initial material, the XRPD patterns of $H_3PO_4$ salt remained the same as that of the initial material, showing that it was physically stable under 80° C. and 80° C./75% RH conditions for 2 weeks.

6.10.5.4. L-Tartrate Salt of Compound 1

The L-tartrate salt of Compound 1 was prepared by evaporation of a solution comprising Compound 1 and L-tartaric acid in ACN, EtOH, EtOAc or acetone.

The XRPD pattern and Raman spectrum of the L-tartrate salt of Compound 1 are provided in FIG. 12 and FIG. 13, respectively.

L-tartrate salt form 1 had a crystalline XRPD pattern as shown in FIG. 88.

A list of X-Ray Diffraction Peaks for L-tartrate salt form 1 is provided below in Table 51.

TABLE 51

X-Ray Diffraction Peaks for L-tartrate salt form 1

| Two-theta angle (°) | d Space (Å) | Height (cps) | Integrated Intensity (cps deg) |
|---|---|---|---|
| 6.04 | 14.62 | 35641.02 | 13962.89 |
| 9.47 | 9.33 | 498.71 | 113.50 |
| 12.14 | 7.28 | 8910.13 | 2777.20 |
| 13.73 | 6.44 | 1380.04 | 819.25 |
| 14.57 | 6.07 | 5574.18 | 1460.05 |
| 15.19 | 5.83 | 5555.62 | 1613.38 |
| 16.19 | 5.47 | 27183.97 | 7267.10 |
| 16.68 | 5.31 | 14358.85 | 4281.40 |
| 17.30 | 5.12 | 13416.42 | 3458.95 |
| 18.27 | 4.85 | 4471.36 | 1050.50 |
| 19.98 | 4.44 | 23979.41 | 9001.06 |
| 20.31 | 4.37 | 11804.09 | 3991.55 |
| 21.14 | 4.20 | 1301.63 | 239.97 |
| 22.08 | 4.02 | 1347.34 | 442.01 |

TABLE 51-continued

X-Ray Diffraction Peaks for L-tartrate salt form 1

| Two-theta angle (°) | d Space (Å) | Height (cps) | Integrated Intensity (cps deg) |
|---|---|---|---|
| 22.75 | 3.90 | 5360.97 | 2162.43 |
| 23.21 | 3.83 | 3574.02 | 3882.23 |
| 23.84 | 3.73 | 11453.82 | 2990.70 |
| 24.33 | 3.66 | 18815.15 | 6865.32 |
| 25.92 | 3.43 | 1449.30 | 312.77 |
| 26.51 | 3.36 | 1104.03 | 183.82 |
| 27.09 | 3.29 | 1496.66 | 230.40 |
| 27.75 | 3.21 | 2573.67 | 1246.17 |
| 28.44 | 3.14 | 2470.19 | 678.86 |
| 29.52 | 3.02 | 4293.56 | 1403.94 |
| 31.15 | 2.87 | 1948.85 | 631.58 |
| 31.83 | 2.81 | 2876.44 | 853.94 |
| 32.73 | 2.73 | 1501.50 | 473.39 |
| 33.31 | 2.69 | 1944.21 | 550.61 |
| 34.99 | 2.56 | 3591.42 | 1161.34 |
| 35.55 | 2.52 | 1870.73 | 746.99 |
| 36.80 | 2.44 | 822.22 | 280.25 |
| 37.25 | 2.41 | 692.53 | 113.17 |
| 37.77 | 2.38 | 2489.26 | 741.25 |
| 38.41 | 2.34 | 449.34 | 44.89 |

L-tartrate salt form 2 had a crystalline XRPD pattern as shown in FIG. 89.

A list of X-Ray Diffraction Peaks for L-tartrate salt form 2 is provided below in Table 52.

TABLE 52

X-Ray Diffraction Peaks for L-tartrate salt form 2

| Two-theta angle (°) | d Space (Å) | Height (cps) | Integrated Intensity (cps deg) |
|---|---|---|---|
| 5.02 | 17.58 | 735.02 | 463.76 |
| 6.29 | 14.04 | 22630.03 | 8352.94 |
| 6.46 | 13.67 | 2622.26 | 2491.62 |
| 9.71 | 9.10 | 1759.68 | 647.27 |
| 12.47 | 7.09 | 224.77 | 399.99 |
| 12.63 | 7.00 | 4859.90 | 1705.70 |
| 15.21 | 5.82 | 1978.51 | 1241.29 |
| 16.51 | 5.36 | 15847.76 | 6108.09 |
| 16.56 | 5.35 | 907.28 | 949.99 |
| 17.23 | 5.14 | 9095.92 | 2351.90 |
| 18.82 | 4.71 | 2721.51 | 994.01 |
| 20.72 | 4.28 | 6070.37 | 5681.20 |
| 22.49 | 3.95 | 1617.44 | 558.47 |
| 22.71 | 3.91 | 567.93 | 116.48 |
| 24.04 | 3.70 | 5177.14 | 3429.03 |
| 24.86 | 3.58 | 1422.20 | 220.06 |
| 24.95 | 3.57 | 4293.73 | 1743.64 |
| 27.08 | 3.29 | 1155.04 | 620.23 |
| 28.25 | 3.16 | 1480.68 | 843.50 |
| 29.30 | 3.05 | 1607.84 | 780.71 |
| 30.78 | 2.90 | 319.68 | 186.67 |
| 31.16 | 2.87 | 516.22 | 54.50 |
| 31.30 | 2.86 | 224.24 | 42.92 |
| 33.13 | 2.70 | 558.74 | 250.00 |
| 33.96 | 2.64 | 300.89 | 31.99 |
| 34.36 | 2.61 | 338.44 | 70.34 |
| 34.87 | 2.57 | 234.44 | 41.74 |
| 35.03 | 2.56 | 472.06 | 23.44 |
| 35.14 | 2.55 | 480.05 | 28.62 |
| 35.29 | 2.54 | 274.42 | 37.01 |
| 36.36 | 2.47 | 572.04 | 197.04 |
| 36.58 | 2.45 | 536.59 | 139.95 |

The L-tartrate salt was a hemi-tartrate dihydrate as indicated from $^1$H NMR in FIG. 14 and TGA/DSC in FIG. 15. The $^1$H NMR indicated a stoichiometric ratio of approximately 2:1 for the Compound 1 free base to L-tartaric acid. The TGA/DSC indicated similar weight loss and dissolvation event when different solvents were used for re-crystallization of L-tartrate salt, which indicated that it was a hydrate.

In the TGA/DSC thermogram of the L-tartrate salt (FIG. 37), 3.97% weight loss upon heating to 119.9° C. on TGA is attributed to the water content in the material. It's corresponding to a dehydration event in DSC with an onset temperature of 89.5° C. This showed that the sample was likely a dihydrate with theoretical value of 4.34% for water content. The dehydrated product melt and decomposed starting around 201.5° C. as evidenced in both TGA and DSC.

The sorption/desorption of L-tartrate salt is presented in FIG. 47. The L-tartrate is a hydrate, but water is partially lost when dried in vacuum oven during salt preparation. Upon exposed to moisture in sorption test, uptaken water is first consumed to satisfy the hydrate formation, therefore the L-tartrate hydrate is only slightly hygroscopic. As shown in FIG. 49, the XRPD pattern of the solid residues after DVS test remained unchanged from that of the initial material. Additional DVS study was performed by pre-heating the L-tartrate salt at 50° C. for 3 hours, immediately started the two-cycle sorption/desorption process (i.e., 0-95-0-95-0% RH). Weight loss of 5.53% was greater than 3.97% observed in TGA for the initial material, showing that L-tartrate salt re-gained water quickly after withdrawn from the vacuum oven. The sorption/desorption isotherms after pre-heat was presented in FIG. 48, clearly demonstrated that a hydrate was formed quickly even at RH as 20% RH. The test reaches 20% RH in less than 2 hours. Cycle 1 sorption at 20% RH was 4.32%, which matches well with the theoretical value of water content (4.34%) in a hemi-tartrate dihydrate salt. The water uptake of the hydrate at 80% RH is estimated as 0.81% (i.e. the difference between 20% RH and 80% RH at Cycle 1 sorption). The sorption/desorption is reproducible through Cycle 2 sorption/desorption at 25° C. At the end of DVS test, the solid residues remained the same XRPD patterns as those of the initial material and the solids from previous DVS test without pre-heating step.

As presented in FIG. 63, the XRPD patterns of Compound 1 L-tartrate salt under stress conditions remained the same as that of the initial material, showing that it was physically stable under 80° C. and 80° C./75% RH conditions for 2 weeks.

A combinational XRD-DSC experiment was carried out on the L-tartrate salt by heating the sample at 5° C./min and scan XRD at 12°/min 2 theta. The data were illustrated in FIG. 64. XRPD pattern (left side) was changed between 96.5° C. and 131.5° C., corresponding to an endothermic peak observed in DSC (right side). It demonstrated the dehydration occurred within the temperature range, resulting in an anhydrate.

In order to isolate the L-tartrate salt anhydrate, a portion of L-tartrate salt was heated in DSC to 130° C. at 10° C./min. The solid residue was immediately analyzed using XRPD. As shown in FIG. 65, the XRPD patterns were identical for the materials before and after heating, implying the anhydrate picks up moisture rapidly to form the hydrate. Therefore, the hydrate is more stable than the anhydrate.

6.10.5.5. L-Lactate Salt of Compound 1

L-lactate salt form 1 was prepared by evaporation of a solution comprising Compound 1 and L-lactic acid in hexane. L-lactate salt form 2 was prepared by evaporation of a solution comprising Compound 1 and L-lactic acid in EtOAc.

The XRPD pattern and Raman spectrum of the L-lactate salt of Compound 1 are provided in FIG. 16 and FIG. 17, respectively.

L-lactate salt form 1 had a crystalline XRPD pattern as shown in FIG. 86.

A list of X-Ray Diffraction Peaks for L-lactate salt form 1 is provided below in Table 53.

TABLE 53

X-Ray Diffraction Peaks for L-lactate salt form 1

| Two-theta angle (°) | d Space (Å) | Height (cps) | Integrated Intensity (cps deg) |
|---|---|---|---|
| 5.77 | 15.31 | 8567.29 | 2702.27 |
| 7.93 | 11.14 | 3707.79 | 805.07 |
| 9.57 | 9.23 | 6536.45 | 1744.37 |
| 9.81 | 9.01 | 5422.84 | 1229.97 |
| 10.01 | 8.83 | 1286.33 | 278.79 |
| 11.69 | 7.57 | 636.44 | 442.22 |
| 12.09 | 7.31 | 659.47 | 257.86 |
| 12.81 | 6.91 | 438.13 | 130.72 |
| 13.72 | 6.45 | 2239.74 | 429.16 |
| 14.39 | 6.15 | 387.11 | 62.28 |
| 14.66 | 6.04 | 646.85 | 76.15 |
| 16.10 | 5.50 | 9044.71 | 1801.13 |
| 16.89 | 5.25 | 1892.98 | 391.34 |
| 17.19 | 5.15 | 4152.74 | 900.30 |
| 17.70 | 5.01 | 3726.05 | 856.48 |
| 18.89 | 4.69 | 4918.54 | 956.25 |
| 19.20 | 4.62 | 2551.89 | 508.03 |
| 19.54 | 4.54 | 3811.47 | 1914.07 |
| 19.72 | 4.50 | 3625.59 | 480.85 |
| 20.16 | 4.40 | 24622.32 | 4477.86 |
| 20.43 | 4.34 | 2054.14 | 585.82 |
| 20.96 | 4.23 | 1108.89 | 182.73 |
| 21.55 | 4.12 | 2279.40 | 428.08 |
| 21.84 | 4.07 | 3342.05 | 708.16 |
| 23.12 | 3.84 | 334.58 | 125.71 |
| 24.22 | 3.67 | 7143.74 | 1642.85 |
| 24.67 | 3.61 | 699.39 | 99.43 |
| 24.92 | 3.57 | 1595.28 | 535.99 |
| 25.21 | 3.53 | 979.84 | 134.85 |
| 26.19 | 3.40 | 900.19 | 141.78 |
| 27.06 | 3.29 | 1508.32 | 552.00 |
| 28.55 | 3.12 | 1353.80 | 327.88 |
| 29.20 | 3.06 | 591.65 | 138.22 |
| 30.43 | 2.93 | 2605.13 | 525.52 |
| 32.82 | 2.73 | 602.22 | 261.32 |
| 34.36 | 2.61 | 665.89 | 425.00 |
| 36.29 | 2.47 | 520.56 | 416.78 |

L-lactate salt form 2 had a crystalline XRPD pattern as shown in FIG. 87.

A list of X-Ray Diffraction Peaks for L-lactate salt form 2 is provided below in Table 54.

TABLE 54

X-Ray Diffraction Peaks for L-lactate salt form 2

| Two-theta angle (°) | d Space (Å) | Height (cps) | Integrated Intensity (cps deg) |
|---|---|---|---|
| 9.69 | 9.12 | 14394.35 | 3150.69 |
| 10.23 | 8.64 | 19279.06 | 4326.72 |
| 12.14 | 7.28 | 4313.13 | 1293.87 |
| 12.74 | 6.94 | 2068.86 | 442.28 |
| 13.29 | 6.66 | 9625.97 | 2982.37 |
| 13.51 | 6.55 | 2764.22 | 395.72 |
| 15.62 | 5.67 | 1891.97 | 318.80 |
| 16.05 | 5.52 | 2662.84 | 703.09 |
| 16.29 | 5.44 | 6298.25 | 1046.32 |
| 16.87 | 5.25 | 6862.45 | 973.00 |
| 17.02 | 5.20 | 27914.56 | 5175.78 |
| 17.55 | 5.05 | 9048.65 | 2680.58 |
| 18.00 | 4.92 | 1471.27 | 529.76 |
| 18.51 | 4.79 | 21485.38 | 3960.06 |
| 18.97 | 4.67 | 53356.51 | 10660.90 |
| 19.47 | 4.55 | 36315.48 | 8047.20 |
| 20.41 | 4.35 | 22065.68 | 4792.69 |
| 20.98 | 4.23 | 2383.55 | 855.63 |
| 21.45 | 4.14 | 5586.68 | 748.31 |
| 22.39 | 3.97 | 4949.80 | 489.75 |
| 22.64 | 3.93 | 4626.59 | 1873.26 |
| 23.08 | 3.85 | 5876.13 | 934.80 |
| 23.50 | 3.78 | 936.23 | 177.40 |
| 23.84 | 3.73 | 14622.61 | 1862.43 |
| 24.03 | 3.70 | 11506.27 | 1924.85 |
| 24.46 | 3.64 | 2237.05 | 807.56 |
| 24.88 | 3.58 | 2294.50 | 303.94 |
| 25.21 | 3.53 | 1877.24 | 193.86 |
| 26.42 | 3.37 | 1045.35 | 469.22 |
| 26.86 | 3.32 | 4712.78 | 900.78 |
| 27.24 | 3.27 | 1985.74 | 467.48 |
| 27.77 | 3.21 | 5853.58 | 947.72 |
| 28.23 | 3.16 | 5844.76 | 983.05 |
| 28.53 | 3.13 | 2717.46 | 528.27 |
| 30.47 | 2.93 | 3981.65 | 827.52 |
| 31.04 | 2.88 | 1908.37 | 610.28 |
| 31.58 | 2.83 | 1072.02 | 246.27 |
| 32.44 | 2.76 | 1114.10 | 614.50 |
| 33.93 | 2.64 | 1246.80 | 704.44 |
| 35.53 | 2.52 | 1078.89 | 391.53 |
| 36.58 | 2.45 | 2105.60 | 666.00 |
| 37.11 | 2.42 | 2175.79 | 352.14 |
| 38.68 | 2.33 | 1282.85 | 404.00 |

In the TGA/DSC thermogram of the L-lactate salt form 2 (FIG. 39), continuous weight loss upon heating was noticed in TGA result starting from around 76.5° C. Total weight loss of 1.74% upon heating to 119.9° C. was attributed to the water content in the sample. An endothermic peak with an onset temperature of 145.3° C. in DSC curve was associated with significant weight loss in the same temperature range of TGA curve, showing the decomposition of the salt, which was confirmed by additional experiments.

The sorption/desorption of the L-lactate salt form 2 is presented in FIG. 52, indicating the L-lactate salt is moderately hygroscopic. As shown in FIG. 53, the XRPD pattern of the solid residues after DVS test is the same as that of the initial material.

As presented in FIG. 67, the XRPD patterns of Compound 1 L-lactate salt form 2 under stress conditions were different from that of the initial material, implying that it was not physically stable under 80° C. and 80° C./75% RH conditions for 2 weeks.

6.10.5.6. L-Malate Salt of Compound 1

L-malate salt form 1 was prepared by evaporation of a solution comprising Compound 1 and L-malic acid in ACN. L-malate salt form 2 was prepared by evaporation of a solution comprising Compound 1 and L-malic acid in MeNO$_2$. L-malate salt form 3 was prepared by evaporation of a solution comprising Compound 1 and L-malic acid in EtOAc. L malate salt form 4 was prepared by evaporation of a solution comprising Compound 1 and L malic acid in IPA. The $^1$H NMR of the L-malate salt indicated the stoichiometry was approximately 1:1 for Compound 1 free base to L-malic acid.

The XRPD pattern and Raman spectrum of the L-malate salt of Compound 1 are provided in FIG. 18 and FIG. 19, respectively.

L-malate salt form 1 had a crystalline XRPD pattern as shown in FIG. 90.

A list of X-Ray Diffraction Peaks for L-malate salt form 1 is provided below in Table 55.

TABLE 55

X-Ray Diffraction Peaks for L-malate salt form 1

| Two-theta angle (°) | d Space (Å) | Height (cps) | Integrated Intensity (cps deg) |
|---|---|---|---|
| 5.52 | 16.00 | 4650.06 | 1374.78 |
| 15.86 | 5.58 | 299.26 | 130.32 |
| 17.18 | 5.16 | 317.48 | 150.50 |
| 11.12 | N/A | N/A | N/A |

L-malate salt form 2 had a crystalline XRPD pattern as shown in FIG. 91.

A list of X-Ray Diffraction Peaks for L-malate salt form 2 is provided below in Table 56.

TABLE 56

X-Ray Diffraction Peaks for L-malate salt form 2

| Two-theta angle (°) | d Space (Å) | Height (cps) | Integrated Intensity (cps deg) |
|---|---|---|---|
| 5.48 | 16.13 | 14241.11 | 3831.12 |
| 6.15 | 14.37 | 14244.61 | 3895.02 |
| 7.56 | 11.68 | 10677.31 | 2313.60 |
| 8.50 | 10.40 | 1379.75 | 235.51 |
| 8.99 | 9.83 | 1009.51 | 155.58 |
| 9.50 | 9.30 | 2937.00 | 553.28 |
| 11.08 | 7.98 | 1857.08 | 413.05 |
| 12.21 | 7.24 | 1578.33 | 648.91 |
| 12.97 | 6.82 | 7502.51 | 2057.41 |
| 15.23 | 5.81 | 9224.98 | 2018.74 |
| 16.09 | 5.50 | 3458.62 | 904.54 |
| 17.16 | 5.16 | 7349.85 | 1813.80 |
| 17.50 | 5.06 | 5177.60 | 943.59 |
| 18.01 | 4.92 | 2362.53 | 418.22 |
| 18.48 | 4.80 | 8401.92 | 2975.75 |
| 19.21 | 4.62 | 774.16 | 76.11 |
| 19.69 | 4.51 | 3989.92 | 797.59 |
| 20.38 | 4.35 | 1302.47 | 133.59 |
| 21.09 | 4.21 | 19457.71 | 4307.14 |
| 21.75 | 4.08 | 1674.61 | 558.12 |
| 22.47 | 3.95 | 3942.16 | 786.38 |
| 22.72 | 3.91 | 2402.73 | 634.11 |
| 23.70 | 3.75 | 878.23 | 191.72 |
| 24.44 | 3.64 | 5993.43 | 1304.05 |
| 24.96 | 3.56 | 2237.93 | 303.32 |
| 25.23 | 3.53 | 1430.80 | 183.14 |
| 25.80 | 3.45 | 1115.60 | 224.93 |
| 26.20 | 3.40 | 1083.00 | 130.42 |
| 26.51 | 3.36 | 602.65 | 101.81 |
| 27.78 | 3.21 | 1833.76 | 663.95 |
| 28.41 | 3.14 | 828.83 | 162.67 |
| 30.01 | 2.98 | 588.93 | 107.33 |
| 30.41 | 2.94 | 5575.15 | 1101.91 |
| 32.95 | 2.72 | 713.94 | 167.61 |
| 34.90 | 2.57 | 1206.98 | 144.36 |
| 35.28 | 2.54 | 381.13 | 132.40 |
| 35.91 | 2.50 | 1060.42 | 208.28 |
| 36.41 | 2.47 | 506.65 | 110.71 |
| 37.63 | 2.39 | 666.57 | 168.88 |

L-malate salt form 3 had a crystalline XRPD pattern as shown in FIG. 92.

A list of X-Ray Diffraction Peaks for L-malate salt form 3 is provided below in Table 57.

TABLE 57

X-Ray Diffraction Peaks for L-malate salt form 3

| Two-theta angle (°) | d Space (Å) | Height (cps) | Integrated Intensity (cps deg) |
|---|---|---|---|
| 4.89 | 18.05 | 733.52 | 196.88 |
| 5.49 | 16.08 | 476.34 | 148.29 |
| 7.25 | 12.19 | 388.59 | 110.60 |
| 11.74 | 7.53 | 161.95 | 23.13 |
| 12.39 | 7.14 | 77.69 | 25.95 |
| 15.76 | 5.62 | 302.26 | 59.64 |
| 16.34 | 5.42 | 92.28 | 11.80 |
| 16.73 | 5.29 | 82.14 | 17.20 |
| 19.79 | 4.48 | 93.50 | 14.98 |
| 20.54 | 4.32 | 139.31 | 31.59 |
| 21.23 | 4.18 | 36.88 | 13.01 |

L-malate salt form 4 had a crystalline XRPD pattern as shown in FIG. 93.

A list of X-Ray Diffraction Peaks for L-malate salt form 4 is provided below in Table 58.

TABLE 58

X-Ray Diffraction Peaks for L-malate salt form 4

| Two-theta angle (°) | d Space (Å) | Height (cps) | Integrated Intensity (cps deg) |
|---|---|---|---|
| 5.91 | 14.94 | 31637.83 | 7073.58 |
| 8.34 | 10.59 | 450.62 | 50.16 |
| 10.45 | 8.46 | 446.51 | 49.28 |
| 10.91 | 8.10 | 7690.41 | 1510.86 |
| 12.67 | 6.98 | 1733.49 | 464.77 |
| 13.10 | 6.75 | 632.99 | 112.97 |
| 13.48 | 6.56 | 1569.65 | 343.67 |
| 15.34 | 5.77 | 915.97 | 115.48 |
| 16.71 | 5.30 | 1049.18 | 138.54 |
| 17.49 | 5.07 | 1003.54 | 201.55 |
| 17.89 | 4.95 | 1244.11 | 301.16 |
| 18.22 | 4.86 | 3801.22 | 515.07 |
| 18.72 | 4.74 | 8609.34 | 1276.65 |
| 18.95 | 4.68 | 1225.87 | 395.20 |
| 19.41 | 4.57 | 584.23 | 104.52 |
| 19.84 | 4.47 | 888.59 | 99.41 |
| 20.21 | 4.39 | 778.79 | 107.30 |
| 20.77 | 4.27 | 7772.45 | 1151.69 |
| 21.22 | 4.18 | 6019.34 | 958.38 |
| 21.62 | 4.11 | 1469.36 | 225.07 |
| 21.91 | 4.05 | 3933.61 | 810.69 |
| 22.60 | 3.93 | 1554.17 | 343.06 |
| 23.99 | 3.71 | 1702.59 | 388.26 |
| 24.56 | 3.62 | 1954.61 | 312.65 |
| 25.03 | 3.55 | 1382.95 | 222.57 |
| 26.20 | 3.40 | 3053.38 | 513.08 |
| 27.19 | 3.28 | 378.84 | 50.65 |
| 27.52 | 3.24 | 1327.44 | 297.07 |
| 28.45 | 3.13 | 1262.11 | 258.60 |
| 29.19 | 3.06 | 1040.34 | 204.72 |
| 29.60 | 3.02 | 375.40 | 39.46 |
| 29.96 | 2.98 | 263.41 | 37.89 |
| 30.24 | 2.95 | 514.98 | 44.48 |
| 30.99 | 2.88 | 644.29 | 151.37 |
| 31.61 | 2.83 | 1501.73 | 260.48 |
| 34.44 | 2.60 | 891.98 | 204.00 |
| 35.66 | 2.52 | 268.17 | 104.49 |
| 36.10 | 2.49 | 187.33 | 47.19 |
| 36.86 | 2.44 | 390.94 | 58.41 |
| 37.19 | 2.42 | 190.16 | 78.86 |
| 37.83 | 2.38 | 689.68 | 97.30 |
| 38.58 | 2.33 | 469.32 | 68.49 |
| 39.05 | 2.30 | 250.12 | 29.00 |

In the TGA/DSC thermogram of the L-malate salt form 2 (FIG. 38), 1.21% weight loss upon heating to 94.8° C. on TGA is attributed to the water content in the material.

Multiple endothermic events were observed in DSC results. The first one with an onset temperature of 100.8° C. was likely a solid-solid transition. The second one was followed by a broad third one, corresponding to the temperature range with continuous and significant weight loss on TGA, implying melting and decomposition occurred.

The sorption/desorption of L-malate salt form 2 is presented in FIG. 50, indicating the L-malate salt is a hygroscopic material. As shown in FIG. 51, the XRPD pattern of the solid residues after DVS test is different from that of the initial material.

As presented in FIG. 66, the XRPD patterns of Compound 1 L-malate salt under stress conditions were different from that of the initial material, showing that it was not physically stable under 80° C. and 80° C./75% RH conditions for 2 weeks.

6.10.5.7. Citrate Salt of Compound 1

The citrate salt of Compound 1 was prepared by evaporation of a solution comprising Compound 1 and citric acid in MTBE, MeNO$_2$, Hexane or MeOAc. The XRPD patterns in FIG. 20 and Raman spectra in FIG. 21 of the citrate salt showed that the citrate salt was amorphous. The $^1$H NMR of the citrate salt indicated that the stoichiometry was approximately 1:1 for Compound 1 free base to citric acid.

6.10.5.8. Succinate Salt of Compound 1

Succinate salt form 1 was prepared by evaporation of a solution comprising Compound 1 and succinic acid in ACN or EtOH. Succinate salt form 2 was prepared by evaporation of a solution comprising Compound 1 and succinic acid in EtOAc. When acetone was used to crystallize the succinate salt, a mix of succinate salt (form 1) and free base (form B) was obtained.

The XRPD patterns and Raman spectra of succinate salt forms 1-2 are provided in FIG. 22 and FIG. 23, respectively.

Succinate salt form 1 had a crystalline XRPD pattern as shown in FIG. 94.

A list of X-Ray Diffraction Peaks for succinate salt form 1 is provided below in Table 59.

TABLE 59

X-Ray Diffraction Peaks for succinate salt form 1

| Two-theta angle (°) | d Space (Å) | Height (cps) | Integrated Intensity (cps deg) |
|---|---|---|---|
| 5.86 | 15.06 | 741560.16 | 134011.71 |
| 8.43 | 10.48 | 3428.24 | 566.75 |
| 11.07 | 7.98 | 8866.34 | 1152.28 |
| 11.79 | 7.50 | 19251.74 | 3571.33 |
| 12.67 | 6.98 | 1055.18 | 744.64 |
| 13.55 | 6.53 | 2868.66 | 662.80 |
| 13.69 | 6.46 | 5459.82 | 1133.49 |
| 14.47 | 6.12 | 481.50 | 186.09 |
| 16.84 | 5.26 | 4915.24 | 643.73 |
| 17.38 | 5.10 | 598.40 | 112.44 |
| 17.74 | 4.99 | 8286.93 | 1474.54 |
| 18.77 | 4.72 | 10169.14 | 1725.47 |
| 18.97 | 4.67 | 1406.15 | 163.65 |
| 19.22 | 4.61 | 3386.12 | 762.14 |
| 20.59 | 4.31 | 729.25 | 113.97 |
| 21.11 | 4.21 | 2468.42 | 599.98 |
| 21.33 | 4.16 | 7483.04 | 1362.99 |
| 21.43 | 4.14 | 4898.23 | 317.40 |
| 21.83 | 4.07 | 4564.87 | 614.73 |
| 21.90 | 4.06 | 12063.81 | 1567.35 |
| 22.23 | 4.00 | 1810.53 | 450.35 |
| 22.78 | 3.90 | 1062.85 | 212.49 |
| 23.74 | 3.75 | 37058.08 | 6170.46 |
| 23.97 | 3.71 | 4975.30 | 962.00 |
| 24.84 | 3.58 | 2097.14 | 474.48 |
| 25.12 | 3.54 | 4306.68 | 1112.62 |
| 26.29 | 3.39 | 12976.02 | 2215.84 |

TABLE 59-continued

X-Ray Diffraction Peaks for succinate salt form 1

| Two-theta angle (°) | d Space (Å) | Height (cps) | Integrated Intensity (cps deg) |
|---|---|---|---|
| 27.42 | 3.25 | 901.22 | 159.21 |
| 28.10 | 3.17 | 1659.85 | 238.74 |
| 28.20 | 3.16 | 2429.80 | 274.68 |
| 28.39 | 3.14 | 2613.39 | 471.94 |
| 28.88 | 3.09 | 530.93 | 114.42 |
| 29.35 | 3.04 | 2131.21 | 381.64 |
| 29.57 | 3.02 | 4295.83 | 753.04 |
| 29.82 | 2.99 | 1459.99 | 215.81 |
| 30.88 | 2.89 | 390.60 | 55.20 |
| 31.61 | 2.83 | 10632.06 | 1942.82 |
| 33.87 | 2.64 | 768.10 | 98.22 |
| 34.33 | 2.61 | 2622.97 | 624.69 |
| 35.36 | 2.54 | 649.18 | 395.76 |
| 39.11 | 2.30 | 155.05 | 61.13 |
| 39.85 | 2.26 | 1061.88 | 215.57 |

Succinate salt form 2 had a crystalline XRPD pattern as shown in FIG. 95.

A list of X-Ray Diffraction Peaks for succinate salt form 2 is provided below in Table 60.

TABLE 60

X-Ray Diffraction Peaks for succinate salt form 2

| Two-theta angle (°) | d Space (Å) | Height (cps) | Integrated Intensity (cps deg) |
|---|---|---|---|
| 5.69 | 15.53 | 3116.38 | 1013.59 |
| 5.90 | 14.96 | 2015.61 | 643.95 |
| 6.18 | 14.28 | 715.27 | 222.85 |
| 11.02 | 8.02 | 207.22 | 62.21 |
| 16.48 | 5.38 | 55.16 | 39.67 |
| 17.31 | 5.12 | 68.01 | 20.03 |
| 18.49 | 4.80 | 176.59 | 105.39 |
| 20.99 | 4.23 | 221.29 | 157.64 |
| 22.30 | 3.98 | 72.49 | 20.83 |
| 23.16 | 3.84 | 52.32 | 12.42 |
| 29.01 | 3.08 | 69.12 | 23.39 |
| 30.85 | 2.90 | 53.51 | 26.22 |

6.10.5.9. Tosylate Salt of Compound 1

Tosylate salt form 1 was prepared by evaporation of a solution comprising Compound 1 and p-toluenesulfonic acid in ACN. Tosylate salt form 2 was prepared by evaporation of a solution comprising Compound 1 and p-toluenesulfonic acid in MeNO$_2$ or acetone. Tosylate salt form 3 was prepared by evaporation of a solution comprising Compound 1 and p-toluenesulfonic acid in EtOAc.

The XRPD patterns and Raman spectra of tosylate salt forms 1-3 are provided in FIG. 24 and FIG. 25, respectively.

Tosylate salt form 1 had a crystalline XRPD pattern as shown in FIG. 96.

A list of X-Ray Diffraction Peaks for tosylate salt form 1 is provided below in Table 61.

TABLE 61

X-Ray Diffraction Peaks for tosylate salt form 1

| Two-theta angle (°) | d Space (Å) | Height (cps) | Integrated Intensity (cps deg) |
|---|---|---|---|
| 4.50 | 19.63 | 1119.48 | 481.74 |
| 6.22 | 14.19 | 24089.25 | 8683.84 |

TABLE 61-continued

X-Ray Diffraction Peaks for tosylate salt form 1

| Two-theta angle (°) | d Space (Å) | Height (cps) | Integrated Intensity (cps deg) |
|---|---|---|---|
| 8.88 | 9.95 | 7912.38 | 2783.78 |
| 9.55 | 9.26 | 2286.05 | 1003.10 |
| 9.67 | 9.14 | 1996.14 | 635.37 |
| 12.19 | 7.25 | 5448.92 | 1717.40 |
| 13.25 | 6.68 | 3136.11 | 1011.98 |
| 13.89 | 6.37 | 7529.57 | 3315.12 |
| 14.86 | 5.96 | 1281.58 | 310.08 |
| 15.71 | 5.64 | 3137.73 | 1037.40 |
| 17.14 | 5.17 | 5481.82 | 1566.01 |
| 17.73 | 5.00 | 3531.02 | 981.24 |
| 18.29 | 4.85 | 1046.09 | 317.43 |
| 18.63 | 4.76 | 3683.67 | 904.17 |
| 19.45 | 4.56 | 3896.87 | 2042.03 |
| 19.90 | 4.46 | 3285.04 | 1187.11 |
| 21.06 | 4.22 | 2293.12 | 665.02 |
| 21.71 | 4.09 | 10614.44 | 4550.98 |
| 22.64 | 3.92 | 3981.34 | 1553.01 |
| 23.12 | 3.84 | 2237.02 | 752.41 |
| 23.88 | 3.72 | 875.58 | 528.34 |
| 24.27 | 3.66 | 1288.84 | 419.54 |
| 25.43 | 3.50 | 2133.47 | 487.47 |
| 25.84 | 3.45 | 2652.92 | 1354.57 |
| 26.06 | 3.42 | 780.65 | 259.53 |
| 26.37 | 3.38 | 1293.11 | 194.96 |
| 27.71 | 3.22 | 1001.90 | 400.92 |
| 28.45 | 3.13 | 241.26 | 52.80 |
| 28.82 | 3.10 | 650.54 | 207.73 |
| 29.20 | 3.06 | 983.94 | 309.44 |
| 30.62 | 2.92 | 745.67 | 355.19 |
| 31.45 | 2.84 | 837.77 | 432.24 |
| 33.81 | 2.65 | 163.76 | 156.52 |
| 34.89 | 2.57 | 833.87 | 343.43 |
| 35.38 | 2.54 | 547.37 | 179.19 |

Tosylate salt form 2 had a crystalline XRPD pattern as shown in FIG. 97.

A list of X-Ray Diffraction Peaks for tosylate salt form 2 is provided below in Table 62.

TABLE 62

X-Ray Diffraction Peaks for tosylate salt form 2

| Two-theta angle (°) | d Space (Å) | Height (cps) | Integrated Intensity (cps deg) |
|---|---|---|---|
| 5.78 | 15.28 | 3129.35 | 882.17 |
| 6.24 | 14.15 | 6413.58 | 1705.19 |
| 6.48 | 13.64 | 6310.57 | 1602.31 |
| 7.01 | 12.60 | 1270.40 | 460.48 |
| 8.13 | 10.87 | 12819.37 | 3032.70 |
| 9.79 | 9.02 | 1209.06 | 355.63 |
| 11.67 | 7.57 | 12054.78 | 2902.12 |
| 12.04 | 7.35 | 749.22 | 232.59 |
| 12.60 | 7.02 | 4656.33 | 1144.98 |
| 14.25 | 6.21 | 5771.80 | 1204.84 |
| 15.04 | 5.88 | 8508.73 | 1766.00 |
| 15.57 | 5.69 | 1201.06 | 370.24 |
| 16.42 | 5.39 | 4471.53 | 1074.22 |
| 17.53 | 5.05 | 1492.46 | 287.52 |
| 18.13 | 4.89 | 976.97 | 133.25 |
| 18.31 | 4.84 | 4582.65 | 1701.91 |
| 18.89 | 4.69 | 5274.72 | 1700.42 |
| 19.55 | 4.54 | 1069.93 | 261.06 |
| 19.90 | 4.46 | 1094.61 | 247.10 |
| 21.36 | 4.16 | 4435.48 | 761.82 |
| 21.61 | 4.11 | 3758.93 | 882.67 |
| 21.94 | 4.05 | 853.73 | 88.40 |
| 22.49 | 3.95 | 3570.30 | 888.13 |
| 22.74 | 3.91 | 1446.33 | 273.00 |
| 23.05 | 3.85 | 1650.81 | 342.85 |

TABLE 62-continued

X-Ray Diffraction Peaks for tosylate salt form 2

| Two-theta angle (°) | d Space (Å) | Height (cps) | Integrated Intensity (cps deg) |
|---|---|---|---|
| 23.35 | 3.81 | 3441.60 | 887.49 |
| 23.59 | 3.77 | 7432.65 | 1530.88 |
| 24.36 | 3.65 | 2344.93 | 768.09 |
| 24.55 | 3.62 | 1568.96 | 315.09 |
| 25.53 | 3.49 | 1864.52 | 430.70 |
| 25.78 | 3.45 | 1116.10 | 249.08 |
| 26.54 | 3.36 | 2153.07 | 378.46 |
| 27.40 | 3.25 | 1360.83 | 449.11 |
| 28.07 | 3.18 | 408.48 | 52.86 |
| 28.49 | 3.13 | 415.91 | 113.26 |
| 29.32 | 3.04 | 386.23 | 223.04 |
| 30.44 | 2.93 | 478.73 | 207.01 |
| 32.58 | 2.75 | 266.35 | 98.77 |
| 33.16 | 2.70 | 222.84 | 50.13 |
| 33.62 | 2.66 | 556.86 | 70.67 |
| 35.52 | 2.53 | 601.40 | 341.07 |
| 36.88 | 2.44 | 534.83 | 121.80 |

Tosylate salt form 3 had a crystalline XRPD pattern as shown in FIG. 98.

A list of X-Ray Diffraction Peaks for tosylate salt form 3 is provided below in Table 63.

TABLE 63

X-Ray Diffraction Peaks for tosylate salt form 3

| Two-theta angle (°) | d Space (Å) | Height (cps) | Integrated Intensity (cps deg) |
|---|---|---|---|
| 5.59 | 15.79 | 587.67 | 198.25 |
| 7.44 | 11.88 | 122.67 | 29.86 |
| 8.91 | 9.92 | 100.60 | 21.68 |
| 11.22 | 7.88 | 908.65 | 230.37 |
| 13.13 | 6.74 | 292.80 | 68.40 |
| 13.78 | 6.42 | 103.28 | 18.68 |
| 14.05 | 6.30 | 72.35 | 12.99 |
| 14.89 | 5.95 | 79.41 | 16.05 |
| 15.62 | 5.67 | 121.73 | 36.04 |
| 17.78 | 4.98 | 171.13 | 57.59 |
| 18.15 | 4.88 | 374.03 | 77.57 |
| 19.24 | 4.61 | 99.69 | 17.63 |
| 19.70 | 4.50 | 63.03 | 11.84 |
| 20.77 | 4.27 | 326.32 | 112.46 |
| 21.72 | 4.09 | 94.50 | 25.96 |
| 21.96 | 4.04 | 194.16 | 45.94 |
| 22.40 | 3.97 | 445.42 | 103.56 |
| 23.49 | 3.78 | 147.54 | 26.77 |
| 24.97 | 3.56 | 24.38 | 28.69 |
| 25.97 | 3.43 | 126.49 | 21.65 |
| 26.66 | 3.34 | 74.56 | 26.28 |
| 28.92 | 3.08 | 51.12 | 17.05 |
| 31.46 | 2.84 | 36.16 | 13.37 |

6.10.5.10. Mesylate Salt of Compound 1

Mesylate salt form 1 was prepared by evaporation of a solution comprising Compound 1 and methanesulfonic acid in ACN/IPA, EtOH/IPA or acetone. Mesylate salt form 2 was prepared by evaporation of a solution comprising Compound 1 and methanesulfonic acid in EtOAc.

The XRPD patterns and Raman spectra of mesylate salt forms 1-2 are provided in FIG. 26 and FIG. 27, respectively.

Mesylate salt form 1 had a crystalline XRPD pattern as shown in FIG. 99. A list of X-Ray Diffraction Peaks for mesylate salt form 1 is provided below in Table 64.

TABLE 64

X-Ray Diffraction Peaks for mesylate salt form 1

| Two-theta angle (°) | d Space (Å) | Height (cps) | Integrated Intensity (cps deg) |
|---|---|---|---|
| 5.78 | 15.27 | 49300.59 | 12429.36 |
| 7.87 | 11.22 | 2955.99 | 658.99 |
| 10.30 | 8.58 | 2325.51 | 514.54 |
| 10.71 | 8.25 | 5639.75 | 1233.98 |
| 11.61 | 7.62 | 4822.73 | 1387.64 |
| 11.86 | 7.46 | 2031.41 | 388.49 |
| 12.39 | 7.14 | 280.99 | 157.12 |
| 13.50 | 6.55 | 445.26 | 64.79 |
| 13.83 | 6.40 | 598.23 | 211.63 |
| 14.17 | 6.24 | 465.14 | 78.92 |
| 15.05 | 5.88 | 1537.55 | 238.83 |
| 15.56 | 5.69 | 825.59 | 180.11 |
| 15.80 | 5.60 | 786.43 | 131.94 |
| 16.29 | 5.44 | 1183.68 | 265.49 |
| 17.06 | 5.19 | 785.26 | 127.66 |
| 17.49 | 5.07 | 5376.19 | 1043.67 |
| 17.74 | 5.00 | 3356.48 | 525.78 |
| 18.10 | 4.90 | 6521.33 | 3902.46 |
| 18.30 | 4.84 | 8803.15 | 1056.35 |
| 18.54 | 4.78 | 4331.78 | 791.47 |
| 19.25 | 4.61 | 2827.22 | 485.65 |
| 19.89 | 4.46 | 827.43 | 147.02 |
| 20.18 | 4.40 | 2395.10 | 581.27 |
| 20.58 | 4.31 | 1565.50 | 448.98 |
| 20.98 | 4.23 | 1329.32 | 121.57 |
| 21.56 | 4.12 | 1098.02 | 435.12 |
| 21.95 | 4.05 | 1906.89 | 639.52 |
| 23.41 | 3.80 | 5886.15 | 1445.90 |
| 24.22 | 3.67 | 1175.84 | 298.88 |
| 24.82 | 3.58 | 1168.28 | 343.54 |
| 25.53 | 3.49 | 999.98 | 330.62 |
| 26.08 | 3.41 | 1605.90 | 277.36 |
| 26.77 | 3.33 | 543.62 | 69.86 |
| 27.27 | 3.27 | 620.56 | 264.06 |
| 28.17 | 3.16 | 1296.21 | 233.73 |
| 28.38 | 3.14 | 713.11 | 401.95 |
| 29.03 | 3.07 | 659.20 | 119.89 |
| 29.31 | 3.04 | 983.25 | 231.03 |
| 29.87 | 2.99 | 568.74 | 211.56 |
| 30.81 | 2.90 | 272.77 | 78.25 |
| 32.02 | 2.79 | 557.29 | 117.37 |
| 32.99 | 2.71 | 273.87 | 49.72 |
| 34.03 | 2.63 | 287.44 | 60.05 |
| 35.01 | 2.56 | 561.92 | 118.83 |
| 35.45 | 2.53 | 369.17 | 165.89 |
| 35.72 | 2.51 | 436.77 | 75.30 |
| 36.33 | 2.47 | 223.38 | 39.78 |
| 37.65 | 2.39 | 433.85 | 164.84 |

Mesylate salt form 2 had a crystalline XRPD pattern as shown in FIG. 100.

A list of X-Ray Diffraction Peaks for mesylate salt form 2 is provided below in Table 65.

TABLE 65

X-Ray Diffraction Peaks for mesylate salt form 2

| Two-theta angle (°) | d Space (Å) | Height (cps) | Integrated Intensity (cps deg) |
|---|---|---|---|
| 5.14 | 17.18 | 1551.90 | 358.84 |
| 5.26 | 16.79 | 2300.19 | 281.94 |
| 10.45 | 8.46 | 736.68 | 139.37 |
| 16.37 | 5.41 | 85.61 | 14.32 |
| 18.36 | 4.83 | 379.10 | 102.32 |
| 20.41 | 4.35 | 215.89 | 34.85 |
| 20.95 | 4.24 | 741.91 | 110.48 |
| 21.59 | 4.11 | 428.99 | 62.04 |
| 21.86 | 4.06 | 169.85 | 23.59 |
| 22.14 | 4.01 | 60.71 | 4.84 |
| 22.63 | 3.93 | 75.07 | 9.44 |
| 23.33 | 3.81 | 152.57 | 17.25 |
| 24.24 | 3.67 | 77.04 | 21.74 |
| 25.76 | 3.46 | 62.57 | 6.96 |
| 26.16 | 3.40 | 162.16 | 28.53 |
| 28.41 | 3.14 | 88.28 | 19.20 |
| 31.70 | 2.82 | 102.91 | 24.75 |

6.10.5.11. Besylate Salt and Fumarate Salt of Compound 1

Only one sample was prepared for each acid, respectively. Both salts were crystalline. The fumarate salt of Compound 1 was prepared by evaporation of a solution comprising Compound 1 and fumaric acid in ACN. The besylate salt of Compound 1 was prepared by evaporation of a solution comprising Compound 1 and benzenesulfonic acid in MeNO$_2$. The $^1$H NMR spectrum of the fumarate salt indicated that the fumarate salt was likely a hemi-fumarate, i.e., stoichiometry of free base to fumaric acid was 2:1.

The XRPD patterns and Raman spectra of besylate salt and fumarate salt of compound 1 were presented in FIG. 28 and FIG. 29, respectively.

Besylate salt had a crystalline XRPD pattern as shown in FIG. 101.

A list of X-Ray Diffraction Peaks for besylate salt is provided below in Table 66.

TABLE 66

X-Ray Diffraction Peaks for besylate salt

| Two-theta angle (°) | d Space (Å) | Height (cps) | Integrated Intensity (cps deg) |
|---|---|---|---|
| 6.29 | 14.04 | 10079.20 | 3370.84 |
| 7.84 | 11.27 | 792.75 | 108.46 |
| 9.64 | 9.17 | 1715.74 | 623.01 |
| 11.32 | 7.81 | 3068.41 | 767.79 |
| 12.63 | 7.00 | 714.46 | 137.04 |
| 14.38 | 6.15 | 4085.73 | 987.11 |
| 15.89 | 5.57 | 598.93 | 455.05 |
| 16.81 | 5.27 | 2062.26 | 484.07 |
| 17.44 | 5.08 | 985.62 | 403.57 |
| 19.09 | 4.64 | 1730.10 | 327.29 |
| 19.39 | 4.57 | 2021.88 | 847.60 |
| 19.82 | 4.48 | 413.42 | 87.69 |
| 20.31 | 4.37 | 753.15 | 141.36 |
| 20.79 | 4.27 | 2156.74 | 598.02 |
| 21.63 | 4.10 | 624.78 | 148.57 |
| 22.35 | 3.97 | 913.49 | 366.36 |
| 22.82 | 3.89 | 1781.71 | 366.74 |
| 23.87 | 3.72 | 1699.23 | 656.68 |
| 25.30 | 3.52 | 1057.85 | 298.77 |
| 26.12 | 3.41 | 637.04 | 289.25 |
| 27.64 | 3.22 | 1214.57 | 597.64 |
| 28.94 | 3.08 | 613.67 | 331.12 |
| 34.90 | 2.57 | 274.40 | 63.34 |

Fumarate salt had a crystalline XRPD pattern as shown in FIG. 102.

A list of X-Ray Diffraction Peaks for fumarate salt is provided below in Table 67.

TABLE 67

X-Ray Diffraction Peaks for fumarate salt

| Two-theta angle (°) | d Space (Å) | Height (cps) | Integrated Intensity (cps deg) |
|---|---|---|---|
| 5.97 | 14.80 | 252492.33 | 70173.05 |
| 8.31 | 10.64 | 2370.62 | 521.48 |
| 11.09 | 7.97 | 6488.86 | 2230.80 |
| 11.92 | 7.42 | 633.10 | 177.24 |
| 12.38 | 7.15 | 1824.49 | 447.50 |
| 12.97 | 6.82 | 3300.75 | 845.78 |
| 13.53 | 6.54 | 2169.17 | 551.07 |
| 14.72 | 6.01 | 749.76 | 283.35 |
| 15.81 | 5.60 | 1083.00 | 318.56 |
| 16.66 | 5.32 | 1114.36 | 220.75 |
| 18.51 | 4.79 | 1692.29 | 391.66 |
| 18.92 | 4.69 | 5992.99 | 1732.71 |
| 20.94 | 4.24 | 2922.64 | 569.38 |
| 21.36 | 4.16 | 13242.36 | 2930.78 |
| 21.76 | 4.08 | 4393.51 | 1792.16 |
| 22.34 | 3.98 | 1433.13 | 337.27 |
| 23.33 | 3.81 | 578.80 | 247.32 |
| 24.08 | 3.69 | 3172.91 | 1022.18 |
| 24.65 | 3.61 | 2885.09 | 647.85 |
| 25.58 | 3.48 | 599.14 | 238.98 |
| 26.31 | 3.38 | 11075.59 | 2579.03 |
| 28.74 | 3.10 | 2691.70 | 1069.09 |
| 29.20 | 3.06 | 2323.12 | 711.80 |
| 29.83 | 2.99 | 1118.39 | 279.20 |
| 30.96 | 2.89 | 118.24 | 128.75 |
| 31.72 | 2.82 | 6110.27 | 1748.30 |
| 34.86 | 2.57 | 774.22 | 423.28 |
| 36.34 | 2.47 | 414.89 | 293.99 |

6.10.6. Salt Scale-Up Results

The crystalline salt forms observed from the screening study, i.e., HCl (form 2), $H_2SO_4$ (form 1), $H_3PO_4$ (form 1), L-tartrate (form 1, hemi-tartrate hydrate), L-malate (form 2) and L-lactate (form 2), were successfully scaled up and characterized along with the free base.

The concentrations of acids were different from those used in the salt screening experiments. The amounts of Compound 1 and acids used for salt scale-up were summarized in Table 68.

TABLE 68

Compound 1 Salt Scale-up

| Sample | Cmpd 1 (mg) | Cmpd 1 (mmole) | MeOH/DCM (mL) | Acid conc. (mol/L) | Acid used (µL) | Molar ratio of Cmpd 1/Acid |
|---|---|---|---|---|---|---|
| HCl | 361.4 | 1.124 | 20.0 | 12.0 | 94.0 | 1 |
| $H_2SO_4$ | 311.9 | 0.970 | 20.0 | 18.4 | 53.0 | 1 |
| $H_3PO_4$ | 299.5 | 0.932 | 20.0 | 15.2 | 62.0 | 1 |
| L-lactate | 357.7 | 1.113 | 20.0 | 0.649 | 1715.0 | 1 |
| L-tartrate | 262.5 | 0.817 | 20.0 | 0.525 | 779.0 | 2 |
| L-malate | 277.0 | 0.862 | 20.0 | 0.479 | 1801.0 | 1 |

The free base of Compound 1 was weighed and dissolved in MeOH/DCM, then mixed with the acidic counter-ion solution based on the specified molar ratio in a 40 mL clear glass vial. The vial was then capped and shaken at 200 RPM at ambient temperature for 2 hours. Afterwards, the cap was removed and the vial was stored in fume hood for drying under nitrogen purge. Re-crystallization solvent was then added to the sample to generate a suspension sample. All salts were prepared in the same procedure. The final 6 mL of re-crystallization solvents were added into the samples as follows:

IPA to the HCl salt sample;
IPA to the $H_2SO_4$ salt sample;
EtOAc to the $H_3PO_4$ salt sample;
Acetone to the L-tartrate salt sample;
Nitromethane and acetone of 1 mL to the L-malate salt sample; and
n-Hexane to the L-lactate salt sample.

In addition, both L-malate sample and L-lactate sample were seeded with crystalline sample obtained during salt screening using the corresponding counter-ion, respectively.

All samples in the re-crystallization solvents were stirred with stirring bars at ambient temperature for approximately 3 days. They were filtered using 0.2 µm Nylon-membraned centrifuge tube filters at 14000 RPM for 5 min, respectively. The solids were covered and dried in vacuum oven at ambient temperature for 2 days. Both the HCl salt and L-malate salt were further dried in vacuum oven at 60° C. for one day after $^1$H NMR tests indicated they contained small amount of re-crystallization solvents. The $H_2SO_4$ salt was re-slurried in n-Hexane and recovered through filtration and drying in vacuum oven at 60° C. overnight.

At the end, both salts and free base were stored in closed vials at ambient temperature prior to analyses using a variety of solid state characterization techniques. The compounds used were free base (form A), HCl salt (form 2), $H_2SO_4$ salt (form 1), $H_3PO_4$ salt (form 1), L-tartrate salt (form 1), L-malate salt (form 2) and L-lactate salt (form 2).

6.10.7. Solid State Stability

Physical Stability:

A portion of the sample was loaded to a 4 mL clear glass vial. Four samples were prepared for each salt. The vials (open) were stored under 4 different stress conditions, respectively. The stress conditions were 40° C., 40° C./75% RH, 80° C. and 80° C./75% RH. Temperature was controlled using ovens and 75% RH was controlled using saturated sodium chloride solution in water. At the two-week time point, the samples stored at 80° C. and 80° C./75% RH were removed for analysis using XRPD.

Chemical Stability:

Approximately 1 mg of Compound 1 was accurately weighed to a 4 mL clear glass vial. Six vials were prepared for each salt. Two samples were stored in the refrigerator. The other four samples in open vials were stored under 4 stress conditions, respectively. At the two-week time point, the samples stored at 80° C. and 80° C./75% RH were removed, dissolved in solvent and assayed using HPLC with UV detection after appropriate dilution. One set of samples stored in the refrigerator were used to prepare the stock and standard solutions. The HPLC method was presented in Table 69.

TABLE 69

HPLC Method

| | |
|---|---|
| HPLC System | alliance e2695 Separation Module with 2998 Photodiode Array Detector |
| Software | Empower2 |
| Mobile Phase A | 0.1% (v/v) formic acid in water |
| Mobile Phase B | 0.1% (v/v) formic acid in MeOH |
| Column | Phenomenex Gemini-NX, 5µ C18, 110Å, 250 × 4.6 mm, Cat# 00G-4454-E0, SN# 614022-11 |
| Column Temperature | Ambient |
| Flow Rate | 1.0 mL/min |
| Injection Volume | 10 µL |
| Detection | PDA range of 210-400 nm and UV at 254 nm |
| Run Time | 25 minutes |

| Gradient profile | Time (minute) | % A | % B |
|---|---|---|---|
| | 0.0 | 85 | 15 |
| | 0.25 | 85 | 15 |
| | 20.0 | 0 | 100 |
| | 23.0 | 0 | 100 |

TABLE 69-continued

| HPLC Method | | |
|---|---|---|
| 24.0 | 85 | 15 |
| 25.0 | 85 | 15 |

As presented in Table 70, the remaining percentages for free base and salts were within %100±2 except for the L-malate salt, showing the free base and salts were chemically stable under 80° C. and 80° C./75% RH conditions for 2 weeks except for the L-malate salt. The chromatograms are presented in FIG. 68, FIG. 69, FIG. 70, FIG. 71, FIG. 72, FIG. 73 and FIG. 74, respectively. Although extra peaks were observed for the salt except for the free base and L-malate salt, the peak area percentage was <0.1%. As to the L-malate salt, significant degradations occurred, therefore it was not chemically stable under stress conditions.

TABLE 70

Remaining Percentage of Compound 1 Free Base and Salts under Stress Conditions

| Compound | Free base | HCl | H$_2$SO$_4$ | H$_3$PO$_4$ | L-tartrate | L-malate | L-lactate |
|---|---|---|---|---|---|---|---|
| % Remaining at 80° C. | 101.8 | 101.2 | 100.0 | 101.1 | 98.7 | 87.7 | 100.4 |
| % Remaining at 80° C./75% RH | 100.8 | 100.4 | 100.1 | 99.9 | 98.3 | 92.9 | 100.5 |

6.10.8. Conclusions

Crystalline salts were obtained from 11 of 13 acidic counter-ions used in this study. All salts exhibited higher solubility than the free base in water. Except for the L-malate salt, all salts and free base were chemically stable under 80° C. and 80° C./75% RH for 2 weeks. Compound 1 (free base), the H$_3$PO$_4$ salt and L-tartrate salt were physically stable under stress conditions. The HCl salt and H$_2$SO$_4$ salt were stable under 80° C. condition but not under 80° C./75% RH. The L-lactate salt was not physically stable under stress conditions. The L-malate salt was neither physically nor chemically stable under stress condition. Compound 1 (free base), the H$_3$PO$_4$ salt and L-tartrate salt (hydrate) were not hygroscopic. The L-lactate salt was moderately hygroscopic and other salts were hygroscopic.

A number of references have been cited, the disclosures of which are incorporated herein by reference in their entirety.

What is claimed is:

1. A pharmaceutical composition comprising about 20-40% by weight of 2-(tert-butylamino)-4-((1R,3R,4R)-3-hydroxy-4-methylcyclohexylamino)-pyrimidine-5-carboxamide or a pharmaceutically acceptable salt, stereoisomer, solvate, hydrate, isotopologue or solid form thereof, about 30-50% by weight of microcrystalline cellulose, about 20-40% by weight of mannitol, about 1-10% by weight of carboxymethyl cellulose, about 1-10% by weight of hydroxypropyl methylcellulose and about 0.1-2% by weight of magnesium stearate.

2. A pharmaceutical composition comprising about 28.57% by weight of 2-(tert-butylamino)-4-((1R,3R,4R)-3-hydroxy-4-methylcyclohexylamino)-pyrimidine-5-carboxamide or a pharmaceutically acceptable salt, stereoisomer, solvate, hydrate, isotopologue or solid form thereof, about 37.43% by weight of microcrystalline cellulose, about 26% by weight of mannitol, about 4% by weight of carboxymethyl cellulose, about 3% by weight of hydroxypropyl methylcellulose and about 1% by weight of magnesium stearate.

3. A pharmaceutical composition comprising about 20-40% by weight of 2-(tert-butylamino)-4-((1R,3R,4R)-3-hydroxy-4-methylcyclohexylamino)-pyrimidine-5-carboxamide or a pharmaceutically acceptable salt, stereoisomer, solvate, hydrate, isotopologue or solid form thereof, about 20-40% by weight of microcrystalline cellulose, about 20-40% by weight of mannitol, about 1-20% by weight of carboxymethyl cellulose, about 1-10% by weight of hydroxypropyl methylcellulose and about 0.1-2% by weight of magnesium stearate.

4. A pharmaceutical composition comprising about 28.57% by weight of 2-(tert-butylamino)-4-((1R,3R,4R)-3-hydroxy-4-methylcyclohexylamino)-pyrimidine-5-carboxamide or a pharmaceutically acceptable salt, stereoisomer, solvate, hydrate, isotopologue or solid form thereof, about 33.43% by weight of microcrystalline cellulose, about 26% by weight of mannitol, about 8% by weight of carboxymethyl cellulose, about 3% by weight of hydroxypropyl methylcellulose and about 1% by weight of magnesium stearate.

5. A pharmaceutical composition comprising about 28.57% by weight of 2-(tert-butylamino)-4-((1R,3R,4R)-3-hydroxy-4-methylcyclohexylamino)-pyrimidine-5-carboxamide or a pharmaceutically acceptable salt, stereoisomer, solvate, hydrate, isotopologue or solid form thereof, about 31.93% by weight of microcrystalline cellulose, about 26% by weight of mannitol, about 8% by weight of carboxymethyl cellulose, about 4.5% by weight of hydroxypropyl methylcellulose and about 1% by weight of magnesium stearate.

6. A pharmaceutical composition comprising about 20-40% by weight of 2-(tert-butylamino)-4-((1R,3R,4R)-3-hydroxy-4-methylcyclohexylamino)-pyrimidine-5-carboxamide or a pharmaceutically acceptable salt, stereoisomer, solvate, hydrate, isotopologue or solid form thereof, about 20-50% by weight of microcrystalline cellulose, about 20-40% by weight of mannitol, about 1-10% by weight of carboxymethyl cellulose, about 1-10% by weight of hydroxypropyl methylcellulose and about 0.1-2% by weight of magnesium stearate.

7. A pharmaceutical composition comprising about 28.57% by weight of 2-(tert-butylamino)-4-((1R,3R,4R)-3-hydroxy-4-methylcyclohexylamino)-pyrimidine-5-carboxamide or a pharmaceutically acceptable salt, stereoisomer, solvate, hydrate, isotopologue or solid form thereof, about 35.93% by weight of microcrystalline cellulose, about 26% by weight of mannitol, about 4% by weight of carboxymethyl cellulose, about 4.5% by weight of hydroxypropyl methylcellulose and about 1% by weight of magnesium stearate.

* * * * *